(12) United States Patent
Alexandrov et al.

(10) Patent No.: US 11,077,090 B2
(45) Date of Patent: Aug. 3, 2021

(54) COMPOUNDS AND COMPOSITIONS AND USES THEREOF

(71) Applicants: Sunovion Pharmaceuticals Inc., Marlborough, MA (US); PGI Drug Discovery LLC, Paramus, NJ (US)

(72) Inventors: Vadim Alexandrov, Tarrytown, NY (US); Carrie A. Bowen, Uxbridge, MA (US); Taleen G. Hanania, Valhalla, NY (US); Noel Aaron Powell, Westford, MA (US)

(73) Assignees: Sunovion Pharmaceuticals Inc., Marlborough (MA); PGI Drug Discovery LLC, Paramus, NJ (US)

( * ) Notice: Subject to any disclaimer, the term of this patent is extended or adjusted under 35 U.S.C. 154(b) by 0 days.

(21) Appl. No.: 15/663,672

(22) Filed: Jul. 28, 2017

(65) Prior Publication Data

US 2018/0028492 A1 Feb. 1, 2018

Related U.S. Application Data

(60) Provisional application No. 62/368,575, filed on Jul. 29, 2016.

(51) Int. Cl.
| | |
|---|---|
| *C07D 311/76* | (2006.01) |
| *A61K 31/353* | (2006.01) |
| *A61K 31/13* | (2006.01) |
| *C12P 17/06* | (2006.01) |
| *C07D 313/08* | (2006.01) |
| *A61K 45/06* | (2006.01) |
| *A61K 31/352* | (2006.01) |

(52) U.S. Cl.
CPC ............ *A61K 31/353* (2013.01); *A61K 31/13* (2013.01); *A61K 31/352* (2013.01); *A61K 45/06* (2013.01); *C07D 311/76* (2013.01); *C07D 313/08* (2013.01); *C12P 17/06* (2013.01)

(58) Field of Classification Search
CPC .................................................. C07D 311/76
See application file for complete search history.

(56) References Cited

U.S. PATENT DOCUMENTS

| | | | |
|---|---|---|---|
| 3,438,995 A | 4/1969 | Faust et al. | |
| 3,470,179 A | 9/1969 | Ott | |
| 3,536,809 A | 10/1970 | Applezweig | |
| 3,549,624 A | 12/1970 | Conover et al. | |
| 3,551,427 A | 12/1970 | Ott | |
| 3,598,123 A | 8/1971 | Zaffaroni | |
| 3,845,770 A | 11/1974 | Theeuwes et al. | |
| 3,916,899 A | 11/1975 | Theeuwes et al. | |
| 3,995,052 A | 11/1976 | Jirkovsky et al. | |
| 4,008,719 A | 2/1977 | Theeuwes et al. | |
| 4,021,451 A | 5/1977 | Dobson et al. | |
| 4,021,452 A | 5/1977 | Floyd | |
| 4,036,842 A | 7/1977 | Dobson et al. | |
| 4,041,169 A | 9/1977 | Demerson et al. | |
| 4,066,648 A | 1/1978 | Oka et al. | |
| 4,127,665 A | 11/1978 | Sarges et al. | |
| 4,337,343 A | 6/1982 | Maillard et al. | |
| 4,500,543 A | 2/1985 | Debernardis et al. | |
| 4,556,656 A | 12/1985 | McAll | |
| 4,904,300 A * | 2/1990 | Schneider | A01N 43/50 504/225 |
| 4,963,568 A | 10/1990 | Schoenleber et al. | |
| 4,994,486 A | 2/1991 | Schoenleber et al. | |
| 4,999,359 A | 3/1991 | Vecchietti et al. | |
| 5,032,598 A | 7/1991 | Baldwin et al. | |
| 5,041,451 A | 8/1991 | Colle et al. | |
| 5,059,595 A | 10/1991 | Le Grazie | |
| 5,073,543 A | 12/1991 | Marshall et al. | |
| 5,109,008 A | 4/1992 | Scopes et al. | |

(Continued)

FOREIGN PATENT DOCUMENTS

| | | |
|---|---|---|
| AU | 2010325925 A1 | 6/2011 |
| AU | 2016200448 A1 | 2/2016 |
| CA | 2031684 | 6/1991 |
| CN | 1072411 | 5/1993 |

(Continued)

OTHER PUBLICATIONS

Akdemir, A., et al. "Identification of novel α7 nicotinic receptor ligands by in silico screening against the crystal structure of a chimeric α7 receptor ligand binding domain." Bioorganic and Medicinal Chemistry. (2012), vol. 20, pp. 5992-6002 (Year: 2012).*

(Continued)

*Primary Examiner* — John S Kenyon
(74) *Attorney, Agent, or Firm* — Lauren L. Stevens; Dennis A. Bennett

(57) ABSTRACT

Compounds of formula I:

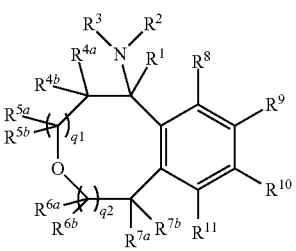

are disclosed, as are pharmaceutical compositions containing such compounds. Methods of treating neurological or psychiatric diseases and disorders in a subject in need thereof are also disclosed.

45 Claims, 8 Drawing Sheets

(56) References Cited

U.S. PATENT DOCUMENTS

| | | | |
|---|---|---|---|
| 5,120,548 A | 6/1992 | McClelland et al. |
| 5,134,127 A | 7/1992 | Stella et al. |
| 5,288,749 A | 2/1994 | Meyer et al. |
| 5,304,657 A | 4/1994 | Toki et al. |
| 5,354,556 A | 10/1994 | Sparks et al. |
| 5,391,556 A | 2/1995 | Heckel et al. |
| 5,393,759 A | 2/1995 | Combourieu et al. |
| 5,464,834 A | 11/1995 | Peligion et al. |
| 5,532,203 A | 7/1996 | Fory et al. |
| 5,532,233 A | 7/1996 | Weber et al. |
| 5,591,767 A | 1/1997 | Mohr et al. |
| 5,621,133 A | 4/1997 | Deninno et al. |
| 5,639,476 A | 6/1997 | Oshlack et al. |
| 5,646,173 A | 7/1997 | Bos et al. |
| 5,656,658 A | 8/1997 | Hammarberg et al. |
| 5,674,533 A | 10/1997 | Santus et al. |
| 5,684,020 A | 11/1997 | Peligion et al. |
| 5,733,566 A | 3/1998 | Lewis |
| 6,031,099 A | 2/2000 | Moltzen et al. |
| 6,235,774 B1 | 5/2001 | Fagrig et al. |
| 6,262,044 B1 | 7/2001 | Møller et al. |
| 6,313,309 B1 | 11/2001 | Baxter et al. |
| 6,436,943 B1 | 8/2002 | Stoltefuss et al. |
| 6,503,913 B1 | 1/2003 | Goldmann et al. |
| 7,019,026 B1 | 3/2006 | Andersen et al. |
| 7,282,499 B2 | 10/2007 | Arjona et al. |
| 7,297,704 B2 | 11/2007 | Sabb et al. |
| 7,414,068 B2 | 8/2008 | Lim et al. |
| 7,544,717 B2 | 6/2009 | Hom et al. |
| 7,745,462 B2 | 6/2010 | Fairhurst et al. |
| 7,884,109 B2 | 2/2011 | Ohlmeyer et al. |
| 8,227,625 B2 | 7/2012 | Corbera-Arjona et al. |
| 8,710,245 B2 | 4/2014 | Shao et al. |
| 9,216,975 B2 | 12/2015 | Napoletano et al. |
| 9,351,954 B2 | 5/2016 | Shao et al. |
| 10,085,968 B2 | 10/2018 | Shao et al. |
| 10,196,403 B2 | 2/2019 | Hanania et al. |
| 10,336,732 B2 | 7/2019 | Xie et al. |
| 2003/0073687 A1 | 4/2003 | Bebbington et al. |
| 2003/0149057 A1 | 8/2003 | Want et al. |
| 2004/0180883 A1 | 9/2004 | Gilmore et al. |
| 2004/0220402 A1 | 11/2004 | Chow et al. |
| 2005/0032873 A1 | 2/2005 | Hatzenbuhler et al. |
| 2005/0075366 A1 | 4/2005 | Heidelbaugh et al. |
| 2005/0187281 A1 | 8/2005 | Hinze et al. |
| 2005/0239832 A1 | 10/2005 | John et al. |
| 2005/0267199 A1 | 12/2005 | Hom et al. |
| 2006/0047127 A1 | 3/2006 | Arjona |
| 2006/0148872 A1 | 7/2006 | Chow et al. |
| 2006/0258714 A1 | 11/2006 | Heffernan et al. |
| 2007/0032481 A1 | 2/2007 | Dvorak et al. |
| 2007/0072926 A1 | 3/2007 | Chow et al. |
| 2007/0154534 A1 | 7/2007 | Sheitman et al. |
| 2007/0185144 A1 | 8/2007 | Zhong et al. |
| 2008/0081910 A1 | 4/2008 | Saab et al. |
| 2008/0113961 A1 | 5/2008 | Nishi et al. |
| 2008/0255239 A1 | 10/2008 | Chow et al. |
| 2008/0306082 A1 | 12/2008 | Dahnke et al. |
| 2009/0069305 A1 | 3/2009 | Gaul et al. |
| 2009/0118283 A1 | 5/2009 | Defert et al. |
| 2009/0318690 A1 | 12/2009 | Sasaki et al. |
| 2010/0035887 A1 | 2/2010 | Ricciardi |
| 2010/0178299 A1 | 7/2010 | Sitkovsky et al. |
| 2010/0197714 A1 | 8/2010 | Wunsch et al. |
| 2010/0295881 A1 | 11/2010 | Yao et al. |
| 2012/0171199 A1 | 7/2012 | Dobson et al. |
| 2013/0109677 A1 | 5/2013 | Shao et al. |
| 2014/0256712 A1 | 9/2014 | Shao et al. |
| 2015/0031709 A1 | 1/2015 | Campbell et al. |
| 2016/0083399 A1 | 3/2016 | Shao et al. |
| 2016/0264597 A1 | 9/2016 | Chytil et al. |
| 2017/0001987 A1 | 1/2017 | Xie et al. |
| 2018/0030064 A1 | 2/2018 | Xie et al. |
| 2018/0057506 A1 | 3/2018 | Chytil et al. |
| 2018/0093974 A1 | 4/2018 | Xie et al. |
| 2018/0118727 A1 | 5/2018 | Campbell et al. |
| 2019/0038594 A1 | 2/2019 | Bowen et al. |
| 2019/0256525 A1 | 8/2019 | Bauer et al. |
| 2019/0308990 A1 | 10/2019 | Xie et al. |
| 2020/0129477 A1 | 4/2020 | Hopkins et al. |
| 2020/0179336 A1 | 6/2020 | Hopkins |

FOREIGN PATENT DOCUMENTS

| | | |
|---|---|---|
| CN | 1300291 A | 6/2001 |
| CN | 1860112 | 11/2006 |
| CN | 100384824 | 4/2008 |
| CN | 101468986 | 7/2009 |
| CN | 101468987 | 7/2009 |
| CN | 101759710 | 6/2010 |
| CN | 102731574 | 10/2012 |
| DE | 3827727 | 2/1990 |
| EP | 368175 | 5/1990 |
| EP | 416740 | 3/1991 |
| EP | 0431421 | 6/1991 |
| GB | 984365 | 2/1965 |
| JP | 01006267 | 1/1989 |
| JP | H2243691 | 9/1990 |
| JP | H 03163068 B2 | 7/1991 |
| JP | H 03223277 B2 | 10/1991 |
| JP | 049367 | 1/1992 |
| JP | 03223277 B2 | 10/2001 |
| JP | 2002512233 | 4/2002 |
| JP | 2002512244 | 4/2002 |
| JP | 2003261566 A | 9/2003 |
| JP | 2004269449 A | 9/2004 |
| JP | 2005145859 A | 6/2005 |
| JP | 2006117568 A | 5/2006 |
| JP | 2014214130 A | 11/2014 |
| JP | 2015510513 | 4/2015 |
| WO | WO 91/08205 A1 | 6/1991 |
| WO | WO 9203434 | 3/1992 |
| WO | WO 1992003434 | 3/1992 |
| WO | WO 92/14465 | 9/1992 |
| WO | WO 92/15592 A1 | 9/1992 |
| WO | WO 94/00441 A1 | 1/1994 |
| WO | WO 96/04287 A1 | 2/1996 |
| WO | WO 96/38435 | 12/1996 |
| WO | WO 99/01437 | 1/1999 |
| WO | WO 99/46237 A1 | 9/1999 |
| WO | WO 99/46267 A1 | 9/1999 |
| WO | WO 0000487 | 1/2000 |
| WO | WO 2000/023445 | 4/2000 |
| WO | WO 2000/035915 | 6/2000 |
| WO | WO 2000/043397 | 7/2000 |
| WO | WO 2000/068230 | 11/2000 |
| WO | 2000078742 A1 | 12/2000 |
| WO | WO 2000/078742 | 12/2000 |
| WO | WO 2001/017516 | 3/2001 |
| WO | WO 2001/19831 A1 | 3/2001 |
| WO | WO 2001/0132610 A1 | 5/2001 |
| WO | WO 2001/0132655 A2 | 5/2001 |
| WO | WO 2001032610 | 5/2001 |
| WO | WO 2001032655 | 5/2001 |
| WO | WO 2001062233 | 8/2001 |
| WO | WO 2001072745 | 10/2001 |
| WO | WO 2002/012189 | 2/2002 |
| WO | WO 2002/022614 | 3/2002 |
| WO | WO 2002/02066443 A2 | 8/2002 |
| WO | WO 2001080893 | 10/2002 |
| WO | WO 2002083667 | 10/2002 |
| WO | WO 2002/02102387 A1 | 12/2002 |
| WO | WO 2003/006455 A1 | 1/2003 |
| WO | WO 2003/03035065 A1 | 5/2003 |
| WO | WO 2003092374 | 11/2003 |
| WO | WO 2004/004726 A1 | 1/2004 |
| WO | WO 2004024081 | 3/2004 |
| WO | WO 2004/035812 A2 | 4/2004 |
| WO | WO 2004/066912 A2 | 8/2004 |
| WO | WO 2004/078723 A1 | 9/2004 |
| WO | WO 2004/082687 A1 | 9/2004 |
| WO | WO 2004/087680 A1 | 10/2004 |
| WO | WO 2004089913 | 10/2004 |
| WO | WO 2004/112719 A2 | 12/2004 |

(56) References Cited

FOREIGN PATENT DOCUMENTS

| | | |
|---|---|---|
| WO | WO 2005012291 | 2/2005 |
| WO | WO 2005/035518 A1 | 4/2005 |
| WO | WO 2005/072412 A2 | 8/2005 |
| WO | WO 2005/073236 A2 | 8/2005 |
| WO | WO 2005/079800 A1 | 9/2005 |
| WO | WO 2005/087779 A1 | 9/2005 |
| WO | WO 2005087714 | 9/2005 |
| WO | WO 2005095326 | 10/2005 |
| WO | WO 2005111025 | 11/2005 |
| WO | WO 2006/014135 A1 | 2/2006 |
| WO | WO 2006/014136 A1 | 2/2006 |
| WO | WO 2006/015259 A2 | 2/2006 |
| WO | WO 2006/030124 | 3/2006 |
| WO | WO 2006/053274 A2 | 5/2006 |
| WO | WO 2006066172 | 6/2006 |
| WO | WO 2006089053 | 8/2006 |
| WO | WO 2006/117305 | 11/2006 |
| WO | WO 2007/001939 A1 | 1/2007 |
| WO | WO 2007/002681 A2 | 1/2007 |
| WO | WO 2007/006546 A1 | 1/2007 |
| WO | WO 2007/095586 A2 | 8/2007 |
| WO | WO 2007/102999 A2 | 9/2007 |
| WO | WO 2007/120594 A1 | 10/2007 |
| WO | WO 2007/126041 A1 | 11/2007 |
| WO | WO 2008011560 | 1/2008 |
| WO | WO 2008/042422 A2 | 4/2008 |
| WO | WO 2008/048981 A2 | 4/2008 |
| WO | WO 2008/058342 A1 | 5/2008 |
| WO | WO 2008/119689 A1 | 10/2008 |
| WO | WO 2008/125348 | 10/2008 |
| WO | WO 2008/155132 A1 | 12/2008 |
| WO | WO 2009/009550 A1 | 1/2009 |
| WO | WO 2009/057974 A2 | 5/2009 |
| WO | WO 2009/067202 A1 | 5/2009 |
| WO | WO 2009/068467 A1 | 6/2009 |
| WO | WO 2009/072621 A1 | 6/2009 |
| WO | WO 2009/085256 A1 | 7/2009 |
| WO | WO 2010/053583 A2 | 5/2010 |
| WO | WO 2010/092180 A1 | 8/2010 |
| WO | WO 2010/092181 A1 | 8/2010 |
| WO | WO 2010090716 | 8/2010 |
| WO | WO 2010093425 | 8/2010 |
| WO | WO 2011017389 | 2/2011 |
| WO | WO 2011/036889 A1 | 3/2011 |
| WO | WO 2011/060035 A1 | 5/2011 |
| WO | WO 2011/060217 A1 | 5/2011 |
| WO | WO 2011/069063 A2 | 6/2011 |
| WO | WO 2011/081205 A1 | 7/2011 |
| WO | WO 2011/133729 A2 | 10/2011 |
| WO | WO 2012/020133 A1 | 2/2012 |
| WO | WO 2012/122340 A1 | 9/2012 |
| WO | WO 2013/010453 A1 | 1/2013 |
| WO | WO 2013050334 | 4/2013 |
| WO | WO 2013/067248 A1 | 5/2013 |
| WO | WO 2013091773 | 6/2013 |
| WO | WO 2013119895 | 8/2013 |
| WO | WO 2013/192346 A1 | 12/2013 |
| WO | 2014078454 A1 | 5/2014 |
| WO | WO 2014/078454 | 5/2014 |
| WO | WO 2014/106238 A1 | 7/2014 |
| WO | WO 2006/066950 A2 | 6/2016 |
| WO | WO 2018/023072 | 2/2018 |
| WO | WO 2011/094740 | 8/2018 |
| WO | WO 2018151861 | 8/2018 |
| WO | WO 2019161236 | 8/2019 |
| WO | WO 2019161238 | 8/2019 |
| WO | WO 2020118032 | 6/2020 |
| ZA | 9102744 A | 2/1992 |

OTHER PUBLICATIONS

Anxiety and Depression Association of America. "Depression." Accessed Mar. 16, 2019. (Jan. 29, 2009). Available from: < https://adaa.org/understanding-anxiety/depression/treatment >. (Year: 2009).*

National Institute of Mental Health. "Bipolar Disorder." (Apr. 2016). Accessed Mar. 16, 2019. Available from: < https://www.nimh.nih.gov/health/topics/bipolar-disorder/index.shtml >. (Year: 2016).*

Nemade, R., et al. "Schizophrenia Medication Treatment Options." (Feb. 15, 2006). Accessed Mar. 16, 2019. Available from: < https://www.mentalhelp.net/articles/schizophrenia-medication-treatment-options/ >. (Year: 2006).*

National Institute of Mental Health. "Obsessive-Compulsive Disorder." (Jan. 2016). Accessed Mar. 16, 2019. Available from: < https://www.nimh.nih.gov/health/topics/obsessive-compulsive-disorder-ocd/index.shtml >. (Year: 2016).*

CDC. "Treatment of ADHD." (Jan. 30, 2016). Accessed Mar. 16, 2019. Available from: < https://www.cdc.gov/ncbddd/adhd/treatment.html >. (Year: 2016).*

"Find the Best Epilepsy Treatment for You." (May 23, 2015). Accessed Mar. 16, 2019. Available from: < https://share.upmc.com/2015/05/epilepsy-treatment/ >. (Year: 2016).*

Wilkinson, D., et al. "Cholinesterase Inhibitors Used in the Treatment of Alzheimer's Disease." Drugs Aging (2004), vol. 21, Issue 7, pp. 453-478. (Year: 2004).*

Werber, E.A., et al. "The beneficial effect of cholinesterase inhibitors on patients suffering from Parkinson's disease and dementia." J. Neural Transm. (2001), vol. 108, pp. 1319-1325. (Year: 2001).*

Berge, S., et al. "Pharmaceutical Salts." Journal of Pharmaceutical Sciences. (Jan. 1977), vol. 66, No. 1, pp. 1-19 (Year: 1977).*

Nguyen, Lien, Ai., et al. "Chiral Drugs: An Overview." Int. J. Biomed Sci. (Jun. 2006), vol. 2, Issue 2, pp. 85-100. (Year: 2006).*

Bianchi, et al, "Model studies towards stephaoxocanes: Construction of the 2-oxa-4-azaphenalene core of stephaoxocanidine and eletefine", European Journal of Organic Chemistry (2003), (24), 4731-4736.

Ram et al., "Synthesis and structure-activity relationships of 1-substituted-aminomethyl-3-phenyl/methyl-1,3-dihydroisobenzofurans and 4-substituted-amino-1-phenyl/methylisochromans—a new class of antihistaminics", Indian Journal of Chemistry, Section B: Organic Chemistry Including Medicinal Chemistry (1984), 23B(12), 1261-7.

Rekka et al., "Structural features of some diphenhydramine analogs that determine the interaction with rat liver cytochrome P-450", Agents and Actions (1989), 27(1-2), 184-7.

The list of search results of CAPLUS, Apr. 21, 2016. (Total 20 pages.)

Answer Summary, from the search of CAPLUS, Apr. 21, 2016 (Total 29 pages.)

International Search Report and Written Opinion, dated Dec. 21, 2017, in the corresponding PCT Appl. No. PCT/US17/44511.

Ahmad, I and Snieckus, V., "A Convenient Entro into the Rhoeadan Skelton. Total Synthesis of (±)-cis-alpinigenine", Canadian Journal of Chemistry, 60(12):2678-2686 (1982).

American Chemical Society, STN Database RN 63463-05-8 entered Nov. 16, 1984.

Antoz, F.J., et al., "The Structure and Chemistry of Actinobolin", Journal of American Chemical Society, 92(16):4933-4942 (1970).

AU Application No. 2013216935, Examination Report No. 2 dated Aug. 1, 2017.

Bakshi, et al., "Antagonism of Phencyclidine-Induced Deficits in Prepulse Inhibition by the Putative Atypical Antipsychotic Olanzapine," Psychopharamcology, 122(2):198-201, 1995.

Berardi, et al., "4-(Tetralin-1-yl)-and-4-(Naphthalen-1yl)akyl] Derivatives of 1-Cyclohexylpiperazine as σ Receptor Ligands with Agonists $\sigma_2$ Activity", Journal of Medicinal Chemistry, American Chemical Society, 47(9):2308-23-17 (2004).

Berardi, et al., "A Multireceptorial Binding Reinvestigation on an Extended Class of σ Ligands: N-[ω-(Indan-1-yl and Tetralin-1-yl)alkyl] Derivatives of 3,3-Dimethylpiperdine Reveal High Affinities Towards $\sigma_1$ and EBP Sites", Bioorganic & Medicinal Chemistry, 9(5):1325-1335 (2001).

Berardi, et al., "Novel Potent σ1 Ligands: N-[ω-(Tetralin-1-yl)alkyl] piperdine Derivatives", Journal of Medicinal Chemistry, American Chemical Society, 38(21):4255-4260 (1996).

Berge, S.M., et al., "Pharmaceutical Salts", Journal of Pharmaceutical Sciences, 66(1):1-19 (1977).

(56) References Cited

OTHER PUBLICATIONS

Boger, D.L., et al., "Thermal Cycloaddition of 1,3,5-Triazine with Enamines: Regiospecific Pyrimidine Annulation", Journal of Organic Chemistry, 47:2673-2675 (1982).
Böhme, H. And Hitzel, V., "Homoisochroman-Derivative mit basischer Seitenkette in 1-Stellung", Archiv der Pharmazie 306:948-953 (1973) No English Translation.
Böhme, H. and Ziegler, F., "The Aminomethylation of 1-cyano-isochromane and 1-cyano-isothiochromane", Arch Pharm (Weinheim), 307(4):287-290 (1974) with English Translation.
CAPULUS Search Results of Apr. 6, 2016; 102 pages.
CAS Database Regisry 444792-99-8 (XP-002742897) Aug. 24, 2002; 1 page.
CAS Database Regisry 444793-00-4 (XP-002742898) Aug. 24 ,2002; 1 page.
CAS Database Regisry 444796-01-5 (XP-002742896) Aug. 24, 2002; 1 page.
CAS Database Regisry 46490-93-1 (XP-002742899) Nov. 16, 1984; 1 page.
CAS Database Regisry 738532-48-4 (XP-002742900) Sep. 3, 2004; 1 page.
CAS Database Regisry Accession No. 1022058-43-0, May 23, 2008.
CAS Database Regisry Accession No. 1022339-80-5, May 25, 2008.
CAS Database Regisry Accession No. 1022468-83-2, May 25, 2008.
CAS Database Regisry Accession No. 1022813-67-7, May 27, 2008.
CAS Database Regisry Accession No. 1023480-64-9, May 29, 2008.
CAS Database Regisry Accession No. 1024262-27-8 Jun. 1, 2008.
CAS Database Regisry Accession No. 3549452-84-9, Sep. 28, 2001.
CAS Database Regisry Accession No. 3594552-83-8, Sep. 28, 2001.
CAS Database Registry Accession Nos. 131022-75-8, 1310059-007-4, 1310059-06-3, 1310059-08-5 and 1310059-09-6 as cited in the Japanese Office Action dated Mar. 14, 2017 for Japanese Application No. 2014-556702.
CAS Database Registry Accession No. 340968-07-2, Jun. 14, 2001.
CAS Database Registry Accession No. 359452-60-1, Sep. 28, 2001.
CAS Database Registry No. 1027177-28-1 Jun. 11, 2008.
CAS Database Registry No. 1935196-69-2 Jun. 20, 2016.
CAS Registry No. 724648-33-5; STN entry date Sep. 10, 2004; Chemical name: Quinazoline, 4-benzo[b]thien-2-yl-1,4-dihydro- (cited Aug. 1, 2017, obtained from https://scifinder.cas.org on Aug. 10, 2017).
CAS Registry No. 736880-30-1; STN entry date Sep. 1, 2004; Chemical name: Quinazoline, 4-benzo[b]thien-2-yl-1,4-dihydro-2-methyl- (cited Aug. 1, 2017, obtained from https://scifinder.cas.org on Aug. 10, 2017).
CAS Registry No. 775528-08-0; STN entry date Nov. 7, 2004; Chemical name: Quinazoline, 4-benzo[b]thien-2-yl-1,4-dihydro-2-methyl (cited Aug. 1, 2017, obtained from https://scifinder.cas.org on Aug. 10, 2017).
CAS Registry No. 790156-85-3; STN entry date Nov. 28, 2004; Chemical name: Quinazoline, 4-benzo[b]thien-2-yl-1,4-dihydro- (cited Aug. 1, 2017, obtained from https://scifinder.cas.org on Aug. 10, 2017).
CAS Registry No. 933704-221-3, Apr. 30, 2007.
CAS Registry No. 1541037-08-04 date unknown.
Chemical Abstracts STN Registry Database, record for RN 1784628-34-7, Entered into STN on Jun. 19, 2015. (Year: 2015).
Chihara, et al., "Preparation of Benzothiiophene Derivatives as Blood Platelt Aggregation Inhibitors", Retrieved from STN Database Ascession No. 1992:128652 and JP03223277a, Yoshitomi Pharmacetuical Industries Ltd., Oct. 2, 1991.
CN Office Action in Application No. 201410333332.1, dated Nov. 2, 2015 with translation.

Corbera, et al., "A Medicinal-Chemistry-Guided Approach to Selective and Druglike Sigma 1 Ligands", ChemMedChem, 1(1):140-154 (2006).
Dammacco, M., et al., "Lithiation of N-Alkyl-(o-totyl)aziridine: Stereoselective Synthesis of Isochromans", Journal of Organic Chemistry, 74:6319-6322 with supplemental material pp. S1-S34 (2009).
Debernadis, J.F., et. al., "Conformationally Defined Adrenergic Agents. 4. 1-(Aminomethyl)phthalans: Synthesis and Pharmacological Consequences of the Phtalan Ring Oxygen Atom", Journal of Medicinal Chemistry, 30:178-184 (1987).
Dehaven-Hudkins, et al., "Characterization of the Binding of [3H](+)pentazocine to σ Recognition Sites in Guinea Pig Brain", European Journal of Pharmacology—Molecular Pharmacology Section 227:371-378 (1992).
Deninno, M.P., et al., "Synthesis and Dopaminergic Activity of 3-Substituted 1- (Aminomethyl)-3,4-dihydro-5,6-dihydroxy-1H-2-benzopyrans: Characterization of an Auxiliary Binding Region in the D1 Receptor", Journal of Medicinal Chemistry, 34:2561-2569 (1991).
Disabled World Towards Tomorrow, "Neurological Disorders: Types, Research & Treatment" URL: https://www.disabled-world.com/health/neurology downloaded on Nov. 1, 2017; 5 pages.
Dobson, et al., "Pyrano Heterocycles I. The Synthesese of Isochromans and the Novel Thieno[3,2-c]pyran, Benzothieno[3,2-c]pyran, and Pyrano[4,3-b]benxofuran Systems", Journal of Hetercyclic Chemistry, 12(3):591-594, 1975, 4 pages.
Ellis, "Affective Disorders (Mood Disorders)", Healthline Part 1 of 7 Overview; URL: http://www.healthline.com/health/affective-disorders, 5 pages, downloaded Jul. 25, 2015.
Emedicine Health, "Brain Cancer: Get Facts on Treatment, Causes and Symptoms", URL: https://www,emedicinehealth.com/brain_cancer/article_em.htm?pf=2; 15 pages downloaded 2015.
EP Application No. 123747266.8, Communication Pursuant to Article 94(63) EPC dated Dec. 21, 2017.
EP Application No. 13747266.8, Partial Supplementary European Search Report dated Aug. 14, 2015; 11 pages.
EP Application No. 10835185.9, Extended European Search Report dated Apr. 4, 2013, 15 pages.
EP Patent Application No. 13747266.8, Communication Pursuant to Article 94(3) dated Nov. 18, 2016.
Gaur,S., et al. "CoMFA and CoMSIA Studies on a set of Benzyl Piperazines, Piperadines, Pyrazinopyridoindoles, Pyrazinoisoquinolines and Semi Rigid analogs of Diphenydramine", Medicinal Chemistry Research, 13(8-9):746-757 (2004).
Ghaemi, et al., "Does Olanzapine have Antidepressant Properties? A Retrospective Preliminary Study", Bipolar Disorders, 2:196-199, 2000.
Ghasemi, et al., "The Role of NMDA Receptors in the Pathophysiology and Treatment of Mood Disorders", Neuroscience and Biobehavioral Reviews, 47:336-358, 2014.
Girke, W.P.K., "Elektrophile Aromatische Substitutionsreaktionen Mit Protonierten 1,3- Diazinen II. Darstellung and Eigenschaften 4-arylsubstituierter 3,4-Dichrochinazolin-Derivate", European Journal of Inorganic Chemistry, 112(4):1348-1358 (1979) [English Abstract and machine translation of entire referenc- 24 pages].
Gleason, et al., "Blockade of Phencyclidine-Induced Hyperlocomotion by Olanzapine, Clozapine and Serotonin Receptor Subtype Selective Antagnoists in Mice", Psychopharmacology, 129:79-84, 1997.
Gould, P.L., "Sale Selection for Basic Drugs", International Journal of Pharmaceutics, 33:201-217 (1986).
Grilliot, A-L and Hart, D.J., "Guanidinium Carboxylates: Preparation of 3-Carboxyoctahydro-9aH-Pyrimidin-9a-Ylium Chloride", Hetercoycles, 39(2):435-438 (1994).
Gronowitz, et al, The Reaction of 5-Bromo- and 2-Bromopyrimidine with Organolithium Compounds, Acta Chemica Scandinavica 19(7):8 pages (1965).
Hanner, et al., "Purification Molecular Cloning, and Expression of the Mammalian Sigma$_1$-Binding Site", Proc. Natl. Aca. Sci., 93:8072-8077 (1996).
Hayakawa, K., et al., "Addition Reactions of (Phenylsulfonyl)propadiene with 1-Pryrrolidinyl Enamines of Cyclic Ketones: Syntheses and

(56) References Cited

OTHER PUBLICATIONS

Reactions of 1,3-Dienes Possessing an Allyl Sulfone Moiety", Journal of Organic Chemistry, 51:5100-5105 (1986).
Hejl, et al., "Prepulse Inhibition in Patients with Alzheimer's Disease", Neurobiology of Aging, 25:1045-1050 (2004).
Hörig, H. and Pullman, W., "From Bendch to Clinic and Back: Perspective on the 1st IQPC Translational Research Conference", Journal of Translational Medicine, 2:44, 8 pages (2004).
Huang, N-A, et al., "Thiation Reactions of Some Active Carbonyl Compoounds with Sulfur Transfer Reagents", The Journal of Organic Chemistry, 52(2):169-172 (1987).
Ingebrigsten, T., et al., "Palladium-Catalysed Synthesis of Pyrimidines", Heterocycles, 65(11):2593-2603 (2005).
International Application No. PCT/US2010/05884, International Search Report and Written Opinion dated Aug. 25, 2011, 10 pages.
International Application No. PCT/US2013/025260, International Preliminary Report on Patentability issued by the International Searching Authority, dated Aug. 21, 2014 (10 pages).
International Application No. PCT/US2013/025260, International Search Report and Written Opinion issued by the International Searching Authority, dated Apr. 17, 2013 (10 pages).
International Application No. PCT/US2016/017527 International Search Report dated Apr. 4, 2016.
International Application No. PCT/US2016/017539, International Search Report dated Apr. 21, 2016.
International Application No. PCT/US2016/017539, Written Opinion dated Apr. 21, 2016.
International Application No. PCT/US2017/044517, International Search Report and Written Opinion dated Jan. 11, 2018.
International Application No. PCT/US2018/044854, International Search Report and Written Opinion dated Apr. 10, 2018, 13 pages.
Ito, N., et al., "A Medium-Term Rat Live Bioassy for Rapid in vivo Dection of Carcinogenic Potential of Chemicals", Cancer Science, 94(1):3-8 (2003).
Jacobs, et al., "1-Imidizolyl(alkyl)-Substituted Di- and Tetrahydroquinolines and Analogues: Syntheses and Evaluation fo Dual Inhibitors of Thromboxane A2 Synthase and Aromatase", Journal of Medicinal Chemistry, 43(9):1841-1851, 2000.
Jaskowska, J. and Kowalski, P., "N-Alkylation of Imides Using Phase Transfer Catalysts Under Solvent-Free Conditions", Journal Heterocyclic Chemistry, 45:1371-1375 (2008).
Jentsch, et al., "The Neuropsychopharmacology of Phencyclidine: From NMDA Receptor Hypfunction to the Dopamine Hypothesis of Schizophrenia", Neurpsychopharmacology, 20(3):201-225, 1999.
JP Application No. 2012-542219, Office Action dated Nov. 21, 2014, 9 pages including translation.
JP Application No. 2014-556702 , Notice of Reasons for Rejection dated Jul. 19, 2016 (with translation).
JP Application No. 2014-556702 , Notice of Reasons for Rejection dated Mar. 14, 2017 (with translation).
Kapur, et al., "NMDA Receptor Antagonists Ketamine and PCP Have Direct Effects on the Dopamine D2 and Serotonin 5-HT2 Receptors—Implications for Models of Schizophrenia", Molecular Psychiatry, 7:837-844, 2002.
Karran, et al., "The Amyloid Cascade Hypothesis for Alzheimer's Disease: An Appraisal for the Development of Therapeutics", Nature, 10:698-712 (2011).
Katsuki, et al., "Excitotoxic Degeneration of Hypthalamic Orexin Neurons in Slice Culture", Neurobiology of Disease, 15:61-69, 2004.
Kornev, et al. CAS STN Abstrack , publ 2009 RN 1202851-83-9.
Kostin, et al., "Lack of Hypocretin Attenuates Behavioral Changes Produced by Glutamatergic Activation of the Perifornical-Lateral Hypthalamic Area", Sleep, 37(5):1011-1020, 2014.
Krogsgaard-Larsen, et al., Texbook of Drug Design and Discovery Madsen, U. (Ed.). (2009). Textbook of Drug Design and Discovery, Fourth Edition. Boca Raton: CRC Press. (2002).

Kumar, A., et al., "Catecholamines in a Semi-Rigid Framework: Synthesis & Biological Activity of N-Substituted I-Aminomethyl-5,6- & 6,7-dihydroxyisochromans", Indian Journal of Chemistry 26B:47-51 (1987).
Kumar, A., et al., "Phenethylamine in a Semi-Rigid Framework: Synthesis & Biological Activity of N-Substituted I-Aminomethyl-5,6- & 6,7-dimethoxyisochromans", Indian Journal of Chemistry 16B:793-796 (1978).
Langa,et al., "Generation and Phenotypic Analysis of Sigma Receptor type 1 (σ1) Knockout Mice", European Journal of Neuroscience, 18:2188-2196 (2003).
Lima, et al., Bioisosterism: A Useful Strategy for Molecular Modification and Drug Design, Current Medicinal Chemistry, 12:23-49 (2005).
Lindvall, O. and Kokaia, Z., "Stem Cells for the Treatment of Neurological Disorders", Nature, 441:1094-1096 (2006).
Lowry, et al., "Protein Measurement with the Folin Phenol Reagent", Journal Biochemistry, 193:265 (1951).
Macchia, B., et al., "Conformationally Restrained Analogs of Sympathomimetic Catecholamines, Synthesis Conformational Analysis, and Adrenergic Activity of Isochroman Derivatives", Journal of Medicinal Chemistry, 36:3077-3086 (1993).
Maier, et al., "Novel Spiropiperdines as Highly Potent and Subtype Selective σ-Receptor Ligands. Part 1", Journal of Medicinal Chemistry, 45:438-448 (2002), Journal Medicinal Chemistry, 45:4923-4930 (2002).
Maier, et al., "Novel a Receptor Ligands, Part 2. SAR of Spiro[[2]benxopyran-1,4-piperdines] and Spiro [[2]benzofuran-1,4'-piperidines] with Carbon Substituents in Position 3", Journal Medicinal Chemistry, 45:4923-4930 (2002).
Marcus, et al., "The Efficacy and Safety of Aripiprazole as Adjunctive Therapy in Major Depressive Disorder. A Second Multicenter, Randomized, Double-Blind, Placebo-Controlled Study", Journal of Clinical Psybhopharmacology, 28(2):156-165, 2008.
Mashkovskiy, Drugs, Moscow, New Wave, LLC, vol. 1, p. 11 (2002) with translation.
Mayo Clinic Symptoms and Causes, "Seasonal Affective Disorder (SAD)", URL: https://www.mayoclinic.org/diseases-conditions/seasonal-affective-disorder/syymptoms-causes; 2 pages, downloaded 2015.
Mokrosz, et al., "Structure-Activity Relationship Studies of CNS Agents. Part 14:3 Structural Requirements for the 5-HT1A and 5-HT2A Receptor of Simple 1-(2-pyrimidinyl)piperazine Derivatives", Pharmazie, 49(H11) 6 pages (1994).
Moreno, et al., "Preclinical Models of Antipsychotic Drug Action", International Journal of Neuropsychopharmacology, 16:2131-2144, 2013.
Movassaghi, M. and Hill, M.D., "Single-Step Synthesis of Pyrimidine Derivatives", Journal of American Chemical Society, 128:14254-14255 (2006).
MX Application No. MX/a/2012/006326, Examination Report dated Jul. 4, 2013, with English translation, 6 pages.
Nakashima, T., et al., "Regulation of Folding and Photochromic Reactivity of Teraylenes Through a Host-Guest Interaction", Chem. European Journal, 17:10951-10957 (2011).
Nishimura, Y., et al., "Syntheses and Activities of some Bactobolin Derivatives", Journal of Antibiotics, 45(5):735-741 (1992).
Nordquist, et al., "Effects of Aripiprazole/OPC-14597 on Motor Activity, Pharmacological Models of Psychosis, and Brain Activity in Rats", Neuropharmacology, 54:405-416, 2008.
NZ Application No. 600008, Firstt Examination Report dated Mar. 11, 2013 in NZ , 3 pages.
NZ Application No. 626068 Examination Report dated Oct. 8, 2015, 3 pages.
NZ Application No. 711802 Examination Report dated Oct. 8, 2015, 5 pages.
Papillion, J.P.N., et al., "Structure-Activity Relationships, Pharmacokinetics, and in Vivo Activity of CYP11B2 and CYP11B1 Inhibitors", Journal of Medicinal Chemistry, 58:4749-4770 (2015).
Pittenger, et al., "The NMDA Receptor as a Therapeutic Target in Major Depressive Disorder", CNS & Neuroological Distorders—Drug Targets, 6(2): 101-115, 2007.

(56) References Cited

OTHER PUBLICATIONS

PUBCHEM CID 1215079, create date Feb. 7, 2007, p. 3 compound; accessed Nov. 13, 2017; 9 pages.
Quirion, et al., "A Proposal for the Classification of Sigma Binding Sites", Trends in Pharamcology Science, 13:85-86 (1992).
Quiroz, T., et al., "A Practical Method for the Synthesis of Pyrrolizidine, Indolizidine and Pyrroloazepinolizidine Nucleus", Tetrahedron Letters, 48:1571-1575 (2007).
Radesca, et al., "Synthesis and Receptor Binding of Enantiomeric N-Substituted cis-N-[2-(3,4-Dichlorophenyl)ethyl]-1-(1-pyrrolidinyl) cyclohexylamines as High-Affinity σ Receptor Ligands", Journal of Medicinal Chemistry, 34:3058-3065 (1991).
Ross, L.O., et al., "Potential Anticancer Agents. XVIII. Synthesis of Substituted 4,5-Trimethylenepyrimidines", Journal of American Chemical Society, 84(12):3108-3114 (1959).
Sakai, et al., "Facile and Efficient Synthesis of Polyfunctionalized Benzofurans: Three-Component Coupling Reactions from an Alkynylsilane, and o-Hydroxybenzaldehyde Derivative, and a Secondary Amine by a Cu(1)-Cu(II) Cooperative Calatytic System", RwreHWSEON IWRRWEA, 49:3437-3440 (2008).
Salomone, A., et al., "Preparation of Polysubstituted Isochromanes by Addition of ortho-Lithiated Aryloxiranes to Enaminones", Journal of Organic Chemistry, 78:11059-11065 (2013).
Saxena, M., et al., "Synthesis of some Substituted Pyrazinopyridoindoles and 3D QSAR Stuies along with Related Compounds: Piperazines, Piperidines, Pyrazinoisoquinolines. And Diphenhydramine, and its Semi-Rigid Analogs as Antihistamines (H1)", Bioorganic & Medicinal Chemistry 14:8249-8258 (2006).
Schäfer, S., "Failure is an Option: Learning from Unsuccessful Proof-of-Concept Trials", Drug Discovery Today, 13(21/22):913-916 (2008).
Schmitz, et al., "Hippocampal Neuron Loss Exceeds Amyloid Plaque Load in a Transgenic Mouse Model of Alzheimer's Disease", American Journal of Pathology, 164(4):1045-1050 (2004).
Schow, et al., "Novel Sigma Receptor Ligands 2.", Bioorganic & Medicinal Chemistry Letters, 3(2):221-224 (1993).
SG Application No. 201204089-5, Written Opinion dated Sep. 20, 2013, 12 pages.
Singapore Application No. 10201401661, Search Report and Written Opinion dated Jun. 15, 2015, 10 pages.
Snyder, et al., "Receptor Mechanisms in Antipsychotic Drug Action: Focus on Sigma Receptors", Journal of Neuropsychiatry, 1(1):7-15 (1989).
Steliou, K., et al., "Group 14 Metal Assisted Carbon-Sulfur Bond Formation", Journal of Organic Chemistry, 50(24):4969-4971 (1985).
Strekowski, et al., "Synthesis of 2-Chloro-4,6-di(heteraryl)pyrimidines", Journal of Heterocyclic Chemistry, 27:1393-1400 (1989).
Swerdlow et al., "Seroquel Restores Sensorimotor Gating in Phencyclidine-Treated Rats," Journal of Pharmacology and Experimental Therapeutics, vol. 279, No. 3, pp. 1290-1299, Dec. 1996.
Toffano, M., et al., "Asymmetric Routes Towards Polyfunctionalized Pyrrolidines: Application to the Synthesis of Alkaloid Analogues", Tetrahedron: Asymmetry, 14:3365-3370 (2003).
Torrado, et al., "Novel Selective and Potent 5-HT Reuptake Inhibitors with 5-HT$_{1D}$ Antagonist Activity: Chemistry and Pharmacological Evaluation of a Series of Thienopyran Derivatives", Bioorganic & Medicinal Chemistry, 12(20):5277-5295, 2004, 19 pages.
Trehan, "A New Synthesis of 13-aza-18-nor-17oxo-A-nor-3-thiaestra-1,5(10), 9(11)- triene" Retrieved from STN Database Accession No. 1986:225089 & Indian Journal of Chemistry, Section 6: Organic Chemistry Including Medicinal Chemistry, 24B(6):659-661 (1985).
Trehan, "Synthesis of 2,3,13-Triaza-18-nor-17-oxo-3-phenyl-A-nor-estra-1,5(10), 9(11)triene & 2,3,13-Triaza-7,7-dimethyl-18-nor-17-oxo-3-phenyl-A-nor-estra-1,5(10), 9(11)-triene", Indian Journal of Chemistry, 19B:243-245 (1980).
Van Der Stoel, et al., "Di-TT-methane Regarrangement of 4-Heteroaryl-1,4(or 3,4)-dihydropyrimidines", Journal of the Chemical Society, Perkin Transactions 1, 4 pages Nov. 2, 1978.
Vecchietti, et al.,"(1S)-1-(Aminomethyl)-2-(arylacetyl)-1,2,3,4-tetrahydroisoquinoline and Heterocycle-Condensed Tetrahydropyridine Derivatives: Members of a Novel Class of Very Potent K Opiod Analgesics", Journal of Medicinal Chemistry, 34(8):2624-2633 1991.
Walker, et al., "Sigma Receptors: Biology and Function", Phamacological Reviews, 42(4):355-402 (1990).
Weis, et al., "The Crystal and Molecular Structure of 4,6,6-trimethyl-2-phenyl-1,6- dihydropyrimidine", Hetercycles, 19(3):6 pages (1982).
Williams, M., et al., "Emerging Molecular Approaches to Pain Therapy", Journal of Medicinal Chemistry, 42(9):1481-1500 (1999).
Winhusen, T.M., et al., "A Placebo-Controlled Screening Trial of Tiagabine, Sertraline and Donepezil as Cocaine Dependence Treatments", Addiction, 100(Suppl.1):68-77 (2005).
Xi, Z., et al., Preparation of Partially Substituted 1-Halo- and 1,4-Dihalo-1,3-Dienes via Reagent-Controlled Desilyation of Halogenated 1,3-Dienes, Journal of Organic Chemistry, 71:3154-3158 (2006).
US Food and Drug Administration, "Highlights of Prescribing Information: Abilify," FDA label, last revised Dec. 2014, 84 pages.
International Application No. PCT/US2017/044511, International Preliminary Report on Patentability issued by the International Searching Authority, dated Jan. 29, 2019, 8 pages.
International Application No. PCT/US2017/044517, International Preliminary Report on Patentability issued by the International Searching Authority, dated Jan. 29, 2019, 6 pages.
CAS Registry No. 1027834-86-1, Entered STN: Jun. 13, 2008, 4 pages.
CAS Registry No. 1071058-54-2, Entered STN: Nov. 6, 2008, 4 pages.
CAS Registry No. 40196-92-7, Entered STN: Nov. 16, 1984, 2 pages.
CAS Registry No. 40196-93-8, Entered STN: Nov. 16, 1984, 2 pages.
Datta et al., "Studies in Sulphur Heterocycles. Part 5. Further Use of 6,7-Dihydribenzo[b]thiphen-4[5H]-one in the Synthesis of Substituted Benzo[b]thiophene Derivatives", J. Chem. Research (S), 1988, 72-73.
Davis et al., "Benzothiophene Containing Rho Kinase Inhibitors: Efficacy in an Animal Model of Glaucoma", Bioorganic & Medicinal Chemistry Letters, Jun. 1, 2010, 20(11):3361-3366.
Devani et al., "Synthesis of 2-Aminothiophenes & Thieno[2,3-d]pyrimidines", Indian Journal of Chemistry, May 1976, 14B:357-360.
Extended European Search Report in EP Appln. No. 17835384.3, dated Mar. 9, 2020, 10 pages.
Frohlich et al., "A Novel Synthesis of 3,3-(Spiro)Substituted Azetidines", Heterocycles, 1994, 37(3):1897-1891.
Google.com [online] "Parkinson's Disease—Symptoms, Diagnosis and Treatment." Jan. 22, 2006, [Retrieved on Dec. 28, 2018] Retrieved from URL <https://www.google.com/search?q=Parkinson+disease+treatment&source=Int&tbs=cdr%3A1%2Ccd_max%3A2%2F8%2F2012&tbm=>, 2 pages.
Hopkinsmedicine.org [online] "Treatment for Tourette Syndrome: Johns Hopkins Pediatric Neurology," Apr. 2006, [Retrieved on Dec. 28, 2018] Retrieved from URL <https://www.hopkinsmedicine.org/neurology_neurosurgery/centers_clinics/pediatric-neurology/conditions/tourettes_syndrome/treatment.html>, 1 page.
International Preliminary Report on Patentability in PCT Appln. No. PCT/US2018/044854, dated Feb. 4, 2020, 8 pages.
Mayoclinic.org [online] "Fibromyalgia Treatment: Is Neurontin Effective?" Jul. 2009, [Retrieved Oct. 18, 2019], Retrieved from URL <https://www.mayoclinic.org/diseases-conditions/fibromyalgia/expert-answers/fibromyalgia-treatment/faq-20058273>, 3 pages.
Medicinenet.com [online] "Alzheimer's Disease Treatment, Symptoms, Stages & Life Expectancy." Jul. 2007, [Retrieved on Dec. 28, 2018], Retrieved from URL <https://www.medicinenet.com/alzheimers_disease_causes_stages_and_symptoms/article.htm#alzheimers_disease_medications>, 16 pages.
Medlineplus.gov [online] "Symptoms, Diagnosis and Treatment: Alzheimer's Disease." Fall 2010, [Retrieved on Dec. 28, 2018], Retrieved from URL <https://medlineplus.gov/magazine/issues/fall10/articles/fall10pg19.html>, 5(3):19.

(56) References Cited

OTHER PUBLICATIONS

Michaeljfox.org [online] "Parkinson's Disease," May 2007, [Retrieved Dec. 28, 2018] Retrieved from URL <https://www.michaeljfox.org/understanding-parkinsons/living-with-pd/topic.php?causes>, 5 pages.
Ng, et al., "Design and synthesis of hydroxyethylamine (HEA) BACE-1 inhibitors: prime side chromane-containing inhibitors," Bioorganic & Medicinal Chemistry Letters, 2013, 23(16):4674-4679.
PUBCHEM CID 4878038, create date Sep. 17, 2005, accessed Feb. 22, 2019; 12 pages.
PUBCHEM CID 4878041, create date Sep. 17, 2005, accessed Feb. 22, 2019; 14 pages.
Ross et al., "α2 Adrenoceptor Agonists as Potential Analgesic Agents. 2. Discovery of 4-(4-Imidazo)-1,3-dimethyl-6,7-dihydrothianaphthene as a High-Affinity Ligand for the α2D Adrenergic Receptor", J. Med. Chem., 2000, 43:1423-1426.
Shklyaeva et al., "2-Amino-6-(3,4-ethylenedioxythiophen-2-yl)-4-(2-thienyl)-pyrimidine: Synthesis and Properties", Russian Journal of Organic Chemistry, 2010, 46(6):938-940.
Sridhar et al., "Synthesis and Anticancer Activity of Some Novel Pyrimidine Derivatives", International Journal of Pharmaceutical Sciences and Research, Sep. 29, 2011, 2(10):2562-2565.
Stanetty et al., "Heterocyclische Spiroverbindungen Spiroverbindungen: Spiro [benzo[b]thiophen-4(5H),3'-pyrrolidine]", Arch. Pharm., 1984, 317:168-176 With English Abstract.
Togna, et al., "1-Phenil-6, 7-dihydroxy-isochroman inhibits inflammatory activation of microglia," Brain Research Bulletin, 2013, 95:33-39.
Caira "Crystalline Polymorphism of Organic Compounds," Topics in Current Chemistry, 1998, 163-208.
Correll et al. "Safety and Effectiveness of SEP-363856 in Schizophrenia: Results of a 6-Month, Open-Label Extension Study", American College of Neuropsychopharmacology, Poster. Dec. 2019, 1 page.
Dedic et al. "SEP-363856, A Novel Psychotropic Agent With a Unique, Non-D2 Receptor Mechanism of Action", The Journal of Pharmacology and Experimental Therapeutics, vol. 371, Pages 1-14. Oct. 2019.
Dedic et al. "The Novel, Non-D2 Psychotropic Agent SEP-363856 Modulates Presynaptic Dopamine Function in Mice", American College of Neuropsychopharmacology, Poster. Dec. 9, 2019, 1 page.
Fujima et al. "Synthesis of (s)-3-(N-Methylamino)-1-(2-thienyl)propan-1-ol: Revisiting Eli Lilly's Resolution-Racemization-Recycle Synthesis of Duloxetine for it's Robust Processes", Organic Process Research and Development, 2006, 10(5):905-913.
Hopkins et al. "Effects of SEP-363856 on Negative Symptoms in Schizophrenia: Analysis of an Acute, Placebo-Controlled Trial of a Novel Psychotropic Agent With No Dopamine-D2/5-Ht2a Antagonist Activity", American College of Neuropsychopharmacology, Poster. Dec. 2019, 1 page.
INTL Application No. PCT/US2018/000078 International Search Report and Written Opinion, dated May 25, 2018, 9 pages.
INTL Application No. PCT/US2019/018263 International Search Report and Written Opinion, dated Apr. 2, 2019, 8 pages.
INTL Application No. PCT/US2019/018265 International Search Report and Written Opinion dated May 29, 2019, 17 pages.
INTL Application No. PCT/US2019/064646, International Search Report and Written Opinion, dated Mar. 9, 2020, 13 pages.
Jones et al. "SEP-0363856, A Novel Psychotropic Agent With a Unique, Non-D2 Mechanism of Action", European College of Neuropsychopharmacology Congress, Poster. Sep. 2019.
Kay et al., "The positive and negative syndrome scale (PANSS) for schizophrenia," Schizophrenia Bulletin, 1987, 13(2):261-276.
Koblan et al. "A Non-D2-Receptor-Binding Drug for the Treatment of Schizophrenia", The New England Journal of Medicine, Apr. 16, 2020, 382(16):1497-1506.
Koblan et al. "A Phase 1 Open Label Safety and Tolerability Study of SEP-363856, A Novel Non-D2 Mechanism of Action Molecule, in Patients With Schizophrenia", American College of Neuropsychopharmacology, Poster. Dec. 2016, 1 page.
Koblan et al. "Efficacy and Safety of SEP-363856 in the Treatment of Schizophrenia: A 4-Week, Randomized, Placebo-Controlled Trial of a Novel Compound With a Non-D2 Mechanism of Action", American College of Neuropsychopharmacology Annual Meeting, Poster. Dec. 2018, 1 page.
Koblan et al. "Efficacy and Safety of SEP-363856, A Novel Non-D2 Agent, in the Treatment of Schizophrenia: A 4-Week, Randomized, Placebo-Controlled Trial", European College of Neuropsychopharmacology Congress, Poster. Sep. 2019, 1 page.
Koblan et al. "Efficacy and Safety of SEP-363856, A Novel Psychotropic Agent With a Non-D2 Mechanism of Action, in the Treatment of Schizophrenia: A 4-Week, Randomized, Placebo-Controlled Trial", American Psychiatric Association, Poster. May 2019, 1 page.
Koblan et al. "Efficacy and Safety of SEP-363856, A Novel Psychotropic Agent With a Non-D2 Mechanism of Action, in the Treatment of Schizophrenia: A 4-Week, Randomized, Placebo-Controlled Trial", American Society of Clinical Psychopharmacology, Poster. May 2019, 1 page.
Koblan et al. "Efficacy and Safety of SEP-363856, A Novel Psychotropic Agent With a Non-D2 Mechanism of Action, in the Treatment of Schizophrenia: A 4-Week, Randomized, Placebo-Controlled Trial", US Psychiatric and Mental Health Congress, Poster. Oct. 2019, 1 page.
Koblan et al. "Efficacy and Safety of SEP-363856, A Novel Psychotropic Agent With a Non-D2 Mechanism of Action, in the Treatment of Schizophrenia: A Randomized, Placebo-Controlled Trial", Neuroscience Education Institute, Poster. Nov. 2019, 1 page.
Koblan et al. "SEP-363856, A Novel Psychotropic Agent With a Non-D2 Mechanism of Action for the Treatment of Schizophrenia", The 2019 Congress of the Schizophrenia International Research Society, Oral Presentation. 20 pages. Apr. 2019.
Koblan, "SEP-363856, A Candidate Antipsychotic and Antidepressant Compound With a Novel Non-D2 Mechanism of Action", 6th Biennial Schizophrenia International Research Society Conference, Oral Presentation. 31 pages. Apr. 2018.
Mahableshwarkar et al., "Replication of a statistical method to reduce pseudospecificity and enhance understanding of score changes among PANSS factors," Presented at the International Society of CNS Clinical Trials and Methodology, Paris, France, Aug. 31-Sep. 2, 2017, 1 page.
Poola et al. "Pharmacokinetics, Safety, and Tolerability of SEP-363856 in Healthy Adult Male Subjects and in Adult Patients With Schizophrenia Following Oral Administration", American College of Clinical Pharmacology, Poster. Sep. 2018, 1 page.

* cited by examiner

Effect of compound treatment on DA release in the PFC.
(Data expressed as DA concentration as % of baseline ± SEM).

Effect of compound treatment on 5-HT release in the PFC.

(Data expressed as 5-HT concentration as % of baseline± SEM).

Effect of compound treatment on NE release in the PFC.
(Data expressed as NE concentration as % of baseline ± SEM).

Effect of compound treatment on ACh release in the PFC (Data expressed as Ach concentration as % of baseline ± SEM).

Effect of compound treatment on DA release in the NAcc.
(Data expressed as DA concentration as % of baseline ± SEM).

Effect of compound treatment on 5-HT release in the NAcc.
(Data expressed as 5-HT concentration as % of baseline ± SEM).

Effect of compound treatment on NE release in the NAcc.
(Data expressed as NE concentration as % of baseline ± SEM ).

Effect of compound treatment on ACh release in the NAcc.

(Data expressed as Ach concentration as % of baseline ± SEM).

COMPOUNDS AND COMPOSITIONS AND USES THEREOF

FIELD OF THE INVENTION

The invention relates to isochroman-4-amines, benzoxepinamines and benzooxacinamines as well as pharmaceutical compositions containing such compounds. The compounds and pharmaceutical compositions are useful for treating neurological or psychiatric diseases and disorders in a subject in need thereof. Such diseases and disorders include, for example, depression, bipolar disorder, pain, schizophrenia, obsessive compulsive disorder, addiction, social disorder, attention deficit hyperactivity disorder, an anxiety disorder, autism, a cognitive impairment, or a neuropsychiatric symptom such as apathy, depression, anxiety, psychosis, aggression, agitation, impulse control disorders, and sleep disorders in neurological disorders such as Alzheimer's and Parkinson's diseases.

All publications, patents, patent applications, and other references cited in this application are incorporated herein by reference in their entirety for all purposes and to the same extent as if each individual publication, patent, patent application or other reference was specifically and individually indicated to be incorporated by reference in its entirety for all purposes. Citation of a reference herein shall not be construed as an admission that such is prior art to the present invention.

BACKGROUND OF THE INVENTION

Central nervous system diseases and disorders affect a wide range of the population with differing severity. Neurological and psychiatric diseases and disorders include major depression, schizophrenia, bipolar disorder, obsessive compulsive disorder (OCD), panic disorder, and posttraumatic stress disorder (PTSD), among others. These diseases and disorders affect a person's thoughts, mood, behavior and social interactions and can significantly impair daily functioning. See, e.g., *Diagnostic and Statistical Manual of Mental Disorders*, 4th Ed., American Psychiatric Association (2000) ("DSM-IV-TR"); *Diagnostic and Statistical Manual of Mental Disorders*, 5th Ed., American Psychiatric Association (2013) ("DSM-5").

While medications exist for some aspects of these diseases and disorders, there remains a need for effective treatments for various neurological and psychiatric diseases and disorders, including mood disorders such as bipolar and related disorders, psychosis and schizophrenia. For example, while mood stabilizers such as lithium and valproate, antidepressants and antipsychotic drugs are used to treat mood disorders, more effective medications are necessary. And current antipsychotics may be successful in treating the positive symptoms of schizophrenia but fare less well for the negative and cognitive symptoms. Additionally, current antidepressants are typically effective only for a proportion of subjects suffering from depression. Furthermore, despite the fact that the behavioral and psychiatric symptoms of neurological disease such as Parkinson's disease and Alzheimer's disease are major reasons for the institutionalization of subjects, few drugs exist to treat them.

SUMMARY OF THE INVENTION

In one aspect, the invention relates to method for treating a neurological or psychiatric disease or disorder comprising administering to a subject in need thereof an effective amount of a compound of formula I:

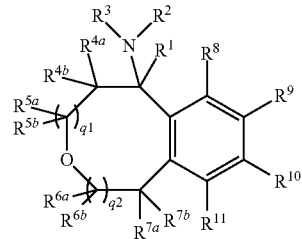

or a pharmaceutically acceptable salt thereof,
wherein:
q1 is 0 or 1,
q2 is 0 or 1, and
the sum of q1 plus q2 is 0 or 1;
$R^1$, $R^2$ and $R^3$ are chosen independently from H and an aliphatic ($C_1$-$C_8$)hydrocarbyl optionally substituted with one or more groups independently selected from halogen, —C≡C—, hydroxyl, ($C_1$-$C_6$)alkoxy, amino, ($C_1$-$C_6$)alkylamino and di($C_1$-$C_6$)alkylamino;
$R^{4a}$, $R^{4b}$, $R^{7a}$, and $R^{7b}$ are chosen independently from H, halogen, ($C_1$-$C_6$)alkyl, ($C_1$-$C_6$)haloalkyl, and ($C_1$-$C_6$)alkoxy;
$R^{5a}$, $R^{5b}$, $R^{6a}$ and $R^{6b}$ are chosen independently from H, halogen, ($C_1$-$C_6$)alkyl and ($C_1$-$C_6$)haloalkyl;
$R^8$, $R^9$, $R^{10}$ and $R^{11}$ are chosen independently from H, halogen, ($C_1$-$C_8$)hydrocarbyl, cyano, —$CF_3$, ($C_1$-$C_6$)haloalkyl, hydroxyl, ($C_1$-$C_6$)alkoxy, aminocarbonyl, ($C_1$-$C_6$)alkylaminocarbonyl, di($C_1$-$C_6$)alkylaminocarbonyl, ($C_1$-$C_6$)acyl, ($C_1$-$C_6$)haloalkoxy, hydroxy($C_1$-$C_6$)alkyl, carboxy, ($C_1$-$C_6$)alkoxycarbonyl, acetoxy, nitro, amino, ($C_1$-$C_6$)alkylamino, di($C_1$-$C_6$)alkylamino, aminosulfonyl, benzyl, aryl, heteroaryl, phenoxy, —OC(O)N(alkyl)$_2$ or benzyloxy;
wherein said benzyl, aryl, heteroaryl, phenoxy or benzyloxy are optionally substituted with one or more substituents independently selected from halogen, ($C_1$-$C_6$)alkyl, cyano, ($C_1$-$C_6$)haloalkyl, hydroxyl, ($C_1$-$C_6$)alkoxy, aminocarbonyl, ($C_1$-$C_6$)alkylaminocarbonyl, di($C_1$-$C_6$)alkylaminocarbonyl, ($C_1$-$C_6$)acyl, ($C_1$-$C_6$)haloalkoxy, hydroxy($C_1$-$C_6$)alkyl, carboxy, ($C_1$-$C_6$)alkoxycarbonyl, acetoxy, nitro, amino, ($C_1$-$C_6$)alkylamino, and di($C_1$-$C_6$)alkylamino;
and further wherein:
any two of $R^8$, $R^9$, $R^{10}$ and $R^{11}$ attached to adjacent carbon atoms, together with the carbon atoms to which they are attached, may form a 5 to 8-membered carbocycle or heterocycle which is optionally substituted with one or more substituents independently selected from halogen, hydroxyl, amino, ($C_1$-$C_6$)alkylamino, di($C_1$-$C_6$)alkylamino, ($C_1$-$C_6$)alkyl, ($C_1$-$C_6$)haloalkyl, ($C_1$-$C_6$)alkoxy, and ($C_1$-$C_6$)haloalkoxy.

In another aspect the invention relates to pharmaceutical compositions comprising compounds of formula I above, wherein at least one of $R^1$, $R^2$, $R^3$, $R^{4a}$, $R^{4b}$, $R^{5a}$, $R^{5b}$, $R^{6a}$, $R^{6b}$, $R^{7a}$, $R^{7b}$, $R^8$, $R^9$, $R^{10}$ and $R^{11}$ is other than hydrogen.

In another aspect, the invention relates to chemical compounds of formula I, with the provisos that:
when q1 and q2 are both zero and NR$^2$R$^3$ is NHCH$_3$ or N(CH$_3$)$_2$, then at least one of $R^1$, $R^{4a}$, $R^{4b}$, $R^8$, $R^9$, $R^{10}$ and $R^{11}$ must be other than hydrogen or methoxy, and
when q1 and q2 are both zero and NR$^2$R$^3$ is NH$_2$, then one of the following four conditions must be met:

at least two of $R^8$, $R^9$, $R^{10}$ and $R^{11}$ must be other than hydrogen, or at least one of $R^8$, $R^9$, $R^{10}$ and $R^{11}$ must be phenyl, or at least one of $R^{4a}$ and $R^{4b}$, must be other than hydrogen, or at least one of $R^{7a}$ and $R^{7b}$ must be methyl and the other of $R^{7a}$ and $R^{7b}$ must be other than methyl, and when q1 or q2 is one and $NR^2R^3$ is $NH_2$, then the following species are excluded:

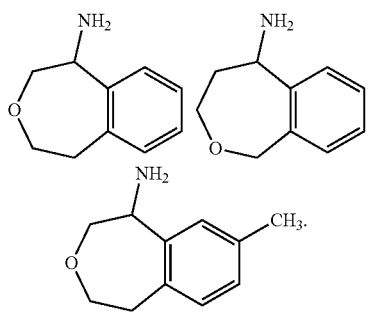

DETAILED DESCRIPTION OF THE INVENTION

Figure 1:
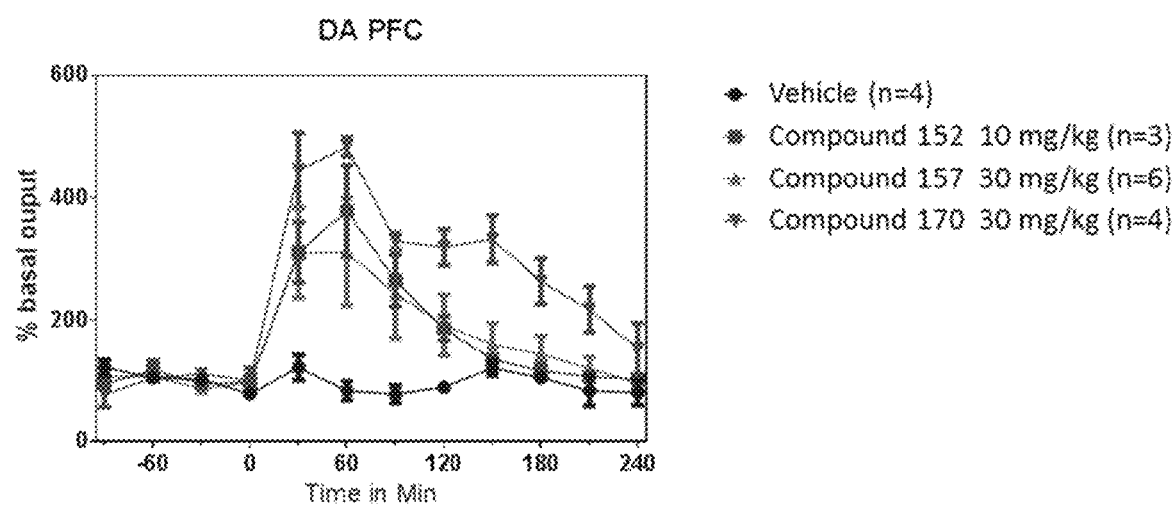
FIG. 1 shows the effect of representative compounds of the invention on treatment on DA release in the PFC.

The methods of the invention relate to the use of compounds and compositions of Formula I above to treat neurological or psychiatric diseases and disorders or impairments. In some embodiments, the neurological or psychiatric disease or disorder is depression, bipolar disorder, pain, schizophrenia, obsessive compulsive disorder, addiction, social disorder, attention deficit hyperactivity disorder, an anxiety disorder, autism or cognitive impairments. In one embodiment, the disorder is depression, particularly treatment-resistant depression (TRD), major depressive disorder (MDD), unipolar depression, bipolar depression or depression associated with another disease or disorder.

In one embodiment relating to the use of compounds of formula I in these methods, any two of $R^8$, $R^9$, $R^{10}$ and $R^{11}$ attached to adjacent carbon atoms, together with the carbon atoms to which they are attached, may form a 5 to 8-membered carbocycle or heterocycle which is optionally substituted with one or more substituents independently selected from halogen, hydroxyl, amino, $(C_1-C_6)$alkylamino, di$(C_1-C_6)$alkylamino, $(C_1-C_6)$alkyl, $(C_1-C_6)$haloalkyl, $(C_1-C_6)$alkoxy, and $(C_1-C_6)$haloalkoxy. In one such embodiment, any two of $R^8$, $R^9$, $R^{10}$ and $R^{11}$ form a phenyl ring, which may be substituted as described.

In another embodiment relating to the use of compounds of formula I in these methods, there are four possibilities: (a) at least one of $R^8$, $R^9$, and $R^{11}$ is chosen from halogen, methyl and ethyl; or (b) $R^{10}$ is methoxy; or (c) $R^8$, $R^9$, $R^{10}$, $R^{11}$, $R^{7a}$, and $R^{7b}$ are hydrogen and at least one of $R^{4a}$ and $R^{4b}$ is methyl, or (d) $R^8$ and $R^9$, together with the carbon atoms to which they are attached, form a 6-membered carbocycle or 7-membered bridged carbocycle. In any of these four possibilities, when q1 and q2 are both zero, $R^{4a}$ may be hydrogen and $R^{4b}$ may be hydrogen or methyl, and $R^2$ and $R^3$ may be hydrogen. In any of these four possibilities, when q1 is one, $R^2$ and $R^3$ may be hydrogen or methyl.

In another embodiment relating to the use of compounds of formula I in these methods, exemplary compounds are those in which $R^2$ and $R^3$ are hydrogen, q1 and q2 are both zero, and (a) both of $R^{7a}$ and $R^{7b}$ are methyl, or (b) both of $R^8$ and $R^9$ are methyl, or (c) $R^9$ is methoxy and at least one of $R^{4a}$ and $R^{4b}$ is methyl, or (d) $R^{11}$ is propyl.

In another embodiment relating to the use of compounds of formula I in these methods, exemplary compounds are those in which $R^{4a}$, $R^{4b}$, $R^{5a}$, $R^{5b}$, $R^{6a}$, $R^{6b}$, $R^{7a}$, and $R^{7b}$ are all hydrogen, and (a) q1 is one and $R^1$, $R^2$, $R^3$, $R^8$, $R^{10}$, and $R^{11}$ are hydrogen, or (b) q1 and q2 are both zero, $R^{10}$ and $R^{11}$ are hydrogen, or (c) q1 and q2 are both zero, $R^8$, $R^9$, and $R^{10}$ are hydrogen and $R^{11}$ is —$(C_1-C_3)$alkyl.

In another embodiment relating to the use of compounds of formula I in these methods, exemplary compounds are those in which $R^1$, $R^{4a}$, $R^{4b}$, $R^{5a}$, $R^{5b}$, $R^{6a}$, $R^{6b}$, $R^{7a}$, and $R^{7b}$ are all hydrogen, and (a) q1 is one, $R^2$ and $R^3$ are hydrogen or methyl, and $R^{10}$ and $R^{11}$ are hydrogen or methyl, or (b) q1 and q2 are both zero and $R^8$, $R^9$, $R^{10}$ and $R^{11}$ are chosen from hydrogen, methyl, methoxy and chloro.

In a pharmaceutical composition aspect, the invention relates to compositions comprising a pharmaceutically acceptable carrier and a compound of formula I above, wherein at least one of $R^1$, $R^2$, $R^3$ $R^{4a}$, $R^{4b}$, $R^{5a}$, $R^{5b}$, $R^6a$, $R^{6b}$, $R^{7a}$, $R^{7b}$, $R^8$, $R^9$, $R^{10}$ and $R^{11}$ is other than hydrogen.

In a chemical compound aspect, the invention relates to compounds of formula I:

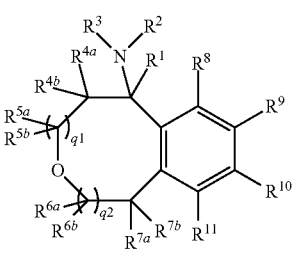

I or a pharmaceutically acceptable salt thereof, wherein:
q1 is 0 or 1,
q2 is 0 or 1, and
the sum of q1 plus q2 is 0 or 1;
$R^1$, $R^2$ and $R^3$ are chosen independently from H and an aliphatic $(C_1-C_8)$hydrocarbyl optionally substituted with one or more groups independently selected from halogen, —C≡C—, hydroxyl, $(C_1-C_6)$alkoxy, amino, $(C_1-C_6)$alkylamino and di$(C_1-C_6)$alkylamino;

$R^{4a}$, $R^{4b}$, $R^{7a}$, and $R^{7b}$ are chosen independently from H, halogen, $(C_1-C_6)$alkyl, $(C_1-C_6)$haloalkyl, and $(C_1-C_6)$alkoxy;

$R^{5a}$, $R^{5b}$, $R^{6a}$ and $R^{6b}$ are chosen independently from H, halogen, $(C_1-C_6)$alkyl and $(C_1-C_6)$haloalkyl;

$R^8$, $R^9$, $R^{10}$ and $R^{11}$ are chosen independently from H, halogen, $(C_1-C_8)$hydrocarbyl, cyano, —$CF_3$, $(C_1-C_6)$haloalkyl, hydroxyl, $(C_1-C_6)$alkoxy, aminocarbonyl, $(C_1-C_6)$alkylaminocarbonyl, di$(C_1-C_6)$alkylaminocarbonyl, $(C_1-C_6)$acyl, $(C_1-C_6)$haloalkoxy, hydroxy$(C_1-C_6)$alkyl, carboxy, $(C_1-C_6)$alkoxycarbonyl, acetoxy, nitro, amino, $(C_1-C_6)$alkylamino, di$(C_1-C_6)$alkylamino, aminosulfonyl, benzyl, aryl, heteroaryl, phenoxy, —OC(O)N(alkyl)$_2$ or benzyloxy;

wherein said benzyl, aryl, heteroaryl, phenoxy or benzyloxy are optionally substituted with one or more substituents independently selected from halogen, $(C_1-C_6)$alkyl, cyano, $(C_1-C_6)$haloalkyl, hydroxyl, $(C_1-C_6)$alkoxy, aminocarbonyl, $(C_1-C_6)$alkylaminocarbonyl, di$(C_1-C_6)$alkylaminocarbonyl, $(C_1-C_6)$acyl, $(C_1-C_6)$haloalkoxy, hydroxy$(C_1-C_6)$alkyl, carboxy, $(C_1-C_6)$alkoxycarbonyl, acetoxy, nitro, amino, $(C_1-C_6)$alkylamino, and di$(C_1-C_6)$alkylamino;

and further wherein:

any two of $R^8$, $R^9$, $R^{10}$ and $R^{11}$ attached to adjacent carbon atoms, together with the carbon atoms to which they are attached, may form a 5 to 8-membered carbocycle or heterocycle which is optionally substituted with one or more substituents independently selected from halogen, hydroxyl, amino, $(C_1-C_6)$alkylamino, di$(C_1-C_6)$alkylamino, $(C_1-C_6)$alkyl, $(C_1-C_6)$haloalkyl, $(C_1-C_6)$alkoxy, and $(C_1-C_6)$haloalkoxy;

with the provisos that, when q1 and q2 are both zero and $NR^2R^3$ is $NHCH_3$ or $N(CH_3)_2$, then at least one of $R^1$, $R^{4a}$, $R^{4b}$, $R^8$, $R^9$, $R^{10}$ and $R^{11}$ must be other than hydrogen or methoxy; or when q1 and q2 are both zero and $NR^2R^3$ is $NH_2$, then one of the following four conditions must be met:
at least two of $R^8$, $R^9$, $R^{10}$ and $R^{11}$ must be other than hydrogen, or
at least one of $R^8$, $R^9$, $R^{10}$ and $R^{11}$ must be phenyl, or
at least one of $R^8$, $R^9$, $R^{10}$ and $R^{11}$ must be phenyl, or
at least one of $R^{4a}$ and $R^{4b}$ must be other than hydrogen, or
at least one of $R^{7a}$ and $R^{7b}$ must be methyl and the other of $R^{7a}$ and $R^{7b}$ must be other than methyl, and when q1 or q2 is one, then the following species are excluded:

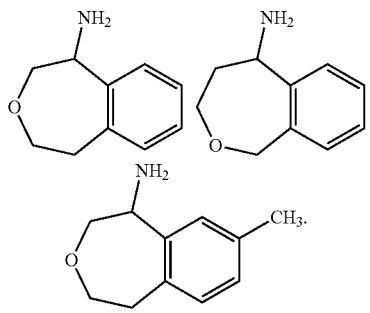

In one embodiment relating to the compounds, q1 and q2 are both zero, and the compounds are chroman-1-amines of formula II:

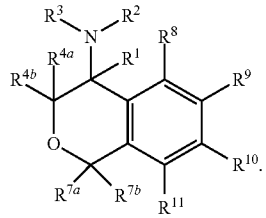

In another embodiment relating to the compounds, q1 is one, and the compounds are 1,3,4,5-tetrahydrobenzo[c]oxepin-5-amines of formula III:

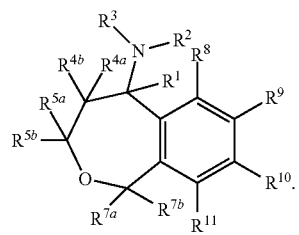

In another embodiment relating to the compounds, q2 is one, and the compounds are 1,2,4,5-tetrahydrobenzo[d]oxepin-1-amines of formula IV:

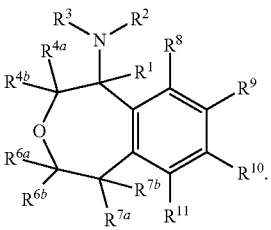

In some embodiments, $R^{4a}$, $R^{4b}$, $R^{7a}$, and $R^{7b}$ are hydrogen.

In some embodiments, $R^7$ and $R^8$ form a 5 to 8-membered carbocycle or heterocycle which is optionally substituted with one or more substituents independently selected from halogen, hydroxyl, amino, $(C_1-C_6)$alkylamino, di$(C_1-C_6)$alkylamino, $(C_1-C_6)$alkyl, $(C_1-C_6)$haloalkyl, $(C_1-C_6)$alkoxy, and $(C_1-C_6)$haloalkoxy. In some embodiments, the carbocycle or heterocycle may be chosen from phenyl, pyridine, cyclohexene, thiazole, bicycloheptene, and dihydropyran.

In some embodiments, $R^9$ and $R^{10}$ form a 5 to 8-membered carbocycle or heterocycle which is optionally substituted with one or more substituents independently selected from halogen, hydroxyl, amino, $(C_1-C_6)$alkylamino, di$(C_1-C_6)$alkylamino, $(C_1-C_6)$alkyl, $(C_1-C_6)$haloalkyl, $(C_1-C_6)$alkoxy, and $(C_1-C_6)$haloalkoxy. In some embodiments, the carbocycle or heterocycle may be chosen from phenyl, pyridine, cyclohexene, thiazole, bicycloheptene, and dihydropyran.

In some embodiments, $R^9$ is a phenyl which is unsubstituted or substituted with 1 to 4 substituents independently selected from halo, —OH, —$NH_2$, methyl, ethyl, methoxy, trifluoromethyl and trifluoromethoxy; in others, $R^9$ is a 5- or 6-membered heteroaryl which is unsubstituted or substituted with 1 to 4 substituents independently selected from halo, —OH, —$NH_2$, methyl, ethyl, methoxy, trifluoromethyl and trifluoromethoxy.

In some embodiments, two of $R^8$, $R^9$, $R^{10}$ and $R^{11}$ are chosen from methyl and chloro and the other two are hydrogen.

In some embodiments, $R^2$ is hydrogen and $R^3$ is chosen from methyl, ethyl, propyl, isopropyl, and hydroxyethyl.

In some embodiments, $R^1$ is hydrogen or methyl; in some embodiments $R^1$ is hydrogen.

In some embodiments, $R^{4a}$ and $R^{4b}$ are chosen independently from hydrogen and $(C_1-C_6)$alkyl.

In some embodiments of tetrahydrobenzo[c]oxepin-5-amines of formula III or 1,2,4,5-tetrahydrobenzo[d]oxepin-1-amines of formula IV, $R^8$ and $R^9$ form a 5 to 8-membered carbocycle or heterocycle which is optionally substituted with one or more substituents independently selected from halogen, hydroxyl, amino, $(C_1-C_6)$alkylamino, di$(C_1-C_6)$alkylamino, $(C_1-C_6)$alkyl, $(C_1-C_6)$haloalkyl, $(C_1-C_6)$alkoxy, and $(C_1-C_6)$haloalkoxy. In particular embodiments, the carbocycle is phenyl, which may be substituted as described.

In some embodiments of tetrahydrobenzo[c]oxepin-5-amines of formula III or 1,2,4,5-tetrahydrobenzo[d]oxepin-1-amines of formula IV, $R^{4a}$ and $R^{4b}$ are chosen from hydrogen and methyl.

In some embodiments of tetrahydrobenzo[c]oxepin-5-amines of formula III or 1,2,4,5-tetrahydrobenzo[d]oxepin-1-amines of formula IV, $R^2$ is hydrogen and $R^3$ is hydrogen or methyl.

In some embodiments of chroman-1-amines of formula II, tetrahydrobenzo[c]oxepin-5-amines of formula III or 1,2,4,5-tetrahydrobenzo[d]oxepin-1-amines of formula IV, one or two of $R^8$, $R^9$, $R^{10}$ and $R^{11}$ are chosen from methyl and chloro and the remaining two or three of $R^8$, $R^9$, $R^{10}$ and $R^{11}$ are hydrogen.

In one embodiment, provided are compounds of formula (I) which are greater than 90% enantiomerically pure. In another embodiment, provided are compounds of formula I which are greater than 95% enantiomerically pure.

In one embodiment, provided is a compound according to formula I, wherein said compound is:

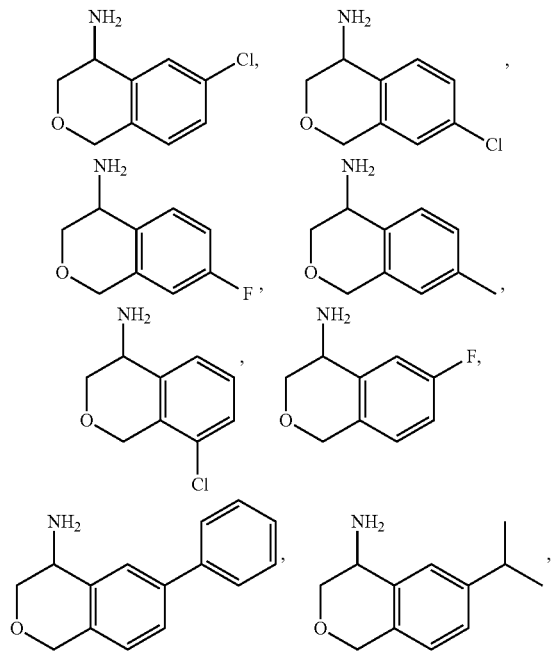

-continued

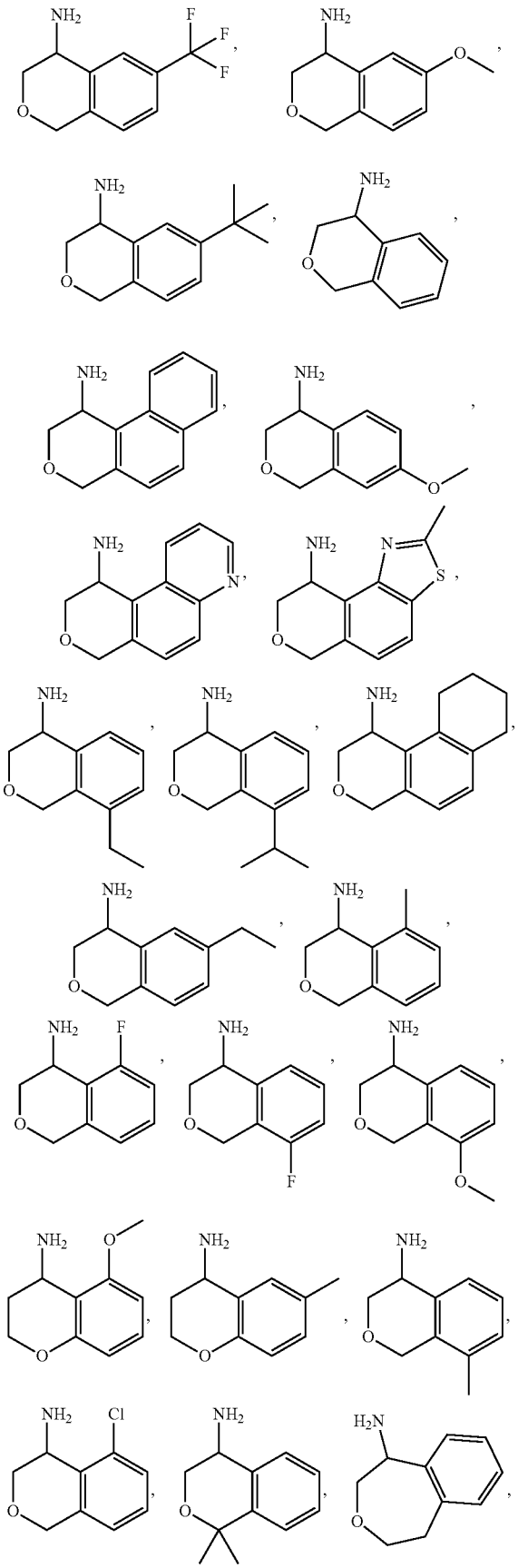

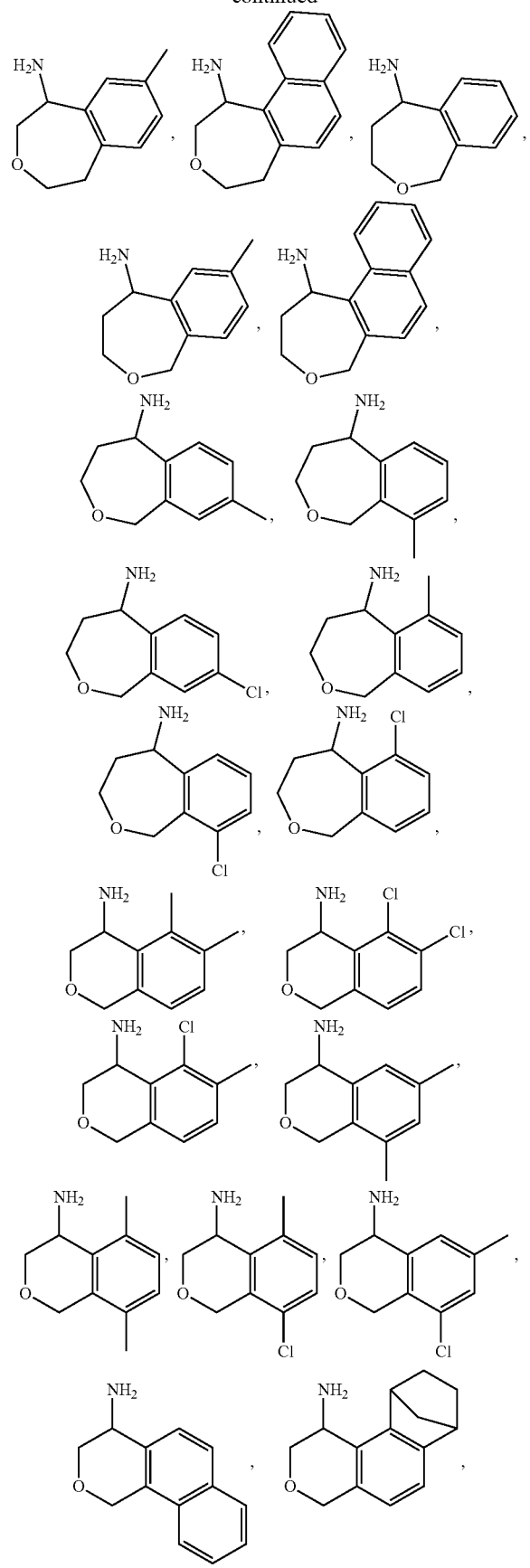
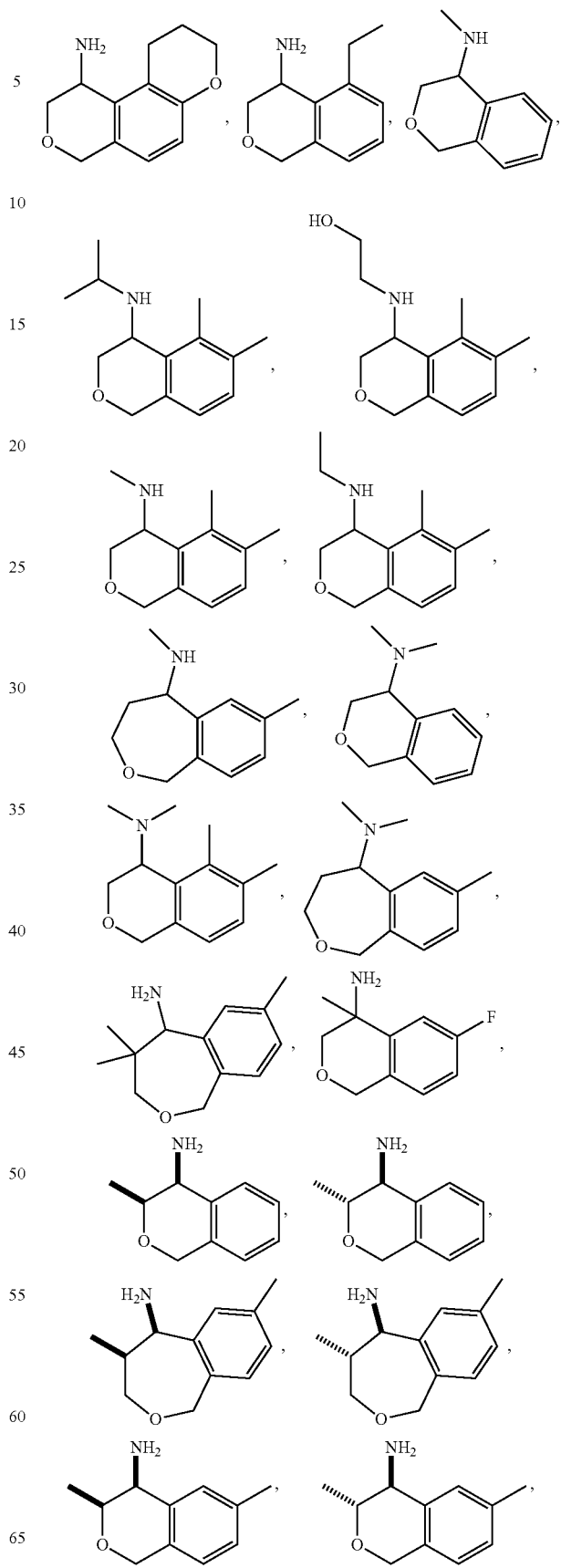

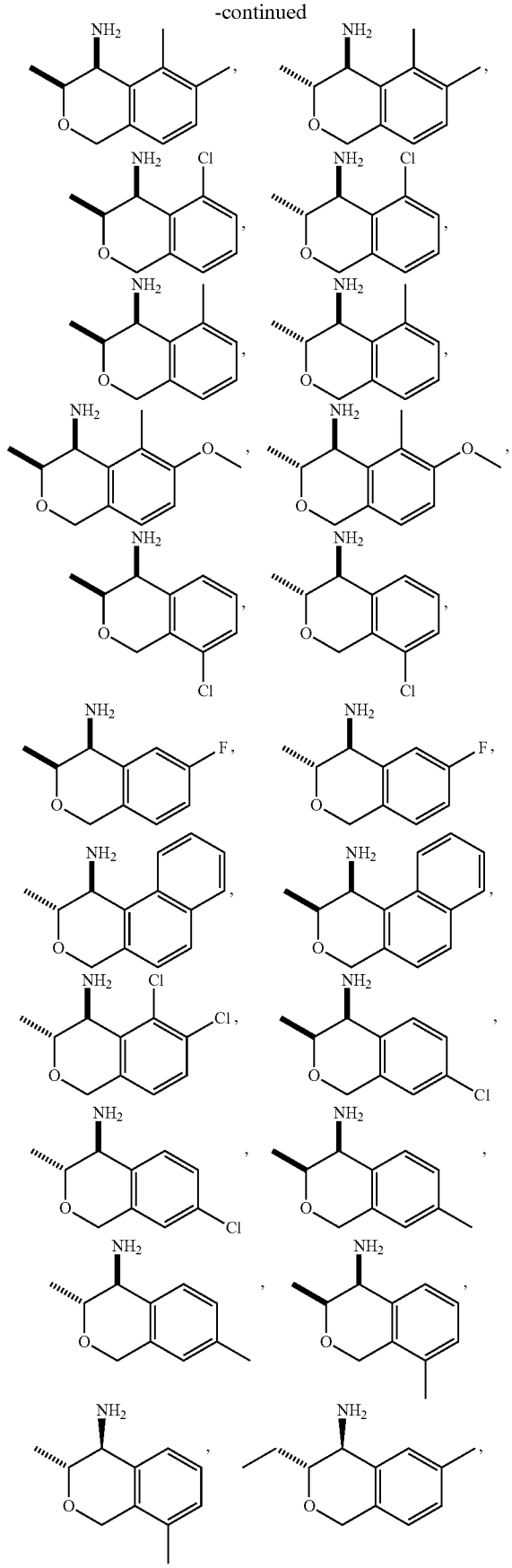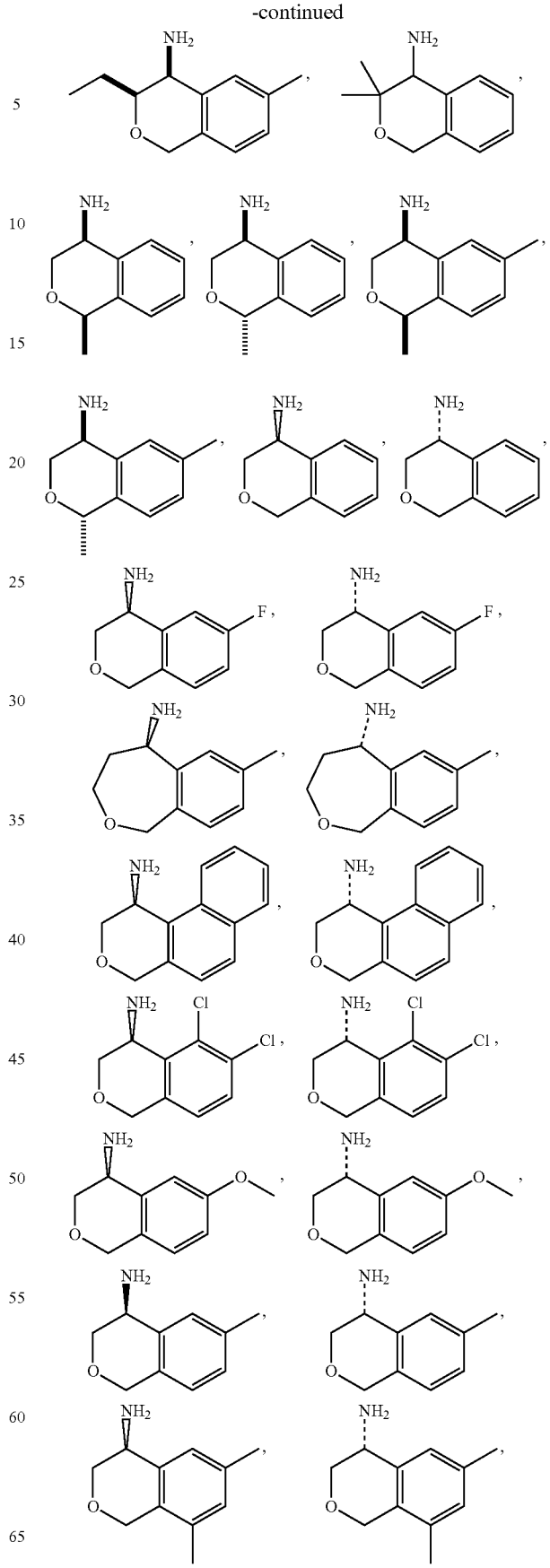

-continued

-continued
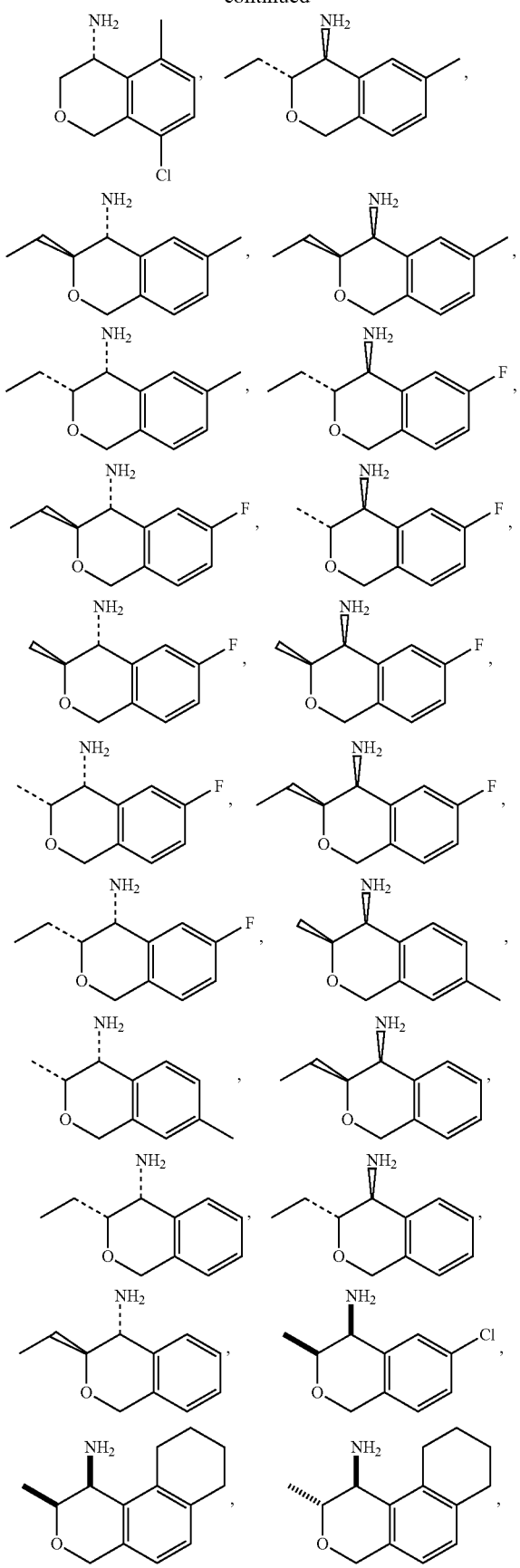
-continued
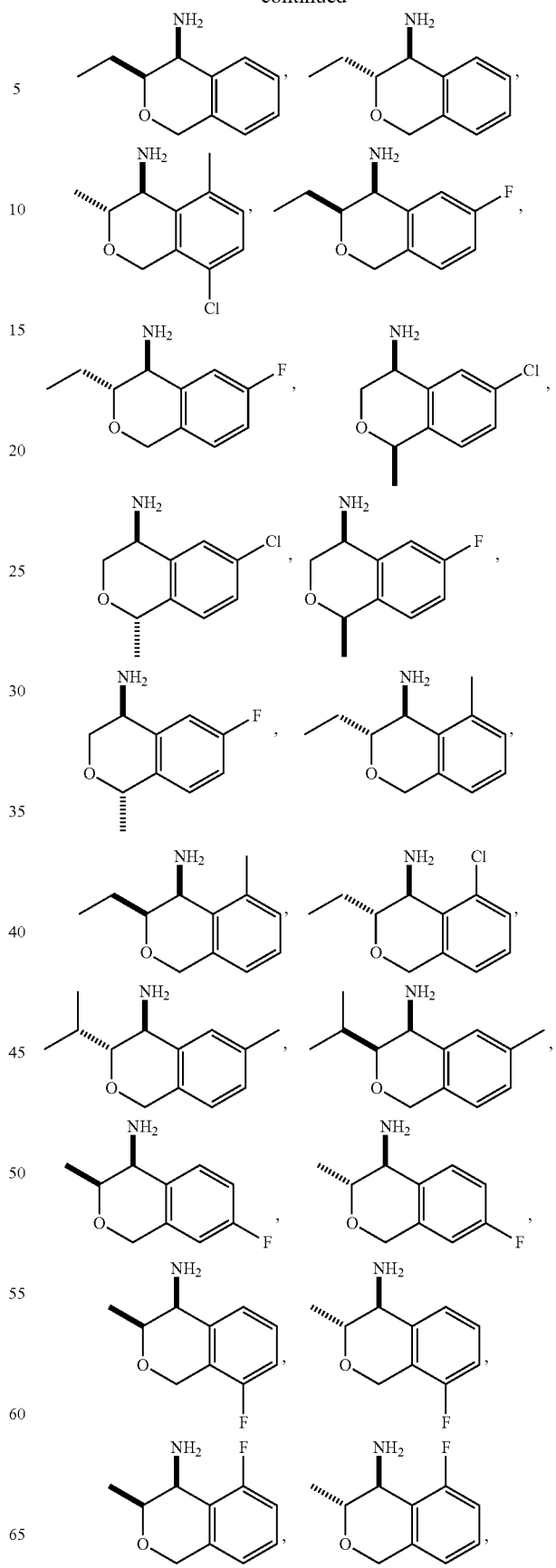

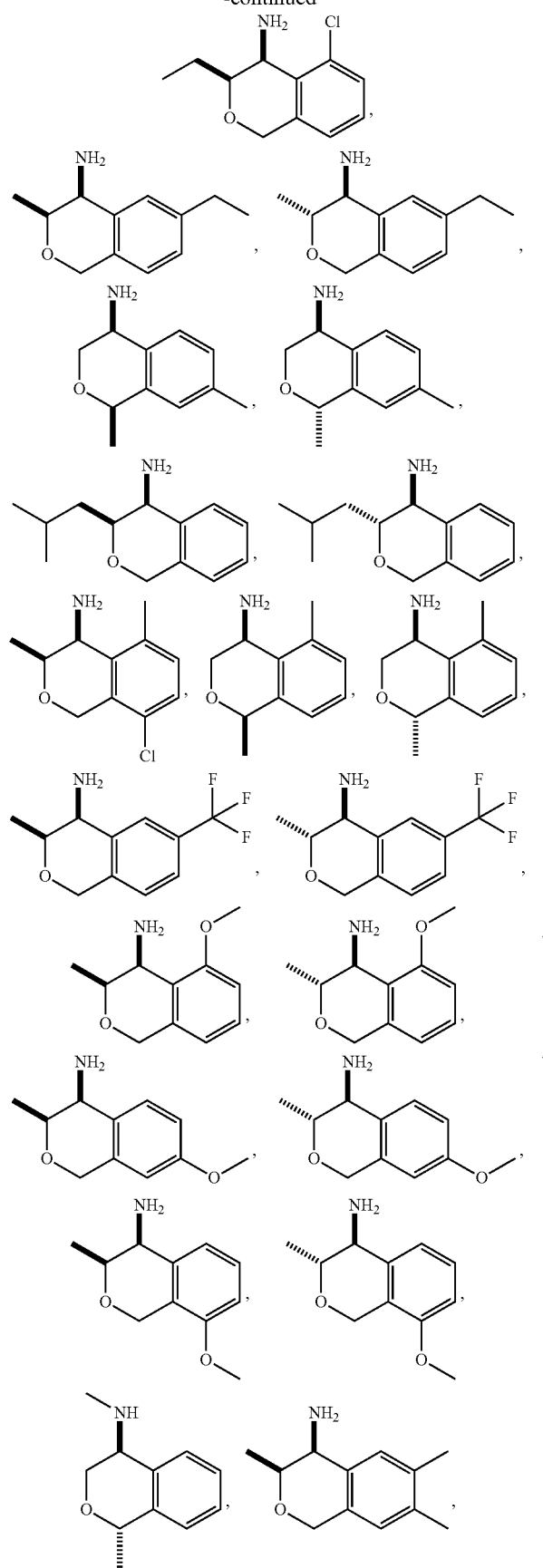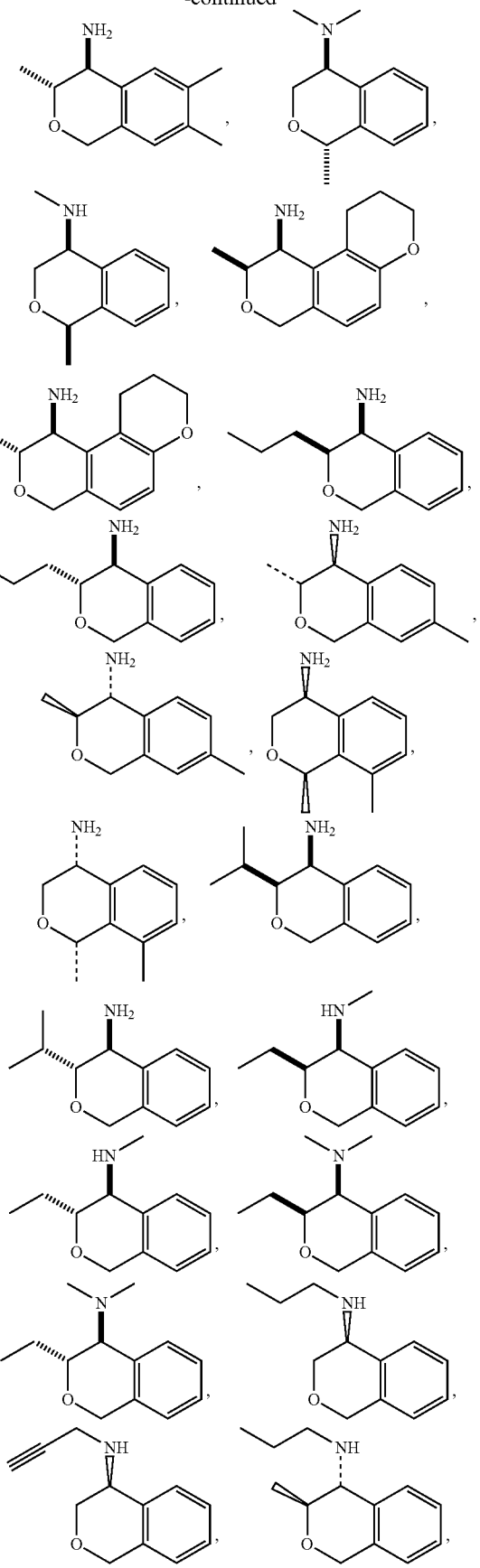

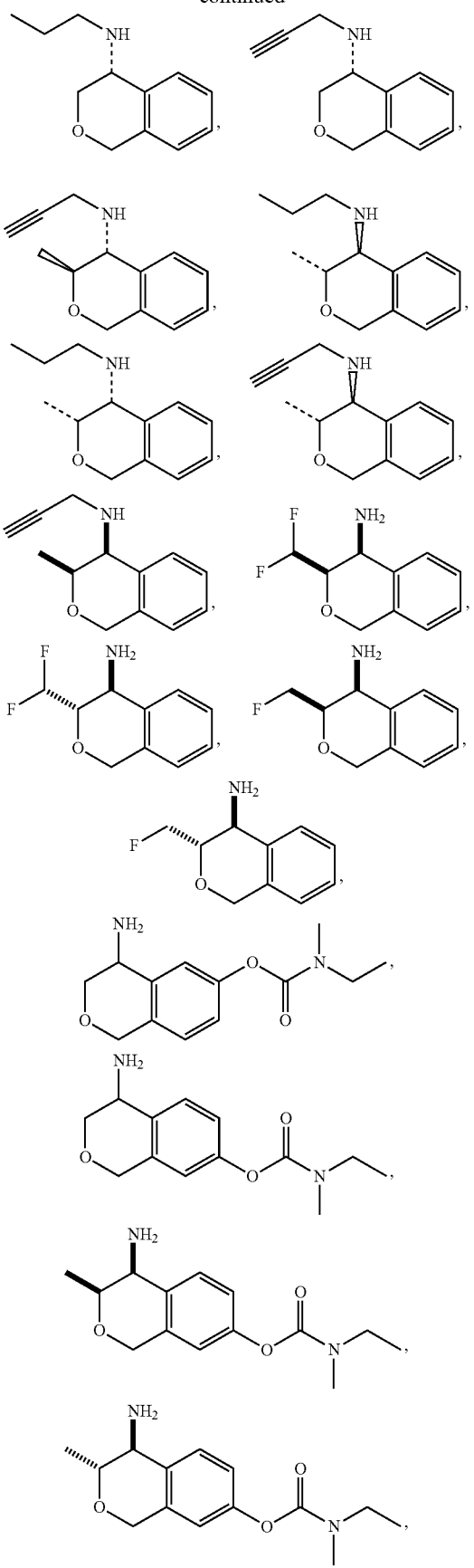
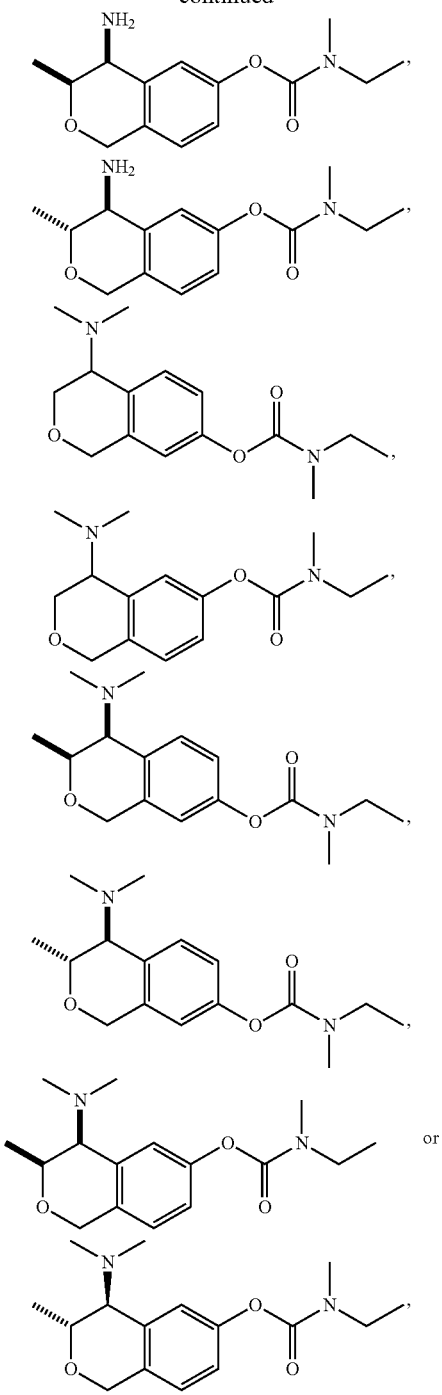
or a pharmaceutically acceptable salt thereof.
In one embodiment, provided are compounds according to formula I wherein said compound is:
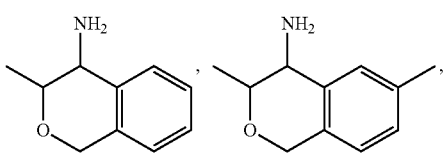

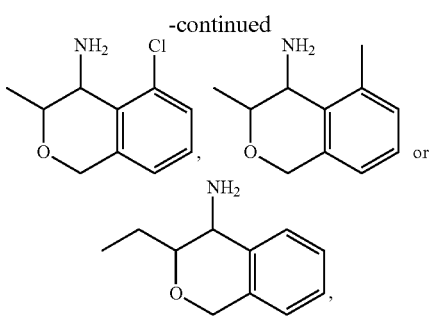

or a pharmaceutically acceptable salt thereof.

In another embodiment, provided are compounds according to formula I wherein said compound is:

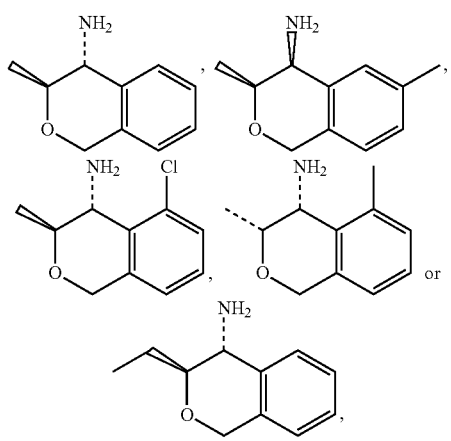

or a pharmaceutically acceptable salt thereof.

In another embodiment, provided are compounds according to formula I wherein said compound is:

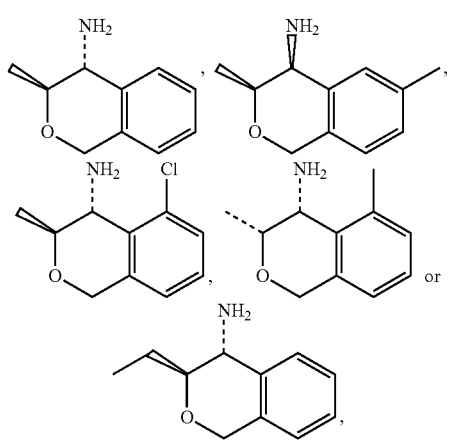

and has greater than 90% enantiomeric purity. In another embodiment, said compound has greater than 95% enantiomeric purity.

Compounds and Compositions and Definitions

Compounds and compositions of this invention include those described generally above, and are further illustrated by the classes, subclasses, and species disclosed herein. As used herein, the following definitions shall apply unless otherwise indicated. A comprehensive list of abbreviations utilized by organic chemists (i.e. persons of ordinary skill in the art) appears in the first issue of each volume of the Journal of Organic Chemistry. The definitions therein, which are typically presented in a table entitled "Standard List of Abbreviations" are the definitions used herein.

The graphic representations of racemic, ambiscalemic and scalemic or enantiomerically pure compounds used herein are a modified version of the denotations taken from Maehr J. Chem. Ed. 62, 114-120 (1985): simple lines provide no information about stereochemistry and convey only connectivity; solid and broken wedges are used to denote the absolute configuration of a chiral element; solid and broken bold lines are geometric descriptors indicating the relative configuration shown but not necessarily denoting racemic character; and wedge outlines and dotted or broken lines denote enantiomerically pure compounds of the indicated relative stereochemistry of indeterminate absolute configuration. For example, the graphic representation

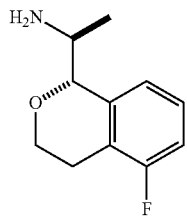

indicates a trans relationship between the two chiral centers, that is, either or both of the two representations below:

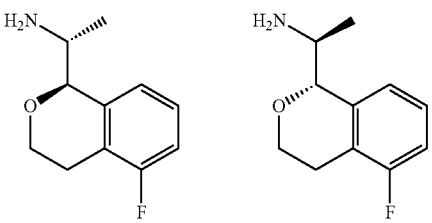

in any ratio, from pure enantiomers to racemates, while the representation:

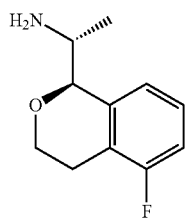

indicates a single enantiomer with the absolute configuration depicted, e.g., ((R)-1-((R)-5-fluoroisochroman-1-yl)ethan-1-amine in the illustration above. Further, the open wedge/broken line depiction as shown in the example below:

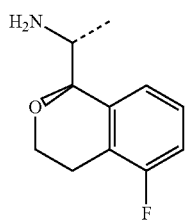

represents a single enantiomer of the indicated relative stereochemistry of an undetermined absolute configuration. In the text describing the stereochemistry of the examples, the convention of Chemical Abstracts is used. Thus "(R)-1-((R)-5-rel- . . . " indicates that the two chiral centers are in that relative relationship, which would be depicted in a structural diagram by solid bold and dashed lines, whereas "(R)-1-((R)-5- . . . " without the "rel" indicates a single enantiomer of that absolute configuration, which would be depicted in a structural diagram by solid and broken wedges.

The "enantiomeric excess" or "% enantiomeric excess" of a composition can be calculated using the equation shown below. In the example shown below, a composition contains 90% of one enantiomer, e.g., the S enantiomer, and 10% of the other enantiomer, e.g., the R enantiomer. ee=(90-10)/100=80%.

Thus, a composition containing 90% of one enantiomer and 10% of the other enantiomer is said to have an enantiomeric excess of 80%. Some compositions described herein contain an enantiomeric excess of at least about 50%, 75%, 90%, 95%, or 99% of the S enantiomer. In other words, the compositions contain an enantiomeric excess of the S enantiomer over the R enantiomer. In other embodiments, some compositions described herein contain an enantiomeric excess of at least about 50%, 75%, 90%, 95%, or 99% of the R enantiomer. In other words, the compositions contain an enantiomeric excess of the R enantiomer over the S enantiomer.

For instance, an isomer/enantiomer can, in some embodiments, be provided substantially free of the corresponding enantiomer, and can also be referred to as "optically enriched," "enantiomerically enriched," "enantiomerically pure" and "non-racemic," as used interchangeably herein. These terms refer to compositions in which the percent by weight of one enantiomer is greater than the amount of that one enantiomer in a control mixture of the racemic composition (e.g., greater than 1:1 by weight). For example, an enantiomerically enriched preparation of the S enantiomer, means a preparation of the compound having greater than about 50% by weight of the S enantiomer relative to the R enantiomer, such as at least about 75% by weight, further such as at least about 80% by weight. In some embodiments, the enrichment can be much greater than about 80% by weight, providing a "substantially enantiomerically enriched," "substantially enantiomerically pure" or a "substantially non-racemic" preparation, which refers to preparations of compositions which have at least about 85% by weight of one enantiomer relative to other enantiomer, such as at least about 90% by weight, and further such as at least 95% by weight. In certain embodiments, the compound provided herein is made up of at least about 90% by weight of one enantiomer. In other embodiments, the compound is made up of at least about 95%, 98%, or 99% by weight of one enantiomer.

In some embodiments, the compound is a racemic mixture of (S)- and (R)-isomers. In other embodiments, provided herein is a mixture of compounds wherein individual compounds of the mixture exist predominately in an (S)- or (R)-isomeric configuration. For example, the compound mixture has an (S)-enantiomeric excess of greater than about 55%, about 60%, about 65%, about 70%, about 75%, about 80%, about 85%, about 90%, about 95%, about 96%, about 97%, about 98%, about 99%, about 99.5%, or more. In other embodiments, the compound mixture has an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

In other embodiments, the compound mixture has an (R)-enantiomeric purity of greater than about 55%, about 60%, about 65%, about 70%, about 75%, about 80%, about 85%, about 90%, about 95%, about 96%, about 97%, about 98%, about 99%, about 99.5% or more. In some other embodiments, the compound mixture has an (R)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In other embodiments, the compound mixture contains identical chemical entities except for their stereochemical orientations, namely (S)- or (R)-isomers. For example, if a compound disclosed herein has —CH(R)— unit, and R is not hydrogen, then the —CH(R)— is in an (S)- or (R)-stereochemical orientation for each of the identical chemical entities. In some embodiments, the mixture of identical chemical entities is a racemic mixture of (S)- and (R)-isomers. In another embodiment, the mixture of the identical chemical entities (except for their stereochemical orientations), contain predominately (S)-isomers or predominately (R)-isomers. For example, the (S)-isomers in the mixture of identical chemical entities are present at about 55%, about 60%, about 65%, about 70%, about 75%, about 80%, about 85%, about 90%, about 95%, about 96%, about 97%, about 98%, about 99%, about 99.5%, or more, relative to the (R)-isomers. In some embodiments, the (S)-isomers in the mixture of identical chemical entities are present at an (S)-enantiomeric excess of greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5% or more.

In another embodiment, the (R)-isomers in the mixture of identical chemical entities (except for their stereochemical orientations), are present at about 55%, about 60%, about 65%, about 70%, about 75%, about 80%, about 85%, about 90%, about 95%, about 96%, about 97%, about 98%, about 99%, about 99.5%, or more, relative to the (S)-isomers. In some embodiments, the (R)-isomers in the mixture of identical chemical entities (except for their stereochemical orientations), are present at a (R)-enantiomeric excess greater than about 55% to about 99.5%, greater than about 60% to about 99.5%, greater than about 65% to about 99.5%, greater than about 70% to about 99.5%, greater than about 75% to about 99.5%, greater than about 80% to about 99.5%, greater than about 85% to about 99.5%, greater than about 90% to about 99.5%, greater than about 95% to about 99.5%, greater than about 96% to about 99.5%, greater than about 97% to about 99.5%, greater than about 98% to greater than about 99.5%, greater than about 99% to about 99.5%, or more.

Hydrocarbyl refers to any substituent comprised of hydrogen and carbon as the only elemental constituents. $C_1$ to $C_{20}$ hydrocarbon includes, for example, alkyl, cycloalkyl, polycycloalkyl, alkenyl, alkynyl, aryl and combinations thereof. Examples include benzyl, phenethyl, cyclohexylmethyl, adamantyl, camphoryl and naphthylethyl. Aromatic hydrocarbons include benzene (phenyl), naphthalene (naphthyl), anthracene, etc. Aliphatic hydrocarbons are hydrocarbons that are not aromatic; they may be saturated or unsaturated, cyclic, linear or branched, or combinations thereof. Aliphatic hydrocarbons include, for example, alkyl, alkenyl, alkynyl, cycloalkyl, cycloalkenyl, cycloalkynyl, and combinations thereof. Non-limiting examples of aliphatic hydrocarbons include isopropyl, 2-butenyl, 2-butynyl, cyclopentyl, cyclopropylmethyl, norbornyl, and the like.

Unless otherwise specified, alkyl (or alkylene) is intended to include linear or branched saturated hydrocarbon structures and combinations thereof. Alkyl refers to alkyl groups from 1 to 20 carbon atoms, preferably 1 to 10 carbon atoms, more preferably 1 to 6 carbon atoms. Examples of alkyl groups include methyl, ethyl, propyl, isopropyl, n-butyl, s-butyl, t-butyl and the like.

Cycloalkyl is a subset of hydrocarbon and includes cyclic hydrocarbon groups of from 3 to 8 carbon atoms. Examples of cycloalkyl groups include cyclopropyl, cyclobutyl, cyclopentyl, norbornyl and the like.

Unless otherwise specified, the term "carbocycle" is intended to include ring systems in which the ring atoms are all carbon but of any oxidation state. Thus ($C_3$-$C_{10}$) carbocycle refers to both non-aromatic and aromatic systems, including such systems as cyclopropane, benzene (phenyl) and cyclohexene; ($C_8$-$C_{12}$) carbopolycycle refers to such systems as norbornane, decalin, indane and naphthalene. Carbocycle, if not otherwise limited, refers to monocycles, bicycles and polycycles, including bridged structures.

Heterocycle means an aliphatic or aromatic carbocycle residue in which from one to four carbons is replaced by a heteroatom selected from the group consisting of N, O, and S. The nitrogen and sulfur heteroatoms may optionally be oxidized, and the nitrogen heteroatom may optionally be quaternized. Unless otherwise specified, a heterocycle may be non-aromatic (heteroaliphatic) or aromatic (heteroaryl). Heterocycle, if not otherwise limited, refers to monocycles, bicycles and polycycles, including bridged structures. Examples of heterocycles include, but are not limited to, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, atrophine, dioxane, tetrahydrofuran and the like. Examples of heterocyclyl residues include piperazinyl, piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl (also historically called thiophenyl), benzothienyl, thiamorpholinyl, oxadiazolyl, triazolyl and tetrahydroquinolinyl.

Hydrocarbyloxy refers to groups of from 1 to 20 carbon atoms, preferably 1 to 10 carbon atoms, more preferably 1 to 6 carbon atoms attached to the parent structure through an oxygen. Alkoxy is a subset of hydrocarbyloxy and includes groups of a straight or branched configuration. Examples include methoxy, ethoxy, propoxy, isopropoxy and the like. Lower-alkoxy refers to groups containing one to four carbons.

The term "halogen" means fluorine, chlorine, bromine or iodine. In one embodiment, halogen may be fluorine or chlorine.

Unless otherwise specified, acyl refers to formyl and to groups of 1, 2, 3, 4, 5, 6, 7 and 8 carbon atoms of a straight, branched, cyclic configuration, saturated, unsaturated and aromatic and combinations thereof, attached to the parent structure through a carbonyl functionality. Examples include acetyl, benzoyl, propionyl, isobutyryl and the like. Lower-acyl refers to groups containing one to four carbons. The double bonded oxygen, when referred to as a substituent itself is called "oxo".

As used herein, the term "optionally substituted" may be used interchangeably with "unsubstituted or substituted". The term "substituted" refers to the replacement of one or more hydrogen atoms in a specified group with a specified radical. For example, substituted alkyl, aryl, cycloalkyl, heterocyclyl etc. refer to alkyl, aryl, cycloalkyl, or heterocyclyl wherein one or more H atoms in each residue are replaced with halogen, haloalkyl, hydrocarbyl, acyl, alkoxyalkyl, hydroxy lower alkyl, carbonyl, phenyl, heteroaryl, benzenesulfonyl, hydroxy, hydrocarbyloxy, haloalkoxy, oxaalkyl, carboxy, alkoxycarbonyl [—C(═O)O-alkyl], alkoxycarbonylamino [HNC(═O)O-alkyl], aminocarbonyl (also known as carboxamido) [—C(═O)NH$_2$], alkylaminocarbonyl [—C(═O)NH-alkyl], dialkylaminocarbonyl [—C(═O)N(alkyl)$_2$], cyano, acetoxy, nitro, amino, alkylamino, dialkylamino, (alkyl)(aryl)aminoalkyl, alkylaminoalkyl (including cycloalkylaminoalkyl), dialkylaminoalkyl, dialkylaminoalkoxy, heterocyclylalkoxy, mercapto, alkylthio, sulfoxide, sulfone, sulfonylamino, alkylsulfinyl, alkylsulfonyl, acylaminoalkyl, acylaminoalkoxy, acylamino, amidino, aryl, benzyl, heterocyclyl, heterocyclylalkyl, phenoxy, benzyloxy, heteroaryloxy, hydroxyimino, alkoxyimino, oxaalkyl, aminosulfonyl, trityl, amidino, guanidino, ureido, benzyloxyphenyl, and benzyloxy. "Oxo" is also included among the substituents referred to in "optionally substituted"; it will be appreciated by persons of skill in the art that, because oxo is a divalent radical, there are circumstances in which it will not be appropriate as a substituent (e.g. on phenyl). In one embodiment, 1, 2, or 3 hydrogen atoms are replaced with a specified radical. In the case of alkyl and cycloalkyl, more than three hydrogen atoms can be replaced by fluorine; indeed, all available hydrogen atoms could be replaced by fluorine. In particular embodiments, substituents are halogen, halo($C_1$-$C_4$)hydrocarbyl, halo($C_1$-$C_4$)hydrocarbyloxy, cyano, thiocyanato, ($C_1$-$C_4$)hydrocarbylsulfinyl, ($C_1$-$C_4$)hydrocarbyl-sulfonyl, aminosulfonyl, nitro, acetyl, and acetamido. Preferred substituents are halogen, ($C_1$-$C_4$)alkyl, ($C_1$-$C_4$)alkoxy, ($C_1$-$C_4$) fluoroalkyl, ($C_1$-$C_4$)fluoroalkoxy, hydroxy, amino, ($C_1$-$C_4$) alkylamino, di($C_1$-$C_4$)alkylamino, ($C_1$-$C_4$)acylamino, ($C_1$-$C_4$)fluoroalkyl and ($C_1$-$C_4$)fluoroalkoxy.

Substituents R" are generally defined when introduced and retain that definition throughout the specification and claims.

As used herein, and as would be understood by the person of skill in the art, the recitation of "a compound"—unless expressly further limited—is intended to include salts of that compound. Thus, for example, the recitation "a compound of formula I" as depicted above, which contains a basic amine residue —$NR^2R^3$, would include salts —$NHR^2R^{3+}X^-$ wherein $X^-$ is any counterion. In a particular embodiment, the term "compound of formula I" refers to the compound or a pharmaceutically acceptable salt thereof; this term refers to a pharmaceutically acceptable salt of the compound, even if not explicitly stated. Unless otherwise stated or depicted, structures depicted herein are also meant to include all stereoisomeric (e.g., enantiomeric, diastereomeric, and cis-trans isomeric) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and cis-trans isomeric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. In addition to therapeutic uses, such compounds are useful, for example, as analytical tools or probes in biological assays.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in *J. Pharmaceutical Sciences*, 1977, 66, 1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Although pharmaceutically acceptable counter ions will be preferred for preparing pharmaceutical formulations, other anions are quite acceptable as synthetic intermediates. Thus X may be pharmaceutically undesirable anions, such as iodide, oxalate, trifluoromethanesulfonate and the like, when such salts are chemical intermediates.

Unless otherwise specified, the word "includes" (or any variation thereon, e.g., "include", "including", etc.) is intended to be open-ended. For example, "A includes 1, 2 and 3" means that A includes but is not limited to 1, 2 and 3.

Unless otherwise specified, the phrase "such as" is intended to be open-ended. For example, "A can be a halogen, such as chlorine or bromine" means that A can be, but is not limited to, chlorine or bromine.

According to another embodiment, the invention provides a composition comprising a compound of this invention (or its pharmaceutically acceptable salt) and a pharmaceutically acceptable carrier, adjuvant, or vehicle. In some embodiments, the amount of compound in compositions of this invention (also referred to herein as "effective amount" or "therapeutically effective amount") is such that is effective to treat, prevent, and/or manage various neurological and/or psychiatric diseases and disorders and/or symptoms in a subject. In some embodiments, a composition of this invention is formulated for administration to a subject in need of such composition. In some embodiments, a composition of this invention is formulated for oral administration to a subject.

As used herein, the term "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

In certain embodiments, provided herein is a composition (e.g., a pharmaceutical composition) comprising a compound described herein and a pharmaceutically acceptable excipient or carrier. In some embodiments, provided herein is a method of treating neurological or psychiatric diseases and disorders in a subject in need thereof in a subject, comprising administering an effective amount of a compound or a pharmaceutical composition described herein. Examples of carriers and excipients are well known to those skilled in the art and are described in detail in, e.g., Ansel, Howard C., et al., Ansel's Pharmaceutical Dosage Forms and Drug Delivery Systems. Philadelphia: Lippincott, Williams & Wilkins, 2004; Gennaro, Alfonso R., et al. Remington: The Science and Practice of Pharmacy. Philadelphia: Lippincott, Williams & Wilkins, 2000; and Rowe, Raymond C. Handbook of Pharmaceutical Excipients. Chicago, Pharmaceutical Press, 2005. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. Pharmaceutically acceptable compositions of this invention may be orally administered in any orally acceptable dosage form including capsules, tablets, aqueous suspensions or solutions.

The amount of compounds of the present invention that may be combined with the carrier materials to produce a composition in a single dosage form will vary depending upon a variety of factors, including the host treated and the particular mode of administration. It should also be understood that a specific dosage and treatment regimen for any particular subject will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In one embodiment, the invention provides for a method for treating a neurological or psychiatric disease or disorder, wherein the neurological or psychiatric disease or disorder is anxiety or attention deficit hyperactivity disorder.

In one embodiment, provided is a method of treating anxiety or attention deficit hyperactivity disorder in a subject in need thereof, comprising the step of administering to said subject an effective amount of a compound selected from:

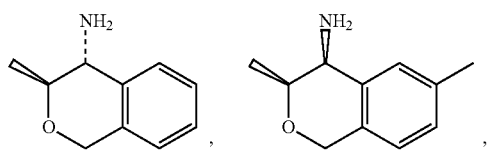

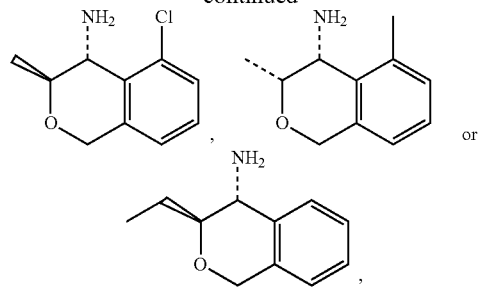

or a pharmaceutically acceptable salt thereof.

In one embodiment, provided is a method of treating anxiety in a subject in need thereof, comprising the step of administering to said subject an effective amount of a compound selected from:

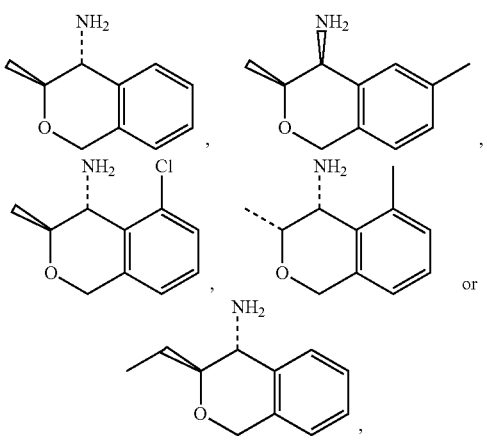

or a pharmaceutically acceptable salt thereof.

In one embodiment of the invention, provided is a method of treating attention deficit hyperactivity disorder in a subject in need thereof, comprising the step of administering to said subject an effective amount of a compound selected from:

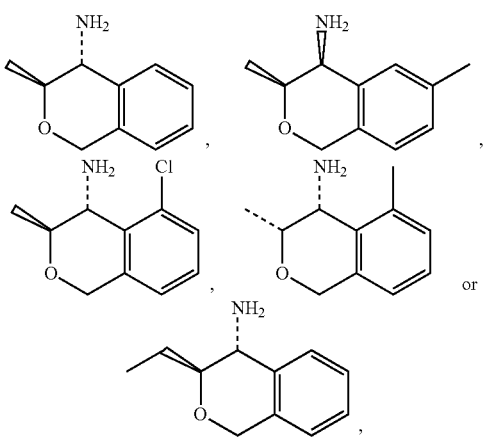

or a pharmaceutically acceptable salt thereof.

In some embodiments, the invention provides a method for treating a neurological or psychiatric diseases or disorder in a subject, comprising administering to the subject an effective amount of a compound of this invention (or its pharmaceutically acceptable salt), or composition comprising a compound of this invention (or its pharmaceutically acceptable salt). Neurological and/or psychiatric diseases and disorders diseases can exhibit a variety of psychiatric and behavioral symptoms, including apathy, depression, anxiety, cognitive impairment, psychosis, aggression, agitation, poor impulse control and sleep disruptions.

In some embodiments, the neurological or psychiatric diseases or disorder is selected from a psychosis, including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (e.g., phencyclidine, ketamine and other dissociative anesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both positive, negative, and cognitive symptoms of schizophrenia and other psychoses; cognitive disorders including dementia (semantic dementia, frontotemporal dementia, dementia with depressive features, persisting, subcortical dementia, dementia with Lewy Bodies, Parkinsonism-ALS Dementia Complex, and dementia associated with Alzheimer's disease, ischemia, multi-infarct dementia, trauma, vascular problems, stroke, HIV disease, Parkinson's disease, Huntington's disease, Down syndrome, Pick's disease, Creutzfeldt-Jacob disease, perinatal hypoxia, or substance abuse), delirium, amnestic disorders or age related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa, pica and compulsive eating disorders; bipolar disorders, mood disorders including depressive disorders; depression including unipolar depression, seasonal depression and postpartum depression, atypical depression, catatonic depression, elderly depression, endogenous depression, melancholic depression, perinatal depression, situational depression, chronic depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; disorders such as autism, depression, benign forgetfulness, childhood learning disorders, specific learning disorders, intellectual development disorders, and closed head injury; movement disorders; epilepsy; urinary incontinence; neuronal damage including ocular damage, retinopathy or macular degeneration of the eye, tinnitus, hearing impairment and loss, and brain edema; emesis; and sleep disorders including insomnia and narcolepsy.

In some embodiments, the neurological or psychiatric disease or disorder is Alzheimer's disease, Parkinson's disease, depression, cognitive impairment, stroke, schizophrenia, Down syndrome, or Fetal Alcohol Syndrome. In some embodiments, the neurological or psychiatric disease or disorder is Alzheimer's disease. In some embodiments, the neurological or psychiatric disease or disorder is Parkinson's disease. In some embodiments, the neurological or psychiatric disease or disorder is depression. In some embodiments, the neurological or psychiatric disease disorder is cognitive impairment. In some embodiments, the cognitive impairment is cognitive dysfunction associated with depression, for example, major depressive disorder. In some embodiments, the neurological or psychiatric disorder is stroke. In some embodiments, the neurological or psychiatric disease or disorder is schizophrenia. In some embodiments, the neurological or psychiatric disease or disorder is Down syndrome. In some embodiments, the neurological or psychiatric disorder is Fetal Alcohol Syndrome.

In some embodiments, the neurological or psychiatric disease or disorder is bipolar disease. Bipolar disorder is a serious psychiatric disorder that has a prevalence of approximately 2% of the population, and affects both genders alike. It is a relapsing-remitting condition characterized by cycling between elevated (i.e., manic) and depressed moods, which distinguishes it from other disorders such as major depressive disorder and schizophrenia. Bipolar I is defined by the occurrence of a full manic episode, although most individuals experience significant depression. Symptoms of mania include elevated or irritable mood, hyperactivity, grandiosity, decreased need for sleep, racing thoughts and in some cases, psychosis. The depressive episodes are characterized by anhedonia, sad mood, hopelessness, poor self-esteem, diminished concentration and lethargy. Bipolar II is defined as the occurrence of a major depressive episode and hypomanic (less severe mania) episode although subjects spend considerable more time in the depressive state. Other related conditions include cyclothymic disorder.

In some embodiments, the neurological or psychiatric disease or disorder is schizophrenia. Schizophrenia is a disorder of unknown origin, which usually appears for the first time in early adulthood and is marked by characteristics such as psychotic symptoms, phasic progression and development, and/or deterioration in social behavior and professional capability. Characteristic psychotic symptoms are disorders of thought content (e.g., multiple, fragmentary, incoherent, implausible or simply delusional contents, or ideas of persecution) and of mentality (e.g., loss of association, flight of imagination, incoherence up to incomprehensibility), as well as disorders of perceptibility (e.g., hallucinations), emotions (e.g., superficial or inadequate emotions), self-perceptions, intentions, impulses, and/or inter-human relationships, and psychomotoric disorders (e.g., catatonia). Other symptoms are also associated with this disorder. Schizophrenia is classified into subgroups: the paranoid type, characterized by delusions and hallucinations and absence of thought disorder, disorganized behavior, and affective flattening; the disorganized type, also named "hebephrenic schizophrenia," in which thought disorder and flat affect are present together; the cataconic type, in which prominent psychomotor disturbances are evident, and symptoms may include catatonic stupor and waxy flexibility; and the undifferentiated type, in which psychotic symptoms are present but the criteria for paranoid, disorganized, or catatonic types have not been met. The symptoms of schizophrenia normally manifest themselves in three broad categories: positive, negative and cognitive symptoms. Positive symptoms are those which represent an "excess" of normal experiences, such as hallucinations and delusions. Negative symptoms are those where the subject suffers from a lack of normal experiences, such as anhedonia and lack of social interaction. The cognitive symptoms relate to cognitive impairment in schizophrenics, such as lack of sustained attention and deficits in decision making.

In some embodiments, the neurological or psychiatric disease or disorder is anxiety disorder. Anxiety disorders are characterized by fear, worry, and uneasiness, usually generalized and unfocused as an overreaction to a situation. Anxiety disorders differ in the situations or types of objects that induce fear, anxiety, or avoidance behavior, and the associated cognitive ideation. Anxiety differs from fear in that anxiety is an emotional response to a perceived future threat while fear is associated with a perceived or real immediate threat. They also differ in the content of the associated thoughts or beliefs. Examples of anxiety disorders include separation anxiety disorder, selective mutism, specific phobia, social anxiety disorder (social phobia), panic disorder, panic attack specifier, agoraphobia, generalized anxiety disorder, substance/medication-induced anxiety disorder, anxiety disorder due to another medical condition, illness anxiety disorder, social (pragmatic) communication disorder, other specified anxiety disorder, and unspecified anxiety disorder; stressor-related disorders, including reactive attachment disorder, disinhibited social engagement disorder, posttraumatic stress disorder (PTSD), acute stress disorder, and adjustment disorders.

Cognitive impairment includes a decline in cognitive functions or cognitive domains, e.g., working memory, attention and vigilance, verbal learning and memory, visual learning and memory, reasoning and problem solving (e.g., executive function, speed of processing and/or social cognition). In particular, cognitive impairment may indicate deficits in attention, disorganized thinking, slow thinking, difficulty in understanding, poor concentration, impairment of problem solving, poor memory, difficulties in expressing thoughts, and/or difficulties in integrating thoughts, feelings and behavior, or difficulties in extinction of irrelevant thoughts.

In some embodiments, the neurological or psychiatric disease or disorder involves a deficit in cognition (cognitive domains as defined by the DSM-5 are: complex attention, executive function, learning and memory, language, perceptual-motor, social cognition). In some embodiments, the neurological or psychiatric disorder is associated with a deficit in dopamine signaling. In some embodiments, the neurological or psychiatric disorder is associated with basal ganglia dysfunction. In some embodiments, the neurological or psychiatric disorder is associated with dysregulated locomotor activity. In some embodiments, the neurological or psychiatric disorder is associated with impairment of prefrontal cortex functioning.

In some embodiments, the present invention provides a method of treating one or more symptoms of a neurological and/or psychiatric disease or disorder provided herein. Such diseases and disorders include mood disorders, including bipolar I disorder, bipolar II disorder, bipolar depression, mania, cyclothymic disorder, sub stance/medication-induced bipolar and related disorders, bipolar and related disorder due to another medical condition, other specified bipolar and related disorder, and unspecified bipolar and related disorders; psychotic disorders, including schizophrenia, schizophrenia spectrum disorder, acute schizophrenia, chronic schizophrenia, NOS schizophrenia, schizoid personality disorder, schizotypal personality disorder, delusional disorder, psychosis, psychotic disorder, brief psychotic disorder, shared psychotic disorder, psychotic disorder due to a general medical condition, drug-induced psychosis (e.g., cocaine, alcohol, amphetamine), schizoaffective disorder, agitation, aggression, delirium, catalepsy, catatonia, dissociative identity disorder, paranoid personality disorder, psychotic depression, Schizotypical Personality Disorder, Childhood Disintegrative Disorder (Heller's Syndrome), Disintegrative Psychosis, Dissociative Amnesia, Somatic Symptom Disorder, Parkinson's psychosis, excitative psychosis, Tourette's syndrome, and organic or NOS psychosis; depressive disorders, including disruptive mood dysregulation disorder, major depressive disorder (MDD) (including major depressive episode), dysthymia, persistent depressive disorder (dysthymia), treatment resistant depression, premenstrual dysphoric disorder, substance/medication-induced depressive disorder, depressive disorder due to another medical condition, other specified depressive disorder, and unspecified depressive disorder; anxiety disorders; and other disorders including substance abuse or dependency (e.g., nicotine, alcohol, cocaine), addiction, internet gaming disorder, eating disorders, behavior disorder, seizure, vertigo, epilepsy, agitation, aggression, neurodegenerative disease, Alzheimer's disease, Parkinson's disease, dyskinesias, Huntington's disease, dementia, premenstrual dysphoria, attention deficit disorder (ADD) and attention deficit hyperactivity disorder (ADHD)), hyperkinetic syndrome, autism, autism spectrum disorder, obsessive-compulsive disorder, pain, fibromyalgia, migraine, cognitive impairment, movement disorder, restless leg syndrome (RLS), multiple sclerosis, Primary Progressive Multiple Sclerosis, multiple sclerosis, sleep disorder, sleep apnea, narcolepsy, excessive daytime sleepiness, jet lag, drowsy side effect of medications, insomnia, sexual dysfunction, hypertension, emesis, Lesche-Nyhane disease, Wilson's disease, Rett syndrome, and Huntington's chorea. In some embodiments, the neurological and/or psychiatric disorders include agitation and aggression.

In some embodiments, the agitation and aggression are associated with Alzheimer's disease, Parkinson's disease, and/or autism.

In some embodiments, the neurological and/or psychiatric diseases or disorders are obsessive-compulsive disorder and related disorders (e.g., body dysmorphic disorder, hoarding disorder, trichotillomania, excoriation disorder).

In some embodiments, the neurological and/or psychiatric diseases or disorders are disruptive, impulse-control, and conduct disorders including oppositional defiant disorder, intermittent explosive disorder, conduct disorder, antisocial personality disorder, pyromania, kleptomania, other specified disruptive, impulse-control, and conduct disorder, unspecified disruptive, impulse-control, and conduct disorder.

Depressive disorders include major depressive disorder and dysthymia, and are associated with depressed mood (sadness), poor concentration, insomnia, fatigue, appetite disturbances, excessive guilt and thoughts of suicide.

In some embodiments, the present invention provides a method of treating one or more symptoms including depression (e.g., major depressive disorder or dysthymia); bipolar disorder, seasonal affective disorder; cognitive deficit; sleep related disorder (e.g., sleep apnea, insomnia, narcolepsy, cataplexy) including those sleep disorders which are produced by psychiatric conditions; chronic fatigue syndrome;

anxieties (e.g., general anxiety disorder, social anxiety disorder, panic disorder); obsessive compulsive disorder; postmenopausal vasomotor symptoms (e.g., hot flashes, night sweats); neurodegenerative disease (e.g., Parkinson's disease, Alzheimer's disease, amyotrophic lateral sclerosis, primary lateral sclerosis, progressive muscular atrophy, progressive bulbar (atrophy) palsy, pseudobulbar palsy spinal muscular atrophy diseases (e.g., SMA type I, also called Werdnig-Hoffmann disease, SMA type II, SMA type III, also called Kugelberg-Welander disease, and Kennedy Disease, also called progressive spinobulbar muscular atrophy), Hallervorden-Spatz disease, Seitelberger disease (Infantile Neuroaxonal Dystrophy), adrenoleukodystrophy, Alexander Disease, autosomal dominant cerebellar ataxia (ADCA), pure autonomic failure (Bradbury-Eggleston Syndrome), CADASIL Syndrome, and neuronal ceroids lipofuscinose disorders such as Batten Disease (Spielmeyer-Vogt-Sjögren)); manic disorder; dysthymic disorder; and obesity.

In some embodiments, a depressive disorder is associated with acute suicidality or suicide ideation. The United States Food and Drug Administration has adopted a "black box" label warning indicating that antidepressants may increase the risk of suicidal thinking and behavior in some children, adolescents and young adults (up to age 24) with a depressive disorder such as MDD. In some embodiments, a provided compound does not increase the risk of suicidal thinking and/or behavior in children, adolescents and/or young adults with a depressive disorder, e.g., with MDD. In some embodiments, the present invention provides a method of treating one or more symptoms of a depressive disorder (e.g., MDD) in children, adolescents and/or young adults without increasing the risk of suicidal thinking and/or behavior.

In some embodiments, the present invention provides a method of treating one or more symptoms including senile dementia, Early Onset Alzheimer's Disease, Alzheimer's type dementia, cognition, memory loss, amnesia/amnestic syndrome, disturbances of consciousness, coma, lowering of attention, speech disorder, agnosia, aphasia, apraxia, Mild Cognitive Impairment (MCI), benign forgetfulness, mild neurocognitive disorder, major neurocognitive disorder, neurocognitive disorder due to disease (e.g., Huntington's Disease, Parkinson's disease, Prion Disease, Traumatic Brain Injury, HIV or AIDS), Binswanger's Disease (subcortical leukoencephalopathy), and Capgras Syndrome.

In some embodiments, the present invention provides a method of treating one or more symptoms of pain, e.g., neuropathic pain, sensitization accompanying neuropathic pain, or inflammatory pain. In some embodiments, the pain is neuropathic pain, including post herpetic (or post-shingles) neuralgia, reflex sympathetic dystrophy/causalgia or nerve trauma, phantom limb pain, carpal tunnel syndrome, and peripheral neuropathy (such as diabetic neuropathy or neuropathy arising from chronic alcohol use). In some embodiments, the pain is acute pain, nociceptive pain, arthritis pain, rheumatoid arthritis, osteoarthritis, joint pain, muscoskeletal pain, back pain, dorsalgia, bulging disc, hip pain, visceral pain, headache, tension headache, acute tension headache, chronic tension headache, chronic cluster headache, common migraine, classic migraine, cluster headache, mixed headache, post-traumatic headache, eye strain headache, Short-lasting Unilateral Neuralgiform (SUNCT) headache, SUNCT Syndrome, herpes zoster, acute herpes zoster, shingles, postherpetic neuralgia (shingles), causalgia, central pain, central pain syndrome, chronic back pain, neuralgia, neuropathic pain syndrome, neuropathy, diabetic neuropathy, diabetes-related neuropathy, diabetes-related nerve pain, fibrositis, peripheral neuropathy caused by chemotherapy, peripheral nerve disease, peripheral neuropathy, nerve pain, nerve trauma, sensitization accompanying neuropathic pain, complex regional pain syndrome, compression neuropathy, craniofacial pain, chronic joint pain, chronic knee pain, chronic pain syndrome, cancer pain, trigeminal neuralgia, tic doloreaux, reflex sympathetic causalgia, painful peripheral neuropathy, spinal nerve injury, arachnoiditis, spinal pain, Bernhardt-Roth Syndrome (meralgia parasthetica), carpal tunnel syndrome, cerebrospinal fluid syndrome, Charcot-Marie-tooth disease, hereditary motor and sensory neuropathy, peroneal muscular atrophy, cluster-tic syndrome, coccygeal pain syndromes, compartment syndrome, degenerative disc disease, failed back surgery syndrome, genito-pelvic pain/penetration disorder, gout, inflammatory pain, lumbar radiculopathy, neuroma (painful scar), pain associated with multiple sclerosis, pelvic floor disorders, phantom limb pain, *piriformis* syndrome, psychogenic pain, radicular pain syndrome, Raeder's syndrome, referred pain, reflex sympathetic dystrophy syndrome, sciatica, sciatica pain, scoliosis, slipped disc, somatic pain, spinal stenosis, stiff-person syndrome/stiff-man syndrome, stump pain, sympathetically maintained pain, tolosahunt syndrome, whiplash, or pain associated with Lyme disease.

In some embodiments, the present invention provides a method of treating one or more symptoms including obesity; migraine or migraine headache; and sexual dysfunction, in men or women, including without limitation sexual dysfunction caused by psychological and/or physiological factors, erectile dysfunction, premature ejaculation, vaginal dryness, lack of sexual excitement, inability to obtain orgasm, and psycho-sexual dysfunction, including without limitation, inhibited sexual desire, inhibited sexual excitement, inhibited female orgasm, inhibited male orgasm, functional dyspareunia, functional vaginismus, and atypical psychosexual dysfunction.

In some embodiments, the present invention provides a method of suppressing rapid eye movement (REM) during both sleep and daytime equivalent.

In some embodiments, the present invention provides a method of suppressing or eliminating pathological or excessive REM during the night or daytime equivalent.

In some embodiments, the present invention provides a method of treating one or more symptoms including cataplexy (sudden involuntary transient bouts of muscle weakness or paralysis while awake); nighttime sleep disturbance/sleep fragmentation associated with narcolepsy or other conditions; sleep paralysis associated with narcolepsy or other conditions; hypnagogic and hypnapompic hallucinations associated with narcolepsy or other conditions; and excessive daytime sleepiness associated with narcolepsy, sleep apnea or shift work disorder and other medical conditions such as cancer, chronic fatigue syndrome and fibromyalgia.

In some embodiments, the present invention provides a method of treating one or more symptoms of movement disorders, including akinesias, akinetic-rigid syndromes, dyskinesias and dystonias. Examples of akinesias and akinetic-rigid syndromes include Parkinson's disease, drug-induced Parkinsonism, postencephalitic Parkinsonism, secondary Parkinsonism, Parkinson plus syndromes, atypical Parkinsonism, idiopathic Parkinsonism, progressive supranuclear palsy, multiple system atrophy, corticobasal degeneration, Parkinsonism-ALS dementia complex and basal ganglia calcification, medication-induced Parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de la Tourette's syndrome, epilepsy, muscular spasms and disorders associated with muscular spasticity or weakness including tremors. Examples of dyskinesias include drug (e.g. L-DOPA) induced dyskinesia tremor (such as rest tremor, postural tremor, intention tremor), chorea (such as Sydenham's chorea, Huntington's disease, benign hereditary chorea, neuroacanthocytosis, symptomatic chorea, drug-induced chorea and hemiballism), myoclonus (including generalised myoclonus and focal myoclonus), tics (including simple tics, complex tics and symptomatic tics). Examples of dystonias include generalised dystonia, iodiopathic dystonia, drug-induced dystonia, symptomatic dystonia, paroxymal dystonia, focal dystonia, blepharospasm, oromandibular dystonia, spasmodic dysphonia, spasmodic torticollis, axial dystonia, dystonic writer's cramp and hemiplegic dystonia. Other examples of movement disorders include stereotypic movement disorder, persistent (chronic) motor disorder, medication-Induced movement disorder, psychogenic movement disorders, sub stance/medication-Induced movement disorder, extrapyramidal movement disorders, hyperkinetic movement disorders, hypokinetic movement disorders, alternating hemiplegia, Angelman syndrome, Hallervorden-Spatz Disease, ataxia, dentate cerebellar ataxia, ataxia telangiectasia (Louis-Bar syndrome), Friedreich's Ataxia, hereditary spinal ataxia, hereditary spinal sclerosis, Machado-Joseph Disease, spinocerebellar ataxia, progressive myoclonic ataxia, athetosis, ballismus, blepharospasm (eye twitching), cerebral palsy, tardive dystonia, tardive dyskinesia, idiopathic torsion dystonia, torsion dystonia, focal dystonia, idiopathic familial dystonia, Idiopathic nonfamilial dystonia, cervical dystonia (spasmodic torticollis), primary dystonia, orofacial dystonia, developmental coordination disorder, bulbospinal muscular atrophy (Kennedy's Disease), Shy-Drager Syndrome, and Stiff-Person (Stiff-Man) Syndrome.

In some embodiments, the present invention provides a method of treating one or more symptoms of epilepsy and/or seizures, including abdominal epilepsy, absence seizure, acquired epilepsy, acquired epileptiform aphasia, Aicardi syndrome, Alpers' disease, Alpers-Huttenlocher syndrome, Angelman syndrome, benign focal epilepsy, benign focal epilepsy of childhood, benign intracranial hypertension, benign rolandic epilepsy (BRE), CDKL5 disorder, childhood absence epilepsy, dentate cerebellar ataxia, Doose syndrome, Dravet syndrome, dyscognitive focal seizure, epilepsy with grand mal seizures, epilepsy with myoclonic-absences, epileptic hemiplegia, febrile seizures, focal seizure, frontal lobe epilepsy, generalized tonic-clonic seizures, genetic epilepsy, Glut1 deficiency syndrome, hypothalmic hamartoma, idiopathic epilepsy, idiopathic generalized epilepsy, idopathic localization-related epilepsies, idopathic partial epilepsy, idopathic seizure, juvenile absence epilepsy, juvenile myoclonic epilepsy, Lafora disease, Lafora progressive myoclonus epilepsy, Landau-Kleffner syndrome, Lassueur-Graham-Little syndrome, Lennox syndrome, Lennox-Gastaut syndrome, medically refractory epilepsy, mesial-temporal lobe sclerosis, myoclonic seizure, neonatal epilepsy, occipital lobe epilepsy, Ohtahara syndrome, Panayiotopoulos syndrome, parietal lobe epilepsy, PCDH19 epilepsy, photosensitive epilepsy, progressive myoclonic epilepsies, Rasmussen's encephalitis, Rasmussen's syndrome, refractory epilepsy, seizure disorder, status epilepticus, Sturge-Weber syndrome, symptomatic generalized epilepsy, symptomatic parital epilepsy, TBCK-related ID syndrome, temporal lobe epilepsy, temporal lobe seizures, tonic-clonic seizure, West syndrome, tremor, cerebellar tremor, cerebellar outflow tremor, intention tremor, essential tremor, benign essential tremor, Parkinsonian tremor, and medication-induced postural tremor.

In some embodiments, the present invention provides a method of treating a neurological and/or psychiatric disease or disorder described herein, comprising administering a compound of the invention in conjunction with one or more pharmaceutical agents. Suitable pharmaceutical agents that may be used in combination with the compounds of the present invention include anti-Parkinson's drugs, anti-Alzheimer's drugs, anti-depressants, anti-psychotics, anti-ischemics, CNS depressants, anti-cholinergics, nootropics, epilepsy medication, attention (e.g., ADD/ADHD) medications, sleep-promoting medications, wakefulness-promoting medications, and pain medications. In some embodiments, suitable pharmaceutical agents are anxiolytics.

Suitable anti-Parkinson's drugs include dopamine replacement therapy (e.g. L-DOPA, carbidopa, COMT inhibitors such as entacapone or tolcapone), dopamine agonists (e.g. D1 agonists, D2 agonists, mixed D1/D2 agonists, bromocriptine, pergolide, cabergoline, ropinirole, pramipexole, piribedil, or apomorphine in combination with domperidone), histamine H2 antagonists, monoamine oxidase inhibitors (such as selegiline, rasagiline, safinamideand tranylcypromine), certain atypical antipsychotics such as pimavanserin (a non-dopaminergic atypical antipsychotic and inverse agonist of the serotonin 5-HT$_{2A}$ receptor), and amantadine.

In some embodiments, compounds of the invention can be used in combination with levodopa (with or without a selective extracerebral decarboxylase inhibitor such as carbidopa or benserazide), anticholinergics such as biperiden (optionally as its hydrochloride or lactate salt) and trihexyphenidyl(benzhexyl)hydrochloride, COMT inhibitors such as entacapone or tolcapone, MAO A/B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate. Lisuride and pramipexole are commonly used in a non-salt form.

Suitable anti-Alzheimer's drugs include beta-secretase inhibitors, gamma-secretase inhibitors, cholinesterase inhibitors such as donepezil, galantamine or rivastigmine, HMG-CoA reductase inhibitors, NSAID's including ibuprofen, vitamin E, and anti-amyloid antibodies. In some embodiments, an anti-Alzheimer's drug is memantine.

Suitable anti-depressants and anti-anxiety agents include norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists.

Specific suitable anti-depressant and anti-anxiety agents include amitriptyline, clomipramine, doxepin, imipramine and trimipramine; amoxapine, desipramine, citalopram, escitalopram, maprotiline, nortriptyline and protriptyline; fluoxetine, fluvoxamine, paroxetine and sertraline; isocarboxazid, phenelzine, tranylcypromine and selegiline; moclobemide: venlafaxine; desvenlafaxine, duloxetine; aprepitant; bupropion, vilazodone, mirtazapine, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, reboxetine, vortioxetine, clorazepate, and pharmaceutically acceptable salts thereof. In some embodiments, suitable anti-depressant and anti-anxiety agents are tianeptine, or pharmaceutically acceptable salts thereof.

Suitable anti-psychotic and mood stabilizer agents include D2 antagonists, 5HT2A antagonists, atypical antipsychotics, lithium, and anticonvulsants.

Specific suitable anti-psychotic and mood stabilizer agents include chlorpromazine, fluphenazine, haloperidol, amisulpride, perphenazine, thioridazine, trifluoperazine, aripiprazole, asenapine, clozapine, olanzapine, paliperidone, quetiapine, risperidone, ziprasidone, lurasidone, flupentixol, levomepromazine, pericyazine, perphenazine, pimozide, prochlorperazine, zuclopenthixol, olanzapine and fluoxetine, lithium, carbamazepine, lamotrigine, valproic acid, iloperidone, thiothixene and pharmaceutically acceptable salts thereof.

Suitable epilepsy medications include levetiracetam, oxcarbazepine, clobazam, retigabine, zonisamide, felbamate, esclicarbazepine acetate, lacosamide, carbamazepine, tiagabine, methsuximide, progabide, valproic acid, lamotrigine, brivaracetam, rufinamide, topiramate and perampanel.

Suitable attention medications include methyl phenidate, atomoxetine, guanfacine, D-amphetamine, lisdexamphetamine, methylamphetamine, and clonidine.

Suitable sleep-promoting medications include ramelteon, triazolam, zopiclone, eszopiclone, zolpidem, temazepam, and trazodone.

Suitable wakefulness-promoting medications include Modafinil, D-Amphetamine, caffeine, and armodafinil.

Suitable pain medications include dextromethorphan, tapentadol, buprenorphine, codeine, fentanyl, hydrocodone, hydromorphone, morphine, naloxegol, oxycodone, tramadol, gabapentil, difluprednate, pregabalin, acetyl salicyclic acid, bromfenac, diclofenac, diflunisal, indomethacin, ketorolac, meoxican, and naproxen.

In some embodiments, compounds of the invention may be used in combination with other therapies. Suitable therapies include psychotherapy, cognitive behavioral therapy, electroconvulsive therapy, transcranial magnetic stimulation, vagus nerve stimulation, and deep-brain stimulation.

The exact amount required will vary from subject to subject, depending on the species, age, and general condition of the subject, the severity of the condition, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the present invention will be decided by the attending physician within the scope of sound medical judgment.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease or disorder being treated. In some embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

In some embodiments, a combination of two or more therapeutic agents may be administered together with the compounds of the invention. In some embodiments, a combination of three or more therapeutic agents may be administered with the compounds of the invention.

Other examples of agents the compounds of this invention may also be combined with include: vitamins and nutritional supplements, antiemetics (e.g. 5-HT3 receptor antagonists, dopamine antagonists, NK1 receptor antagonists, histamine receptor antagonists, cannabinoids, benzodiazepines, or anticholinergics), agents for treating Multiple Sclerosis (MS) such as beta interferon (e.g., Avonex® and Rebif®, dalfampridine, alemtuzumab), Copaxone®, and mitoxantrone; treatments for Huntington's disease such as tetrabenazine; treatments for asthma such as albuterol and Singulair®; anti-inflammatory agents such as corticosteroids, TNF blockers, IL-1 RA, azathioprine, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, agents for treating cardiovascular disease such as beta-blockers, ACE inhibitors, diuretics, nitrates, calcium channel blockers, and statins, fibrates, cholesterol absorption inhibitors, bile acid sequestrants, and niacin; agents for treating liver disease such as corticosteroids, cholestyramine, interferons, and anti-viral agents; agents for treating blood disorders such as corticosteroids, anti-leukemic agents, and growth factors; agents for treating immunodeficiency disorders such as gamma globulin; and anti-diabetic agents such as biguanides (metformin, phenformin, buformin), thiazolidinediones (rosiglitazone, pioglitazone, troglitazone), sulfonylureas (tolbutamide, acetohexamide, tolazamide, chlorpropamide, glipizide, glyburide, glimepiride, gliclazide), meglitinides (repaglinide, nateglinide), alpha-glucosidase inhibitors (miglitol, acarbose), incretin mimetics (exenatide, liraglutide, taspoglutide), gastric inhibitory peptide analogs, DPP-4 inhibitors (vildagliptin, sitagliptin, saxagliptin, linagliptin, alogliptin), amylin analogs (pramlintide), and insulin and insulin analogs.

In some embodiments, a compound of the present invention, or a pharmaceutically acceptable salt thereof, is administered in combination with an antisense agent, a monoclonal or polyclonal antibody, or a siRNA therapeutic.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another, normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of formula I, or a pharmaceutically acceptable salt thereof, an additional therapeutic agent, and a pharmaceutically acceptable carrier, adjuvant, or vehicle.

The amount of both, an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In some embodiments, the present invention provides a medicament comprising at least one compound of formula I, or a pharmaceutically acceptable salt thereof, and a pharmaceutically acceptable carrier, adjuvant, or vehicle.

In some embodiments, the present invention provides the use of a compound of formula I, or a pharmaceutically acceptable salt thereof, in the manufacture of a medicament for the treatment of a neurological and/or psychiatric disease or disorder.

EXAMPLES

As depicted in the Examples below, in some embodiments, compounds are prepared according to the following procedures. It will be appreciated that, although the general methods depict the synthesis of certain compounds of the present invention, the following methods, and other methods known to persons skilled in the art, can be applied to all compounds and subclasses and species of each of these, as described herein.

Example 1. 6-Chloroisochroman-4-amine hydrochloride

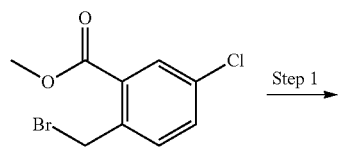

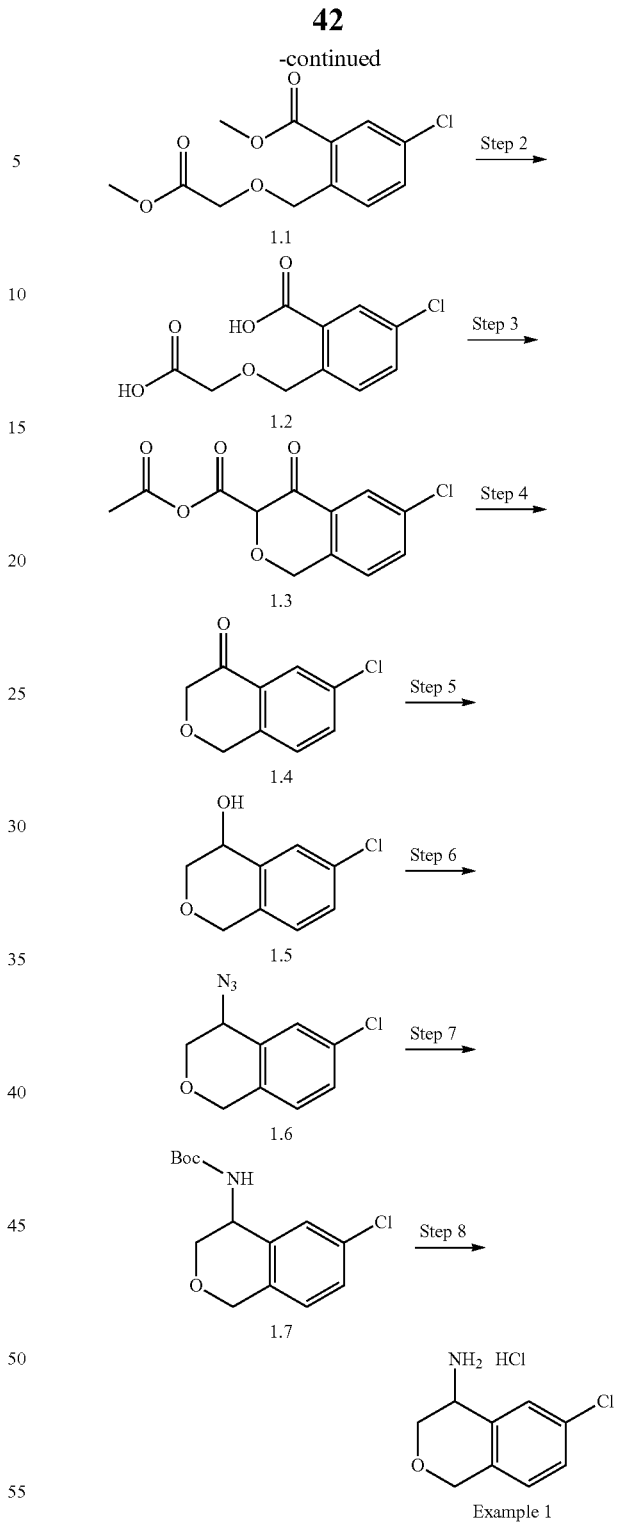

Step 1.

Methyl 2-hydroxyacetate (1.72 g, 19.2 mmol) was dissolved in DMF (50 mL) and treated with sodium hydride (460 mg, 19.2 mmol, 95%). The reaction mixture was stirred at room temperature for 30 min, and then cooled in an ice bath. A solution of 2.53 g (9.60 mmol) of methyl 2-(bromomethyl)-5-chlorobenzoate (Thorarensen, A., et al WO2004018414) in DMF (5 mL) was added, and the reaction mixture was stirred at 0° C. for 10 min. Excess hydride was carefully quenched by the dropwise addition of saturated aqueous NH$_4$Cl (20 mL). The mixture was diluted with water (50 mL) and extracted with EtOAc (4×60 mL). The combined organics were washed with brine (2×25 mL), anhydrous Na$_2$SO$_4$, filtered, and concentrated under reduced pressure. Purification by flash column chromatography (SiO$_2$, 5% EtOAc/hexanes) gave methyl 5-chloro-2-((2-methoxy-2-oxoethoxy)methyl)benzoate 1.1 (1.82 g, 70%) as a white solid. MS (ESI): m/z 273 [M+H].

Step 2.

A solution of compound 1.1 (1.83 g, 6.71 mmol) in EtOH (10 mL) was treated with a solution of NaOH (1.2 g, 30.1 mmol) in water (7 mL), and stirred at room temperature for 1 h. The mixture was acidified to pH=3-4 by the addition of 1M aqueous HCl. The aqueous phase was extracted with DCM (4×50 mL). The combined organics were washed with brine (2×20 mL), dried over anhydrous Na$_2$SO$_4$, filtered, and concentrated under reduced pressure to provide 2-((carboxymethoxy)methyl)-5-chlorobenzoic acid 1.2 (1.59 g, 97%) as a white solid. LC-MS (ESI): m/z 243 [M−H].

Step 3.

Potassium acetate (2.56 g, 26.1 mmol) was added to a solution of compound 1.2 (1.6 g, 6.54 mmol) in Ac$_2$O (30 mL). The reaction mixture was heated to 140° C. and stirred for 2 h. Ice water (100 mL) and Et$_2$O (100 mL) was added to the reaction vessel and the resulting biphasic mixture was transferred to a separatory funnel. The layers were separated and the aqueous phase was extracted with Et$_2$O (5×50 mL). The combined organics were washed with brine (2×20 mL), dried over anhydrous Na$_2$SO$_4$, filtered, and concentrated under reduced pressure to provide acetic 6-chloro-4-oxoisochroman-3-carboxylic anhydride 1.3 (1.02 g, 15%) as brown oil, which was used without further purification.

Step 4.

A solution of compound 1.3 (1.02 g, 3.83 mmol) in EtOH (30 mL) was treated with a solution of NaOH (306 mg, 7.66 mmol) in water (10 mL). The reaction mixture was stirred at ambient temperature for 15 min and then extracted with EtOAc (4×10 mL). The combined organics were washed with brine, dried over anhydrous Na$_2$SO$_4$, filtered, and concentrated under reduced pressure. Purification by flash column chromatography (SiO$_2$, 5% EtOAc/hexanes) afforded 6-chloroisochroman-4-one 1.4 (0.505 g, 72%) as a white solid. $^1$H NMR (300 MHz, DMSO-d$_6$) δ 8.03 (d, J=1.1 Hz, 1H), 7.55 (dd, J=8.1, 2.1 Hz, 1H), 7.21 (d, J=8.1 Hz, 1H), 4.89 (s, 2H), 4.38 (s, 2H).

Step 5.

To a solution of compound 1.4 (506 mg, 2.77 mmol) in EtOH (9 mL) was added NaBH$_4$ (104 mg, 2.77 mmol). The reaction was stirred at ambient temperature for 1 h. EtOAc (20 mL) and saturated aqueous NH$_4$Cl (15 mL) was added to the reaction vessel and the resulting biphasic mixture was transferred to a separatory funnel. The layers were separated and the aqueous phase was extracted with EtOAc (3×20 mL). The combined organics were washed with brine, dried over anhydrous Na$_2$SO$_4$, filtered, and concentrated under reduced pressure to provide crude 6-chloroisochroman-4-ol 1.5 (478 mg, 94%) as colorless oil, which was used without further purification. $^1$H NMR (300 MHz, CDCl$_3$) δ 7.47 (d, J=2.1 Hz, 1H), 7.25 (d, J=7.2 Hz, 1H), 6.98 (d, J=8.4 Hz, 1H), 4.79 (d, J=15.3 Hz, 1H), 4.66 (d, J=15.3 Hz, 1H), 4.55 (s, 1H), 4.08 (dd, J=12.0, 3.3 Hz, 1H), 3.88 (dd, J=12.0, 2.7 Hz, 1H), 3.73 (dd, J=14.1, 6.9 Hz, 1H), 2.36 (br s, 1H).

Step 6.

A solution of compound 1.5 (480 mg, 2.59 mmol) in toluene (7 mL) was treated with diphenyl phosphoryl azide (853 mg, 3.10 mmol), and cooled in an ice bath. A solution of DBU (777 mg, 3.10 mmol) in toluene (1.5 mL) was added, and the reaction was stirred at ambient temperature for 16 h. The reaction mixture was directly concentrated under reduced pressure and purified by flash column chromatography (SiO$_2$, gradient elution from 5% EtOAc/hexanes to 10% EtOAc/hexanes) to afford 4-azido-6-chloroisochroman 1.6 (329 mg, 61%) as a colorless oil. $^1$H NMR (300 MHz, CDCl$_3$) δ 7.39 (d, J=2.1 Hz, 1H), 7.32 (dd, J=8.1, 2.1 Hz, 1H), 7.04 (d, J=8.1 Hz, 1H), 4.86 (d, J=15.3 Hz, 1H), 4.70 (d, J=15.3 Hz, 1H), 4.24-2.19 (m, 2H), 3.97 (dd, J=11.4, 2.4 Hz, 1H).

Step 7.

A solution of compound 1.6 (330 mg, 1.57 mmol) in THF (15 mL) was treated with LiAlH$_4$ (59.5 mg, 1.57 mmol) at room temperature. The reaction mixture was stirred at room temperature for 30 min. A solution of Na$_2$CO$_3$ (164 mg, 1.55 mmol) in water (10 mL), EtOAc (15 mL) and di-tert-butyl dicarbonate (0.676 g, 3.1 mmol) was added and the resulting mixture was stirred at ambient temperature for 4 h. The mixture was diluted with water (10 mL) was added to the reaction vessel and aqueous phase was extracted with EtOAc (3×25 mL). The combined organics were washed with brine, dried over anhydrous Na$_2$SO$_4$, filtered, and concentrated under reduced pressure. Purification by flash column chromatography (SiO$_2$, gradient elution from 100% hexanes to 5% EtOAc/hexanes) gave tert-butyl (6-chloroisochroman-4-yl)carbamate 1.7 (349 mg, 78%) as a white solid. LC-MS (ESI): m/z 284 [M+H].

Step 8.

A solution of compound 1.7 (349 mg, 1.23 mmol) in Et$_2$O (2 mL) was treated with a saturated solution of HCl in Et$_2$O (5 mL). The reaction mixture was stirred at room temperature for 16 h and then concentrated under reduced pressure. The resulting solid residue was triturated with Et$_2$O (2×5 mL) to provide the compound of Example 1 (165 mg, 61%) as a white solid. LC-MS (ESI): m/z 184 [M+H]. $^1$H NMR (300 MHz, DMSO-d$_6$) δ 8.52 (brs, 3H), 7.64 (d, J=1.8 Hz, 1H), 7.46 (dd, J=8.4, 2.1 Hz, 1H), 7.24 (d, J=8.4 Hz, 1H), 4.83 (d, J=15.9 Hz, 1H), 4.68 (d, J=15.9 Hz, 1H), 4.38 (s, 1H), 4.14 (dd, J=12.3, 1.8 Hz, 1H), 3.89 (dd, J=12.6, 3.0 Hz, 1H).

TABLE 1

Compounds prepared as described in Example 1 using the appropriately substituted starting materials.

| Example | Structure | Characterization Data |
|---|---|---|
| 2 | 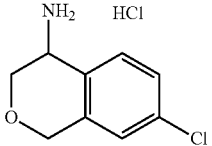 [SMILES: NC1COCc2cc(Cl)ccc21 ; Cl] | MS (ESI): m/z 184 [M + H]. $^1$H NMR (300 M Hz, DMSO-d$_6$) δ 8.58 (br s, 3H), 7.58 (d, J = 8.4 Hz, 1H), 7.42 (dd, J = 8.4, 2.1 Hz, 1H), 7.32 (d, J = 1.8 Hz, 1H), 4.83 (d, J = 15.6 Hz, 1H), 4.69 (d, J = 15.9 Hz, 1H), 4.36 (s, 1H), 4.18 (dd, J = 12.6, 1.8 Hz, 1H), 3.88 (dd, J = 12.6, 2.4 Hz, 1H). |

TABLE 1-continued

Compounds prepared as described in Example 1 using the appropriately substituted starting materials.

| Example | Structure | Characterization Data |
|---|---|---|
| 3 | 4-amino-7-fluoroisochroman HCl | MS (ESI): m/z 168 [M + H]. $^1$H NMR (300 M Hz, DMSO-$d_6$) δ 8.61 (br s, 3H), 7.65-7.61 (m, 1H), 7.23-7.12 (m, 1H), 7.01 (dd, J = 9.6, 2.7 Hz, 1H), 4.83 (d, J = 15.9 Hz, 1H), 4.69 (d, J = 15.6 Hz, 1H), 4.35 (s, 1H), 4.20 (dd, J = 12.6, 1.8 Hz, 1H), 3.88 (dd, J = 12.6, 2.7 Hz, 1H). |
| 4 | 4-amino-7-methylisochroman HCl | MS (ESI): m/z 164 [M + H]. $^1$H NMR (300 M Hz, DMSO-$d_6$) δ 8.50 (br s, 1H), 7.42 (d, J = 7.8 Hz, 1H), 7.14 (d, J = 7.8 Hz, 1H), 6.98 (s, 1H), 4.78 (d, J = 15.3 Hz, 1H), 4.67 (d, J = 15.3 Hz, 1H), 4.28 (s, 1H), 4.17 (dd, J = 12.3, 1.8 Hz, 1H), 3.87 (dd, J = 12.3, 2.7 Hz, 1H), 2.30 (s, 3H). |
| 5 | 4-amino-8-chloroisochroman HCl | MS (ESI): m/z 184 [M + H]. $^1$H NMR (300 M Hz, DMSO-$d_6$) δ 8.76 (s, 3H), 7.60 (d, J = 7.5 Hz, 1H), 7.51 (d, J = 7.2 Hz, 1H), 7.40 (t, J = 7.8 Hz, 1H), 4.82 (d, J = 15.9 Hz, 1H), 4.63 (d, J = 15.9 Hz, 1H), 4.39 (s, 1H), 4.24 (d, J = 12.3 Hz, 1H), 3.89 (dd, J = 12.6, 2.4 Hz, 1H). |
| 6 | 4-amino-6,7-difluoroisochroman HCl | MS (ESI): m/z 167 [M + H]. $^1$H NMR (300 M Hz, DMSO-$d_6$) δ 8.57 (br s, 2H), 7.43 (d, J = 9.6 Hz, 1H), 7.24 (d, J = 12.0 Hz, 2H), 4.82 (d, J = 15.3 Hz, 1H), 4.68 (d, J = 15.3 Hz, 1H), 4.37 (s, 1H), 4.14 (d, J = 12.6 Hz, 1H) 3.90 (dd, J = 12.6, 3.0 Hz, 1H). |

Example 7: 6-Phenylisochroman-4-amine hydrochloride

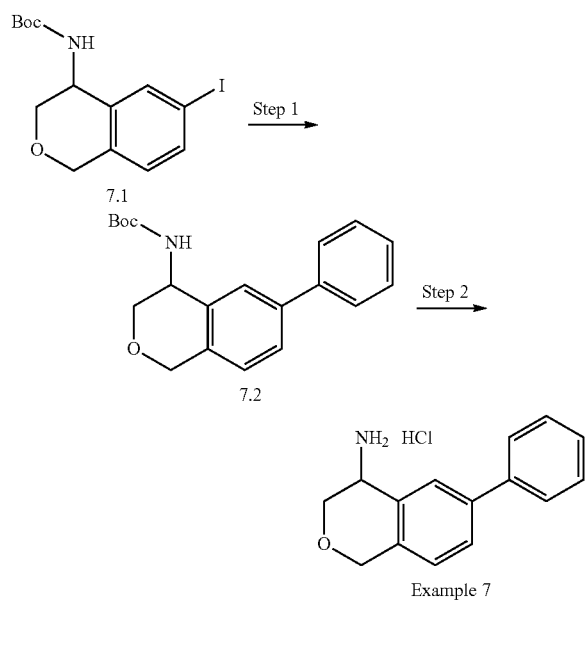

Step 1.

A solution of 170 mg (0.45 mmol) of tert-butyl (6-iodoisochroman-4-yl)carbamate 7.1 (prepared from methyl 2-(bromomethyl)-5-iodobenzoate (Hayakawa, I., et al, WO2011068171) as described in Example 1) in 1,4-dioxane (4 mL) was treated with phenyl boronic acid (110 mg, 0.90 mmol) and Pd(PPh$_3$)$_4$(52.3 mg, 0.045 mmol) and stirred at room temperature for 15 min. Aqueous 3M K$_2$CO$_3$ (0.76 mL, 2.3 mmol) was added, and the reaction mixture was heated to 100° C. with stirring for 5 h. After cooling to room temperature, the mixture was diluted with water (5 mL) and extracted with EtOAc (3×15 mL). The combined organics were dried over anhydrous Na$_2$SO$_4$, filtered, and concentrated under reduced pressure. Purification by flash column chromatography (SiO$_2$, gradient elution from 1% EtOAc/hexanes to 5% EtOAc/hexanes) gave tert-butyl (6-phenylisochroman-4-yl) carbamate 7.2 (110 mg, 75%) as a white solid. LC-MS (ESI): m/z 326 [M+H].

Step 2.

The compound of Example 7 was prepared as previously described in Example 1. MS (ESI): m/z 226 [M+H]. $^1$HNMR (300 MHz, DMSO) δ 8.50 (s, 3H), 7.87 (s, 1H), 7.11 (d, J=7.5 Hz, 3H), 7.53-7.37 (m, 3H), 7.28 (d, J=8.1 Hz, 1H), 4.88 (d, J=15.9 Hz, 1H), 4.75 (d, J=15.3 Hz, 1H), 4.42 (s, 1H), 4.17 (d, J=12.6 Hz, 1H), 3.95 (dd, J=12.3, 2.4 Hz, 1H).

Example 8: 6-Isopropylisochroman-4-amine hydrochloride

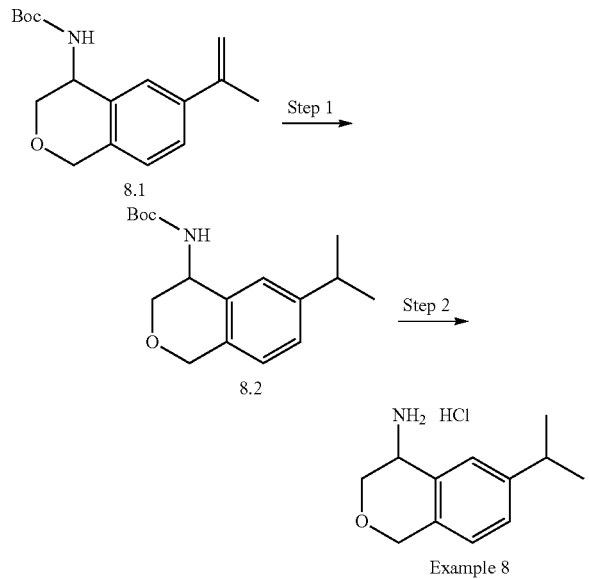

Step 1.

10% Pd/C (25 mg) was added to 250 mg (0.86 mmol) of tert-butyl (6-(prop-1-en-2-yl)isochroman-4-yl)carbamate 8.1 (prepared as described in Example 7 using isopropenylboronic acid pinacol ester) in CH$_3$OH (25 mL). The reaction mixture was stirred at room temperature under a H$_2$ atmosphere for 16 h. After filtering through a Celite pad, the filtrate was concentrated under reduced pressure. Purification by flash column chromatography (SiO$_2$, 5% EtOAc/hexanes) afforded tert-butyl (6-isopropylisochroman-4-yl)carbamate 8.2 (180 mg, 72%) as a brown oil. $^1$H NMR (300 MHz, CDCl$_3$) δ 7.29 (s, 1H), 7.15 (dd, J=8.1, 1.5 Hz, 1H), 6.95 (d, J=8.1 Hz, 1H), 5.10 (d, J=9.0 Hz, 1H), 4.81-4.68 (m, 3H), 4.07 (dd, J=9.0, 1.8 Hz, 1H), 3.87 (dd, J=12.0, 3.0 Hz, 1H), 2.95-2.86 (m, 1H), 1.60 (s, 9H), 0.97 (d, J=7.2 Hz, 6H).

Step 2.

The compound of Example 8 was prepared as described in Example 1. MS (ESI): m/z 192 [M+H]. $^1$HNMR (300 MHz, DMSO-d$_6$) δ 8.38 (br s, 3H), 7.42 (s, 1H), 7.27 (d, J=8.1 Hz, 1H), 7.09 (d, J=8.1 Hz, 1H), 4.79 (d, J=15.0 Hz, 1H), 4.67 (d, J=15.6 Hz, 1H), 4.31 (s, 1H), 4.14 (d, J=12.3 Hz, 1H), 3.87 (d, J=12.6 Hz, 1H), 2.91-2.86 (m, 1H), 1.21 (d, J=6.9 Hz, 6H).

Example 9: 6-Trifluoromethylisochroman-4-amine hydrochloride

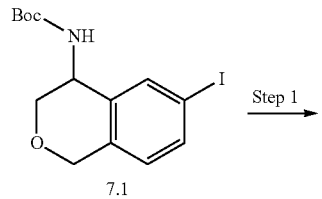

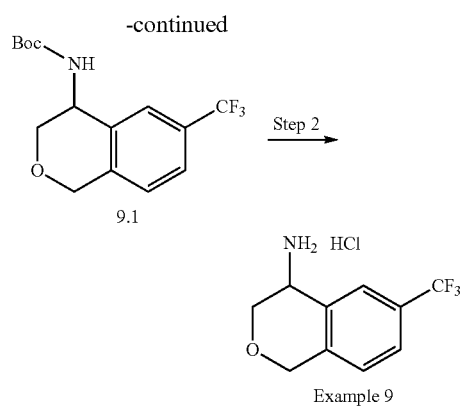

Step 1.

A solution of compound 7.1 (227 mg, 605 µmol) in anhydrous DMF (8 mL) under a N$_2$ atmosphere was treated with copper(I) iodide (230 mg, 1.21 mmol) and hexamethylphosphoramide (541 mg, 3.02 mmol), and stirred at ambient temperature for 10 min. Methyl 2,2-difluoro-2-(fluorosulfonyl)acetate (580 mg, 3.02 mmol) was added, and the reaction mixture was heated to 80° C. and stirred for 6 h. After cooling to room temperature, the mixture was diluted with saturated aqueous NaHCO$_3$ (20 mL) and partitioned with EtOAc (20 mL). The aqueous phase was extracted with EtOAc (2×30 mL). The combined organics were dried over anhydrous Na$_2$SO$_4$, filtered, and concentrated under reduced pressure. Purification by flash column chromatography (SiO$_2$, gradient elution from 5% EtOAc/hexanes to 10% EtOAc/hexanes) afforded tert-butyl (6-(trifluoromethyl) isochroman-4-yl)carbamate 9.1 (85.0 mg, 44%) as a white solid. MS (ESI): m/z 340 [M+Na].

Step 2.

The compound of Example 9 was prepared as previously described in Example 1. MS (ESI): m/z 218 [M+H]. $^1$HNMR (300 MHz, DMSO-d$_6$) δ 8.57 (s, 3H), 7.96 (s, 1H), 7.75 (d, J=7.5 Hz, 1H), 7.44 (d, J=8.1 Hz, 1H), 4.92 (d, J=16.2 Hz, 1H), 4.77 (d, J=15.6 Hz, 1H), 4.95 (s, 1H), 4.18 (d, J=12.3 Hz, 1H), 3.93 (dd, J=12.6, 2.4 Hz, 1H).

Example 10: 6-Methoxyisochroman-4-amine hydrochloride

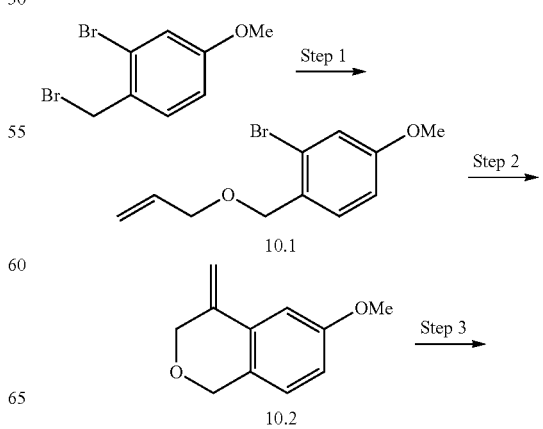

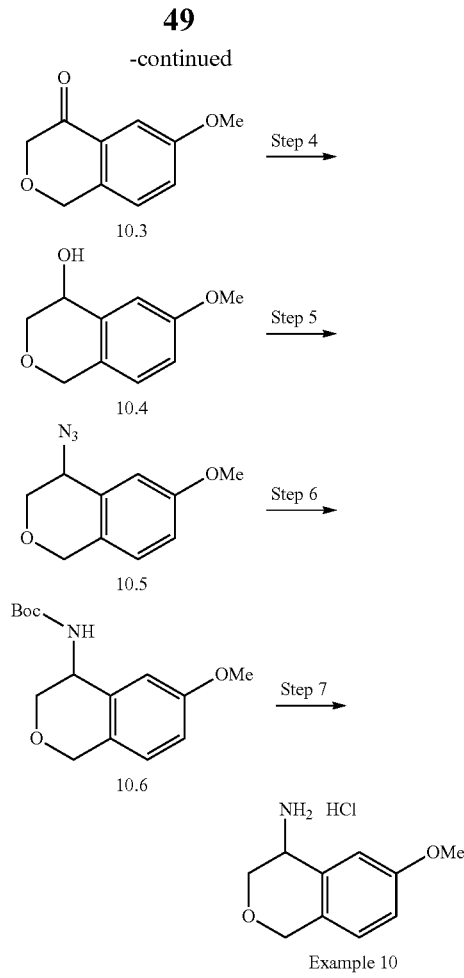

Example 10

Step 1.

To a solution of prop-2-en-1-ol (6.38 g, 110 mmol) in DMF (400 mL) was added 95% sodium hydride (4.38 g, 110 mmol) and 2-bromo-1-(bromomethyl)-4-methoxybenzene (15.5 g, 55.3 mmol) at 0° C. The resulting suspension was stirred at room temperature for 30 min. Excess hydride was quenched by the dropwise addition of water (200 mL), and the mixture was extracted with EtOAc (3×500 mL). The combined organics were washed with brine (2×300 mL), dried over anhydrous Na$_2$SO$_4$, filtered, and concentrated under reduced pressure. The resulting oil was purified by flash column chromatography (SiO$_2$, gradient elution from 100% hexanes to 5% EtOAc/hexanes) to provide 1-((allyloxy)methyl)-2-bromo-4-methoxy benzene 10.1 (12.9 g, 91%) as a yellow oil. $^1$HNMR (300 MHz, CDCl$_3$) δ 7.42 (d, J=8.7 Hz, 1H), 7.10 (d, J=3.3 Hz, 1H), 6.72 (dd, J=8.7, 3.3 Hz, 1H), 6.05-5.94 (m, 1H), 5.40 (ddd, J=17.1, 3.3, 1.5 Hz, 1H), 5.25 (dd, J=10.5, 1.5 Hz, 1H), 4.57 (s, 2H), 4.14 (m, 2H), 3.82 (s, 3H).

Step 2.

A solution of compound 10.1 (12.9 g, 50.1 mmol) in DMF (400 mL) was added Cs$_2$CO$_3$ (19.5 g, 60.1 mmol), triphenylphosphine (5.90 g, 22.5 mmol) and Pd(OAc)$_2$ (1.68 g, 7.51 mmol). The reaction mixture was heated to 90° C. for 1 h. Water (300 mL) and EtOAc (300 mL) were added to the reaction vessel and the resulting biphasic mixture was transferred to a separatory funnel. The layers were separated and the aqueous phase was extracted with EtOAc (2×500 mL). The organic phase was washed with brine (3×500 mL). The combined organics were dried over anhydrous Na$_2$SO$_4$, filtered, and concentrated under reduced pressure. The resulting oil was purified by flash column chromatography (SiO$_2$, gradient elution from 100% hexanes to 5% EtOAc/hexanes) to afford 6-methoxy-4-methylene isochroman 10.2 (5.70 g, 64%) as a yellow oil. $^1$H NMR (300 MHz, CDCl$_3$) δ 7.64 (d, J=8.7 Hz, 1H), 6.82 (dd, J=7.2, 2.7 Hz, 1H), 6.56 (d, J=2.7 Hz, 1H), 5.48 (s, 1H), 4.91 (s, 1H), 4.80 (s, 2H), 4.44 (s, 2H), 3.82 (s, 3H).

Step 3.

NaIO$_4$ (20.7 g, 96.8 mmol) and OsO$_4$ (81.8 mg, 322 μmol) were added to a solution of 12.2 (5.7 g, 32.3 mmol) in THF (200 mL) and water (100 mL), and the reaction mixture was stirred at room temperature for 4 h. The mixture was diluted with water (200 mL) and extracted with EtOAc (3×200 mL). The combined organics were dried over anhydrous Na$_2$SO$_4$, filtered, and concentrated under reduced pressure. The resulting oil was purified by flash column chromatography (SiO$_2$, gradient elution from 5% EtOAc/hexanes to 10% EtOAc/hexanes) to provide 6-methoxyisochroman-4-one 10.3 (3.10 g, 54%) as a white solid. $^1$HNMR (300 MHz, CDCl$_3$) δ 7.53 (s, 1H), 7.27 (d, J=6.6 Hz, 1H), 7.16 (d, J=1.5 Hz, 1H), 4.87 (s, 2H), 4.37 (s, 2H), 3.88 (s, 3H).

Step 4.

6-Methoxyisochroman-4-ol 10.4 (3.00 g, 96%) was prepared as described in Example 1. $^1$H NMR (300 MHz, CDCl$_3$) δ 7.03-6.98 (m, 2H), 6.88 (m, 1H), 4.79 (A of AB, J$_{AB}$=14.7 1H), 4.66 (B of AB, J$_{BA}$=14.7 1H), 4.54 (m, 1H), 4.12 (A of ABX, J$_{AB}$=12.0 Hz, J$_{AX}$=2.7 Hz, 1H), 3.88 (B of ABX, J$_{BA}$=12.0 Hz, J$_{BX}$=2.7 Hz, 1H), 3.80 (s, 3H), 2.23 (d, J=9.6 Hz, 1H).

Step 5.

4-Azido-6-methoxyisochroman 10.5 (2.70 g, 79%) was prepared as described in Example 1. $^1$H NMR (300 MHz, CDCl$_3$) δ 7.01 (d, J=8.1 Hz, 1H), 6.94-6.90 (m, 2H), 4.84 (A of AB, J$_{AB}$=14.7 Hz, 1H), 4.69 (B of AB, J$_{BA}$=14.7 Hz, 1H), 4.33-3.97 (m, 2H), 3.92 (dd, J=12.9, 2.4 Hz, 1H), 3.85 (s, 3H).

Step 6.

tert-Butyl (6-methoxyisochroman-4-yl)carbamate 10.6 (2.49 g, 68%) was prepared as described in Example 1. LC-MS (ESI): m/z 316 [M+H].

Step 7.

The compound of Example 10 (90.0 mg, 94%) was prepared as described in Example 1. MS (ESI): m/z 180 [M+H]. $^1$H NMR (300 MHz, DMSO-d$_6$) δ 8.50 (s, 3H), 7.16 (d, J=2.1 Hz, 1H), 7.10 (d, J=8.4 Hz, 1H), 6.97 (dd, J=8.4, 2.4 Hz, 1H), 4.76 (d, J=14.7 Hz, 1H), 4.64 (d, J=15.0 Hz, 1H), 4.31 (s, 1H), 4.12 (d, J=12.9 Hz, 1H), 3.88 (dd, J=12.3, 2.7 Hz, 1H), 3.77 (s, 3H).

TABLE 2

Compounds prepared as described in Example 10.

| Example | Structure | Characterization Data |
|---|---|---|
| 11 | (4-amino-7-tert-butyl-isochroman · HCl) | MS (ESI): m/z 206 [M + H]. $^1$H NMR (300 M Hz, DMSO-$d_6$) δ 8.53 (br s, 3H), 7.60 (s, 1H), 7.41 (dd, J = 8.1, 1.8 Hz, 1H), 7.09 (d, J = 8.1 Hz, 1H), 4.79 (d, J = 15.0 Hz, 1H), 4.66 (d, J = 15.3 Hz, 1H), 4.31 (s, 1H), 4.15 (d, J = 12.3 Hz, 1H), 3.89 (dd, J = 12.6, 2.7 Hz, 1H), 1.29 (s, 9H). |
| 12 | (isochroman-4-amine · HCl) | MS (ESI): m/z 150 [M + H]. $^1$H NMR (300 M Hz, CD$_3$OD) δ 7.48-7.34 (m, 3H), 7.20 (d, J = 7.5 Hz, 1H), 4.95 (d, J = 15.3 Hz, 1H), 4.81 (d, J = 15.6 Hz, 1H), 4.38 (s, 1H), 4.26 (dd, J = 12.9, 1.5 Hz, 1H), 3.99 (dd, J = 10.5, 2.1 Hz, 1H). |
| 13 | (benzo-fused isochroman-amine · HCl) | MS (ESI): m/z 200 [M + H]. $^1$H NMR (300 M Hz, DMSO-$d_6$) δ 8.46 (br s, 3H), 8.17 (d, J = 8.4 Hz, 1H), 7.99 (d, J = 8.4 Hz, 2H), 7.65-7.60 (m, 2H), 7.31 (d, J = 8.4 Hz, 1H), 5.05-4.88 (m, 3H), 4.38 (d, J = 12.3 Hz, 1H), 3.96 (dd, J = 12.6, 1.8 Hz, 1H). |
| 14 | (7-methoxy-isochroman-4-amine · HCl) | MS (ESI): m/z 180 [M + H]. $^1$H NMR (300 M Hz, CD$_3$OD) δ 7.36 (d, J = 8.4 Hz, 1H), 6.91 (dd, J = 8.4, 2.7 Hz, 1H), 6.75 (d, J = 2.1 Hz, 1H), 4.90 (d, J = 15.6 Hz, 1H), 4.75 (d, J = 15.6 Hz, 1H), 4.30 (s, 1 H), 4.22 (dd, J = 12.6, 1.2 Hz, 1H), 3.94 (dd, J = 12.6, 2.1 Hz, 1H), 3.82 (s, 3H). |
| 15 | (pyridine-fused isochroman-amine · HCl) | MS (ESI): m/z 201 [M + H]. $^1$H NMR (300 M Hz, CD$_3$OD) δ 9.43 (d, J = 8.7 Hz, 1H), 9.29 (d, J = 5.1 Hz, 1H), 8.32 (d, J = 9.0 Hz, 1H), 8.22 (dd, J = 8.7, 5.1 Hz, 1H), 7.99 (d, J = 9.0 Hz, 1H), 5.25 (d, J = 17.7 Hz, 2H), 5.11 (t, J = 17.7 Hz, 1H), 4.50 (d, J = 12.9 Hz, 1H), 4.12 (d, J = 14.7 Hz, 1H). |
| 16 | (methylthiazole-fused isochroman-amine · HCl) | MS (ESI): m/z 221 [M + H]. $^1$H NMR (300 M Hz, DMSO-$d_6$) δ 8.04 (d, J = 8.4 Hz, 1H), 7.22 (d, J = 8.4 Hz, 1H), 4.95 (d, J = 15.6 Hz, 1H), 4.79 (d, J = 16.2 Hz, 2H), 4.23 (d, J = 12.3 Hz, 1H), 4.00 (dd, J = 12.6, 2.4 Hz, 1H), 2.85 (s, 3H). |

Example 17: 8-Ethylisochroman-4-amine hydrochloride

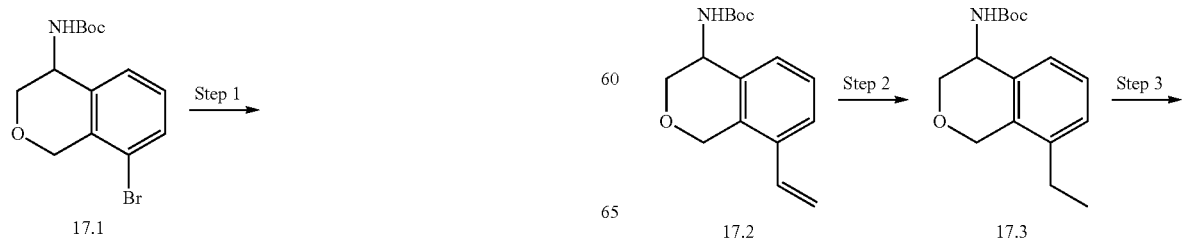

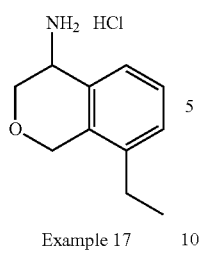

Example 17

Step 1.

tert-Butyl (8-vinylisochroman-4-yl)carbamate 17.2 was prepared from compound 17.1 (prepared from 1,3-dibromo-2-(bromomethyl)benzene as previously described in Example 10) as previously described in Example 7 using vinylboronic acid pinacol ester. $^1$H NMR (300 MHz, CDCl$_3$) δ 7.40-7.35 (m, 2H), 7.27-7.22 (m, 1H), 6.60 (dd, J=18.0, 12.0 Hz, 1H), 5.68 (d, J=18.0 Hz, 1H), 5.36-5.30 (m, 1H), 5.11-5.08 (m, 1H), 4.90 (d, J=15.0 Hz, 1H), 4.75-4.67 (m, 2H), 4.03 (dd, J=12.0, 3.0 Hz, 1H), 3.83 (dd, J=12.0, 3.0 Hz, 1H), 1.46 (s, 9H).

Step 2.

tert-Butyl (8-ethylisochroman-4-yl)carbamate 17.3 was prepared as previously described in Example 8. $^1$H NMR (300 MHz, CDCl$_3$) δ 7.29-7.19 (m, 2H), 7.13-7.10 (m, 1H), 5.10-5.07 (m, 1H), 4.86 (d, J=15.0 Hz, 1H), 4.77-4.71 (m, 2H), 4.04 (dd, J=12.0, 3.0 Hz, 1H), 3.86 (dd, J=12.0, 3.0 Hz, 1H), 2.51-2.44 (m, 2H), 1.46 (s, 9H), 1.20 (t, J 9.0 Hz, 3H).

Step 3.

The compound of Example 17 was prepared as previously described in Example 1. MS (ESI): m/z 178 [M+H]. $^1$H NMR (300 MHz, CD$_3$OD) δ 7.31-7.27 (m, 3H), 5.00 (d, J=18.0 Hz, 1H), 4.76 (d, J=15.0 Hz, 1H), 4.33 (s, 1H), 4.20 (dd, J=15.0, 3 Hz, 1H), 3.92 (dd, J=12.0, 3 Hz, 1H), 2.58-2.50 (m, 2H), 1.21 (t, J=9.0 Hz, 3H).

Example 18: 8-Isopropylisochroman-4-amine hydrochloride

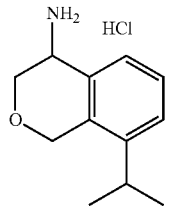

The compound of Example 18 was prepared as described in Example 17 using isopropenylboronic acid pinacol ester. MS (ESI): m/z 192 [M+H]. $^1$H NMR (300 MHz, CD$_3$OD) δ 7.41-7.31 (m, 2H), 7.26-7.23 (m, 1H), 5.08 (d, J=18 Hz, 1H), 4.81 (d, J=21 Hz, 1H), 4.32 (s, 1H), 4.19 (dd, J=12.6, 1.2 Hz, 1H), 3.92 (dd, J=12.9, 2.1 Hz, 1H), 2.86-2.48 (m, 1H), 1.26-1.20 (m, 6H).

Example 19: 2,4,7,8,9,10-Hexahydro-1H-benzo[f]isochromen-1-amine hydrochloride

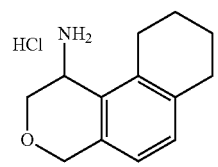

The compound of Example 19 was prepared as described in Example 10 using 5-bromo-6-(bromomethyl)-1,2,3,4-tetrahydronaphthalene 19.6. MS (ESI): m/z 204 [M+H]. $^1$H NMR (300 MHz, DMSO-d6) δ 8.38 (s, 3H), 7.09 (d, J=7.8 Hz, 1H), 6.89 (d, J=7.8 Hz, 1H), 4.82 (d, J=15.6 Hz, 1H), 4.67 (d, J=15.6 Hz, 1H), 4.36 (d, J=3.9 Hz, 1H), 4.23 (d, J=12.3 Hz, 1H), 3.75 (d, J=12.0 Hz, 1H), 2.92-2.84 (m, 1H), 2.73-2.65 (m, 3H), 1.83-1.60 (m, 4H).

Synthesis of 5-bromo-6-(bromomethyl)-1,2,3,4-tetrahydronaphthalene (19.6)

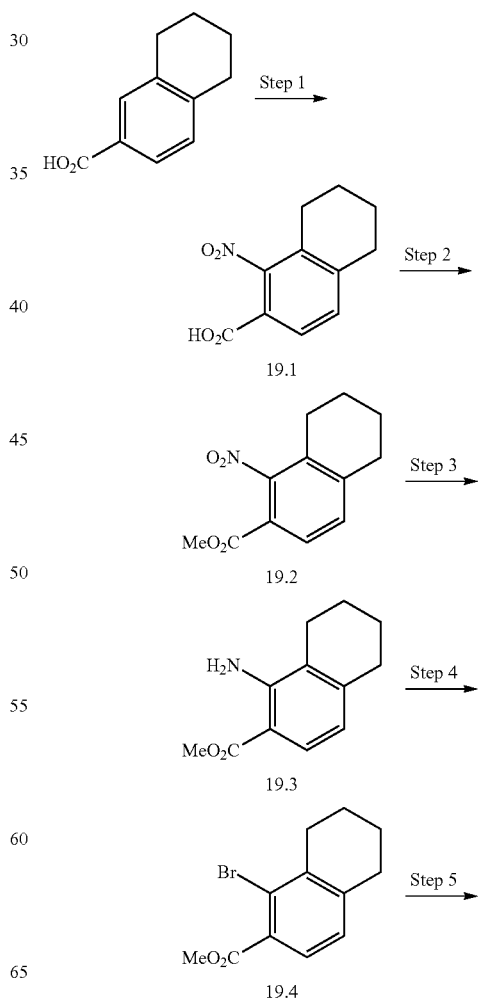

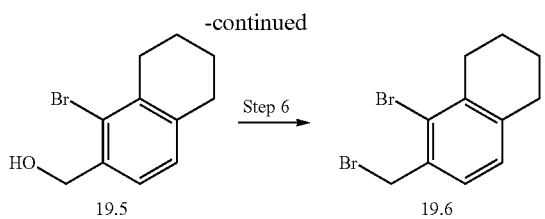

Step 1.

Nitric acid (10.7 mL, 240 mmol) was added to a solution of 5,6,7,8-tetrahydronaphthalene-2-carboxylic acid (10.0 g, 56.7 mmol) in AcOH (70 mL and concentrated $H_2SO_4$ (70 mL). The reaction was stirred at ambient temperature for 1 h and then poured onto ice. The resulting precipitate was collected by filtration to provide 1-nitro-5,6,7,8-tetrahydronaphthalene-2-carboxylic acid 19.1 (11.2 g, 89%) as a yellow solid. MS (ESI-): m/z 220 [M–H]. $^1$H NMR (300 MHz, DMSO-$d_6$) δ 7.75 (d, J=8.1 Hz, 1H), 7.41 (d, J=8.1 Hz, 1H), 2.88-2.81 (m, 2H), 2.69-2.63 (m, 2H), 1.74 (m, 4H).

Step 2.

A solution of compound 19.1 (5.2 g, 11.7 mmol) in $CH_3CN$ (100 mL) was treated with $K_2CO_3$ (4.85 g, 35.1 mmol) and iodomethane (4.98 g, 35.1 mmol). The reaction was stirred at room temperature for 3 h. The mixture was then partitioned between water (100 mL) and EtOAc (600 mL), and the organic phase was washed with brine (2×100 mL), dried over anhydrous Na2SO4, filtered, and concentrated under reduced pressure. The resulting oil was purified by flash column chromatography ($SiO_2$, 100% hexanes) to provide methyl 1-nitro-5,6,7,8-tetrahydronaphthalene-2-carboxylate 19.2 (2.24 g, 81%) as a white solid. $^1$H NMR (300 MHz, $CDCl_3$) δ 7.77 (d, J=8.1 Hz, 1H), 7.26 (d, J=8.4 Hz, 1H), 3.89 (s, 3H), 2.87-2.85 (m, 2H), 2.72-2.66 (m, 2H), 1.83-1.81 (m, 4H).

Step 3.

Compound 19.2 (3.2 g, 9.52 mmol) was dissolved in THF (100 mL). Pd/C (1 g, 10%) was added and the mixture was stirred at room temperature under a $H_2$ atmosphere for 8 h. The mixture was filtered through a Celite pad, and the filtrate was concentrated under reduced pressure. Purification by flash column chromatography ($SiO_2$, 100% hexanes) gave methyl 1-amino-5,6,7,8-tetrahydronaphthalene-2-carboxylate 19.3 (1.80 g, 92%) as a white solid. $^1$H NMR (300 MHz, $CDCl_3$) δ 7.65 (d, J=8.4 Hz, 1H), 6.42 (d, J=8.4 Hz, 1H), 5.88 (brs, 2H), 3.85 (s, 3H), 2.72 (t, J=6.3 Hz, 2H), 2.42 (t, J=6.0 Hz, 2H), 1.92-1.84 (m, 2H), 1.78-1.71 (m, 2H).

Step 4.

A solution of 19.3 (4.3 g, 20.9 mmol) in $CH_3CN$ (200 mL) was cooled in an ice bath, treated with copper(I) bromide (5.99 g, 41.8 mmol), and stirred for 30 min. tert-Butyl nitrite (4.31 g, 41.8 mmol) was added, and the ice bath was removed. The flask was heated to 40° C. and stirred overnight. The mixture was cooled in an ice bath and diluted with $NH_4OH$ and EtOAc, and the resulting biphasic mixture was separated. The aqueous phase was extracted with EtOAc (3×100 mL). The combined organics were dried over anhydrous $Na_2SO_4$, filtered, and concentrated under reduced pressure. Purification by flash column chromatography ($SiO_2$, 5% EtOAc/hexanes) gave methyl 1-bromo-5,6,7,8-tetrahydronaphthalene-2-carboxylate 19.4 (3.60 g, 63%) as a yellow solid. $^1$H NMR (300 MHz, $CDCl_3$) δ 7.40 (d, J=7.8 Hz, 1H), 7.06 (d, J=7.8 Hz, 1H), 3.91 (s, 3H), 2.80 (t, J=8.1 Hz, 4H), 1.86-1.72 (m, 4H).

Step 5.

Compound 19.4 (3.6 g, 13.3 mmol) was dissolved in anhydrous THF (100 mL) under a $N_2$ atmosphere and cooled to −78° C. in a dry ice/acetone bath. Diisobutylaluminum hydride (17.7 mL, 26.6 mmol, 1.5M in toluene) was added in a dropwise manner. Once addition was complete, the cold bath was removed and the reaction mixture was allowed to warm to room temperature for 1 h. Excess hydride was carefully quenched by the dropwise addition of aqueous 3M HCl (50 mL) and the biphasic mixture was transferred to a separatory funnel. The aqueous phase was washed with EtOAc (3×150 mL). The combined organics were dried over anhydrous $Na_2SO_4$, filtered, and concentrated under reduced pressure. Purification by flash column chromatography ($SiO_2$, 10% EtOAc/hexanes) gave (1-bromo-5,6,7,8-tetrahydronaphthalen-2-yl)methanol 19.5 (3.0 g, 94%) as a white solid. $^1$H NMR (300 MHz, $CDCl_3$) δ 7.20 (d, J=7.8 Hz, 1H), 7.06 (d, J=7.8 Hz, 1H), 4.73 (d, J=6.6 Hz, 2H), 2.80-2.75 (m, 4H), 2.02 (t, J=6.6 Hz, 1H), 1.88-1.71 (m, 4H).

Step 6.

Compound 19.5 (3.0 g, 12.4 mmol) was dissolved in 1,2-dichloroethane (120 mL) and cooled in an ice bath. Phosphorous tribromide (0.59 mL, 6.20 mmol) was added and the mixture was stirred at 0° C. for 30 min. The reaction poured into ice water and extracted with $CH_2Cl_2$ (3×50 mL). The combined organics were washed with saturated aqueous $Na_2CO_3$ (100 mL), dried over anhydrous $Na_2SO_4$, filtered, and concentrated under reduced pressure to afford 5-bromo-6-(bromomethyl)-1,2,3,4-tetrahydronaphthalene 19.6 (1.70 g, 45%). $^1$H NMR (300 MHz, $CDCl_3$) δ 7.10 (d, J=7.8 Hz, 1H), 7.02 (d, J=7.5 Hz, 1H), 4.65 (s, 2H), 2.80-2.71 (m, 4H), 1.87-1.70 (m, 4H).

Example 20: 6-Ethylisochroman-4-amine hydrochloride

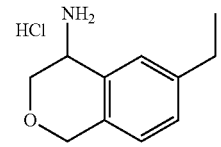

The compound of Example 20 was prepared as described in Example 19 using methyl 2-amino-4-ethylbenzoate. MS (ESI): m/z 178 [M+H]. $^1$H NMR (300 MHz, DMSO-d6) δ 8.44 (s, 3H), 7.35 (s, 1H), 7.23 (d, J=7.8 Hz, 1H), 7.09 (d, J=8.1 Hz, 1H), 4.84 (d, J=11.7 Hz, 1H), 4.70 (d, J=15.3 Hz, 1H), 4.32 (s, 1H), 4.16 (dd, J=12.6, 1.8 Hz, 1H), 3.90 (dd, J=12.6, 2.7 Hz, 1H), 2.64-2.57 (m, 2H), 1.24-1.09 (m, 3H).

Example 21: 5-Methylisochroman-4-amine hydrochloride

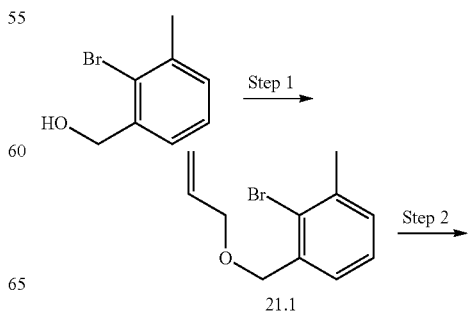

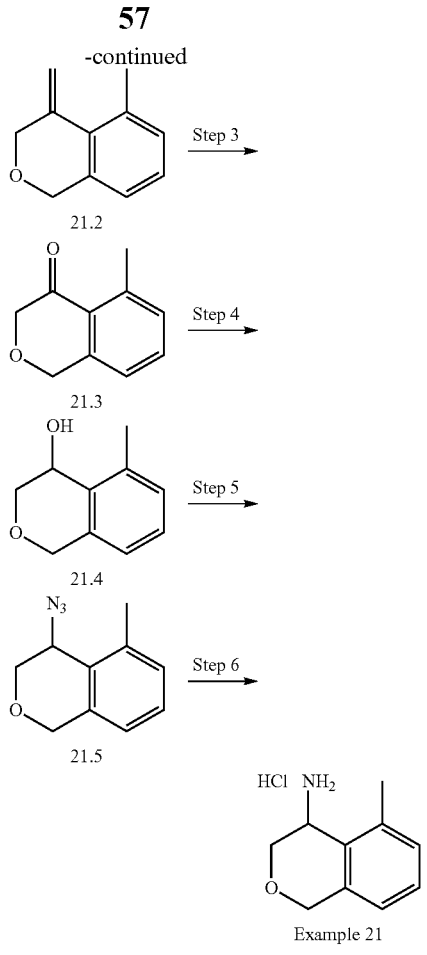

Example 21

Step 1.
Sodium hydride (771 mg, 19.3 mmol, 95%) was added in small portions to a solution of (2-bromo-3-methylphenyl)methanol (2.6 g, 12.9 mmol) in DMF (35 mL) cooled in an ice bath. The resulting slurry was stirred for 15 min, followed by addition of 3-bromoprop-1-ene (1.70 g, 14.1 mmol). The reaction was stirred at 0° C. for 30 min. Excess hydride was quenched by the dropwise addition of saturated aqueous NH₄Cl (75 mL), and the mixture was partitioned with Et₂O (3×40 mL). The combined organics were dried over anhydrous Na₂SO₄, filtered, and concentrated under reduced pressure. The resulting oil was purified by flash column chromatography (SiO₂, 100% hexanes) to provide 1-((allyloxy)methyl)-2-bromo-3-methylbenzene 21.1 (2.30 g, 49%) as a colorless oil. $^1$H NMR (300 MHz, CDCl₃) δ 7.36-7.34 (m, 1H), 7.28-7.18 (m, 2H), 6.08-5.95 (m, 1H), 5.38 (d, J=15.0 Hz, 1H), 5.25 (d, J=10.5 Hz, 1H), 4.62 (s, 2H), 4.14 (d, J=5.7 Hz, 2H), 2.44 (s, 3H).

Step 2.
5-Methyl-4-methyleneisochroman 21.2 was prepared as previously described in Example 10. $^1$H NMR (300 MHz, CDCl₃) δ 7.19-7.15 (m, 2H), 6.96-6.92 (m, 1H), 5.47 (s, 1H), 5.37 (s, 1H), 4.81 (s, 2H), 4.41 (s, 2H), 2.53 (s, 3H).

Step 3.
5-Methylisochroman-4-one 21.3 was prepared as previously described in Example 10. $^1$H NMR (300 MHz, CDCl₃) δ 7.44 (t, J=7.5 Hz, 1H), 7.21 (d, J=7.5 Hz, 1H), 7.08 (d, J=7.8 Hz, 1H), 4.88 (s, 2H), 4.35 (s, 2H), 2.70 (s, 3H).

Step 4.
5-Methylisochroman-4-ol 21.4 was prepared as previously described in Example 1. $^1$H NMR (300 MHz, CDCl₃) δ 7.24-7.19 (m, 1H), 7.13 (d, J=7.5 Hz, 1H), 6.88 (d, J=7.5 Hz, 1H), 4.83 (d, J=15.0 Hz, 1H), 4.70 (d, J=15.0 Hz, 1H), 4.60 (d, J=10.2 Hz, 1H), 4.29 (d, J=12.0 Hz, 1H), 3.81 (dd, J=12.0, 3.3 Hz, 1H), 2.48 (s, 3H), 2.23 (dd, J=13.5, 7.5 Hz, 1H).

Step 5.
4-Azido-5-methylisochroman 21.5 was prepared as previously described in Example 1. $^1$H NMR (300 MHz, CDCl₃) δ 7.26-7.24 (m, 1H), 7.18 (d, J=7.2 Hz, 1H), 6.94 (d, J=7.2 Hz, 1H), 4.91 (d, J=15.3 Hz, 1H), 4.74 (d, J=15.3 Hz, 1H), 4.28 (d, J=12.0 Hz, 1H), 4.08 (s, 1H), 3.92 (dd, J=12.3, 2.1 Hz, 1H), 2.42 (s, 3H).

Step 6.
The compound of Example 21 was prepared as previously described in Example 1. MS (ESI): m/z 164 [M+H]. $^1$H NMR (300 MHz, DMSO-d6) δ 8.26 (s, 3H), 7.29 (t, J=7.5 Hz, 1H), 7.15 (d, J=7.2 Hz, 1H), 6.99 (d, J=7.8 Hz, 1H), 4.87 (d, J=15.6 Hz, 1H), 4.72 (d, J=15.6 Hz, 1H), 4.43 (s, 1H), 4.21 (d, J=12.3 Hz, 1H), 3.80 (dd, J=12.3, 1.2 Hz, 1H), 2.39 (s, 3H).

TABLE 3

Compounds prepared as described in Example 21 using the appropriately substituted starting material.

| Example | Structure | Characterization Data |
|---|---|---|
| 22 | HCl NH₂ F (4-amino-5-fluoroisochroman HCl) | MS (ESI): m/z 168 [M + H]. $^1$H NMR (300 M Hz, CD₃OD) δ 7.52-7.44 (m, 1H), 7.14 (t, J = 9.0 Hz, 1H), 7.06 (d, J = 7.8 Hz, 1H), 4.97 (d, J = 15.9 Hz, 1H), 4.80 (d, J = 15.9 Hz, 1H), 4.58 (s, 1H), 4.28 (d, J = 12.9 Hz, 1H), 3.95 (dd, J = 13.2, 2.4 Hz, 1H). |
| 23 | HCl NH₂ with F (4-amino-8-fluoroisochroman HCl) | MS (ESI): m/z 168 [M + H]. $^1$H NMR (300 M Hz, CD₃OD) δ 7.46-7.39 (m, 1H), 7.30 (d, J = 7.8 Hz, 1H), 7.20 (t, J = 9.3 Hz, 1H), 5.05 (d, J = 15.9 Hz, 1H), 4.77 (d, J = 15.9 Hz, 1H), 4.41 (s, 1H), 4.24 (d, J = 12.0 Hz, 1H), 3.97 (dd, J = 12.9, 2.1 Hz, 1H). |

TABLE 3-continued

Compounds prepared as described in Example 21 using the appropriately substituted starting material.

| Example | Structure | Characterization Data |
| --- | --- | --- |
| 24 | isochroman-4-amine HCl with 8-OMe | MS (ESI): m/z 180 [M + H]. $^1$H NMR (300 M Hz, CD$_3$OD) δ 7.37 (t, J = 6.0 Hz, 1H), 7.05 (d, J = 6.3 Hz, 1H), 4.97 (d, J = 12.3 Hz, 1H), 4.65 (d, J = 12.0 Hz, 1H), 4.34 (s, 1 H), 4.21 (dd, J = 9.6, 0.9 Hz, 1H), 3.93 (dd, J = 9.6, 1.5 Hz, 1H), 3.88 (s, 3H). |
| 25 | isochroman-4-amine HCl with 5-OMe | MS (ESI): m/z 180 [M + H]. $^1$H NMR (300 M Hz, CD$_3$OD) δ 7.38 (t, J = 7.8 Hz, 1H), 6.96 (d, J = 7.5 Hz, 1H), 6.77 (d, J = 7.8 Hz, 1H), 4.89 (d, J = 15.0 Hz, 1H), 4.72 (d, J = 15.3 Hz, 1H), 4.44 (d, J = 1.2 Hz, 1 H), 4.25 (d, J = 12.9 Hz, 1H), 3.93 (s, 3H), 3.90 (dd, J = 13.5, 3.0 Hz, 1H). |
| 26 | isochroman-4-amine HCl with 7-Me | MS (ESI): m/z 164 [M + H]. $^1$H NMR (300 M Hz, DMSO-d6) δ 8.69 (brs, 3H), 7.32 (s, 1H), 7.21 (d, J = 7.8 Hz, 1H), 7.07 (d, J = 7.8 Hz, 1H), 4.80 (d, J = 15.3 Hz, 1H), 4.67 (d, J = 15.3 Hz, 1H), 4.29 (s, 1H), 4.13 (dd, J = 12.6, 1.8 Hz, 1H), 3.88 (dd, J = 12.6, 2.7 Hz, 1H), 2.30 (s, 3H). |
| 27 | isochroman-4-amine HCl with 8-Me | MS (ESI): m/z 164 [M + H]. $^1$H NMR (300 M Hz, CD$_3$OD) δ 7.29-7.25 (m, 3H), 4.94 (d, J = 17.7 Hz, 1H), 4.71 (d, J = 15.9 Hz, 1H), 4.35 (s, 1H), 4.23 (d, J = 12.6 Hz, 1H), 3.95(dd, J = 12.6, 1.8 Hz, 1H), 2.21 (s, 3H). |
| 28 | isochroman-4-amine HCl with 5-Cl | MS (ESI): m/z 184 [M + H]. $^1$H NMR (300 M Hz, DMSO-d6) δ 8.49 (s, 3H), 7.48-7.42 (m, 2H), 7.20 (d, J = 6.3 Hz, 1H), 4.89 (d, J = 15.9 Hz, 1H), 4.71 (d, J = 15.6 Hz, 1H), 4.48 (s, 1H), 4.28 (d, J = 12.6 Hz, 1H), 3.76 (d, J = 12.6 Hz, 1H). |
| 29 | 1,1-dimethylisochroman-4-amine HCl | MS (ESI): M/Z 178 [M + H]. $^1$H NMR (300 M Hz, CDCl$_3$) δ 8.78 (brs, 3 H), 7.61 (d, J = 7.5 Hz, 1H), 7.35 (t, J = 7.5 Hz, 1H), 7.26-7.21 (m, 1H), 7.15 (d, J = 7.8 Hz, 1H), 4.36 (s, 1H), 4.29 (d, J = 12 Hz, 1H), 4.04 (d, J = 12 Hz, 1H), 1.78 (s, 3H), 1.50 (s, 3H). |
| 30 | benzoxepin-amine HCl | MS (ESI): m/z 164 [M + H]. $^1$H NMR (300 M Hz, DMSO-d$_6$) δ 8.59 (brs, 3H), 7.36-7.23 (m, 4H), 4.41 (s, 1H), 4.12-4.00 (m, 2H), 3.74 (d, J = 12.6 Hz, 1H), 3.60-3.49 (m, 2H), 2.89-2.80 (m, 1H). |
| 32 | naphtho-oxepin-amine HCl | MS (ESI): m/z 214 [M + H]. $^1$H NMR (300 M Hz, CD$_3$OD) δ 8.23 (d, J = 8.7 Hz, 1H), 7.94 (t, J = 8.4 Hz, 2H), 7.66 (t, J = 7.2 Hz, 1H), 7.56 (t, J = 7.5 Hz, 1H), 7.41 (d, J = 8.4 Hz, 1H), 5.52 (d, J = 4.2 Hz, 1H), 4.46-4.31 (m, 2H), 3.90 (d, J = 14.4 Hz, 1H), 3.84-3.70 (m, 2H), 3.10-3.04 (m, 1H). |

Example 31: 8-Methyl-1,2,4,5-tetrahydrobenzo[d]oxepin-1-amine hydrochloride

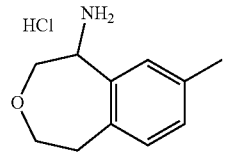

The compound of Example 31 was prepared as previously described in Example 21 using 2-(2-bromo-4-methylphenyl)ethanol. MS (ESI): m/z 178 [M+H]. $^1$H NMR (300 MHz, CDCl$_3$) δ 7.71 (s, 1H), 7.08-7.01 (m, 2H), 4.48 (d, J=11.4 Hz, 1H), 4.37 (s, 1H), 4.16 (d, J=12.6 Hz, 1H), 3.77-3.72 (m, 2H), 3.54 (t, J=11.7 Hz, 1H), 2.77-2.70 (m, 1H), 1.61 (s, 3H).

Synthesis of 2-(2-bromo-4-methylphenyl)ethanol

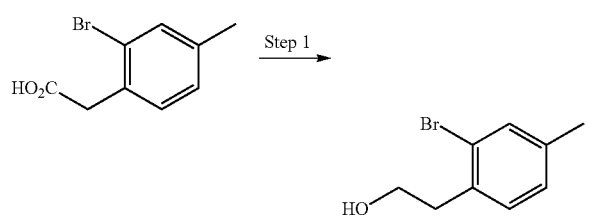

Step 1.

A solution of 2-(2-bromo-4-methylphenyl)acetic acid (7.2 g, 31.43 mmol) in THF (314 mL) was cooled in an ice bath to 0° C., and treated with BH$_3$.THF (62.86 mL, 62.86 mmol, 1M in THF) in a dropwise manner. After addition was complete, the reaction mixture was stirred at 0° C. overnight. Excess borane was quenched by the dropwise addition of 1M HCl (20 mL) at 0° C. The mixture was concentrated under reduced pressure and then partitioned between EtOAc (300 mL) and water (200 mL). The organic layer was washed with brine (200 mL), dried over anhydrous Na$_2$SO$_4$, filtered, and concentrated to give the 2-(2-bromo-4-methylphenyl)ethanol (6.7 g, 94%) as a yellow oil. MS (ESI) m/z 214, 216 [M+H].

Example 33: 1,3,4,5-Tetrahydrobenzo[c]oxepin-5-amine hydrochloride

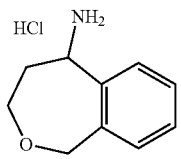 [SMILES: NC1CCOCc2ccccc21 ; Cl]

The compound of Example 33 was prepared as previously described in Example 21 using 4-bromobut-1-ene in place of 3-bromoprop-1-ene. MS (ESI): m/z 164 [M+H]. $^1$H NMR (300 MHz, CD$_3$OD) δ 7.43-7.29 (m, 4H), 4.90-4.76 (m, 3H), 4.22-4.14 (m, 1H), 4.09-4.03 (m, 1H), 2.28-2.20 (m, 2H)

TABLE 4

Compounds prepared as described in Example 33 using the appropriately substituted 2-bromobenzyl alcohol.

| Example | Structure | Characterization Data |
|---|---|---|
| 34 | 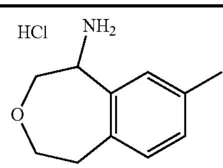 | MS (ESI+): m/z 178 [M + H]. $^1$H NMR (300 M Hz, CD$_3$OD) δ 7.18-7.13 (m, 3H), 4.88-4.71 (m, 3H), 4.20-4.15 (m, 1H), 4.07-4.00 (m, 1H), 2.40 (s, 3H), 2.24-2.16 (m, 2H). |
| 35 | 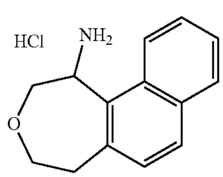 [SMILES: NC1COCCc2ccc3ccccc3c21 ; Cl] | MS (ESI+): m/z 214 [M + H]. $^1$H NMR (300 M Hz, CD$_3$OD) δ 8.26 (d, J = 8.7 Hz, 1H), 7.95 (t, J = 6.6 Hz, 2H), 7.70 (t, J = 7.2 Hz, 1H), 7.59 (t, J = 7.8 Hz, 1H), 7.35 (d, J = 8.7 Hz, 1H), 5.73-5.70 (m, 1H), 5.21 (d, J = 16.5 Hz, 1H), 5.05 (d, J = 16.2 Hz, 1H), 4.27-4.07 (m, 2H), 2.63-2.57 (m, 2H). |
| 36 | 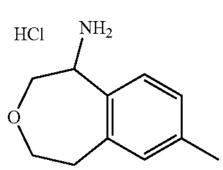 | MS (ESI+): m/z 178 [M + H]. $^1$H NMR (300 M Hz, CD$_3$OD) δ 7.21 (s, 2H), 7.12 (s, 1H), 4.85-4.72 (m, 3H), 4.20-4.12 (m, 1H), 4.07-3.99 (m, 1H), 2.35 (s, 3H), 2.32-2.20 (m, 2H). |
| 37 | 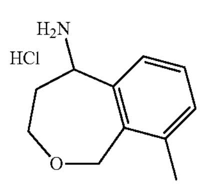 | MS (ESI+): m/z 178 [M + H]. $^1$H NMR (300 M Hz, CD$_3$OD) δ 7.22-7.13 (m, 3H), 5.12 (d, J = 15 Hz, 1H), 4.67-4.62 (m, 2H), 4.16-4.07 (m, 1H), 3.99-3.90 (m, 1H), 2.30-2.25 (m, 5H). |

TABLE 4-continued

Compounds prepared as described in Example 33 using the appropriately substituted 2-bromobenzyl alcohol.

| Example | Structure | Characterization Data |
|---|---|---|
| 38 | 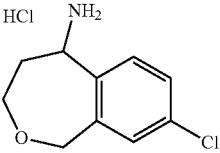 [SMILES: NC1CCOCc2cc(Cl)ccc21 ; Cl] | MS (ESI+): m/z 198 [M + H]. $^1$H NMR (300 M Hz, DMSO-$d_6$): δ 8.85 (brs, 3H), 7.48-7.43 (m, 2H), 7.34-7.30 (m, 1H), 4.78-4.65 (m, 3H), 4.11-4.06 (m, 1H), 3.97-3.89 (m, 1H), 2.13-1.91 (m, 2H). |
| 39 | 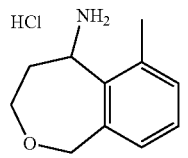 | MS (ESI+): m/z 178 [M + H]. $^1$H NMR (300 M Hz, CDCl$_3$) δ 8.79 (brs, 3H), 7.28-7.13 (m, 2H), 6.95-7.00 (m, 1H), 5.12-5.00 (m, 2H), 4.70 (d, J = 15.3 Hz, 1H), 4.31-4.21 (m, 1H), 4.01-3.95 (m, 1H), 2.70-2.51 (m, 4H), 2.31-2.20 (m, 1H). |
| 40 | 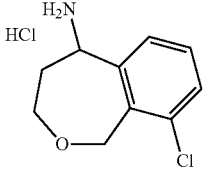 [SMILES: Cl ; NC1CCOCc2c(Cl)cccc21] | MS (ESI+): m/z 198 [M + H]. $^1$H NMR (300 M Hz, DMSO-$d_6$) δ 8.84 (brs, 3H), 7.46 (d, J = 6.0 Hz, 1H), 7.40 (d, J = 5.7 Hz, 1H), 7.33 (d, J = 5.7 Hz, 1H), 5.17 (d, J = 11.1 Hz, 1H), 4.85 (d, J = 5.7 Hz, 1H), 4.74 (d, J = 11.1 Hz, 1H), 4.11-4.06 (m, 1H), 3.99-3.93 (m, 1H), 2.25-2.15 (m, 1H) 2.10-2.00 (m, 1H). |
| 41 | 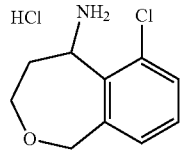 [SMILES: NC1CCOCc2cccc(Cl)c21 ; Cl] | MS (ESI+): m/z 198 [M + H]. $^1$H NMR (300 M Hz, CD$_3$OD) δ 7.47 (d, J = 8.1 Hz, 1H), 7.36 (t, J = 7.5 Hz, 1H), 7.22 (d, J = 7.8 Hz, 1H), 5.26 (d, J = 5.4 Hz, 1H), 5.01 (d, J = 16.2 Hz, 1H), 4.87 (d, J = 16.2 Hz, 1H), 4.15-3.98 (m, 2H), 2.52-2.37 (m, 2H). |

Example 42: 5,6-Dimethylisochroman-4-amine hydrochloride

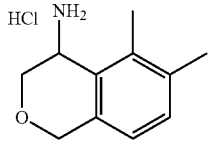

The compound of Example 42 was prepared as previously described in Example 21, using (2-bromo-3,4-dimethylphenyl)methanol (prepared from methyl 2-amino-3,4-dimethylbenzoate as previously described in Example 19). MS (ESI): m/z 178 [M+H]. $^1$H NMR (300 MHz, DMSO-d6) δ 8.32 (s, 3H), 7.20 (d, J=7.8 Hz, 1H), 6.90 (d, J=7.8 Hz, 1H), 4.83 (d, J=15.3 Hz, 1H), 4.68 (d, J=15.3 Hz, 1H), 4.48 (s, 1H), 4.24 (d, J=12.8 Hz, 1H), 3.76 (d, J=11.1 Hz, 1H), 2.25 (s, 6H).

Example 43: 6,7-Dimethyl-1,3,4,5-tetrahydrobenzo[c]oxepin-5-amine hydrochloride

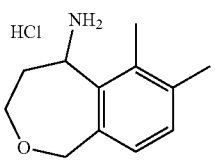

The compound of Example 43 was prepared as previously described in Example 42 using but-3-en-1-ol. MS (ESI): m/z 192 [M+H]. $^1$H NMR (300 MHz, DMSO-d6) δ 8.44 (brs, 3H), 7.13 (d, J=7.5 Hz, 1H), 6.97 (d, J=7.8 Hz, 1H), 5.00 (d, J=15.0 Hz, 1H), 4.94 (s, 1H), 4.60 (d, J=15.0 Hz, 1H), 4.11-4.01 (m, 1H), 3.95-3.90 (m, 1H), 2.33 (s, 3H), 2.27 (s, 3H), 2.19-2.09 (m, 2H).

Example 44: 5,6-Dichloroisochroman-4-amine hydrochloride

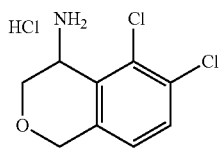 [SMILES: Cl ; NC1COCc2ccc(Cl)c(Cl)c21]

The compound of Example 44 was prepared as previously described in Example 10, using (2-bromo-3,4-dichlorophenyl)methanol 44.5 prepared as described below. MS (ESI): m/z 218 [M+H]. $^1$H NMR (300 MHz, DMSO-d6) δ 8.62 (s, 3H), 7.72 (d, J=7.8 Hz, 1H), 7.26 (d, J=8.4 Hz, 1H), 4.90 (d, J=16.2 Hz, 1H), 4.69 (d, J=16.2 Hz, 1H), 4.52 (s, 1H), 4.31 (d, J=12.6 Hz, 1H), 3.82 (d, J=14.7 Hz, 1H).

Synthesis of (2-bromo-3,4-dichlorophenyl)methanol (44.5)

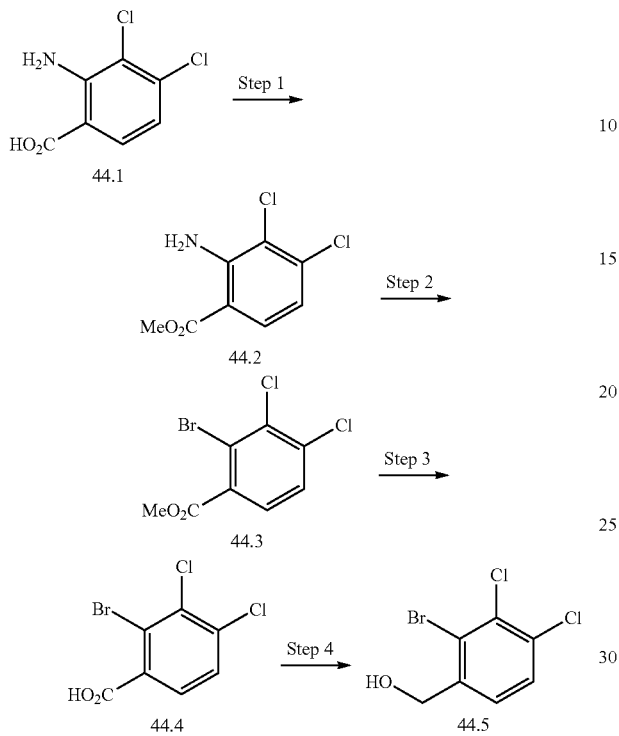

Step 1.

2-Amino-3,4-dichlorobenzoic acid 44.1 (13.6 g, 66.0 mmol, *J. Med. Chem.* 1991, 34, 218) was dissolved in DMF (150 mL) and treated with K$_2$CO$_3$ (45.6 g, 330 mmol) and iodomethane (11.2 g, 79.2 mmol). The resulting slurry was stirred at room temperature for 2 hr. The mixture was diluted with water and extracted with EtOAc (3×100 mL). The combined organics were washed with brine, dried over anhydrous Na$_2$SO$_4$, filtered, and concentrated under reduced pressure. Purification by flash column chromatography (SiO$_2$, gradient elution from 100% hexanes to 10% EtOAc/hexanes) afforded methyl 2-amino-3,4-dichlorobenzoate 44.2 (12.5 g, 86%) as a yellow solid. $^1$H NMR (300 MHz, CDCl$_3$) δ 7.74 (d, J=8.7 Hz, 1H), 6.74 (d, J=8.7 Hz, 1H), 6.47 (br s, 2H), 3.89 (s, 3H).

Step 2.

Methyl 2-bromo-3,4-dichlorobenzoate 44.3 was prepared as previously described in Example 19. $^1$H NMR (300 MHz, CDCl$_3$) δ 7.54 (d, J=9.0 Hz, 1H), 7.49 (d, J=9.0 Hz, 1H), 3.94 (s, 3H).

Step 3.

Compound 44.3 (11.1 g, 39.0 mmol) was dissolved in MeOH (250 mL) and treated with aqueous 2 NNaOH (39.2 mL, 78 mmol), and stirred at room temperature for 2 hr. The mixture was filtered, diluted with water (800 mL), and made acidic to pH=2 by the addition of aqueous 3M HCl. The resulting suspension was extracted with EtOAc (4×400 mL). The combined organics were dried over anhydrous Na$_2$SO$_4$, filtered, and concentrated under reduced pressure to yield 2-bromo-3,4-dichlorobenzoic acid 44.4 (9.85 g, 94%), which was used directly without further purification.

Step 4.

2-Bromo-3,4-dichlorobenzyl alcohol 44.5 was prepared as previously described in Example 31. $^1$H NMR (300 MHz, CDCl$_3$) δ 7.47 (d, J=8.4 Hz, 1H), 7.39 (d, J=8.4 Hz, 1H), 4.75 (s, 2H).

Example 45: 5-Chloro-6-methylisochroman-4-amine hydrochloride

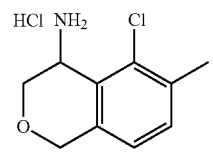

The compound of Example 45 was prepared as previously described in Example 44 from 2-amino-3-chloro-4-methylbenzoic acid (Rewcastle, G. W., et al *J. Med. Chem.* 1991, 34, 217). MS (ESI): m/z 170 [M+H]. $^1$H NMR (300 MHz, CD$_3$OD) δ 7.05 (d, J=0.9 Hz, 1H), 5.00 (d, J=15.3 Hz, 1H), 4.80 (d, J=15.3 Hz, 1H), 4.33 (s, 1H), 4.25 (dd, J=12.9, 1.5 Hz, 1H), 3.84 (dd, J=12.6, 1.8 Hz, 1H), 2.28 (d, J=1.2 Hz, 3H).

Example 46: 6,8-Dimethylisochroman-4-amine hydrochloride

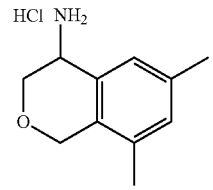

The compound of Example 46 was prepared as previously described in Example 44 from 2-amino-4,6-dimethylbenzoic acid. MS (ESI): m/z 178 [M+H]. $^1$H NMR (300 MHz, CD$_3$OD) δ 7.07 (s, 2H), 4.90 (d, J=18 Hz, 1H), 4.65 (d, J=18 Hz, 1H), 4.27 (s, 1H), 4.18 (dd, J=12, 3 Hz, 1H), 3.90 (dd, J=12, 3 Hz, 1H), 2.32 (s, 3H), 2.15 (s, 1H).

Example 47: 5,8-Dimethylisochroman-4-amine hydrochloride

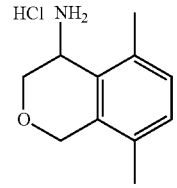

The compound of Example 47 was prepared as previously described in Example 44 from 2-amino-3,6-dimethylbenzoic acid. MS (ESI): m/z 178 [M+H]. $^1$H NMR (300 MHz, DMSO-d$_6$) δ 8.38 (s, 3H), 7.13-7.05 (m, 2H), 4.82 (d, J=15 Hz, 1H), 4.62 (d, J=15 Hz, 1H), 4.39 (s, 1H), 4.25 (d, J=12 Hz, 1H), 3.74 (d, J=12 Hz, 1H), 2.37 (s, 3H), 2.09 (s, 3H).

Example 48: 8-Chloro-5-methylisochroman-4-amine hydrochloride

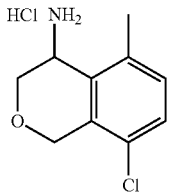

The compound of Example 48 was prepared as previously described in Example 10, using (2-bromo-6-chloro-3-methylphenyl)methanol 48.5 prepared as described below. MS (ESI): m/z 198 [M+H]. $^1$H NMR (300 MHz, DMSO-d$_6$) δ 8.46 (s, 3H), 7.42 (d, J=9.0 Hz, 1H), 7.23 (d, J=9.0 Hz, 1H), 4.85 (d, J=15 Hz, 1H), 4.65 (d, J=15 Hz, 1H), 4.46 (s, 1H), 4.25 (d, J=12 Hz, 1H), 3.79 (d, J=12 Hz, 1H), 2.41 (s, 3H).

Synthesis of (2-bromo-6-chloro-3-methylphenyl)methanol (48.5)

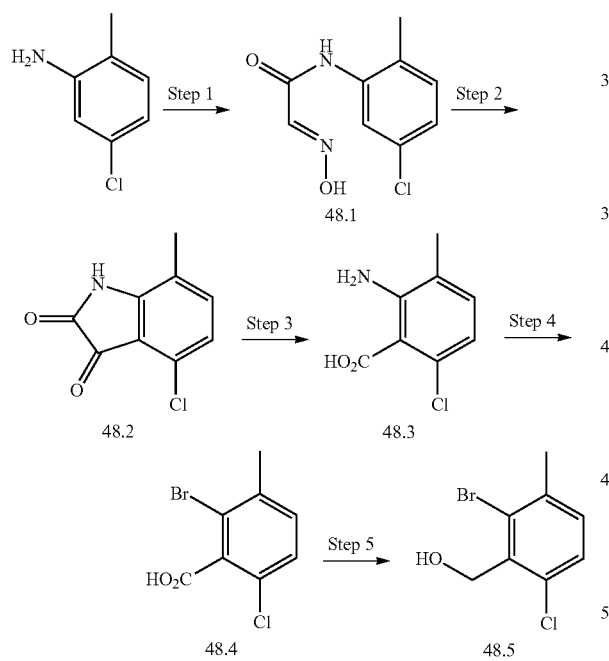

Step 1.

A solution of 5-chloro-2-methylaniline (15 g, 105 mmol) in water (750 mL) was treated with aqueous concentrated HCl (50 mL), hydroxylamine hydrochloride (36.4 g, 525 mmol), 2,2,2-trichloroethane-1,1-diol (25.9 g, 157 mmol) and Na$_2$SO$_4$ (14.9 g, 105 mmol), and heated to reflux for 2 h. After cooling to room temperature, the precipitate was collected by filtration, washed with water, and dried under vacuum to provide (E)-N-(5-chloro-2-methylphenyl)-2-(hydroxyimino)acetamide 48.1 (61.0 g) as a brown solid, which was used without further purification.

Step 2.

Compound 48.1 (51 g, 239 mmol) was dissolved in methanesulfonic acid (350 mL) and heating at 50° C. for 2 h. After cooling to room temperature, the mixture was poured into ice-water. The resulting suspension was collected on a fritted filter, washed with water, and dried under vacuum to provide 4-chloro-7-methylindoline-2,3-dione 48.2 (45.0 g, 96%) as a brown solid. $^1$H NMR (300 MHz, DMSO-d$_6$) δ 10.22 (brs, 1H), 7.01 (dd, J=7.8, 0.6 Hz, 1H), 6.58 (d, J=8.1 Hz, 1H), 2.07 (s, 3H).

Step 3.

Compound 48.2 (15 g, 76.6 mmol) was dissolved in aqueous 0.3M NaOH (1.5 L) and treated with the dropwise addition of 40% hydrogen peroxide (150 mL). The reaction was stirred at room temperature for 4 h. Residual solids were removed by filtration. The filtrate was wasted with CH$_2$Cl$_2$ (3×200 mL), acidified to pH=3-4 with aqueous concentrated HCl, and extracted with EtOAc (3×350 mL). The combined organics were dried over anhydrous Na$_2$SO$_4$, filtered, and concentrated under reduced pressure to yield 2-amino-6-chloro-3-methylbenzoic acid 48.3 (12.7 g, 90%) as a yellow solid. $^1$H NMR (300 MHz, DMSO-d$_6$) δ 7.02 (d, J=7.8 Hz, 1H), 6.58 (d, J=7.8 Hz, 1H), 2.07 (s, 3H).

Step 4.

Compound 48.3 (14.0 g, 75.4 mmol) was dissolved in EtOH (300 mL) and 48% hydrobromic acid (75 mL) and cooled in an ice bath. A solution of NaNO$_2$ (7.79 g, 113 mmol) in water (20 mL) was added in a dropwise manner, and the resulting mixture was stirred at 0° C. for 20 min. Copper(I) bromide (10.8 g, 75.4 mmole) was added in a single portion, the ice bath was removed, and the suspension was heated with stirring to 95° C. for 30 min. After cooling to room temperature, saturated aqueous NH$_4$Cl (200 mL) was added with vigorous stirring. The aqueous phase was extracted with EtOAc (3×200 mL). The combined organics were concentrated under reduced pressure. The residue was dissolved in water (30 mL) and made basic by the addition of aqueous 2N NaOH until pH=10. The aqueous phase was washed with CH$_2$Cl$_2$ (3×200 mL), made acidic to pH=3 by the addition of aqueous 5N HCl, and extracted with EtOAc (4×300 mL). The combined organics were dried over anhydrous Na$_2$SO$_4$, filtered, and concentrated under reduced pressure to yield 2-bromo-6-chloro-3-methylbenzoic acid 48.4. $^1$H NMR (300 MHz, DMSO-d$_6$) δ 7.40-7.49 (m, 2H), 2.36 (s, 3H).

Step 5.

(2-Bromo-6-chloro-3-methylphenyl)methanol 48.5 was prepared as described previously in Example 44. $^1$H NMR (300 MHz, DMSO-d$_6$) δ 7.39 (d, J=8.4 Hz, 1H), 7.32 (d, J=8.1 Hz, 1H), 4.75 (s, 2H), 2.36 (s, 3H).

Example 49: 8-Chloro-6-methylisochroman-4-amine hydrochloride

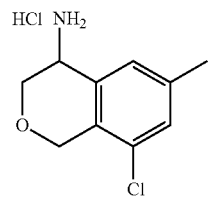

The compound of Example 49 was prepared as previously described in Example 48 from 3-chloro-5-methylaniline. MS (ESI): m/z 198 [M+H]. $^1$H NMR (300 MHz, CD$_3$OD) δ 7.32 (s, 1H), 7.24 (s, 1H), 4.95 (d, J=15 Hz, 1H), 4.64 (d, J=15 Hz, 1H), 4.33 (s, 1H), 4.21 (dd, J=12.0, 3.0 Hz, 1H), 3.92 (dd, J=12.0, 3.0 Hz, 1H), 2.37 (s, 3H).

Example 50: 3,4-Dihydro-1H-benzo[h]isochromen-4-amine hydrochloride

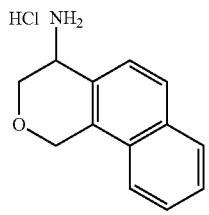 [SMILES: Cl ; NC1COCc2c1ccc1ccccc21]

The compound of Example 50 was prepared as previously described in Example 21 from 2-bromo-1-naphthalenemethanol (Shaik, F. H. et al, Beilstein *J. Org. Chem.* 2009, 5). MS (ESI): m/z 200 [M+H]. $^1$H NMR (300 MHz, DMSO-d6) δ 8.71 (d, J=6.6 Hz, 3H), 7.99-7.85 (m, 3H), 7.66-7.59 (m, 3H), 5.38 (d, J=15.9 Hz, 1H), 5.10 (d, J=15.9 Hz, 1H), 4.46 (s, 1H), 4.30 (d, J=12.6 Hz, 1H), 4.00 (dd, J=12.3, 2.1 Hz, 1H).

Example 51: 2,4,7,8,9,10-Hexahydro-1H-7,10-methanobenzo[f]isochromen-1-amine hydrochloride

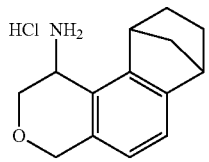 [SMILES: Cl ; NC1COCc2ccc3c(c21)C1CCC3C1]

The compound of Example 51 was prepared as previously described in Example 48 using 1,2,3,4-tetrahydro-1,4-methanonaphthalen-5-amine (Ehrenfreund, J.; et al, WO2004035589). MS (ESI): m/z 216 [M+H]. $^1$H NMR (300 MHz, CD$_3$OD) δ 7.22 (dd, J=7.5, 2.4 Hz, 1H), 6.88 (d, J=7.5 Hz, 1H), 4.97-4.77 (m, 2H), 4.50 (d, J=41.1 Hz, 1H), 4.36-4.24 (m, 1H), 3.91 (d, J=12.9 Hz, 1H), 3.64 (d, J=12.0 Hz, 1H), 3.40-3.33 (m, 1H), 2.06-1.97 (m, 2H), 1.85-1.65 (m, 1H), 1.65-1.62 (m, 1H), 1.19-1.09 (m, 2H).

Example 52: 1,2,4,8,9,10-Hexahydropyrano[4,3-f]chromen-1-amine hydrochloride

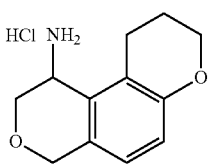

The compound of Example 52 was prepared as previously described in Example 21 using (5-bromochroman-6-yl) methanol 52.5 prepared as described below. MS (ESI): m/z 206 [M+H]. $^1$H NMR (300 MHz, DMSO-d$_6$) δ 8.40 (s, 3H), 6.88 (d, J=8.4 Hz, 1H), 6.80 (d, J=8.4 Hz, 1H), 4.79 (d, J=15.3 Hz, 1H), 4.63 (d, J=15.3 Hz, 1H), 4.34 (s, 1H), 4.22 (d, J=12.6 Hz, 1H), 4.16-4.06 (m, 2H), 3.74 (d, J=12.0 Hz, 1H), 3.00-2.90 (m, 1H), 2.78-2.68 (m, 1H), 1.98-1.89 (m, 2H).

Synthesis of (5-bromochroman-6-yl)methanol (52.5)

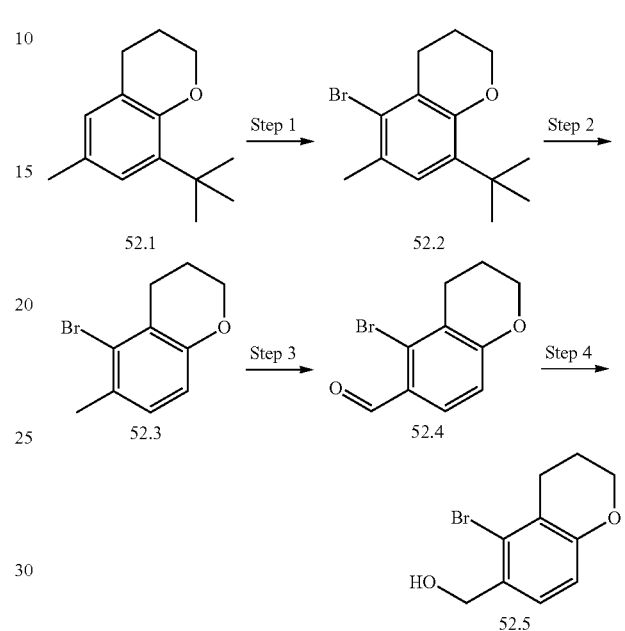

Step 1.

8-(tert-Butyl)-6-methylchroman 52.1 (3.5 g, 17.1 mmol, Mao, C.-H.; et al, *Bioorg. Med. Chem.* 2008, 16, 488) was dissolved in CH$_3$CN (50 mL) and treated with N-bromosuccinimide (3.04 g, 17.1 mmol). The mixture was heated to 80° C. with stirring for 4 hr. After cooling to room temperature, the solvents were removed under reduced pressure, and the residue was purified by flash column chromatography (SiO2, 100% hexanes) to afford 5-bromo-8-(tert-butyl)-6-methylchroman 52.2 (2.5 g, 52%). $^1$H NMR (300 MHz, CDCl$_3$) δ 7.03 (s, 1H), 4.13 (t, J=5.1 Hz, 2H), 2.81 (t, J=6.6 Hz, 2H), 2.37 (s, 3H), 2.08-2.00 (m, 2H), 1.41 (s, 9H).

Step 2.

AlCl$_3$ (3.65 g, 27.4 mmol) was added to a solution of 52.2 (6.5 g, 22.9 mmol) in CH$_2$Cl$_2$ (100 mL) at room temperature and stirred for 2 h. The reaction mixture was carefully quenched by the dropwise addition of 1 M aqueous HCl (30 mL). The mixture was extracted with CH$_2$Cl$_2$ (200 mL). The organic phase was washed with brine (2×50 mL dried over anhydrous Na$_2$SO$_4$, filtered, and concentrated under reduced pressure. The resulting oil was purified by flash column chromatography (SiO$_2$, 100% hexanes) to afford 5-bromo-6-methylchroman 52.3 (4.50 g, 86%) as a green oil. $^1$H NMR (300 MHz, CDCl$_3$) δ 7.04 (d, J=8.4 Hz, 1H), 6.78 (d, J=8.4 Hz, 1H), 4.16 (t, J=5.1 Hz, 2H), 2.83 (t, J=6.6 Hz, 2H), 2.42 (s, 3H), 2.09-2.03 (m, 2H).

Step 3.

Chromium(VI) oxide (9.89 g, 99.0 mmol) was added to a solution of 52.3 (4.5 g, 19.8 mmol) in AcOH (40 mL) and water (20 mL). The reaction was stirred at ambient temperature for 2 h, diluted with water (40 mL), and extracted with EtOAc (200 mL). The organic phase was washed with saturated aqueous NaHCO$_3$ (2×30 mL) and brine (2×30 mL), dried over anhydrous Na$_2$SO$_4$, filtered, and concentrated under reduced pressure. Purification by flash column chromatography (SiO$_2$, 5% EtOAc/hexanes) gave 5-bromochroman-6-carbaldehyde 52.4 (1 g, 21%) as a white solid. $^1$H NMR (300 MHz, CDCl$_3$) δ 10.31 (s, 1H), 7.75 (d, J=8.7 Hz, 1H), 6.87 (d, J=8.7 Hz, 1H), 4.24 (t, J=5.1 Hz, 2H), 2.85 (t, J=6.6 Hz, 2H), 2.13-2.06 (m, 2H).

Step 4.

NaBH$_4$ (376 mg, 9.94 mmol) was added in a single portion to a solution of 52.4 (1.2 g, 4.97 mmol) in CH$_3$OH (30 mL). The reaction mixture was stirred at room temperature for 30 min and then partitioned between water (30 mL) and EtOAc (300 mL). The organic phase was washed with brine (2×40 mL), dried over anhydrous Na$_2$SO$_4$, filtered, and concentrated under reduced pressure to provide (5-bromochroman-6-yl)methanol 52.5 (1.10 g, 91%) as a colorless oil which was used directly without further purification.

Example 53: 5-Ethylisochroman-4-amine hydrochloride

The compound of Example 53 was prepared as previously described in Example 21 using (2-bromo-3-ethylphenyl)methanol 53.4 prepared as described below. MS (ESI): m/z 178 [M+H]. $^1$H NMR (300 MHz, CD$_3$OD) δ 7.36 (t, J=6.0 Hz, 1H), 7.24 (d, J=9.0 Hz, 1H), 7.00 (d, J=6.0 Hz, 1H), 4.95 (d, J=15.0 Hz, 1H), 4.84 (d, J=15.0 Hz, 1H), 4.52 (s, 1H), 4.25 (dd, J=12.0, 3.0 Hz, 1H), 3.92 (dd, J=12.0, 3.0 Hz, 1H), 2.85-2.66 (m, 2H), 1.27 (t, J=6.0 Hz, 3H).

Synthesis of (2-Bromo-3-ethylphenyl)methanol (53.4)

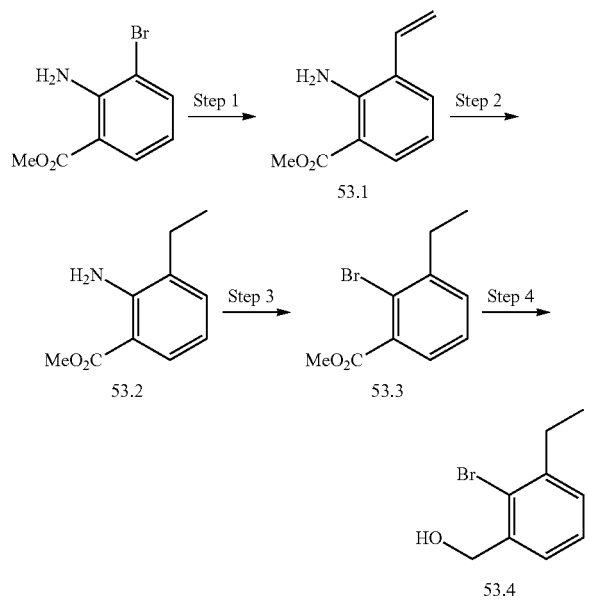

Step 1.

Methyl 2-amino-3-vinylbenzoate 53.1 was prepared as previously described in Example 7 using methyl 2-amino-3-bromobenzoate and vinylboronic acid pinacol ester. $^1$H NMR (300 MHz, CDCl$_3$) δ 7.84 (d, J=9.0 Hz, 1H), 7.38 (d, J=6.0 Hz, 1H), 6.79-6.62 (m, 2H), 5.97 (brs, 2H), 5.62 (dd, J=18.0, 3.0 Hz, 1H), 5.38 (dd, J=12.0, 3.0 Hz, 1H), 3.87 (s, 3H).

Step 2.

Methyl 2-amino-3-ethylbenzoate 53.2 was prepared as previously described in Example 9. $^1$H NMR (300 MHz, CDCl$_3$) δ 7.77 (d, J=9.0 Hz, 1H), 7.20 (d, J=6.0 Hz, 1H), 6.63 (t, J=6.0 Hz, 1H), 5.89 (brs, 2H), 3.86 (s, 1H), 2.54-2.47 (m, 2H), 1.26 (t, J=7.62 Hz, 3H).

Step 3.

Methyl 2-bromo-3-ethylbenzoate 53.3 was prepared as previously described in Example 19. $^1$H NMR (300 MHz, CDCl$_3$) δ 7.45-7.42 (m, 1H), 7.36-7.25 (m, 2H), 3.92 (s, 3H), 2.87-2.80 (m, 2H), 1.24 (t, J=7.5 Hz, 3H).

Step 4.

(2-Bromo-3-ethylphenyl)methanol 53.4 was prepared as previously described in Example 19. $^1$H NMR (300 MHz, CDCl$_3$) δ 7.32-7.23 (m, 2H), 7.19-7.16 (m, 1H), 4.76 (s, 2H), 2.84-2.76 (m, 2H), 2.17 (brs, 1H), 1.23 (t, J=15.0 Hz, 3H).

Example 54: N-Methylisochroman-4-amine hydrochloride

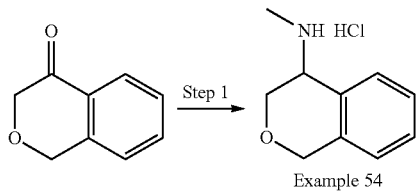

Example 54

Step 1.

Isochroman-4-one (200 mg, 1.35 mmol) was dissolved in EtOH (10 mL) and treated sequentially with 2M NH$_3$ in MeOH (3.4 mol, 6.8 mmol), Ti(Oi-Pr)$_4$ (0.38 g, 1.35 mmol) and NaCNBH$_3$ (0.34 g, 5.4 mmol). The reaction mixture was heated with stirring to reflux for 6 h and then cooled to room temperature and stirred for an additional 16 h. The reaction mixture was partitioned between EtOAc (40 mL) and saturated aqueous Na$_2$CO$_3$ (30 mL). The aqueous layer was extracted with EtOAc (2×15 mL). The combined organics were dried over anhydrous Na$_2$SO$_4$, filtered, and concentrated under reduced pressure to afford N-methylisochroman-4-amine (100 mg, 45%) as a colorless oil, which was converted to the compound of Example 54 as previously described in Example 1. MS (ESI): m/z 164 [M+H]. $^1$H NMR (300 MHz, DMSO-d$_6$) δ 9.37 (brs, 1H), 9.20 (brs, 1H), 7.57 (d, J=7.5 Hz, 1H), 7.45-7.32 (m, 2H), 7.21 (d, J=7.5 Hz, 1H), 4.87 (d, J=15.6 Hz, 1H), 4.73 (d, J=15.6 Hz, 1H), 4.42 (d, J=13.2 Hz, 1H), 4.30 (brs, 1H), 3.87 (dd, J$_1$=12.9, 2.1 Hz, 1H), 2.56-2.50 (m, 3H).

TABLE 5

Compounds prepared as described in Example 54 using the appropriate starting materials.

| Example | Structure | Characterization Data |
|---|---|---|
| 55 | 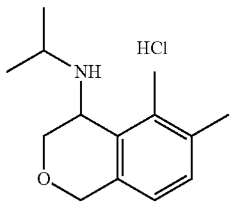 [SMILES: Cc1ccc2c(c1C)C(NC(C)C)COC2 ; Cl] | MS (ESI): m/z 220 [M + H]. $^1$H NMR (300 M Hz, DMSO-$d_6$) δ 8.52 (s, 1H), 8.34 (s, 1H), 7.23 (d, J = 9.0 Hz, 1H), 6.93 (d, J = 9.0 Hz, 1H), 4.90 (d, J = 15.0 Hz, 1H), 4.73 (d, J = 15.0 Hz, 1H), 4.61 (d, J = 9.0 Hz, 1H), 4.43 (d, J = 12.0 Hz, 1H), 3.71 (d, J = 15.0 Hz, 1H), 3.64-3.62 (m, 1H), 2.26 (d, J = 6.0 Hz, 6H), 1.38-1.09 (m, 6H). |
| 56 | 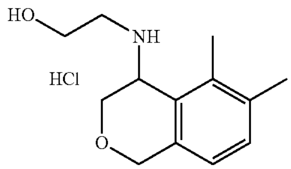 [SMILES: Cc1ccc2c(c1C)C(NCCO)COC2 ; Cl] | MS (ESI): m/z 222 [M + H]. $^1$H NMR (300 M Hz, DMSO-$d_6$) δ 8.80 (d, J = 24.9 Hz, 2H), 7.23 (d, J = 7.5 Hz, 1H), 6.92 (d, J = 7.2 Hz, 1H), 5.32 (s, 1H), 4.88 (d, J = 15.6 Hz, 1H), 4.70 (d, J = 15.3 Hz, 1H), 4.62-4.61 (m, 2H), 4.50 (d, J = 12.6 Hz, 1H), 3.77-3.70 (m, 3H), 3.13-3.07 (m, 2H), 2.26 (d, J = 4.8 Hz, 6H). |

Example 57. N,5,6-Trimethylisochroman-4-amine hydrochloride

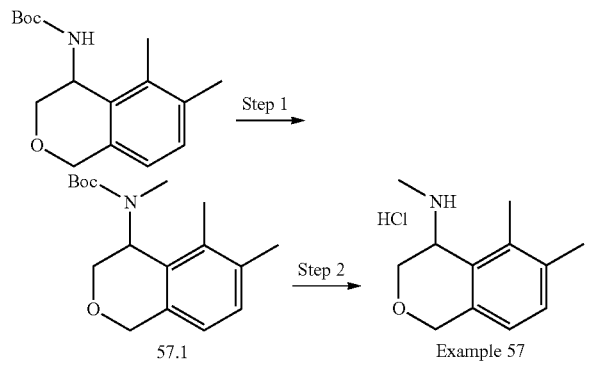

Step 1.

tert-Butyl (5,6-dimethylisochroman-4-yl)carbamate (400 mg, 1.44 mmol, prepared as described in Example 42) was dissolved in anhydrous THF (4 mL) and treated with a 95% dispersion of sodium hydride in mineral oil (103 mg, 4.31 mmol) at room temperature. Once addition was complete, the reaction mixture was heated to 40° C. and stirred for 15 min. Iodomethane (817 mg, 5.76 mmol) was added and heating at 40° C. was continued overnight. After cooling to room temperature, the reaction mixture was partitioned between brine (15 mL) and EtOAc (10 mL). The aqueous phase was washed with EtOAc (2×10 mL). The combined organics were dried over anhydrous $Na_2SO_4$, filtered, and concentrated under reduced pressure. Purification by flash column chromatography ($SiO_2$, gradient elution from 3% EtOAc/hexanes to 5% EtOAc/hexanes) gave tert-butyl (5,6-dimethylisochroman-4-yl)(methyl)carbamate 57.1 (400 mg, 1.37 mmol) as a yellow oil. MS (ESI): m/z 292 [M+H].

Step 2.

The compound of Example 57 was prepared as previously described in Example 1. MS (ESI): m/z 192 [M+H]. $^1$H NMR (300 MHz, DMSO-$d_6$) δ 8.85 (brs, 2H), 7.23 (d, J=7.8 Hz, 1H), 6.92 (d, J=7.8 Hz, 1H), 4.87 (d, J=15.3 Hz, 1H), 4.70 (d, J=15.3 Hz, 1H), 4.47 (d, J=9.3 Hz, 2H), 3.76 (dd, J=13.2, 1.8 Hz, 1H), 2.62 (s, 3H), 2.26 (s, 6H).

TABLE 6

Compounds prepared as described in Example 57 using the appropriate Boc-protected intermediates and alkyl halide.

| Example | Structure | Characterization Data |
|---|---|---|
| 58 | 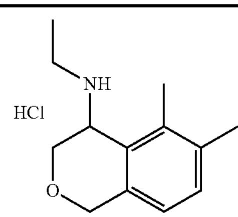 | MS (ESI): m/z 206 [M + H]. $^1$H NMR (300 M Hz, DMSO-$d_6$) δ 8.81 (s, 1H), 8.50 (s, 1H), 7.23 (d, J = 9.0 Hz, 1H), 6.93 (d, J = 9.0 Hz, 1H), 4.88 (d, J = 15.0 Hz, 1H), 4.71 (d, J = 15.0 Hz, 1H), 4.51-4.43 (m, 2H), 3.74 (d, J = 12.0 Hz, 1H), 3.12-3.09 (m, 1H), 2.25 (d, J = 6.0 Hz, 6H), 1.26 (t, J = 9.0 Hz, 3H). |
| 59 | 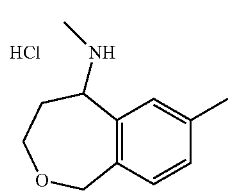 | MS (ESI): m/z 192 [M + H]. $^1$H NMR (300 M Hz, $CD_3OD$) δ 7.26-7.16 (m, 3H), 5.01 (d, J = 15.6 Hz, 1H), 4.83 (d, J = 15.3 Hz, 1H), 4.50-4.47 (m, 1H), 4.15-4.09 (m, 1H), 4.03-3.96 (m, 1H), 2.73 (s, 3H), 2.47-2.39 (m, 5H). |

TABLE 6-continued

Compounds prepared as described in Example 57 using the appropriate Boc-protected intermediates and alkyl halide.

| Example | Structure | Characterization Data |
|---|---|---|
| 258 | 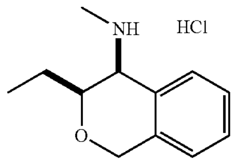 | MS (ESI): m/z 192 [M + H]. $^1$H NMR (300 M Hz, DMSO-d$_6$) δ 9.08 (s, 1H), 8.55 (s, 1H), 7.51 (d, J = 7.8 Hz, 1H), 7.45-7.42 (m, 1H), 7.33 (t, J = 7.2 Hz, 1H), 7.22 (d, J = 7.8 Hz, 1H), 4.97 (d, J = 15.9 Hz, 1H), 4.80 (d, J = 15.9 Hz, 1H), 4.32 (s, 1H), 3.75-3.70 (m, 1H), 2.42 (s, 3H), 1.80-1.70 (m, 2H), 1.02 (t, J = 7.2 Hz, 3H). |
| 259 | 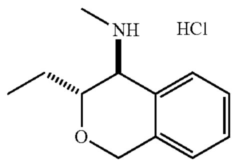 | MS (ESI): m/z 192 [M + H]. $^1$H NMR (300 M Hz, DMSO-d$_6$) δ 9.58 (s, 1H), 9.00 (s, 1H), 7.51 (d, J = 7.5 Hz, 1H), 7.43-7.40 (m, 1H), 7.35-7.30 (m, 1H), 7.21 (d, J = 7.5 Hz, 1H), 4.80 (d, J = 16.2 Hz, 1H), 4.69 (d, J = 16.5 Hz, 1H), 4.29-4.27 (m, 1H), 4.18 (s, 1H), 2.51 (s, 3H), 1.52-1.38 (m, 2H), 0.95 (t, J = 7.5 Hz, 3H). |
| 262 | 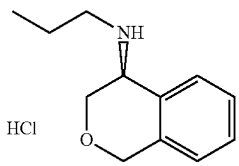 | MS (ESI): m/z 192 [M + H]. $^1$H NMR (300 M Hz, CD$_3$OD) δ 7.48-7.43 (m, 2H), 7.39-7.34 (m, 1H), 7.21 (d, J = 7.5 Hz, 1H), 4.97 (d, J = 15.6 Hz, 1H), 4.81 (d, J = 15.6 Hz, 1H), 4.43 (dd, J = 13.2, 1.2 Hz, 1H), 4.29 (s, 1H), 3.92 (dd, J = 13.2, 1.8 Hz, 1H), 3.11-3.06 (m, 2H), 1.81-1.68 (m, 2H), 1.02 (t, J = 7.4 Hz, 3H). |
| 263 | 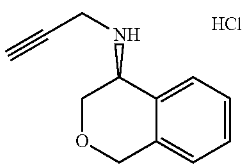 | MS (ESI): m/z 188 [M + H]. $^1$H NMR (300 M Hz, CD$_3$OD) δ 7.47 (t, J = 7.5 Hz, 2H), 7.37 (t, J = 7.8 Hz, 1H), 7.22 (d, J = 7.5 Hz, 1H), 4.98 (d, J = 15.6 Hz, 1H), 4.83 (d, J = 15.6 Hz, 1H), 4.48-4.41 (m, 2H), 4.09-3.90 (m, 3H), 3.33 (t, J = 2.4 Hz, 1H). |
| 264 | 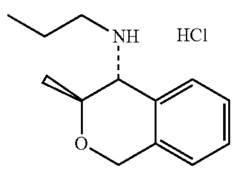 | MS (ESI): m/z 206 [M + H]. $^1$H NMR (300 M Hz, CDCl$_3$) δ 7.42-7.39 (m, 2H), 7.32-7.27 (m, 1H), 7.15 (d, J = 7.8 Hz, 1H), 4.80-4.75 (m, 2H), 4.51-4.48 (m, 1H), 4.08 (s, 1H), 3.01-2.87 (m, 2H), 1.71-1.62 (m, 2H), 1.18 (d, J = 6.6 Hz, 3H), 0.94 (t, J = 7.5 Hz, 3H). |
| 265 | 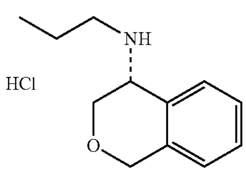 | MS (ESI): m/z 192 [M + H]. $^1$H NMR (300 M Hz, CD$_3$OD) δ 7.45 (t, J = 7.5 Hz, 2H), 7.37 (d, J = 7.8 Hz, 1H), 7.21 (d, J = 7.5 Hz, 1H), 4.97 (d, J = 15.6 Hz, 1H), 4.81 (d, J = 15.6 Hz, 1H), 4.43 (dd, J = 13.2, 1.2 Hz, 1H), 4.29 (s, 1H), 3.92 (dd, J = 13.2, 1.8 Hz, 1H), 3.13-3.06 (m, 2H), 1.81-1.68 (m, 2H), 1.02 (t, J = 7.5 Hz, 3H). |
| 266 | 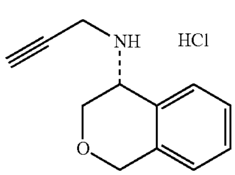 | MS (ESI): m/z 188 [M + H]. $^1$H NMR (300 M Hz, CD$_3$OD) δ 7.47 (t, J = 7.2 Hz, 2H), 7.37 (t, J = 7.5 Hz, 1h), 7.22 (d, J = 7.5 Hz, 1H), 4.97 (d, J = 15.6 Hz, 1H), 4.82 (d, J = 15.6 Hz, 1H), 4.48-4.41 (m, 2H), 4.08-3.90 (m, 3H), 3.32 (t, J = 2.4 Hz, 1H). |
| 267 | 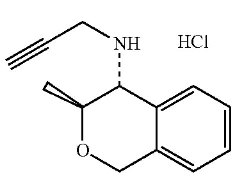 | MS (ESI): m/z 202 [M + H]. $^1$H NMR (300 M Hz, CDCl$_3$) δ 7.62 (d, J = 7.5 Hz, 1H), 7.42-7.28 (m, 2H), 7.10 (d, J = 7.5 Hz, 1H), 5.05-5.00 (m, 2H), 4.78 (d, J = 15.9 Hz, 1H), 4.36 (s, 1H), 4.09 (dd, J = 17.1, 2.4 Hz, 1H), 3.50 (dd, J = 17.1, 2.4 Hz, 1H), 2.60 (t, J = 2.4 Hz, 1H), 1.26 (d, J = 6.6 Hz, 3H). |

TABLE 6-continued

Compounds prepared as described in Example 57 using the appropriate Boc-protected intermediates and alkyl halide.

| Example | Structure | Characterization Data |
|---|---|---|
| 268 | 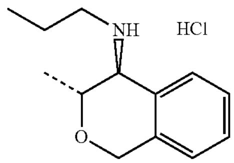 | MS (ESI): m/z 206 [M + H]. $^1$H NMR (300 M Hz, CD$_3$OD) δ 7.42-7.39 (m, 2H), 7.32-7.27 (m, 1H), 7.15 (d, J = 7.8 Hz, 1H), 4.80-4.75 (m, 2H), 4.51-4.48 (m, 1H), 4.08 (s, 1H), 3.01-2.87 (m, 2H), 1.71-1.62 (m, 2H), 1.18 (d, J = 6.6 Hz, 3H), 0.94 (t, J = 7.5 Hz, 3H). |
| 269 | 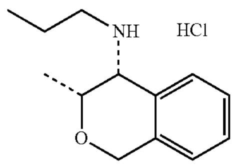 | MS (ESI): m/z 206 [M + H]. $^1$H NMR (300 M Hz, CD$_3$OD) δ 7.27-7.21 (m, 2H), 7.16-7.11 (m, 1H), 7.01 (d, J = 7.8 Hz, 1H), 4.79 (d, J = 15.6 Hz, 1H), 4.65 (d, J = 15.6 Hz, 1H), 4.07 (s, 1H), 3.89-3.86 (m, 1H), 2.70 (t, J = 8.4 Hz, 2H), 1.61-1.41 (m, 2H), 1.26 (d, J = 6.9 Hz, 3H), 0.74 (t, J = 7.5 Hz, 3H). |
| 270 | 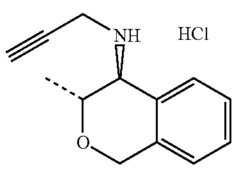 | MS (ESI): m/z 202 [M + H]. $^1$H NMR (300 M Hz, CDCl$_3$) δ 7.62 (d, J = 7.2 Hz, 1H), 7.42-7.28 (m, 2H), 7.10 (d, J = 7.5 Hz, 1H), 5.05-5.00 (m, 2H), 4.78 (d, J = 15.9 Hz, 1H), 4.36 (s, 1H), 4.09 (dd, J = 17.1, 2.4 Hz, 1H), 3.50 (dd, J = 17.1, 2.4 Hz, 1H), 2.60 (t, J = 2.4 Hz, 1H), 1.26 (d, J = 6.6 Hz, 3H). |
| 271 | 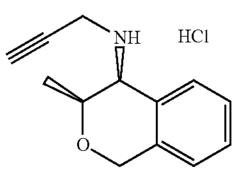 | MS (ESI): m/z 202 [M + H]. $^1$H NMR (300 M Hz, CDCl$_3$) δ 7.68 (d, J = 7.5 Hz, 1H), 7.41-7.26 (m, 2H), 7.09 (d, J = 7.5 Hz, 1H), 5.13 (d, J = 15.6 Hz, 1H), 4.85 (d, J = 15.6 Hz, 1H), 4.38 (s, 1H), 4.21 (dd, J = 16.8, 2.4 Hz, 1H), 4.06 (q, J = 6.9 Hz, 1H), 3.52 (dd, J = 16.8, 2.4 Hz, 1H), 2.57 (t, J = 2.4 Hz, 1H), 1.74 (d, J = 6.9 Hz, 3H). |
| 272 | 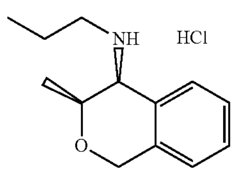 | MS (ESI): m/z 206 [M + H]. $^1$H NMR (300 M Hz, CDCl$_3$) δ 10.09 (brs, 1H), 9.23 (brs, 1H), 8.20-8.17 (m, 1H), 7.40-7.37 (m, 2H), 7.12-7.09 (m, 1H), 5.10 (d, J = 15.6 Hz, 1H), 4.82 (d, J = 15.6 Hz, 1H), 4.48 (s, 1H), 4.06-4.02 (m, 1H), 3.20-3.06 (m, 1H), 2.65-2.47 (m, 1H), 2.05-1.74 (m, 2H), 1.75 (d, J = 6.9 Hz, 3H), 0.88 (t, J = 7.2 Hz, 3H). |

Example 60. N,N-dimethylisochroman-4-amine hydrochloride

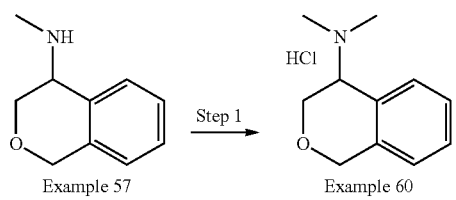

Step 1.

The compound of Example 57 (200 mg, 1.04 mmol) was dissolved in CH$_3$OH (4 mL). Paraformaldehyde (93.6 mg, 3.12 mmol), NaBH$_3$CN (196 mg, 3.12 mmol), and acetic acid (187 mg, 3.12 mmol) were added, and the reaction was stirred at room temperature for 1 h. The reaction mixture was poured into saturated aqueous Na$_2$CO$_3$ (10 mL) and extracted with EtOAc (4×10 mL). The combined organics were dried over anhydrous Na$_2$SO$_4$, filtered, and concentrated under reduced pressure. Purification by flash column chromatography (SiO$_2$, 100% EtOAc) gave N,N,-dimethylisochroman-4-amine (120 mg, 56%) as a white oil. The compound of Example 60 was prepared as described previously in Example 1 as an off-white solid. MS (ESI): m/z 178 [M+H]. $^1$H NMR (300 MHz, DMSO-d$_6$) δ 10.65 (brs, 1H), 7.54 (d, J=7.5 Hz, 1H), 7.48-7.43 (m, 1H), 7.37 (t, J=7.5 Hz, 1H), 7.23 (d, J=7.8 Hz, 1H), 4.89 (d, J=15.6 Hz, 1H), 4.73-4.65 (m, 2H), 4.49 (s, 1H), 3.85 (dd, J=13.8, 2.7 Hz, 1H), 2.82 (d, J=4.8 Hz, 3H), 2.64 (d, J=4.5 Hz, 3H).

TABLE 7

Compounds prepared as described in Example 60 using the appropriate amine.

| Example | Structure | Characterization Data |
|---|---|---|
| 61 | 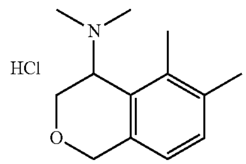 | MS (ESI): m/z 206 [M + H]. ¹H NMR (300 M Hz, CD₃OD) δ 7.31 (d, J = 8.1 Hz. 1H), 6.98 (d, J = 7.8 Hz, 1H), 4.97 (d, J = 15.6 Hz, 1H), 4.79 (d, J = 15.6 Hz, 1H), 4.67 (d, J = 12.6 Hz, 2H), 3.88 (d, J = 12.6 Hz, 1H), 2.92 (s, 6H), 2.35 (d, J = 2.7 Hz, 6H). |
| 62 | 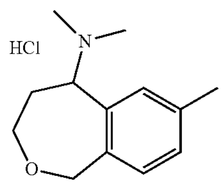 | MS (ESI): m/z 206 [M + H]. ¹H NMR (300 M Hz, CD₃OD) δ 7.29-7.26 (m, 2H), 7.19 (d, J = 7.8 Hz, 1H), 5.14 (d, J = 15.9 Hz, 1H), 4.81 (d, J = 15.9 Hz, 1H), 4.45 (d, J = 3.6 Hz, 1H), 4.21-4.15 (m, 1H), 4.00-3.96 (m, 1H), 3.13 (s, 3H), 2.72-2.68 (m, 1H), 2.66 (s, 3H), 2.41-2.48 (m, 1H), 2.38 (s, 3H). |
| 260 | 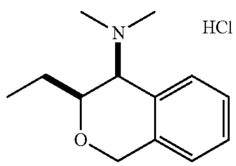 | MS (ESI): m/z 206 [M + H]. ¹H NMR (300 M Hz, DMSO-d₆) δ 7.55-7.50 (m, 2H), 7.37 (t, J = 7.2 Hz, 1H), 7.27 (d, J = 7.5 Hz, 1H), 5.02 (d, J = 15.9 Hz, 1H), 4.79 (d, J = 15.9 Hz, 1H), 4.55 (s, 1H), 3.80-372 (m, 1H), 2.86 (d, J = 5.1 Hz, 3H), 2.46 (d, J = 4.8 Hz, 3H), 1.97-1.87 (m, 2H), 1.03 (t, J = 7.2 Hz, 3H). |
| 261 | 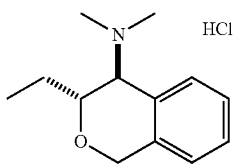 | MS (ESI): m/z 206 [M + H]. ¹H NMR (300 M Hz, DMSO-d₆) δ 7.63 (d, J = 7.5 Hz, 1H), 7.49-7.44 (m, 1H), 7.36 (t, J = 7.2 Hz, 1H), 7.23 (d, J = 7.8 Hz, 1H), 4.83 (d, J = 16.5 Hz, 1H), 4.66 (d, J = 16.5 Hz, 1H), 4.54-49 (m, 1H), 4.38 (s, 1H), 2.70 (s, 6H), 1.50-1.39 (m, 2H), 0.96 (t, J = 7.2 Hz, 3H). |
| 283 | 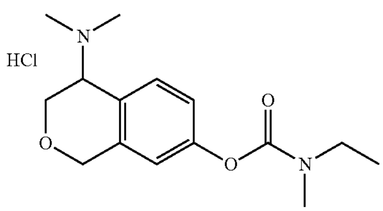 [SMILES: Cl ; CCN(C)C(=O)Oc1ccc2c(c1)COCC2N(C)C] | MS (ESI): m/z 279 [M + H]. ¹H NMR (300 M Hz, CD₃OD) δ 7.48 (d, J = 8.4 Hz, 1H), 7.06 (d, J = 8.4 Hz, 1H), 6.94 (s, 1H), 4.87 (d, J = 15.9 Hz, 1H), 4.68 (d, J = 15.9 Hz, 1H), 4.57 (d, J = 13.9 Hz, 1H), 4.31 (s, 1H), 3.86-3.79 (m, 1H), 3.44-3.26 (m, 2H), 2.95 (d, J = 33.9 Hz, 3H), 2.85 (s, 3H), 2.81 (s, 3H), 1.17 (dt, J = 22.5, 6.9 Hz, 3H). |
| 284 | 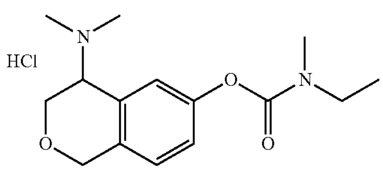 [SMILES: Cl ; CCN(C)C(=O)Oc1ccc2c(c1)C(N(C)C)COC2] | MS (ESI): m/z 279 [M + H]. ¹H NMR (300 M Hz, CD₃OD) δ 7.25 (d, J = 1.8 Hz, 1H), 7.20-7.15 (m, 2H), 4.88 (d, J = 15.9 Hz, 1H), 4.68 (d, J = 15.6 Hz, 1H), 4.55 (d, J = 13.8 Hz, 1H), 4.27 (s, 1H), 3.82 (dd, J = 14.1, 2.4 Hz, 1H), 3.43-3.27 (m, 2H), 2.95 (d, J = 36.0 Hz, 3H), 2.82 (s, 6H), 1.20-1.06 (m, 3H). |
| 285 | 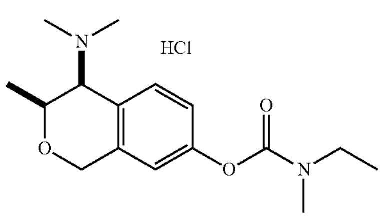 [SMILES: CCN(C)C(=O)Oc1ccc2c(c1)CO[C@@H](C)[C@H]2N(C)C ; Cl] | MS (ESI): m/z 293 [M + H]. ¹H NMR (300 M Hz, CD₃OD) δ 7.34-7.27 (m, 3H), 5.05 (d, J = 15.9 Hz, 1H), 4.89 (d, J = 15.9 Hz, 1H), 4.48-4.45 (m, 1H), 4.20-4.11 (m, 1H), 3.50-3.36(m, 2H), 3.06 (d, J = 36.3 Hz, 3H), 3.05 (s, 3H), 2.70 (s, 3H), 1.58 (d, J = 6.9 Hz, 3H), 1.24 (dt, J = 25.1, 7.2 Hz, 3H). |
| 286 | 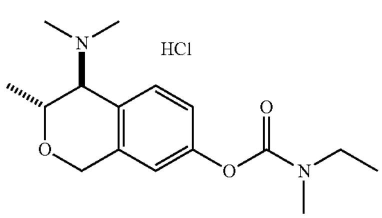 [SMILES: CCN(C)C(=O)Oc1ccc2c(c1)CO[C@H](C)[C@H]2N(C)C ; Cl] | MS (ESI): m/z 293 [M + H]. ¹H NMR (300 M Hz, CD₃OD) δ 7.34-7.26 (m, 3H), 4.90-4.88 (m, 2H), 4.83-4.76 (m, 1H), 4.26 (s, 1H), 3.58-3.36 (m, 2H), 3.06 (d, J = 36.0 Hz, 3H), 2.95 (s, 3H), 2.88 (s, 3H), 1.31-1.18 (m, 6H). |

TABLE 7-continued

Compounds prepared as described in Example 60 using the appropriate amine.

| Example | Structure | Characterization Data |
|---|---|---|
| 287 | 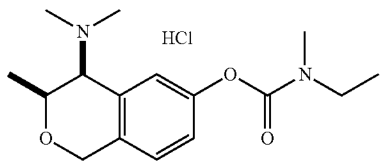 [SMILES: CCN(C)C(=O)Oc1ccc2c(c1)[C@H](N(C)C)[C@H](C)OC2 ; Cl] | MS (ESI): m/z 293 [M + H]. $^1$H NMR (300 M Hz, CD$_3$OD) δ 7.26-7.16 (m, 3H), 4.99 (d, J = 15.6 Hz, 1H), 4.85 (d, J = 15.6 Hz, 1H), 4.28 (s, 1H), 4.05 (q, J = 6.6 Hz, 1H), 3.57-3.31 (m, 2H), 3.05 (d, J = 34.1 Hz, 3H), 1.41 (d, J = 6.6 Hz, 3H), 1.24 (dt, J = 23.7, 7.2 Hz, 3H). |
| 288 | 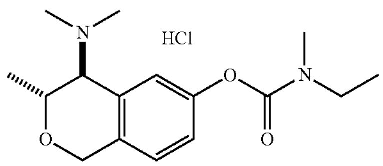 [SMILES: CCN(C)C(=O)Oc1ccc2c(c1)[C@H](N(C)C)[C@@H](C)OC2 ; Cl] | MS (ESI): m/z 293 [M + H]. $^1$H NMR (300 M Hz, CD$_3$OD) δ 7.09-7.00 (m, 3H), 4.69 (s, 2H), 4.17-4.04 (m, 2H), 3.40-3.32 (m, 2H), 2.89 (d, J = 34.8 Hz, 3H), 1.17 (d, J = 6.6 Hz, 3H), 1.09 (dt, J = 24.6, 7.2 Hz, 3H). |

Example 63. 4,4,7-Trimethyl-1,3,4,5-tetrahydrobenzo[c]oxepin-5-amine hydrochloride

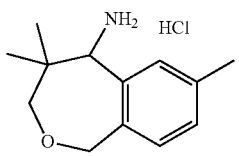

The compound of Example 63 was prepared as previously described in Example 1, using 4,4,7-trimethyl-3,4-dihydrobenzo[c]oxepin-5(1H)-one (prepared as described below). MS (ESI): m/z 206 [M+H]. $^1$H NMR (300 MHz, CD$_3$OD) δ 7.24-7.16 (m, 3H), 4.93-4.76 (m, 2H), 4.29 (s, 1H), 3.80 (d, J=12.6 Hz, 1H), 3.61 (d, J=12.6 Hz, 1H), 2.39 (s, 3H), 1.06 (s, 3H), 0.97 (s, 3H).

Synthesis of 4,7-methyl-3,4-dihydrobenzo[c]oxepin-5(1H)-one and 4,4,7-trimethyl-3,4-dihydrobenzo[c]oxepin-5(1H)-one

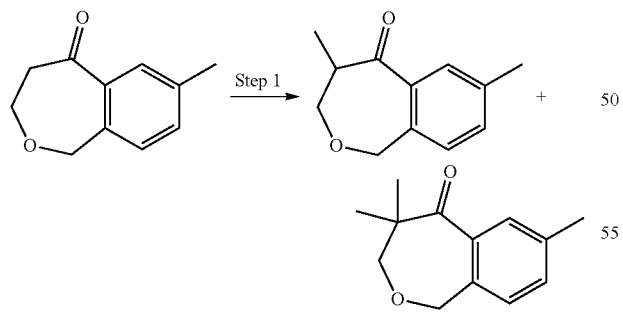

Step 1.

A solution of 1.2 g (6.8 mmol) of 7-methyl-3,4-dihydrobenzo[c]oxepin-5(1H)-one (prepared as previously described in Example 34) in DMF (100 mL) was treated with iodomethane (9.63 g, 67.9 mmol) and cesium carbonate (11.0 g, 33.9 mmol). The reaction was heated with stirring at 50° C. for 2 h, and then partitioned between EtOAc (250 mL) and water (300 mL). The organic phase was washed with brine (100 mL) dried over anhydrous Na$_2$SO$_4$, filtered, and concentrated under reduced pressure. Purification by flash column chromatography (SiO$_2$, gradient elution from 100% hexanes to 5% EtOAc/hexanes) gave 4,7-dimethyl-3,4-dihydrobenzo[c]oxepin-5(1H)-one (550 mg, 43%) as a colorless oil and 4,4,7-trimethyl-3,4-dihydrobenzo[c]oxepin-5(1H)-one (320 mg, 23%) as a colorless oil.

4,7-dimethyl-3,4-dihydrobenzo[c]oxepin-5(1H)-one: MS (ESI)

m/z 190 [M+H].

4,4,7-trimethyl-3,4-dihydrobenzo[c]oxepin-5(1H)-one

MS (ESI): m/z 204 [M+H].

Example 68. 6-Fluoro-4-methylisochroman-4-amine hydrochloride

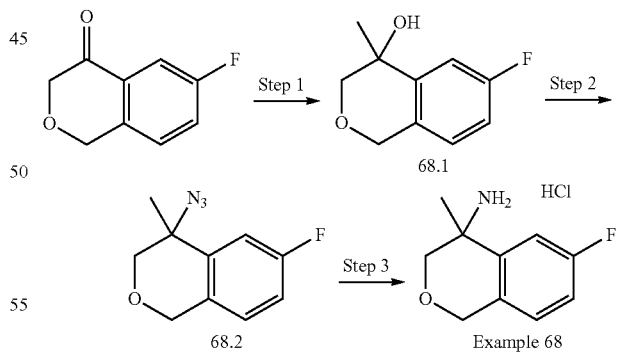

Step 1.

A solution of 6-fluoroisochroman-4-one (420 mg, 2.52 mmol, prepared as described in Example 6) in diethyl ether (40 mL) was cooled in an ice bath and treated with methylmagnesium bromide (3.78 mL, 3.78 mmol, 1M in THF). The reaction was stirred at 0° C. for 1 h. Saturated aqueous NH$_4$Cl (60 mL) and EtOAc (40 mL) were added to the reaction vessel and the resulting biphasic mixture was transferred to a separatory funnel. The layers were separated and the aqueous phase was washed with EtOAc (2×40 mL). The combined organics were dried over anhydrous Na$_2$SO$_4$, filtered, and concentrated under reduced pressure to provide 6-fluoro-4-methylisochroman-4-ol 68.1 (455 mg, 99%) as yellow oil. GC-MS (ESI) m/z 182 [M+H].

Step 2.

Compound 68.1 (250 mg, 1.37 mmol) was dissolved in toluene (6 mL) and cooled in an ice bath. Azidotrimethylsilane (394 mg, 3.42 mmol) and BF$_3$-Et$_2$O (1.24 g, 4.11 mmol) were added, the ice bath was removed, and the reaction was stirred at 30° C. for 2 days. The reaction mixture was carefully quenched by the slow addition of NH$_4$OH and extracted with EtOAc (3×50 mL). The combined organic layers were washed with brine, dried over anhydrous Na$_2$SO$_4$, filtered, and concentrated under reduced pressure. Purification by flash column chromatography (SiO$_2$, 100% hexanes) afforded 4-azido-6-fluoro-4-methyl isochroman 68.2 (240 mg, 84%) as yellow oil. $^1$HNMR (300 MHz, CDCl3) δ 7.19 (d, J=1.8 Hz, 1H), 7.05-6.99 (m, 2H), 4.86 (d, J=15.0 Hz, 1H), 4.74 (d, J=14.7 Hz, 1H), 4.05 (d, J=11.7 Hz, 1H), 3.78 (d, J=12.0 Hz, 1H), 1.49 (s, 3H).

Step 3.

Compound 68.2 (240 mg, 1.15 mmol) was dissolved in THF (10 mL), cooled in an ice bath, and treated with LiAlH$_4$ (87.2 mg, 2.30 mmol) in a single portion. The ice bath was removed, and the reaction mixture was stirred at room temperature for 2 h. Excess hydride was quenched by the sequential addition of water (0.5 mL) and aqueous 2M NaOH (0.5 mL). The resulting mixture was partitioned between aqueous 1M HCl (40 mL) and CH$_2$Cl$_2$ (50 mL). The aqueous phase was washed with CH$_2$Cl$_2$ (2×50 mL) and then made basic by the addition of aqueous 1M NaOH (40 mL). The aqueous phase was extracted with CH$_2$Cl$_2$ (4×50 mL). The combined organics were dried over anhydrous Na$_2$SO$_4$, filtered, and concentrated under reduced pressure to give crude 6-fluoro-4-methylisochroman-4-amine, which was purified by preparative HPLC and converted to the compound of Example 68 (67 mg, 27%) as a white solid as described previously in Example 1. MS (ESI): m/z 182 [M+H]. $^1$H NMR (300 MHz, CD$_3$OD) δ 7.39 (dd, J=9.9, 2.4 Hz, 1H), 7.24-7.15 (m, 2H), 4.94 (d, J=15.2 Hz, 1H), 4.83 (d, J=15.3 Hz, 1H), 4.06 (d, J=12.6 Hz, 1H), 3.82 (d, J=12.6 Hz, 1H), 1.66 (s, 3H).

Example 72. cis-3-methylisochroman-4-amine hydrochloride

Example 73. trans-3-methylisochroman-4-amine hydrochloride

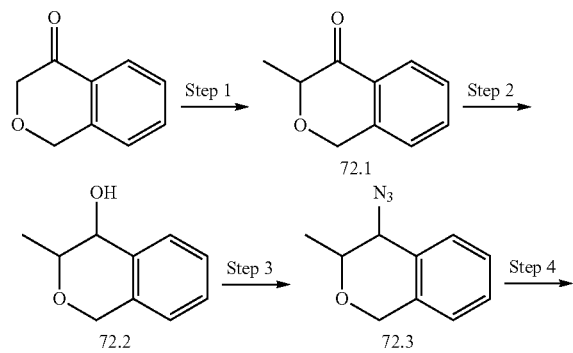

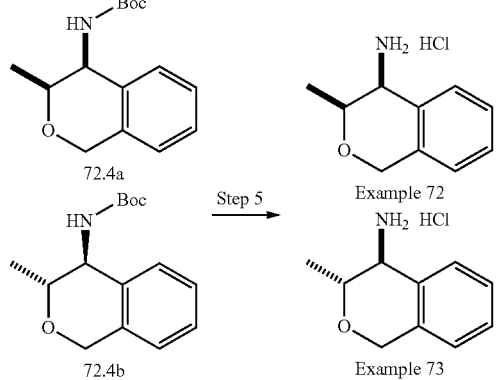

Step 1.

3-Methylisochroman-4-one 72.1 was prepared as previously described in Example 69 using isochroman-4-one (prepared as previously described in Example 12) and iodomethane. MS (ESI): m/z 163 [M+H]. $^1$HNMR (300 MHz, CDCl$_3$) δ 8.05 (d, J=7.5 Hz, 1H), 7.59-7.53 (m, 1H), 7.49-7.39 (m, 1H), 7.21 (d, J=7.5 Hz, 1H), 5.18 (s, 2H), 4.28 (q, J=6.6 Hz, 1H), 1.75 (d, J=6.6 Hz, 3H).

Step 2.

3-Methylisochroman-4-ol 72.2 was prepared as previously described in Example 1. $^1$H NMR (300 MHz, CDCl$_3$) δ 7.56-7.45 (m, 1H), 7.34-7.24 (m, 2H), 7.07-7.01 (m, 1H), 4.89-4.82 (m, 2H), 4.46-4.40 (m, 0.5H), 4.40-4.25 (m, 0.5H), 4.15-4.13 (m, 0.5H), 3.69-3.64 (m, 0.5H), 1.44 (d, J=6.3 Hz, 3H).

Step 3.

4-Azido-3-methylisochroman 72.3 was prepared as previously described in Example 1. $^1$H NMR (300 MHz, CDCl$_3$) δ 7.45 (d, J=8.7 Hz, 1H), 7.43-7.24 (m, 2H), 7.02 (d, J=8.4 Hz, 1H), 4.80 (d, J=2.7 Hz, 2H), 4.11 (d, J=7.8 Hz, 1H), 3.80-3.76 (m, 1H), 1.44 (d, J=6.3 Hz, 3H).

Step 4.

LiAlH$_4$ (119 mg, 3.15 mmol) was added to a room temperature solution of compound 72.3 (200 mg, 1.05 mmol) in THF (10 mL) in a single portion, and the reaction was stirred for 1 h. A solution of aqueous 1M NaOH (5 mL), di-tert-butyl dicarbonate (916 mg, 4.20 mmol) and Na$_2$CO$_3$ (333 mg, 3.15 mmol) were added to the reaction vessel, and the biphasic mixture was stirred vigorously for 2 h. After transferring to a separatory funnel, the mixture was partitioned between water (20 mL) and EtOAc (100 mL). The organic phase was washed with brine (40 mL), dried over anhydrous Na$_2$SO$_4$, filtered, and concentrated under reduced pressure. Purification by flash column chromatography (SiO$_2$, gradient elution from 100% hexanes to 5% EtOAc/hexanes) provided tert-butyl ((3S,4S)-3-methylisochroman-4-yl) carbamate 72.4a (90.0 mg, 32%) as a white solid and tert-butyl ((3R,4S)-3-methylisochroman-4-yl)carbamate 72.4b (70.0 mg, 25%) as a white solid.

Rac-tert-butyl ((3 S,4S)-3-methylisochroman-4-yl)carbamate 72.4a TLC higher Rf. MS (ESI): m/z 286 [M+Na]. $^1$HNMR (300 MHz, CDCl$_3$) δ 7.457.42 (m, 1H), 7.28-7.25 (m, 2H), 7.03-7.00 (m, 1H), 4.954.81 (m, 1H), 4.82 (s, 2H), 4.64 (d, J=8.7 Hz, 1H), 3.91-3.84 (m, 1H), 1.46 (s, 9H), 1.34 (d, J=6.3 Hz, 3H).

Rac-tert-butyl ((3R,4S)-3-methylisochroman-4-yl)carbamate 72.4b TLC lower Rf. MS (ESI): m/z 286 [M+Na]. $^1$HNMR (300 MHz, CDCl$_3$) δ 7.42-7.37 (m, 1H), 7.28-7.21

(m, 2H), 7.02-7.00 (m, 1H), 4.81 (s, 2H), 4.79-4.65 (m, 2H), 3.72-3.67 (m, 1H), 1.48 (s, 9H), 1.38 (d, J=6.3 Hz, 3H).

Step 5.

The compounds of Example 72 and Example 73 were prepared as previously described in Example 1.

Example 72

MS (ESI): m/z 164 [M+H]. ¹H NMR (300 MHz, CDCl₃) δ 7.42-7.33 (m, 3H), 7.18 (d, J=6.9 Hz, 1H), 4.99-4.83 (m, 2H), 4.25 (s, 1H), 4.03-4.05 (m, 1H), 1.40 (d, J=6.6 Hz, 3H).

Example 73

MS (ESI): m/z 164 [M+H]. ¹H NMR (300 MHz, CD₃OD) δ 7.46-7.37 (m, 3H), 7.21 (d, J=7.2 Hz, 1H), 4.97-4.78 (m, 2H), 4.37-4.20 (m, 2H), 1.33 (d, J=6.6 Hz, 3H).

Example 74.
cis-4,7-dimethyl-1,3,4,5-tetrahydrobenzo[c]oxepin-5-amine hydrochloride

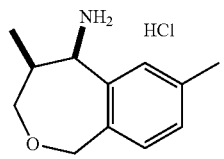

The compound of Example 74 was prepared as previously described in Example 72, using 4,7-methyl-3,4-dihydrobenzo[c]oxepin-5(1H)-one (prepared as described in Example 63). MS (ESI): m/z 192 [M+H]. ¹H NMR (300 MHz, CD₃OD) δ 7.23-7.06 (m, 3H), 5.07 (d, J=15.3 Hz, 1H), 4.79 (d, J=15.3 Hz, 1H), 4.28 (s, H), 4.21-4.15 (m, 1H), 3.61-3.54 (m, 1H), 2.52-2.44 (m, 1H), 2.38 (s, 3H), 0.93 (d, J=7.2 Hz, 3H).

Example 75.
trans-4,7-dimethyl-1,3,4,5-tetrahydrobenzo[c]oxepin-5-amine hydrochloride

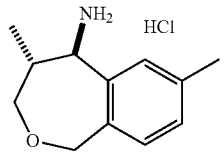

The compound of Example 75 was prepared as previously described in Example 72, using 4,7-methyl-3,4-dihydrobenzo[c]oxepin-5(1H)-one (prepared as described in Example 63). MS (ESI): m/z 192 [M+H]. ¹H NMR (300 MHz, CD₃OD) δ 7.20-7.17 (m, 2H), 7.11 (s, 1H), 4.82-4.69 (m, 3H), 4.10-4.05 (m, 1H), 3.88-3.82 (m, 1H), 2.50-2.41 (m, 1H), 2.40 (s, 3H). 0.94 (d, J=6.9 Hz, 3H).

Example 76. cis-3,6-Dimethylisochroman-4-amine hydrochloride

Example 77.
trans-3,6-Dimethylisochroman-4-amine hydrochloride

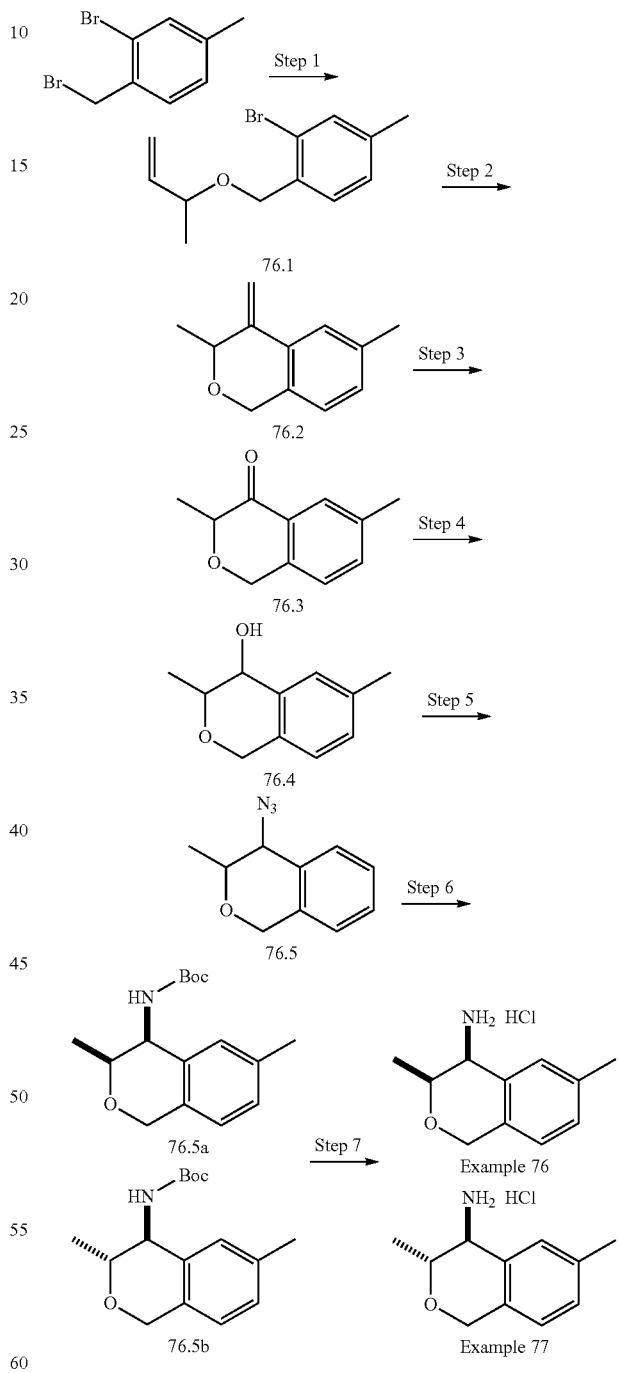

Step 1.

2-Bromo-1-((but-3-en-2-yloxy)methyl)-4-methylbenzene 76.1 was prepared as previously described in Example 10 using 2-bromo-1-(bromomethyl)-4-methylbenzene and but-3-en-2-ol. MS (ESI): m/z 256 [M+H]. ¹H NMR (300 MHz, CDCl₃) δ 7.38 (s, 1H), 7.37 (d, J=7.8 Hz, 1H), 7.12 (d, J=7.8

Hz, 1H), 5.89-5.78 (m, 1H), 5.29-5.18 (m, 2H), 4.57 (d, J=12.9 Hz, 1H), 4.45 (d, J=12.9 Hz, 1H), 2.33 (s, 3H), 1.33 (d, J=6.3 Hz, 3H).

Step 2.

3,6-Dimethyl-4-methyleneisochroman 76.2 was prepared as previously described in Example 10. MS (ESI): m/z 175 [M+H]. $^1$H NMR (300 MHz, CDCl$_3$) δ 7.49 (s, 1H), 7.08 (d, J=7.8 Hz, 1H), 6.95 (d, J=7.8 Hz, 1H), 5.63 (d, J=0.9 Hz, 1H), 5.07 (d, J=1.5 Hz, 1H), 4.82 (d, J=6.9 Hz, 2H), 4.45-4.36 (m, 1H), 2.37 (s, 3H), 1.51 (d, J=6.6 Hz, 3H).

Step 3.

3,6-Dimethylisochroman-4-one 76.3 was prepared as previously described in Example 10. MS (ESI): m/z 177 [M+H]. $^1$H NMR (300 MHz, CDCl$_3$) δ 7.86 (s, 1H), 7.37 (d, J=7.5 Hz, 1H), 7.11 (d, J=7.5 Hz, 1H), 4.91 (s, 2H), 4.25 (q, J=6.6 Hz, 1H), 2.41 (s, 3H), 1.50 (d, J=6.6 Hz, 3H).

Step 4.

3,6-Dimethylisochroman-4-ol 76.4 was prepared as previously described in Example 1. $^1$H NMR (300 MHz, CDCl$_3$) δ 7.30-7.24 (m, 1H), 7.14-7.06 (m, 1H), 6.95-6.90 (m, 1H), 4.78-4.76 (m, 2H), 4.01-4.35 (m, 0.75H), 4.25-4.21 (m, 0.25H), 3.80-3.77 (m, 0.25H), 3.68-3.60 (m, 0.75H), 2.37 (s, 3H), 1.42 (d, J=6.3 Hz, 3H).

Step 5.

4-Azido-3,3-dimethylisochroman 76.5 was prepared as previously described in Example 1.

Step 6.

Compound 76.5 (500 mg, 2.46 mmol) was dissolved in THF (30 mL) and treated with PPh$_3$ (645 mg, 2.46 mmol). The reaction was stirred at room temperature for 30 min. Water (10 mL) was added, and the solution was heated to 60° C. for 12 h. After cooling to room temperature, the mixture was partitioned between aqueous 1M HCl (30 mL) and EtOAc (50 mL). The aqueous phase was washed with EtOAc (2×30 mL). The aqueous phase was made basic by the addition of Na$_2$CO$_3$ (521 mg, 4.92 mmol), and then treated with di-tert-butyl dicarbonate (1.07 g, 4.92 mmol) and THF (40 mL). The biphasic mixture was stirred vigorously at room temperature for 30 min, and then partitioned between water (30 mL) and EtOAc (50 mL). The aqueous phase was extracted with EtOAc (2×50 mL). The combined organics were washed with brine, dried over anhydrous Na$_2$SO$_4$, filtered, and concentrated under reduced pressure. Purification by flash column chromatography (SiO$_2$, gradient elution from 100% hexanes to 97% EtOAc/hexanes) gave tert-butyl-(cis-3,6-dimethylisochroman-4-yl)carbamate 76.5a (300 mg, 44%) as a white solid and tert-butyl-(trans-3,6-dimethylisochroman-4-yl)carbamate 76.5b (170 mg, 25%) as a white solid.

tert-butyl-(cis-3,6-dimethylisochroman-4-yl)carbamate 76.5a TLC higher Rf. MS (ESI): m/z 300 [M+Na].

tert-butyl-(trans-3,6-dimethylisochroman-4-yl)carbamate 76.5b TLC lower Rf. MS (ESI): m/z 300 [M+Na].

Step 7.

The compounds of Example 76 and Example 77 were prepared as previously described in Example 1.

Example 76

MS (ESI): m/z 178 [M+H]. $^1$H NMR (300 MHz, DMSO-d6) δ 8.27 (brs, 3H), 7.31 (s, 1H), 7.21 (d, J=7.8 Hz, 1H), 7.06 (d, J=7.8 Hz, 1H), 4.86-4.71 (m, 2H), 4.17 (d, J=4.5 Hz, 1H), 3.97-3.91 (m, 1H), 2.31 (s, 3H), 1.31 (d, J=6.6 Hz, 3H).

Example 77

MS (ESI): m/z 178 [M+H]. $^1$H NMR (300 MHz, DMSO-d6) δ 8.5 (brs, 3H), 7.41 (s, 1H), 7.19 (d, J=7.8 Hz, 1H), 7.07 (d, J=8.1 Hz, 1H), 4.71 (s, 2H), 4.11 (d, J=3.6 Hz, 2H), 2.31 (s, 3H), 1.27 (d, J=6.3 Hz, 3H).

TABLE 8

Compounds prepared as described in Example 76 using the appropriately substituted starting materials.

| Example | Structure | Characterization Data |
|---|---|---|
| 78 | HCl NH$_2$ (cis-3-methyl-6,7-dimethylisochroman-4-amine) | MS (ESI): m/z 192 [M + H]. $^1$H NMR (300 M Hz, DMSO-d$_6$) δ 8.17 (brs, 3H), 7.18 (d, J = 7.8 Hz, 1H), 6.88 (d, J = 7.8 Hz, 1H), 4.86-4.70 (m, 2H), 4.36 (s, 1H), 3.90-3.83 (m, 1H), 2.23 (s, 3H), 2.21 (s, 3H), 1.32 (d, J = 6.6 Hz, 3H). |
| 79 | HCl NH$_2$ (trans-3-methyl-6,7-dimethylisochroman-4-amine) | MS (ESI): m/z 192 [M + H]. $^1$H NMR (300 M Hz, DMSO-d$_6$) δ 8.36 (brs, 3H), 7.19 (d, J = 7.8 Hz, 1H), 6.90 (d, J = 7.8 Hz, 1H), 4.74-4.20 (d, J = 5.1 Hz, 2H), 4.43-4.33 (m, 2H), 2.25 (s, 6H), 1.11 (d, J = 6.6 Hz, 3H). |
| 80 | HCl NH$_2$ Cl (cis-5-chloro-3-methylisochroman-4-amine) | MS (ESI): m/z 198 [M + H]. $^1$H NMR (300 M Hz, CD$_3$OD) δ 7.47-7.31 (m, 2H), 7.28-7.17 (m, 1H), 5.01-4.78 (m, 2 H), 4.45 (d, J = 2.1 Hz, 1H), 4.05-3.89 (m, 1H), 1.41 (d, J = 6 Hz, 3H). |
| 81 | HCl NH$_2$ Cl (trans-5-chloro-3-methylisochroman-4-amine) | MS (ESI): m/z 198 [M + H]. $^1$H NMR (300 M Hz, DMSO-d$_6$) δ 8.55 (brs, 3H), 7.50-7.42 (m, 2H), 7.22 (dd, J = 3 Hz, 6 Hz, 1H), 4.85-4.71 (m, 2H), 4.51-4.44 (m, 1H), 4.32 (d, J = 3 Hz, 1H), 1.15 (d, J = 6 Hz, 3H). |

TABLE 8-continued

Compounds prepared as described in Example 76 using the appropriately substituted starting materials.

| Example | Structure | Characterization Data |
|---|---|---|
| 82 | 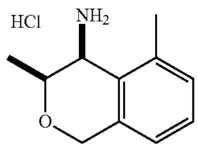 | MS (ESI): m/z 178 [M + H]. $^1$H NMR (300 M Hz, DMSO-$d_6$) δ 8.13 (brs, 3H), 7.29 (t, J = 7.5 Hz, 1H), 7.16 (d, J = 7.5 Hz, 1H), 6.99 (d, J = 7.5 Hz, 1H), 4.92-4.76 (m, 2H), 4.34-4.32 (m, 1H), 3.95-3.89 (m, 1H), 2.37 (s, 3H), 1.33 (d, J = 6.6 Hz, 3H). |
| 83 | 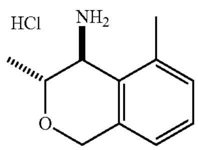 | MS (ESI): m/z 178 [M + H]. $^1$H NMR (300 M Hz, DMSO-$d_6$) δ 8.42 (s, 1H), 7.30 (d, J = 9 Hz, 1H), 7.15 (d, J = 9 Hz, 1H), 7.00 (d, J = 9 Hz, 1H), 4.83-4.69 (m, 2H), 4.46-4.39 (m, 1H), 4.26 (s, 1H), 2.41 (s, 3H), 1.12 (d, J = 9 Hz, 3H). |
| 84 | 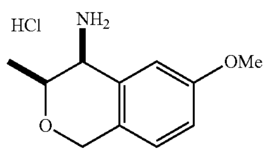 | MS (ESI): m/z 194 [M + H]. $^1$H NMR (300 M Hz, CD$_3$OD) δ 7.09 (d, J = 8.4 Hz, 1H), 7.01-6.97 (m, 1H), 4.92-4.82 (m, 2H), 4.19 (s, 1H), 4.02-3.99 (m, 1H), 3.82 (s, 3H), 1.38 (d, J = 6.9 Hz, 3H). |
| 85 | 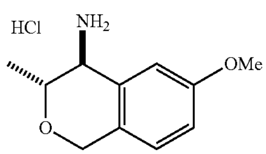 | MS (ESI): m/z 194 [M + H]. $^1$H NMR (300 M Hz, CD$_3$OD) δ 7.12-7.08 (m, 1H), 7.02-6.97 (m, 2H), 4.78 (s, 2H), 4.25-4.20 (m, 1H), 4.14 (d, J = 2.7 Hz, 1H), 3.82 (s, 3H), 1.30 (d, J = 6.6 Hz, 3H). |
| 86 | 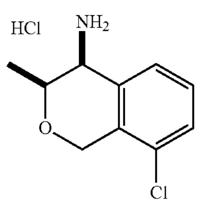 | MS (ESI): m/z 198 [M + H]. $^1$H NMR (300 M Hz, CD$_3$OD) δ 7.50-7.47 (m, 1H), 7.41-7.37 (m, 1H), 5.02 (d, J = 16.5 Hz, 1H), 4.77 (d, J = 16.2 Hz, 1H), 4.29 (s, 1H), 4.04-3.99 (m, 1H), 1.41 (d, J = 6.6 Hz, 3H). |
| 87 | 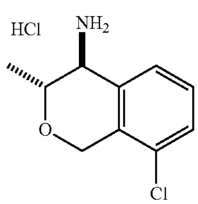 | MS (ESI): m/z 198 [M + H]. $^1$H NMR (300 M Hz, CD$_3$OD) δ 7.52-7.48 (m, 1H), 7.43-7.39 (m, 2H), 4.90-4.73 (m, 2H)-4.33-4.29 (m, 1H), 4.23 (d, J = 2.1 Hz, 1H), 1.29 (d, J = 6.9 Hz, 3H). |
| 88 | 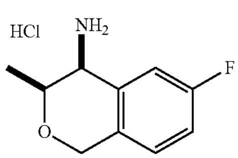 | MS (ESI): m/z 182 [M + H]. $^1$H NMR (300 M Hz, DMSO-$d_6$) δ 8.40 (brs, 3H), 7.43 (dd, J = 8.4 Hz, 1.5 Hz, 1H), 7.29-7.25 (m, 2H), 4.87 (d, J = 12 Hz, 1H), 4.76 (d, J = 11.7 Hz, 1H), 4.27 (s, 1H), 4.00-3.94 (m, 1H), 1.33 (d, J = 4.8 Hz, 3H). |
| 89 | 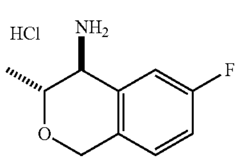 | MS (ESI): m/z 182 [M + H]. $^1$H NMR (300 M Hz, DMSO-$d_6$) δ 8.64 (brs, 3H), 7.53 (d, J = 8.0 Hz, 1H), 7.25 (dd, J = 1.8 Hz, 8.0 Hz, 2H), 4.81-4.71 (m, 2H), 4.21 (d, J = 3.0 Hz, 1H), 4.11-4.08 (m, 1H), 1.31 (t, J = 4.8 Hz, 3H). |
| 90 | 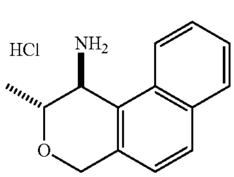 [SMILES: C[C@H]1OCc2ccc3ccccc3c2[C@@H]1N ; Cl] | MS (ESI): m/z 214 [M + H]. $^1$H NMR (300 M Hz, CD$_3$OD) δ 8.13 (d, J = 8.0 Hz, 1H), 8.00 (d, J = 8.0 Hz, 2H), 7.72-7.70 (m, 1H), 7.64-7.62 (m, 1H), 7.31 (d, J = 8.0 Hz, 1H), 5.04 (s, 2H), 4.97 (s, 1H), 4.59-4.57 (m, 1H), 1.35 (d, J = 4.0 Hz, 3H). |

TABLE 8-continued

Compounds prepared as described in Example 76 using the appropriately substituted starting materials.

| Example | Structure | Characterization Data |
|---|---|---|
| 91 | 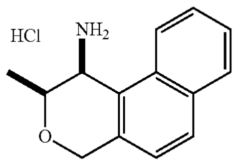 [SMILES: C[C@@H]1OCc2ccc3ccccc3c2[C@@H]1N ; Cl] | MS (ESI): m/z 214 [M + H]. $^1$H NMR (300 M Hz, CD$_3$OD) δ 8.10 (d, J = 8.0 Hz, 1H), 7.99 (d, J = 8.0 Hz, 2H), 7.72-7.70 (m, 1H), 7.64-7.62 (m, 1H), 7.31 (d, J = 8.0 Hz, 1H), 5.13-5.10 (m, 2H), 5.02 (s, 1H), 4.20-4.18 (m, 1H), 1.55 (d, J = 4.0 Hz, 3H). |
| 92 | 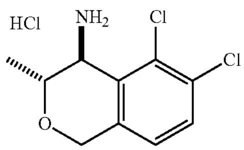 | MS (ESI): m/z 232 [M + H]. $^1$H NMR (300 M Hz, CD$_3$OD) δ 7.64 (d, J = 6.3 Hz, 1H), 7.20 (d, J = 6.3 Hz, 1H), 4.84 (s, 2H), 4.51 (s, 1H), 4.45-4.40 (m, 1H), 1.27 (d, J = 6.3 Hz, 3H). |
| 93 | 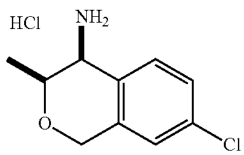 | MS (ESI): m/z 198 [M + H]. $^1$H NMR (300 M Hz, CD$_3$OD) δ 7.43 (d, J = 8.4 Hz, 1H), 7.37-7.33 (m, 1H), 7.25-7.19 (m, 1H), 4.97-4.80 (m, 2H), 4.28-4.25 (m, 1H), 4.05-3.98 (m, 1H), 1.39 (d, J = 6.6 Hz, 3H). |
| 94 | 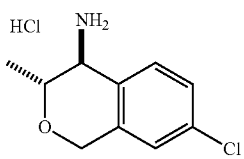 | MS (ESI): m/z 198 [M + H]. $^1$H NMR (300 M Hz, CD$_3$OD) δ 7.44-7.35 (m, 2H), 7.26 (s, 1H), 4.82 (s, 2H), 4.31-4.23(m, 1H), 4.24-4.18 (m, 1H), 1.31 (d, J = 6.6 Hz, 3H). |
| 95 | 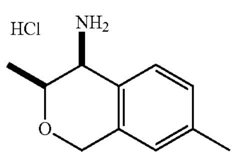 | MS (ESI): m/z 178 [M + H]. $^1$H NMR (300 M Hz, CD$_3$OD) δ 7.29 (d, J = 7.8 Hz, 1H), 7.16 (d, J = 7.8 Hz, 1H), 7.00 (s, 1H), 4.92 (d, J = 15.6 Hz, 1H), 4.82 (d, J = 15.6 Hz, 1H), 4.20 (s, 1H), 4.04-3.91 (m, 1H), 2.34 (s, 3H), 1.38 (d, J = 6.6 Hz, 3H). |
| 96 | 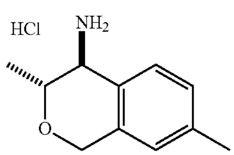 | MS (ESI): m/z 178 [M + H]. $^1$H NMR (300 M Hz, CD$_3$OD) δ 7.31 (d, J = 7.8 Hz, 1H), 7.16 (d, J = 7.8 Hz, 1H), 7.00 (s, 1H), 4.80 (s, 2H), 4.28-4.21 (m, 1H), 4.13 (s, 1H), 2.34 (s, 3H), 1.29 (d, J = 6.9 Hz, 3H). |
| 97 | 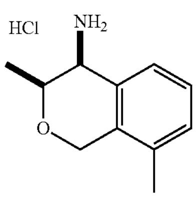 | MS (ESI): m/z 178 [M + H]. $^1$H NMR (300 M Hz, DMSO-d$_6$) δ 8.23 (brs, 3H), 7.31-7.20 (m, 3H), 4.82 (d, J = 15.9 Hz, 1H), 4.69 (d, J = 15.9 Hz, 2H), 4.22-4.21 (m, 1H), 3.97-3.90 (m, 1H), 2.14 (s, 3H), 1.31 (d, J = 6.6 Hz, 3H). |
| 98 | 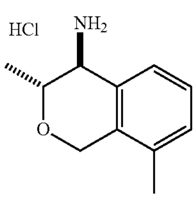 | MS (ESI): m/z 178 [M + H]. $^1$H NMR (300 M Hz, DMSO-d$_6$) δ 8.54 (brs, 3H), 7.42 (d, J = 8.4 Hz, 1H), 7.27-7.18 (m, 2H), 4.68 (s, 2H), 4.20-4.12 (m, 2H), 2.15 (s, 3H), 1.24 (d, J = 6.3 Hz, 3H). |
| 194 | 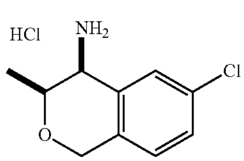 | MS (ESI): m/z 198 [M + H]. $^1$H NMR (300 M Hz, CD$_3$OD) δ 7.50 (d, J = 2.1 Hz, 1H), 7.43 (dd, J = 8.3, 2.1 Hz, 1H), 7.20 (d, J = 8.3 Hz, 1H), 4.95 (d, J = 15.8 Hz, 1H), 4.83 (d, J = 15.8 Hz, 1H), 4.28 (s, 1H), 4.03 (m, 1H), 1.40 (d, J = 6.6 Hz, 3H). |

TABLE 8-continued

Compounds prepared as described in Example 76 using the appropriately substituted starting materials.

| Example | Structure | Characterization Data |
|---|---|---|
| 196 | 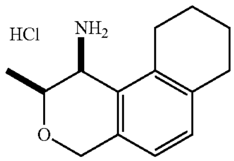 [SMILES: C[C@@H]1OCc2ccc3c(c2[C@@H]1N)CCCC3 ; Cl] | MS (ESI): m/z 218 [M + H]. $^1$H NMR (300 M Hz, CD$_3$OD) δ 7.11 (d, J = 7.9 Hz, 1H), 6.89 (d, J = 7.8 Hz, 1H), 4.90 (d, J = 15.5 Hz, 1H), 4.83 (d, J = 15.5 Hz, 1H), 4.34 (s, 1H), 3.96 (m, 1H), 2.86-2.73 (m, 4H), 1.92-1.72 (m, 4H), 1.39 (d, J = 6.6 Hz, 3H). |
| 197 | 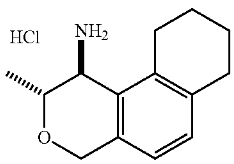 [SMILES: C[C@H]1OCc2ccc3c(c2[C@@H]1N)CCCC3 ; Cl] | MS (ESI): m/z 218 [M + H]. $^1$H NMR (300 M Hz, CD$_3$OD) δ 7.11 (d, J = 7.9 Hz, 1H), 6.89 (d, J = 7.8 Hz, 1H), 4.90 (d, J = 15.5 Hz, 1H), 4.83 (d, J = 15.5 Hz, 1H), 4.34 (s, 1H), 3.96 (m, 1H), 2.86-2.73 (m, 4H), 1.92-1.72 (m, 4H), 1.39 (d, J = 6.6 Hz, 3H). |
| 212 | 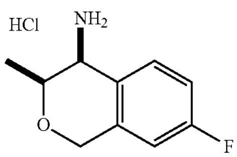 | MS (ESI): m/z 182 [M + H]. $^1$H NMR (300 M Hz, D$_2$O) δ 7.42 (dd, J = 8.6, 5.5 Hz, 1H), 7.08 (td, J = 8.7, 2.6 Hz, 1H), 6.94 (dd, J = 9.4, 2.5 Hz, 1H), 4.99-4.86 (m, 2H), 4.35 (s, 1H), 4.16-4.08 (m, 1H), 1.37 (d, J = 6.7 Hz, 3H). |
| 213 | 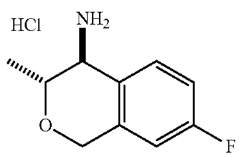 | MS (ESI): m/z 182 [M + H]. $^1$H NMR (300 M Hz, D$_2$O) δ 7.42 (dd, J = 8.6, 5.5 Hz, 1H), 7.10 (td, J = 8.7, 2.7 Hz, 1H), 6.95 (dd, J = 9.3, 2.6 Hz, 1H), 4.89-4.82 (m, 2H), 4.42-4.35 (m, 1H), 4.29 (d, J = 1.7 Hz, 1H), 1.26 (d, J = 6.7 Hz, 3H). |
| 214 | 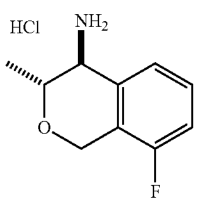 | MS (ESI): m/z 182 [M + H]. $^1$H NMR (300 M Hz, CD$_3$OD) δ 7.45-7.38 (m, 1H), 7.30 (d, J = 7.5 Hz, 1H), 7.24-7.11 (m, 1H), 4.88-4.78 (m, 2H), 4.35-4.21 (m, 2H), 1.32 (d, J = 6.7 Hz, 3H). |
| 215 | 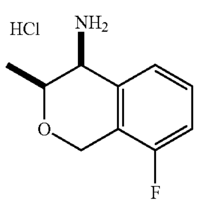 | MS (ESI): m/z 182 [M + H]. $^1$H NMR (300 M Hz, CD$_3$OD) δ 7.45-7.35 (m, 1H), 7.27 (d, J = 7.5 Hz, 1H), 7.22-7.12 (m, 1H), 5.05 (d, J = 16.1 Hz, 1H), 4.83 (d, J = 16.1 Hz, 1H), 4.31 (s, 1H), 4.07-4.00 (m, 1H), 1.41 (d, J = 6.6 Hz, 3H). |
| 216 | 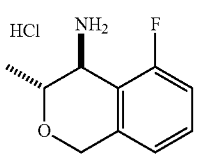 | MS (ESI): m/z 182 [M + H]. $^1$H NMR (300 M Hz, CD$_3$OD) δ 7.41-7.43 (m, 1H), 7.14 (t, J = 9.0 Hz, 1H), 7.06 (d, J = 7.7 Hz, 1H), 4.86 (s, 2H), 4.45-4.27 (m, 2H), 1.30 (d, J = 6.7 Hz, 3H). |
| 217 | 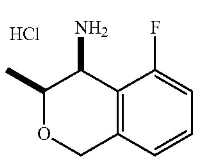 | MS (ESI): m/z 182 [M + H]. $^1$H NMR (300 M Hz, CD$_3$OD) δ 7.50-7.42 (m, 1H), 7.12 (t, J = 9.0 Hz, 1H), 7.04 (d, J = 7.8 Hz, 1H), 4.99 (d, J = 15.9 Hz, 1H), 4.86 (d, J = 16.0 Hz, 1H), 4.49 (s, 1H), 4.04-3.97 (m, 1H), 1.42 (d, J = 6.6 Hz, 3H). |
| 219 | 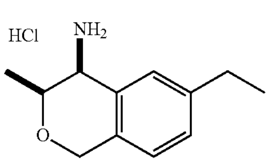 | MS (ESI): m/z 192 [M + H]. $^1$H NMR (300 M Hz, CD$_3$OD) δ 7.28-7.25 (m, 2H), 7.09 (d, J = 8.5 Hz, 1H), 4.94 (d, J = 12.3 Hz, 1H), 4.83 (d, J = 15.4 Hz, 1H), 4.21 (brs, 1H), 4.07-3.98 (m, 1H), 2.71-2.63 (m, 2H), 1.39 (d, J = 6.6 Hz, 3H), 1.25 (t, J = 7.6 Hz, 3H). |

TABLE 8-continued

Compounds prepared as described in Example 76 using the appropriately substituted starting materials.

| Example | Structure | Characterization Data |
| --- | --- | --- |
| 220 | (3-methyl-6-ethyl isochroman-4-amine HCl) | MS (ESI): m/z 192 [M + H]. ¹H NMR (300 M Hz, CD₃OD) δ 7.28-7.25 (m, 2H), 7.10 (d, J = 8.4 Hz, 1H), 4.81 (s, 2H), 4.29-4.21 (m, 1H), 4.15 (d, J = 2.5 Hz, 1H), 2.71-2.63 (m, 2H), 1.31 (d, J = 6.7 Hz, 3H), 1.24 (t, J = 7.8 Hz, 3H). |
| 225 | (3-methyl-5-methyl-8-chloro isochroman-4-amine HCl) | MS (ESI): m/z 212 [M + H]. ¹H NMR (300 M Hz, CD₃OD) δ 7.35 (d, J = 8.2 Hz, 1H), 7.23 (d, J = 8.2 Hz, 1H), 4.99 (d, J = 12.1 Hz, 1H), 4.76 (d, J = 16.4 Hz, 1H), 4.38 (s, 1H), 4.00-3.94 (m, 1H), 2.39 (s, 3H), 1.41 (d, J = 6.6 Hz, 3H). |
| 228 | (3-methyl-6-CF₃ isochroman-4-amine HCl) | MS (ESI): m/z 232 [M + H]. ¹H NMR (300 M Hz, CD₃OD) δ 7.81 (s, 1H), 7.73 (d, J = 8.1 Hz, 1H), 7.42 (d, J = 8.1 Hz, 1H), 4.99 (d, J = 16.5 Hz, 1H), 4.90 (d, J = 16.5 Hz, 1H), 4.39 (brs, 1H), 4.11-4.03 (m, 1H), 1.42 (d, J = 6.6 Hz, 3H). |
| 229 | (3-methyl-6-CF₃ isochroman-4-amine HCl) | MS (ESI): m/z 232 [M + H]. ¹H NMR (300 M Hz, CD₃OD) δ 7.82 (s, 1H), 7.73 (d, J = 8.1 Hz, 1H), 7.42 (d, J = 8.1 Hz, 1H), 4.91 (s, 2H), 4.35-4.28 (m, 2H), 1.30 (d, J = 6.6 Hz, 3H). |
| 230 | (3-methyl-5-OMe isochroman-4-amine HCl) | MS (ESI): m/z 194 [M + H]. ¹H NMR (300 M Hz, CD₃OD) δ 7.39 (t, J = 8.1 Hz, 1H), 6.95 (d, J = 8.1 Hz, 1H), 6.77 (d, J = 7.8 Hz, 1H), 4.91 (d, J = 15.3 Hz, 1H), 4.81 (d, J = 15.6 Hz, 1H), 4.38 (brs, 1H), 4.03-3.93 (m, 1H), 3.93 (s, 3H), 1.40 (d, J = 6.7 Hz, 3H). |
| 231 | (3-methyl-5-OMe isochroman-4-amine HCl) | MS (ESI): m/z 194 [M + H]. ¹H NMR (300 M Hz, CD₃OD) δ 7.39 (t, J = 8.0 Hz, 1H), 6.97 (d, J = 8.3 Hz, 1H), 6.78 (d, J = 7.8 Hz, 1H), 4.86-4.70 (m, 2H), 4.38-4.19 (m, 2H), 3.92 (s, 3H), 1.30 (d, J = 6.7 Hz, 3H). |
| 232 | (3-methyl-7-OMe isochroman-4-amine HCl) | MS (ESI): m/z 194 [M + H]. ¹H NMR (300 M Hz, D₂O) δ 7.35 (d, J = 8.6 Hz, 1H), 6.95 (dd, J = 8.6, 2.6 Hz, 1H), 6.79 (d, J = 2.4 Hz, 1H), 4.83 (brs, 2H), 4.41-4.33 (m, 1H), 4.26 (s, 1H), 3.80 (s, 3H), 1.26 (d, J = 6.7 Hz, 3H). |
| 233 | (3-methyl-7-OMe isochroman-4-amine HCl) | MS (ESI): m/z 194 [M + H]. ¹H NMR (300 M Hz, CD₃OD) δ 7.33 (d, J = 8.6 Hz, 1H), 6.92 (dd, J = 8.6, 2.6 Hz, 1H), 6.76 (d, J = 2.5 Hz, 1H), 4.90-4.85 (m, 2H), 4.29 (s, 1H), 4.13-4.06 (m, 1H), 3.78 (s, 3H), 1.35 (d, J = 6.7 Hz, 3H). |
| 234 | (3-methyl-8-OMe isochroman-4-amine HCl) | MS (ESI): m/z 194 [M + H]. ¹H NMR (300 M Hz, CD₃OD) δ 7.34 (t, J = 8.0 Hz, 1H), 7.01 (dd, J = 8.0, 4.2 Hz, 2H), 4.95 (d, J = 16.2 Hz, 1H), 4.69 (d, J = 16.3 Hz, 1H), 4.22 (s, 1H), 4.02-3.95 (m, 1H), 3.84 (s, 3H), 1.39 (d, J = 6.6 Hz, 3H). |

TABLE 8-continued

Compounds prepared as described in Example 76 using the appropriately substituted starting materials.

| Example | Structure | Characterization Data |
|---|---|---|
| 235 | 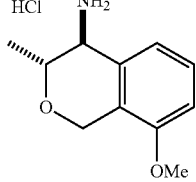 | MS (ESI): m/z 194 [M + H]. $^1$H NMR (300 M Hz, CD$_3$OD) δ 7.36 (t, J = 8.0 Hz, 1H), 7.03 (dd, J = 7.9, 3.4 Hz, 2H), 4.80 (d, J = 16.8 Hz, 1H), 4.70 (d, J = 16.5 Hz, 1H), 4.26-4.21 (m, 1H), 4.15 (s, 1H), 3.85 (s, 3H), 1.29 (d, J = 6.7 Hz, 3H). |
| 237 | 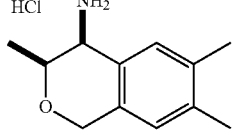 | MS (ESI): m/z 192 [M + H]. $^1$H NMR (300 M Hz, CD$_3$OD) δ 7.36 (t, J = 8.0 Hz, 1H), 7.03 (dd, J = 7.9, 3.4 Hz, 2H), 4.80 (d, J = 16.8 Hz, 1H), 4.70 (d, J = 16.5 Hz, 1H), 4.26-4.21 (m, 1H), 4.15 (s, 1H), 3.85 (s, 3H), 1.29 (d, J = 6.7 Hz, 3H). |
| 238 | 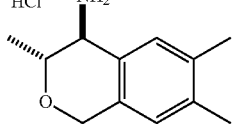 | MS (ESI): m/z 192 [M + H]. $^1$H NMR (300 M Hz, DMSO-$d_6$) δ 8.30 (s, 3H), 7.27 (s, 1H), 6.92 (s, 1H), 4.81-4.67 (m, 2H), 4.13-4.12 (m, 1H), 3.98-3.83 (m, 1H), 2.21 (s, 6H), 1.31 (d, J = 6.6 Hz, 3H). |
| 200 | 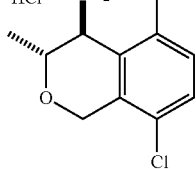 | MS (ESI): m/z 212 [M + H]. $^1$H NMR (300 M Hz, CD$_3$OD) δ 7.38 (d, J = 8.2 Hz, 1H), 7.26 (d, J = 8.0 Hz, 1H), 4.90 (d, J = 17.0 Hz, 1H), 4.72 (d, J = 17.0 Hz, 1H), 4.47-4.30 (m, 2H), 2.42 (s, 3H), 1.22 (d, J = 6.7 Hz, 3H). |
| 248 | 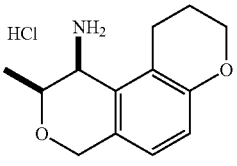 [SMILES: C[C@@H]1OCc2ccc3c(c2[C@@H]1N)CCCO3 ; Cl] | MS (ESI): m/z 220 [M + H]. $^1$H NMR (300 M Hz, DMSO-$d_6$) δ 8.15 (br.s., 3H), 6.89 (d, J = 8.4 Hz, 1H), 6.80 (d, J = 8.4 Hz, 1H), 4.82 (d, J = 15.3 Hz, 1H), 4.71 (d, J = 15.0 Hz, 1H), 4.23 (s, 1H), 4.11-4.08 (m, 2H), 3.89-3.86 (m, 1H), 2.79-2.73 (m, 2H), 1.99-1.92 (m, 2H), 1.31 (d, J = 6.6 Hz, 3H). |
| 249 | 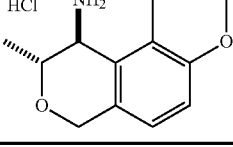 | MS (ESI): m/z 220 [M + H]. $^1$H NMR (300 M Hz, CD$_3$OD) δ 6.89 (d, J = 8.4 Hz, 1H), 6.83 (d, J = 8.7 Hz, 1H), 4.78 (s, 2H), 4.38-4.2 (m, 1H), 4.27 (s, 1H), 4.16 (t, J = 5.4 Hz, 2H), 2.82 (t, J = 6.3 Hz, 2H), 2.12-2.00 (m, 2H), 1.24 (d, J = 6.9 Hz, 3H). |

Example 99.
trans-3-Ethyl-6-methylisochroman-4-amine hydrochloride

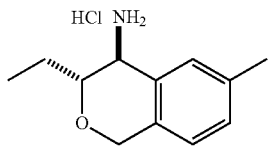

The compound of Example 99 was prepared as previously described in Example 76, using pent-1-en-3-ol. MS (ESI): m/z 192 [M+H]. $^1$H NMR (300 MHz, DMSO-d$_6$) δ 8.39 (brs, 3H), 7.34 (s, 1H), 7.19 (d, J=7.8 Hz, 1H), 7.06 (d, J=7.8 Hz, 1H), 4.69 (s, 2H), 4.18 (s, 1H), 3.90-3.81 (m, 1H), 2.31 (s, 3H), 1.77-1.51 (m, 2H), 0.96 (t, J=5.4 Hz, 3H).

Example 100.
cis-3-Ethyl-6-methylisochroman-4-amine hydrochloride

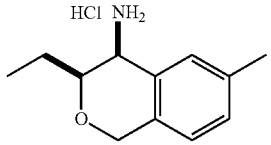

The compound of Example 100 was prepared as previously described in Example 76, using pent-1-en-3-ol. MS (ESI): m/z 192 [M+H]. $^1$H NMR (300 MHz, DMSO-d$_6$) δ 8.18 (brs, 3H), 7.29 (s, 1H), 7.21 (d, J=7.8 Hz, 1H), 7.07 (d, J=7.8 Hz, 1H), 4.87 (d, J=11.7 Hz, 1H), 4.73 (d, J=11.7 Hz, 1H), 4.35 (s, 1H), 3.65-3.62 (m, 1H), 2.31 (s, 3H), 1.66-1.59 (m, 2H), 0.99 (t, J=5.4 Hz, 3H).

TABLE 9

Compounds prepared as described in Examples 99 and 100 using the appropriately substituted starting materials.

| Example | Structure | Characterization Data |
|---|---|---|
| 198 | HCl NH₂, ethyl, isochroman | MS (ESI): m/z 178 [M + H]. $^1$H NMR (300 MHz, CD$_3$OD) δ 7.43-7.39 (m, 2H), 7.37-7.28 (m, 1H), 7.19 (d, J = 7.7 Hz, 1H), 5.00 (d, J = 15.6 Hz, 1H), 4.87 (d, J = 15.6 Hz, 1H), 4.31 (s, 1H), 3.79-3.69 (m, 1H), 1.78-1.61 (m, 2H), 1.12 (t, J = 7.4 Hz, 3H). |
| 199 | HCl NH₂, ethyl, isochroman | MS (ESI): m/z 178 [M + H]. $^1$H NMR (300 MHz, CD$_3$OD) δ 7.43-7.32 (m, 3H), 7.19 (d, J = 7.2 Hz, 1H), 4.82 (s, 2H), 4.22 (d, J = 2.2 Hz, 1H), 4.00-3.95 (m, 1H), 1.71-1.46 (m, 2H), 1.07 (t, J = 7.4 Hz, 3H). |
| 201 | HCl NH₂, ethyl, F-isochroman | MS (ESI): m/z 196 [M + H]. $^1$H NMR (300 MHz, CD$_3$OD) δ 7.27-7.13 (m, 3H), 4.99 (d, J = 15.5 Hz, 1H), 4.82 (d, J = 15.4 Hz, 1H), 4.34 (s, 1H), 3.75-3.69(m, 1H), 1.79-1.58 (m, 2H), 1.11 (t, J = 7.4 Hz, 3H). |
| 202 | HCl NH₂, ethyl, F-isochroman | MS (ESI): m/z 196 [M + H]. $^1$H NMR (300 MHz, CD$_3$OD) δ 7.30-7.11 (m, 3H), 4.77 (s, 2H), 4.25 (d, J = 2.3 Hz, 1H), 4.00-3.94 (m, 1H), 1.76-1.45 (m, 2H), 1.07 (t, J = 7.4 Hz, 3H). |
| 207 | HCl NH₂, ethyl, methyl-isochroman | MS (ESI): m/z 192 [M + H]. $^1$H NMR (300 MHz, CD$_3$OD) δ 7.30 (t, J = 7.6 Hz, 1H), 7.19 (d, J = 7.3 Hz, 1H), 7.00 (d, J = 7.6 Hz, 1H), 4.88 (d, J = 16.2 Hz, 1H), 4.78 (d, J = 16.2 Hz, 1H), 4.37 (d, J = 1.3 Hz, 1H), 4.08-4.03 (m, 1H), 2.42 (s, 3H), 1.66-1.38 (m, 2H), 1.05 (t, J = 7.4 Hz, 3H). |
| 208 | HCl NH₂, ethyl, methyl-isochroman | MS (ESI): m/z 192 [M + H]. $^1$H NMR (300 MHz, CD$_3$OD) δ 7.30 (t, J = 7.6 Hz, 1H), 7.20 (d, J = 7.2 Hz, 1H), 7.00 (d, J = 7.6 Hz, 1H), 5.01 (d, J = 15.7 Hz, 1H), 4.85 (d, J = 15.8 Hz, 1H), 4.42 (s, 1H), 3.72-3.67 (m, 1H), 2.42 (s, 3H), 1.81-1.59 (m, 2H), 1.12 (t, J = 7.4 Hz, 3H). |
| 209 | HCl NH₂ Cl, ethyl, isochroman | MS (ESI): m/z 212 [M + H]. $^1$H NMR (300 MHz, CD$_3$OD) δ 7.49-7.39 (m, 2H), 7.19-7.16 (m, 1H), 4.83 (d, J = 6.5 Hz, 2H), 4.48 (brs, 1H), 4.13-4.07 (m, 1H), 1.67-1.39 (m, 2H), 1.06 (t, J = 7.4 Hz, 3H). |
| 210 | NH₂, isopropyl, methyl-isochroman | MS (ESI): m/z 206 [M + H]. $^1$H NMR (300 MHz, CD$_3$OD) δ 7.25-7.22 (m, 2H), 7.06 (d, J = 8.1 Hz, 1), 4.79 (s, 2H), 4.37 (d, J = 1.9 Hz, 1H), 3.59 (dd, J = 9.7, 2.0 Hz, 1H), 2.36 (s, 3H), 1.82-1.72 (m, 1H), 1.09 (d, J = 6.5 Hz, 3H), 0.94 (d, J = 6.6 Hz, 3H). |
| 211 | NH₂, isopropyl, methyl-isochroman | MS (ESI): m/z 206 [M + H]. $^1$H NMR (300 MHz, CD$_3$OD) δ 7.25-7.22 (m, 2H), 7.07 (d, J = 8.4 Hz, 1H), 4.98 (d, J = 15.3 Hz, 1H), 4.80 (d, J = 15.3 Hz, 1H), 4.43 (s, 1H), 3.36-3.31 (m, 1H), 2.36 (s, 3H), 1.86-1.76 (m, 1H), 1.15 (d, J = 6.4 Hz, 3H), 1.04 (d, J = 6.7 Hz, 3H). |

TABLE 9-continued

Compounds prepared as described in Examples 99 and 100 using the appropriately substituted starting materials.

| Example | Structure | Characterization Data |
|---|---|---|
| 218 | 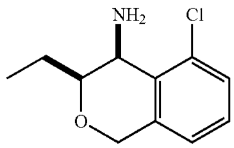 | MS (ESI): m/z 212 [M + H]. $^1$H NMR (300 MHz, CD$_3$OD) δ 7.49-7.38 (m, 2H), 7.22-7.15 (m, 1H), 5.02 (d, J = 15.9 Hz, 1H), 4.85 (d, J = 16.2 Hz, 1H), 4.55 (brs, 1H), 3.76-3.68 (m, 1H), 1.79-1.66 (m, 2H), 1.13 (t, J = 7.4 Hz, 3H). |
| 223 | 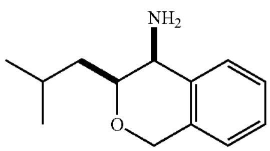 | MS (ESI): m/z 206 [M + H]. $^1$H NMR (300 MHz, CD$_3$OD) δ 7.46-7.30 (m, 3H), 7.19 (d, J = 7.2 Hz, 1H), 4.98 (d, J = 15.6 Hz, 1H), 4.86 (d, J = 15.6 Hz, 1H), 4.26 (brs, 1H), 3.95-3.90 (m, 1H), 1.97-1.89 (m, 1H), 1.70-1.60 (m, 1H), 1.48-1.39 (m, 1H), 1.03 (d, J = 6.6 Hz, 3H), 1.00 (d, J = 6.6 Hz, 3H). |
| 224 | 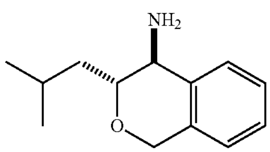 | MS (ESI): m/z 206 [M + H]. $^1$H NMR (300 MHz, CD$_3$OD) δ 7.49-7.29 (m, 3H), 7.19 (d, J = 7.6 Hz, 1H), 4.82 (s, 2H), 4.30-4.13 (m, 2H), 1.94-1.75 (m, 1H), 1.65-1.55 (m, 1H), 1.28-1.19 (m, 1H), 0.98 (t, J = 6.3 Hz, 6H). |
| 250 | 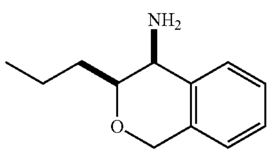 | MS (ESI): m/z 192 [M + H]. $^1$H NMR (300 MHz, DMSO-$d_6$) δ 8.19 (brs, 3H), 7.47 (d, J = 7.5 Hz, 1H), 7.40-7.32 (m, 2H), 7.18 (d, J = 7.5 Hz, 1H), 4.90 (d, J = 15.6 Hz, 1H), 4.79 (d, J = 15.6 Hz, 1H), 4.28 (s, 1H), 3.78 (m, 1H), 1.60-1.56 (m, 2H), 1.52-1.44 (m, 2H), 0.95 (t, J = 7.2 Hz, 3H). |
| 251 | 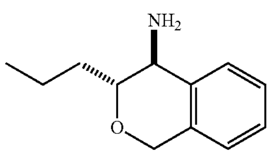 | MS (ESI): m/z 192 [M + H]. $^1$H NMR (300 MHz, DMSO-$d_6$) δ 8.42 (brs, 3H), 7.52 (d, J = 7.5 Hz, 1H), 7.38-7.33 (m, 2H), 7.18 (d, J = 7.5 Hz, 1H), 4.73 (m, 2H), 4.20 (s, 1H), 4.00 (m, 1H), 1.52-1.47 (m, 4H), 0.91 (t, J = 6.9 Hz, 3H). |

Example 101. 3,3-Dimethylisochroman-4-amine hydrochloride

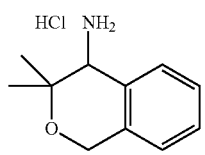

The compound of Example 101 was prepared as previously described in Example 76, using 2-methylbut-3-en-2-ol. MS (ESI): m/z 178 [M+H]. $^1$H NMR (300 MHz, DMSO-d$_6$) δ 8.35 (brs, 3H), 7.49 (d, J=6.9 Hz, 1H), 7.41-7.30 (m, 2H), 7.18 (d, J=7.2 Hz, 1H), 4.86-4.71 (m, 2H), 4.14 (s, 1H), 1.33 (s, 3H), 1.19 (s, 3H).

Example 104. cis-1-Methylisochroman-4-amine hydrochloride

Example 105. trans-1-Methylisochroman-4-amine hydrochloride

Example 104

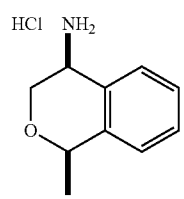

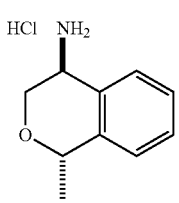

The compounds are Example 104 and Example 105 were prepared as described previously in Example 76 using 1-(1-(allyloxy)ethyl)-2-bromobenzene (prepared as previously described in Example 21 using 1-(2-bromophenyl)ethanol).

Example 105

Example 104. cis-1-Methylisochroman-4-amine hydrochloride

MS (ESI): m/z 164 [M+H]. $^1$H NMR (300 MHz, DMSO-$d_6$) δ 8.66 (brs, 3H), 7.58 (d, J=5.4 Hz, 1H), 7.41-7.31 (m, 2H), 7.25 (d, J 5.7 Hz, 1H), 4.98 (q, J 5.1 Hz, 1H), 4.35 (t, J=2.7, 1H), 4.17 (dd, J=2.7 Hz, 8.7 Hz, 1H), 3.89 (dd, J=3 Hz, 9 Hz, 1H), 1.46 (d, J 5.1 Hz, 3H).

Example 105. trans-(1S,4S)-1-Methylisochroman-4-amine hydrochloride

MS (ESI): m/z 164 [M+H]. $^1$H NMR (300 MHz, DMSO-$d_6$) δ 8.54 (brs, 3H), 7.51 (d, J=7.8 Hz, 1H), 7.41-7.28 (m, 3H), 4.78 (q, J=6.3 Hz, 1H), 4.31-4.29 (m, 1H), 4.21 (d, J=12.6 Hz, 1H), 3.87 (dd, J=2.1 Hz, 12.6 Hz, 1H), 1.53 (d, J=6.6 Hz, 3H).

TABLE 10

Compounds prepared as described in Examples 104 and 105 using the appropriately substituted starting materials.

| Example | Structure | Characterization Data |
|---|---|---|
| 106 | 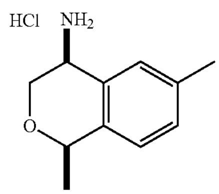 | MS (ESI): m/z 178 [M + H]. $^1$H NMR (300 MHz, CDCl$_3$) δ 8.67 (brs, 3H), 7.43 (s, 1H), 7.12 (d, J = 8.1 Hz, 1H), 6.95 (d, J = 7.8 Hz, 1H), 5.04-4.98 (m, 1H), 4.30 (s, 1H), 4.10 (s, 2H), 2.30 (s, 3H), 1.45 (d, J = 6.6 Hz, 3H). |
| 107 | 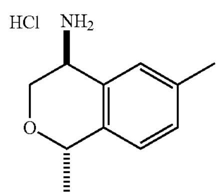 | MS (ESI): m/z 178 [M + H]. $^1$H NMR (300 MHz, CDCl$_3$) δ 8.69 (brs, 3H), 7.46 (s, 1H), 7.14 (d, J = 8.1 Hz, 1H), 7.01 (d, J = 8.1 Hz, 1H), 4.80-4.74 (m, 1H), 4.50 (d, J = 12.3 Hz, 1H), 4.30 (s, 1H), 3.80 (dd, J = 1.8 Hz, 12.6 Hz, 1H), 2.30 (s, 3H), 1.59 (d, J = 6.6 Hz, 3H). |
| 203 | 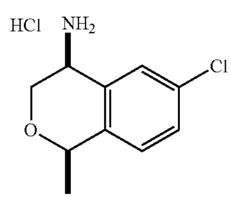 | MS (ESI): m/z 198 [M + H]. $^1$H NMR (300 MHz, DMSO-$d_6$) δ 8.60 (brs, 3H), 7.67 (d, J = 2.1 Hz, 1H), 7.46 (dd, J = 8.4, 2.2 Hz, 1H), 7.30 (d, J = 8.5 Hz, 1H), 4.97-4.93 (m, 1H), 4.39 (t, J = 3.7 Hz, 1H), 4.14 (dd, J = 12.4, 3.5 Hz, 1H), 3.85 (dd, J = 12.3, 4.2 Hz, 1H), 1.43 (d, J = 6.7 Hz, 3H). |
| 204 | 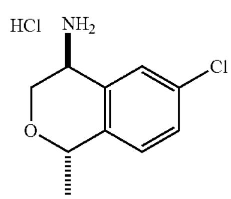 | MS (ESI): m/z 198 [M + H]. $^1$H NMR (300 MHz, DMSO-$d_6$) δ 8.49 (brs, 3H), 7.61 (d, J = 2.2 Hz, 1H), 7.48 (dd, J = 8.4, 2.2 Hz, 1H), 7.34 (d, J = 8.5 Hz, 1H), 4.79-4.73 (m, 1H), 4.35 (s, 1H), 4.16 (d, J = 12.1 Hz, 1H), 3.86 (dd, J = 12.8, 2.3 Hz, 1H), 1.52 (d, J = 6.5 Hz, 3H). |
| 205 | 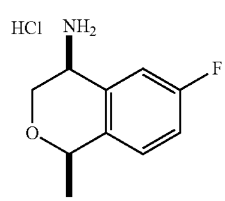 | MS (ESI): m/z 182 [M + H]. $^1$H NMR (300 MHz, D$_2$O) δ 7.26-7.13 (m, 3H), 5.16-5.09 (m, 1H), 4.43 (s, 1H), 4.26 (dd, J = 13.1, 2.3 Hz, 1H), 3.98 (dd, J = 13.2, 2.1 Hz, 1H), 1.47 (d, J = 6.8 Hz, 3H). |

TABLE 10-continued

Compounds prepared as described in Examples 104 and 105 using the appropriately substituted starting materials.

| Example | Structure | Characterization Data |
|---|---|---|
| 206 | HCl, NH₂, F-substituted isochroman | MS (ESI): m/z 182 [M + H]. ¹H NMR (300 MHz, D₂O) δ 7.32-7.27 (m, 1H), 7.22-7.12 (m, 2H), 4.92-4.84 (m, 1H), 4.42 (s, 1H), 4.22 (d, J = 13.2 Hz, 1H), 4.02 (dd, J = 13.1, 2.0 Hz, 1H), 1.53 (d, J = 6.5 Hz, 3H). |
| 221 | NH₂, methyl-substituted isochroman | MS (ESI): m/z 178 [M + H]. ¹H NMR (300 MHz, D₂O) δ 7.30 (t, J = 7.7 Hz, 1H), 7.17 (d, J = 7.4 Hz, 1H), 7.02 (d, J = 7.7 Hz, 1H), 5.18-5.10 (m, 1H), 4.54 (s, 1H), 4.18 (dd, J = 13.2, 1.6 Hz, 1H), 4.01 (dd, J = 13.2, 1.5 Hz, 1H), 2.33 (s, 3H), 1.44 (d, J = 6.8 Hz, 3H). |
| 222 | NH₂, methyl-substituted isochroman | MS (ESI): m/z 178 [M + H]. ¹H NMR (300 MHz, D₂O) δ 7.32 (t, J = 7.7 Hz, 1H), 7.19 (d, J = 7.5 Hz, 1H), 7.10 (d, J = 7.8 Hz, 1H), 4.94-4.89 (m, 1H), 4.55 (s, 1H), 4.19 (d, J = 12.9 Hz, 1H), 3.93 (dd, J = 12.9, 1.3 Hz, 1H), 2.33 (s, 3H), 1.52 (d, J = 6.5 Hz, 3H). |
| 226 | NH₂, methyl-substituted isochroman | MS (ESI): m/z 178 [M + H]. ¹H NMR (300 MHz, D₂O) δ 7.30 (t, J = 7.7 Hz, 1H), 7.18 (d, J = 7.6 Hz, 1H), 7.02 (d, J = 7.7 Hz, 1H), 5.18-5.11 (m, 1H), 4.54 (s, 1H), 4.18 (dd, J = 13.2, 1.6 Hz, 1H), 4.01 (dd, J = 13.2, 1.6 Hz, 1H), 2.33 (s, 3H), 1.44 (d, J = 6.8 Hz, 3H). |
| 227 | NH₂, methyl-substituted isochroman | MS (ESI): m/z 178 [M + H]. ¹H NMR (300 MHz, D₂O) δ 7.32 (t, J = 7.7 Hz, 1H), 7.19 (d, J = 7.5 Hz, 1H), 7.11 (d, J = 7.7 Hz, 1H), 4.95-4.88 (m, 1H), 4.55 (s, 1H), 4.21 (dd, J = 12.9, 1.4 Hz, 1H), 3.94 (dd, J = 12.9, 1.7 Hz, 1H), 2.33 (s, 3H), 1.52 (d, J = 6.5 Hz, 3H). |

Example 236.
trans-N,1-dimethylisochroman-4-amine hydrochloride

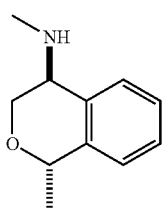

The compound of Example 236 was prepared as previously described in Example 57. MS (ESI): m/z 178 [M+H]. ¹H NMR (300 MHz, DMSO-d₆) δ 9.26 (s, 1H), 9.11 (s, 1H), 7.54 (d, J=7.5 Hz, 1H), 7.45 (d, J=7.5 Hz, 1H), 7.38-7.31 (m, 2H), 4.82-4.80 (m, 1H), 4.40 (d, J=13.1 Hz, 1H), 4.27 (brs, 1H), 3.86 (dd, J=13.1, 2.0 Hz, 1H), 2.56 (t, J=5.4 Hz, 3H), 1.54 (d, J=6.5 Hz, 3H).

Example 239.
cis-N,N,1-trimethylisochroman-4-amine hydrochloride

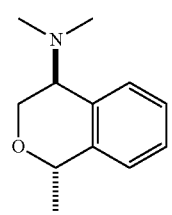

The compound of Example 239 was prepared as previously described in Example 60. MS (ESI): m/z 192 [M+H]. ¹H NMR (300 MHz, CD₃OD) δ 7.59-7.47 (m, 2H), 7.44-7.37 (m, 2H), 4.90-4.84 (m, 1H), 4.64 (d, J=14.1 Hz, 1H), 4.40 (s, 1H), 3.97 (dd, J=14.1, 2.4 Hz, 1H), 2.95 (s, 3H), 2.90 (s, 3H), 1.61 (d, J=6.5 Hz, 3H).

Example 240. cis-N,1-dimethylisochroman-4-amine hydrochloride

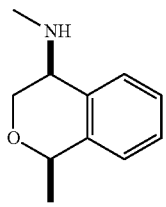

The compound of Example 240 was prepared as previously described in Example 57. MS (ESI): m/z 178 [M+H]. ¹H NMR (300 MHz, CD₃OD) δ 7.51-7.41 (m, 2H), 7.38-7.33 (m, 1H), 7.26 (d, J=7.7 Hz, 1H), 5.18-5.11 (m, 1H), 4.23-4.11 (m, 3H), 2.74 (s, 3H), 1.52 (d, J=6.8 Hz, 3H).

Example 256. cis-3-Isopropylisochroman-4-amine hydrochloride

Example 257. trans-3-Isopropylisochroman-4-amine hydrochloride

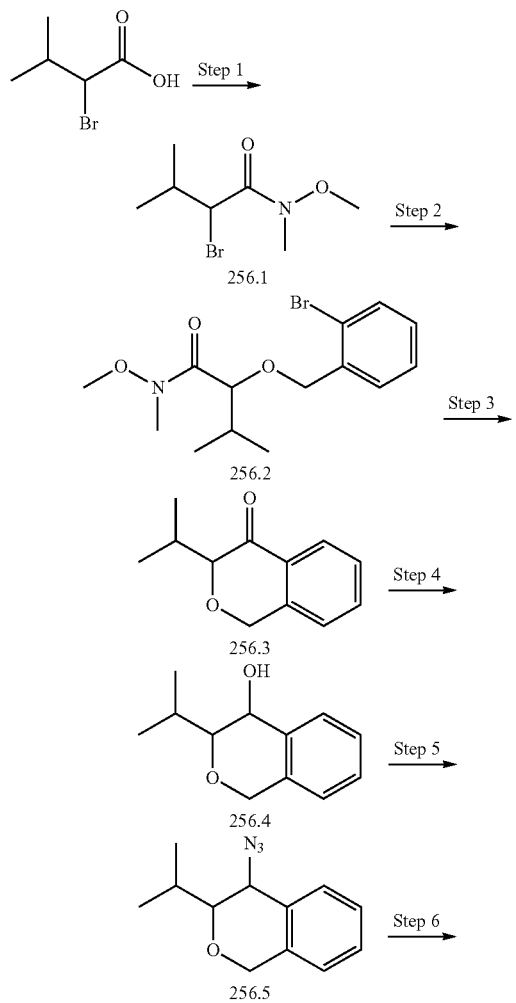

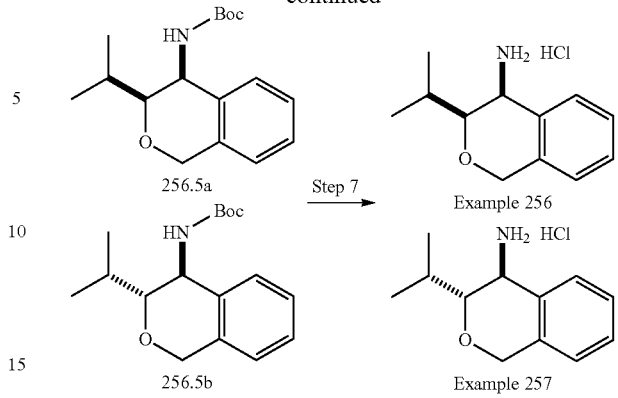

Step 1.

A solution of 2-bromo-3-methylbutanoic acid (5 g, 27.6 mmol) in 100 mL of CH₂Cl₂ was chilled in an ice bath and treated with 1,1-carbonyldiimidazole (4.68 g, 28.9 mmol). The ice bath was removed and the reaction mixture was stirred at ambient temperature for 15 min. N, O-dimethylhydroxylamine (1.76 g, 28.9 mmol) was added to the reaction mixture and stirring at ambient temperature was maintained for 2 h. Water (100 mL) was added to the reaction vessel and the resulting biphasic mixture was transferred to a separatory funnel. The organic phase was washed with 10% aqueous citric acid (2×100 mL), saturated aqueous NaHCO₃ (100 mL), and saturated aqueous NaCl (2×100 mL). The organic phase was dried over anhydrous Na₂SO₄, filtered, and concentrated under reduced pressure to provide 2-bromo-N-methoxy-N,3-dimethylbutanamide 256.1 (2.80 g, crude) as a yellow oil. GC-MS: m/z 223, 225 [M+H]. ¹HNMR (300 MHz, CDCl₃) δ 4.51 (d, J=9.3 Hz, 1H), 3.78 (s, 3H), 3.24 (s, 3H), 2.36-2.28 (m, 1H), 1.16 (d, J=6.9 Hz, 3H), 0.98 (d, J=6.9 Hz, 3H).

Step 2.

A solution of (2-bromophenyl)methanol (3.47 g, 18.6 mmol) in DMF (100 mL) was cooled in an ice bath and treated with sodium hydride (743 mg, 18.6 mmol, 95% in mineral oil). The resulting slurry was stirred for 30 min and then treated with Compound 256.1 (2.8 g, 12.4 mmol). The reaction was stirred at ambient temperature for 1 h and then partitioned between H₂O (100 mL) and EtOAc (100 mL). The aqueous phase was extracted with EtOAc (2×100 mL). The combined organics were washed with saturated aqueous NaCl (2×100 mL), dried over anhydrous Na₂SO₄, filtered, and concentrated under reduced pressure. The resulting oil was purified by flash column chromatography (SiO₂, 100% hexanes gradient to 10% EtOAc/hexanes (90%) to provide 2-((2-bromobenzyl)oxy)-N-methoxy-N,3-dimethylbutanamide 256.2 (4.05 g, 12.2 mmol) as a colorless oil. MS (ESI): m/z 330 [M+H], Step 3.

A solution of Compound 256.2 (4.5 g, 13.6 mmol) in THF (100 mL) was chilled in a dry ice/acetone bath and treated with tert-butyllithium (33.9 mL, 1.7M in pentane). The reaction was stirred in the dry ice/acetone bath for 10 min. Excess base was quenched by the dropwise addition of saturated aqueous NH₄Cl. The mixture was partitioned between saturated aqueous NH₄Cl (100 mL) and EtOAc (100 mL). The aqueous phase was extracted with EtOAc (2×100 mL). The combined organics were dried over anhydrous Na₂SO₄, filtered, and concentrated under reduced pressure. The resulting oil was purified by flash column chromatography (SiO2, 100% hexanes) to afford 3-isopropylisochroman-4-one 256.3 (600 mg, 3.15 mmol) as a yellow oil. ¹H NMR (300 MHz, CDCl3) δ 8.03 (d, J=7.8 Hz, 1H), 7.57-7.52 (m, 1H), 7.40 (t, J=7.5 Hz, 1H), 7.21 (d, J=7.8 Hz, 1H), 4.95 (d, J=15.0 Hz, 1H), 4.86 (d, J=15.0 Hz, 1H), 3.97-3.94 (m, 1H), 2.60-2.53 (m, 1H), 1.15 (d, J=7.5 Hz, 3H), 0.98 (d, J=7.5 Hz, 3H).

Step 4.

3-Isopropylisochroman-4-ol 256.4 was prepared as previously described in Example 1. GC-MS: m/z 192 [M+H]. ¹H NMR (300 MHz, CDCl$_3$) δ 7.54-7.52 (m, 0.4H), 7.43-7.30 (m, 0.6H), 7.31-7.23 (m, 2H), 7.04-6.99 (m, 1H), 4.90-4.49 (m, 3H), 3.33 (dd, J=7.5, 4.5 Hz, 0.4H), 3.08 (dd, J=9.6, 1.2 Hz, 0.6H), 2.13-2.07 (m, 1H), 1.94 (d, J=10.5 Hz, 0.6H), 1.81 (d, J=9.0 Hz, 0.4H), 1.22-1.02 (m, 6H).

Step 5.

4-Azido-3,isopropylisochroman 256.5 was prepared as previously described in Example 1. ¹H NMR (300 MHz, CDCl$_3$) δ 7.46-7.43 (m, 1H), 7.34-7.27 (m, 2H), 7.06-7.03 (m, 1H), 4.83-4.72 (m, 2H), 4.33 (d, J=7.5 Hz, 1H), 3.50-3.46 (m, 1H), 2.11-2.04 (m, 1H), 1.08-1.02 (m, 6H).

Step 6.

Compound s 256.5a and 256.5b were prepared as previously described in Example 73.

tert-butyl-(cis-3-isopropylisochroman-4-yl)carbamate 256.5a TLC higher Rf. ¹H NMR (300 MHz, CDCl$_3$) δ 7.49-7.46 (m, 1H), 7.25-7.22 (m, 2H), 7.00-6.97 (m, 1H), 5.02-4.72 (m, 4H), 3.17 (dd, J=9.6, 1.8 Hz, 1H), 1.91-1.83 (m, 1H), 1.42 (s, 9H), 1.08 (d, J=6.6 Hz, 3H), 0.99 (d, J=6.6 Hz, 3H).

tert-butyl-(trans-3-isopropylisochroman-4-yl)carbamate 256.5b TLC lower Rf. ¹H NMR (300 MHz, CDCl$_3$) δ 7.39-7.36 (m, 1H), 7.24-7.20 (m, 2H), 6.99-6.96 (m, 1H), 4.86-4.69 (m, 4H), 3.32 (dd, J=6.9, 5.1 Hz, 1H), 1.94-1.92 (m, 1H), 1.50 (s, 9H), 1.05 (d, J=6.9 Hz, 6H).

Step 7.

The compounds of Example 256 and Example 257 were prepared as previously described in Example 1.

Example 256

MS (ESI): m/z 292 [M+H]. ¹H NMR (300 MHz, CD$_3$OD) δ 7.49-7.36 (m, 3H), 7.23 (d, J=7.8 Hz, 1H), 5.07 (d, J=15.6 Hz, 1H), 4.94 (d, J=15.6 Hz, 1H), 4.53 (s, 1H), 3.40 (dd, J=10.2, 1.2 Hz, 1H), 1.92-1.85 (m, 1H), 1.20 (d, J=6.3 Hz, 3H), 1.09 (d, J=6.6 Hz, 3H).

Example 257

MS (ESI): m/z 292 [M+H]. ¹H NMR (300 MHz, CD$_3$OD) δ 7.49-7.38 (m, 3H), 7.23 (d, J=7.2 Hz, 1H), 4.88 (s, 2H), 4.47 (d, J=2.1 Hz, 1H), 3.66 (dd, J=9.9, 2.1 Hz, 1H), 1.87-1.80 (m, 1H), 1.14 (d, J=6.6 Hz, 3H), 0.98 (d, J=6.6 Hz, 3H).

Example 273. cis-3-Isopropylisochroman-4-amine hydrochloride

Example 274. trans-3-Isopropylisochroman-4-amine hydrochloride

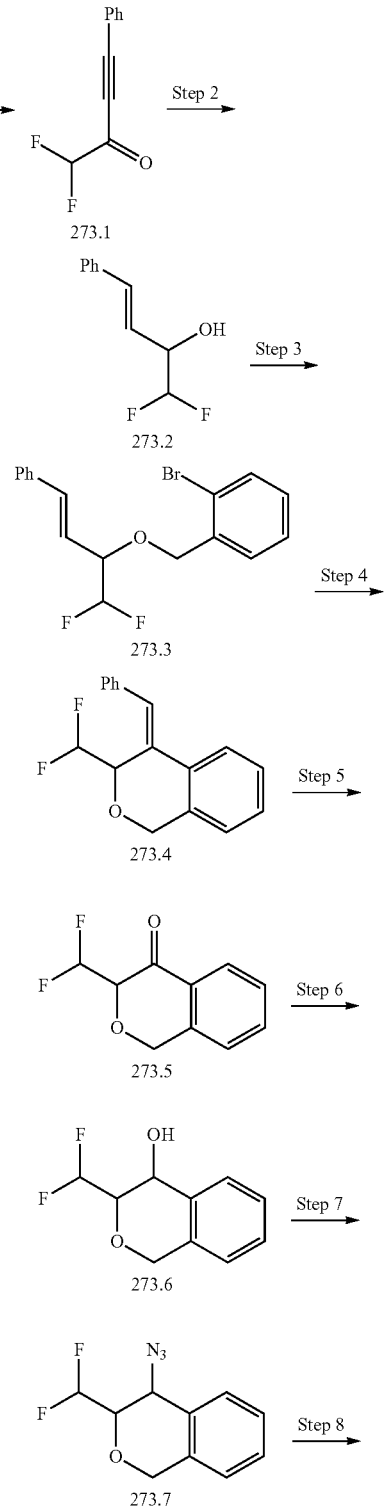

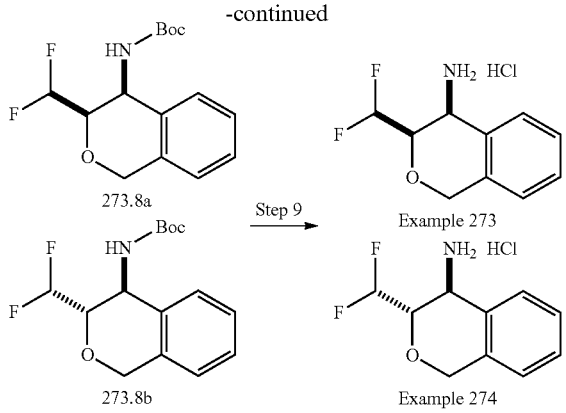

Step 1.

A solution of phenylacetylene (4 g, 39.1 mmol) in 50 mL of anhydrous THF was cooled in a dry ice/acetone bath under a $N_2$ atmosphere. Butyllithium (18.7 mL, 46.9 mmol) was added in a dropwise fashion, and the reaction was stirred at −78° C. for 30 min. A solution of methyl 2,2-difluoroacetate (5.16 g, 46.9 mmol) in THF (5 mL) was added, followed by boron trifluoride etherate (5.91 mL, 46.9 mmol). The cold bath was removed, and the reaction was stirred at ambient temperature for 12 h. Saturated aqueous $NH_4Cl$ (50 mL) was added to the reaction vessel and the reaction mixture was extracted with EtOAc (3×50 mL). The combined organics were washed with saturated aqueous NaCl (2×80 mL), dried over anhydrous $Na_2SO_4$, filtered, and concentrated under reduced pressure. Purification by flash column chromatography ($SiO_2$, 100% hexane) afford 1,1-difluoro-4-phenylbut-3-yn-2-one 273.1 (5.50 g, 30.5 mmol) as a yellow oil. GC-MS: m/z 180 [M+H]. $^1$H NMR (300 MHz, $CDCl_3$) δ 7.67 (d, J=7.2 Hz, 1H), 7.57-7.52 (m, 1H), 7.46-7.41 (m, 2H), 5.88 (t, J=54.0 Hz, 1H).

Step 2.

Compound 273.1 (5.5 g, 30.5 mmol) was dissolved in THF (100 mL) and cooled in an ice bath. $LiAl_4$ (1.73 g, 45.7 mmol) was added slowly in portions and the reaction mixture was stirred 0° C. for 30 min. Excess hydride was quenched by the dropwise addition of H2O (1.8 mL), followed by 1.8 mL of 15% aqueous NaOH. After stirring at room temperature for 0.5 hour, the solid was removed by filtration. The filtrate was concentrated to provide (E)-1,1-difluoro-4-phenylbut-3-en-2-ol 273.2 (5.30 g, 28.7 mmol) as a colorless oil. GC-MS: m/z 184 [M+H]. $^1$H NMR (300 MHz, $CDCl_3$) δ 7.44-7.27 (m, 5H), 6.82 (d, J=15.9 Hz, 1H), 6.25-6.18 (dd, J=15.9, 6.3 Hz, 1H), 5.72 (td, J=56.1, 4.2 Hz, 1H), 4.53-4.43 (m, 1H), 2.25 (d, J=5.1 Hz, 1H).

Step 3.

Compound 273.3 was prepared as previously described in Example 10. $^1$HNMR (300 MHz, $CDCl_3$) δ 7.58-7.50 (m, 2H), 7.49-7.43 (m, 1H), 7.39-7.25 (m, 4H), 7.21-7.15 (m, 2H), 6.81 (d, J=15.9 Hz, 1H), 6.18 (dd, J=16.2, 7.5 Hz, 1H), 5.84-5.64 (m, 1H), 4.79-4.63 (m, 2H), 4.23-4.19 (m, 1H).

Step 4.

Compound 273.4 was prepared as previously described in Example 10. $^1$H NMR (300 MHz, $CDCl_3$) δ 7.66-7.62 (m, 1H), 7.44-7.38 (m, 3H), 7.35-7.29 (m, 3H), 7.25-7.16 (m, 1H), 7.08-7.05 (m, 1H), 6.06-5.67 (td, J=54.9, 5.4 Hz, 1H), 5.20-5.11 (m, 1H), 5.01 (d, J=15.3 Hz, 1H), 4.83 (d, J=15.3 Hz, 1H).

Step 5.

Compound 273.5 was prepared as previously described in Example 10. $^1$H NMR (300 MHz, $CDCl_3$) δ 8.06 (d, J=6.9 Hz, 1H), 7.65-7.59 (m, 1H), 7.48-7.43 (m, 1H), 7.29-7.24 (m, 1H), 6.37 (td, J=53.4, 1.8 Hz, 1H), 5.14 (d, J=15.3 Hz, 1H), 5.02 (d, J=15.3 Hz, 1H), 4.51-4.41 (m, 1H).

Step 6.

Compound 273.6 was prepared as previously described in Example 1. 1H NMR (300 MHz, $CDCl_3$) δ 7.58 (d, J=7.2 Hz, 0.5H), 7.43 (d, J=6.9 Hz, 0.5H), 7.35-7.30 (m, 2H), 7.09-7.02 (m, 1H), 6.24-5.86 (m, 1H), 4.98-4.65 (m, 3H), 3.81-3.74 (m, 1H), 2.34 (d, J=6.6 Hz, 0.5H), 2.12 (d, J=9.9 Hz, 0.5H).

Step 7.

Compound 273.7 was prepared as previously described in Example 1. $^1$H NMR (300 MHz, $CDCl_3$) δ 7.51-7.48 (m, 0.5H), 7.43-7.32 (m, 2.5H), 7.15-7.06 (m, 1H), 6.22-5.82 (m, 1H), 5.04 (d, J=15.3 Hz, 0.5H), 4.91-4.86 (m, 1.5H), 4.62 (d, J=7.8 Hz, 0.5H), 4.34 (s, 0.5H), 3.96-3.88 (m, 1H).

Step 8.

Compound s 273.8a and 273.8b were prepared as previously described in Example 1.

tert-butyl-(cis-3-(difluoromethyl)isochroman-4-yl)carbamate 273.8a TLC higher Rf. $^1$H NMR (300 MHz, $CDCl_3$) □ 7.44-7.41 (m, 1H), 7.34-7.22 (m, 2H), 7.05-7.00 (m, 1H), 6.11-5.73 (m, 1H), 4.99-4.95 (m, 2H), 4.88-4.81 (m, 2H), 3.91-3.85 (m, 1H), 1.44 (s, 9H).

tert-butyl-(trans-3-(difluoromethyl)isochroman-4-yl)carbamate 273.8b TLC lower Rf. $^1$H NMR (300 MHz, $CDCl_3$) □ 7.42-7.40 (m, 1H), 7.32-7.26 (m, 2H), 7.04-7.01 (m, 1H), 6.16-5.78 (m, 1H), 5.02-4.95 (m, 1H), 4.90-4.89 (m, 2H), 4.85-4.80 (m, 1H), 3.84-3.80 (m, 1H), 1.44 (s, 9H).

Step 7.

The compounds of Example 273 and Example 274 were prepared as previously described in Example 1.

Example 273

MS (ESI): m/z 200 [M+H]. $^1$H NMR (300 MHz, $CD_3OD$) δ 7.51-7.45 (m, 2H), 7.42-7.38 (m, 1H), 7.25 (d, J=7.5 Hz, 1H), 6.19 (td, J=54.0, 3.9 Hz, 1H), 5.15 (d, J=15.6 Hz, 1H), 5.02 (d, J=15.6 Hz, 1H), 4.67 (s, 1H), 4.34-4.24 (m, 1H).

Example 274

MS (ESI): m/z 200 [M+H]. $^1$H NMR (300 MHz, $CD_3OD$) δ 7.54-7.40 (m, 3H), 7.25 (d, J=7.5 Hz, 1H), 6.13 (td, J=54.3, 5.1 Hz, 1H), 5.00 (s, 2H), 4.64 (d, J=2.4 Hz, 1H), 4.37-4.27 (m, 1H).

Example 275.
cis-3-(fluoromethyl)isochroman-4-amine hydrochloride

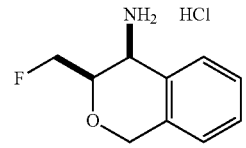 [SMILES: Cl ; N[C@H]1c2ccccc2CO[C@H]1CF]

The compound of Example 275 was prepared as previously described in Example 273 using ethyl 2-fluoroacetate. MS (ESI): m/z 182 [M+H]. $^1$H NMR (300 MHz, DMSO-$d_6$) δ 8.41 (s, 3H), 7.52-7.50 (d, J=7.5 Hz, 1H), 7.44-7.31 (m, 2H), 7.21-7.19 (d, J=7.2 Hz, 1H), 5.0-4.85 (m, 2.5H), 4.83-4.68 (m, 1H), 4.62-4.56 (m, 0.5H), 4.45 (s, 1H), 4.21-4.15 (d, J=17.1 Hz, 1H).

Example 276.
cis-3-(fluoromethyl)isochroman-4-amine hydrochloride

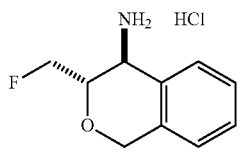

The compound of Example 276 was prepared as previously described in Example 274 using ethyl 2-fluoroacetate. MS (ESI): m/z 182 [M+H]. $^1$H NMR (300 MHz, DMSO-$d_6$) δ 8.8 (s, 3H), 7.68-7.66 (m, 1H), 7.38-7.34 (m, 2H), 7.21-7.20 (m, 1H), 4.91-4.61 (m, 4H), 4.44 (s, 1H), 4.29-4.17 (m, 1H).

Example 277. 4-Aminoisochroman-6-yl ethyl(methyl)carbamate hydrochloride

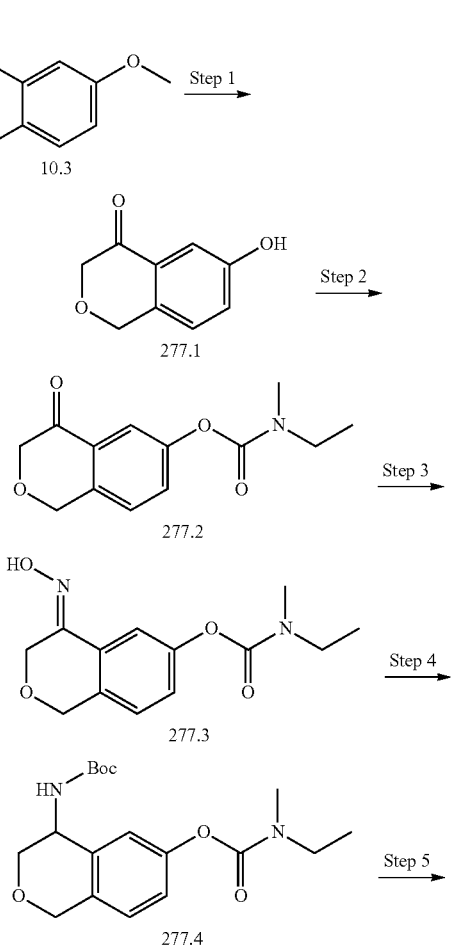

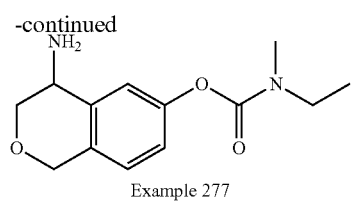

Example 277

Step 1.

6-Methoxyisochroman-4-one 10.3 (1 g, 5.61 mmol) was dissolved in anhydrous DMF (3 mL) under a N2 atmosphere and treated with sodium ethanethiolate (841 mg, 8.41 mmol). The reaction mixture was heated to 140° C. and stirred at that temperature for 15 min. After cooling to room temperature, the mixture was partitioned between H$_2$O (15 mL) and EtOAc (10 mL). The aqueous phase was extracted with EtOAc (2×10 mL). The aqueous phase was acidified with aqueous 1N HCl until pH=2 and extracted with EtOAc (2×10 mL). The combined organics were dried over anhydrous Na$_2$SO$_4$, filtered, and concentrated under reduced pressure to afford 6-hydroxyisochroman-4-one 277.1 (696 mg, 4.24 mmol) as brown oil which was used without further purification. $^1$H NMR (300 MHz, CDCl$_3$) δ 7.45 (d, I=2.1 Hz, 1H), 7.15-7.07 (m, 2H), 4.84 (s, 2H), 4.35 (s, 2H).

Step 2.

A solution of Compound 277.1 (696.5 mg, 4.23 mmol) in CH$_3$CN (15 mL) was treated with ethyl(methyl)carbamic chloride (1.02 g, 8.46 mmol) and K$_2$CO$_3$ (876 mg, 6.34 mmol). The reaction mixture was heated to 55° C. and stirred at that temperature for 5 h. After concentration under reduced pressure, the residue was diluted with water (10 mL) and extracted with EtOAc (3×10 mL). The combined organics were dried over anhydrous Na$_2$SO$_4$, filtered and concentrated under reduced pressure. Purification by flash column chromatography (SiO2, gradient elution from 10% EtOAc/hexanes to 75% EtOAc/hexanes) provided 4-oxoisochroman-6-yl ethyl(methyl)carbamate 277.2 (230 mg, 0.922 mmol) as a yellow oil. $^1$H NMR (300 MHz, CDCl$_3$) δ 7.76 (s, 1H), 7.37 (d, J=8.1 Hz, 1H), 7.23 (d, J=8.4 Hz, 1H), 4.89 (s, 2H), 4.36 (s, 2H), 3.50-3.40 (m, 2H), 3.04 (d, J=24.3 Hz, 3H), 1.28-1.11 (m, 3H).

Step 3.

Compound 277.2 (230 mg, 922 μmol) was dissolved in MeOH (3 mL) and treated with hydroxylamine hydrochloride (319 mg, 4.60 mmol) and pyridine (2 mL). The reaction mixture was heated to 65° C. and stirred at that temperature for 30 min. After cooling to room temperature, the reaction mixture was concentrated under reduced pressure The residue was diluted with H$_2$O (10 mL). The pH was adjusted to 5~6 with 1 N HCl aqueous solution, and the mixture was partitioned with EtOAc (15 mL). The aqueous phase was extracted with EtOAc (2×15 mL). The combined organics were dried over anhydrous Na$_2$SO$_4$, filtered, and concentrated in vacuo to provide crude 4-(hydroxyimino)isochroman-6-yl ethyl(methyl)carbamate 277.3 (228 mg, 862 μmol) as a colorless oil which was used without further purification. $^1$H NMR (300 MHz, CDCl$_3$) □ 7.67 (s, 1H), 7.10 (s, 2H), 4.78 (s, 2H), 4.67 (s, 2H), 3.51-3.38 (m, 2H), 3.03 (d, J=22.5 Hz, 3H), 1.29-1.22 (m, 3H).

Step 4.

A flask containing solution of Compound 277.3 (228 mg, 862 μmol) in MeOH (5 mL) was flushed with H$_2$. Raney Ni (0.5 mL) was added and the reaction mixture was stirred at ambient temperature for 3 h under a H$_2$ balloon. (Boc)2O (375 mg, 1.72 mmol) was added, and the mixture was stirred at ambient temperature for 5 h. The nickel catalyst was removed by filtration through a celite pad, and the filtrate was concentrated under reduced pressure. Purification by flash column chromatography (SiO$_2$, gradient elution from 5% EtOAc/hexanes to 20% EtOAc afforded 4-((tert-butoxycarbonyl)amino)isochroman-6-yl ethyl(methyl)carbamate 277.4 (132 mg, 376 μmol) as a colorless oil. $^1$H NMR (300 MHz, CDCl$_3$) δ 7.16 (s, 1H), 7.04-6.95 (m, 2H), 5.08 (d, J=8.7 Hz, 1H), 4.81-4.65 (m, 3H), 4.02 (dd, J=14.7, 2.7 Hz, 1H), 3.85 (dd, J=14.7, 3.0 Hz, 1H), 3.45-3.39 (m, 2H), 3.02 (d, J=21.9 Hz, 3H), 1.46 (s, 9H), 1.26-1.14 (m, 3H).

Step 5.

The compound of Example 277 was prepared as previously described in Example 1. MS (ESI): m/z 251 [M+H]. 1H NMR (300 MHz, CD$_3$OD) δ 7.24-7.12 (m, 3H), 4.98 (d, J=15.3 Hz, 1H), 4.75 (d, J=15.3 Hz, 1H), 4.33 (s, 1H), 4.19 (d, J=12.9 Hz, 1H), 3.94 (dd, J=12.9, 2.1 Hz, 1H), 3.53-3.35 (m, 2H), 3.05 (d, J=31.8 Hz, 3H), 1.19 (dt, J=24.0, 7.2 Hz, 3H).

General Procedure for Chiral Separation of Racemic Compounds.

The chiral separations were carried out on the racemic amines or N-Boc protected amine intermediates using SFC (supercritical CO$_2$ fluid chromatography) on a preparative Thar SFC-80 system using the specified column and co-solvent system. CO$_2$ total flows were between 60 to 80 g/min with 100 bar back pressure. Additional examples were separated by normal phase preparatory HPLC using the specified column and solvent system.

The Faster Moving Enantiomer (FME) was the earlier eluting enantiomer and the Slower Moving Enantiomer (SME) was the later eluting enantiomer. Following isolation of the separated enantiomers, the Boc protecting groups were removed (if needed) and HCl salts were formed as previously described in Example 1. The compounds in Table 12 are all single enantiomers prepared by chiral separation of previously described racemates. For example, Examples 111 and 112 are the individual enantiomers of Example 12. Each example is a single enantiomer, but the absolute stereochemistry has not been conclusively proven.

TABLE 11

Compounds were prepared as described in Example 277 using the appropriately substituted starting materials.

| Example | Structure | Characterization Data |
|---|---|---|
| 278 | 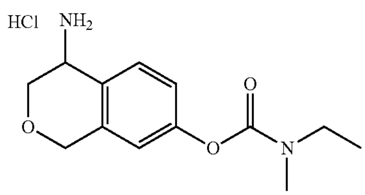 | MS (ESI): m/z 178 [M + H]. $^1$H NMR (300 MHz, CDCl$_3$) δ 8.67 (brs, 3H), 7.43 (s, 1H), 7.12 (d, J = 8.1 Hz, 1H), 6.95 (d, J = 7.8 Hz, 1H), 5.04-4.98 (m, 1H), 4.30 (s, 1H), 4.10 (s, 2H), 2.30 (s, 3H), 1.45 (d, J = 6.6 Hz, 3H). |
| 279 | 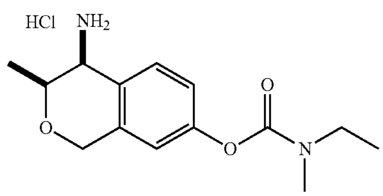 [SMILES: CCN(C)C(=O)Oc1ccc2c(c1)CO[C@@H](C)[C@H]2N ; Cl] | MS (ESI): m/z 265 [M + H]. $^1$H NMR (300 MHz, DMSO-d$_6$) δ 8.30 (brs, 3H), 7.49 (d, J = 8.4 Hz, 1H), 7.08 (dd, J = 8.4, 2.4 Hz, 1H), 6.96 (d, J = 2.4 Hz, 1H), 4.85 (d, J = 15.9 Hz, 1H), 4.75 (d, J = 15.9 Hz, 1H), 4.25 (s, 1H), 3.99-3.92 (m, 1H), 3.44-3.26 (m, 2H), 2.95 (d, J = 36.0 Hz, 3H), 1.32 (d, J = 6.6 Hz, 3H), 1.12 (dt, J = 24.5, 7.2 Hz, 3H). |
| 280 | 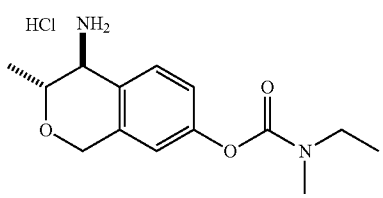 [SMILES: CCN(C)C(=O)Oc1ccc2c(c1)CO[C@H](C)[C@H]2N ; Cl] | MS (ESI): m/z 265 [M + H]. $^1$H NMR (300 MHz, DMSO-d$_6$) δ 8.57 (brs, 3H), 7.59 (d, J = 8.4 Hz, 1H), 7.10 (dd, J = 8.4, 2.1 Hz, 1H), 6.97 (d, J = 2.1 Hz, 1H), 4.73 (s, 2H), 4.18-4.13 (m, 2H), 344-3.26 (m, 2H), 2.95 (d, J = 36.0 Hz, 3H), 1.27 (d, J = 6.3 Hz, 3H), 1.13 (dt, J = 24.4, 6.9 Hz, 3H). |
| 281 | 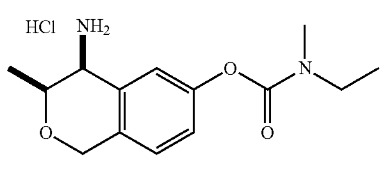 [SMILES: CCN(C)C(=O)Oc1ccc2c(c1)[C@H](N)[C@H](C)OC2 ; Cl] | MS (ESI): m/z 265 [M + H]. $^1$H NMR (300 MHz, CD$_3$OD) δ 7.26-7.16 (m, 3H), 4.99 (d, J = 15.6 Hz, 1H), 4.85 (d, J = 15.6 Hz, 1H), 4.28 (s, 1H), 4.05 (q, J = 6.6 Hz, 1H), 3.57-3.31 (m, 2H), 3.05 (d, J = 34.1 Hz, 3H), 1.41 (d, J = 6.6 Hz, 3H), 1.24 (dt, J = 23.7, 7.2 Hz, 3H). |
| 282 | 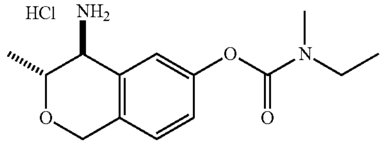 [SMILES: CCN(C)C(=O)Oc1ccc2c(c1)[C@H](N)[C@@H](C)OC2 ; Cl] | MS (ESI): m/z 265 [M + H]. $^1$H NMR (300 MHz, CD$_3$OD) δ 7.09-7.00 (m, 3H), 4.69 (s, 2H), 4.17-4.04 (m, 2H), 3.40-3.32 (m, 2H), 2.89 (d, J = 34.8 Hz, 3H), 1.17 (d, J = 6.6 Hz, 3H), 1.09 (dt, J = 24.6, 7.2 Hz, 3H). |

TABLE 12

Compounds Prepared by Chiral Separation

| Example | Separation Conditions | Analytical Data |
|---|---|---|
| 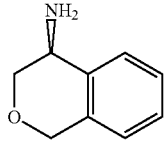 111 | SFC AD-H 20 × 250 mm, 5 μm 65:35 CO₂/MeOH (0.1% NH₄OH) FME | MS (ESI): m/z 150 [M + H]. ¹H NMR (400 MHz, CD₃OD) δ 7.36-7.49 (m, 3H), 7.20 (d, J = 7.6 Hz, 1H), 4.95 (d, J = 15.2 Hz, 1H), 4.82 (d, J = 15.6 Hz, 1H), 4.38 (s, 1H), 4.26 (dd, J = 12.8, 1.6 Hz, 1H), 3.99 (dd, J = 12.8, 2.0 Hz, 1H) |
| 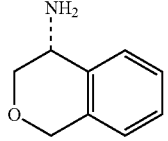 112 | SFC AD-H 20 × 250 mm, 5 μm 65:35 CO₂/MeOH (0.1% NH₄OH) SME | MS (ESI): m/z 150 [M + H]. ¹H NMR (400 MHz, CD₃OD) δ 7.36-7.49 (m, 3H), 7.20 (d, J = 7.6 Hz, 1H), 4.95 (d, J = 15.2 Hz, 1H), 4.82 (d, J = 15.6 Hz, 1H), 4.38 (s, 1H), 4.26 (dd, J = 12.8, 1.6 Hz, 1H,), 3.99 (dd, J = 12.8, 2.0 Hz, 1H) |
| 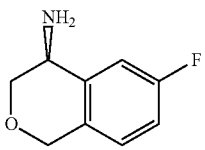 113 | SFC AD 20 × 250 mm, 5 μm 75:25 CO₂/MeOH (0.1% NH₄OH) FME | MS (ESI): m/z 168 [M + H]. ¹H NMR (500 MHz, CD₃OD) δ 7.28-7.18 (m, 3H), 4.94 (d, J = 15.0 Hz, 1H,), 4.78 (d, J = 15.5 Hz, 1H), 4.40 (s, 1H), 4.25 (dd, J = 12.5, 1.5 Hz, 1H), 3.98 (dd, J = 12.5, 2.5 Hz, 1H). |
| 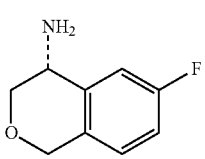 114 | SFC AD 20 × 250 mm, 5 μm 75:25 CO₂/MeOH (0.1% NH₄OH) SME | MS (ESI): m/z 168 [M + H]. ¹H NMR (500 MHz, CD₃OD) δ 7.28-7.18 (m, 3H), 4.94 (d, J = 15.0 Hz, 1H,), 4.78 (d, J = 15.5 Hz, 1H), 4.40 (s, 1H), 4.25 (dd, J = 12.5, 1.5 Hz, 1H), 3.98 (dd, J = 12.5, 2.5 Hz, 1H). |
| 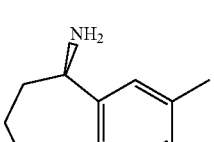 115 | SFC AD 20 × 250 mm, 5 μm 80:20 CO₂/MeOH (0.5% NH₃) FME | MS (ESI): m/z 177 [M + H]. ¹H NMR (500 MHz, CD₃OD) δ 7.17 (d, J = 11.6 Hz, 3H), 4.82 (d, J = 14.6 Hz, 1H), 4.78 (d, J = 8.6 Hz, 1H), 4.74 (d, J = 14.6 Hz, 1H),4.21-4.14 (m, 1H), 4.07-4.02 (m, 1H), 2.40 (s, 3H), 2.19-2.28 (m, 2H). |
| 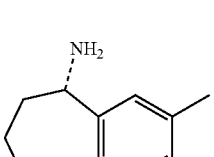 116 | SFC AD 20 × 250 mm, 5 μm 80:20 CO₂/MeOH (0.5% NH₃) SME | MS (ESI): m/z 177 [M + H]. ¹H NMR (500 MHz, CD₃OD) δ 7.17 (d, J = 11.4 Hz, 3H), 4.82 (d, J = 14.6 Hz, 1H), 4.78 (d, J = 8.4 Hz, 1H), 4.74 (d, J = 14.6 Hz, 1H), 4.22-4.14 (m, 1H), 4.07-4.02 (m, 1H), 2.40 (s, 3H), 2.30-2.15 (m, 2H). |
| 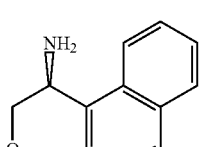 117 | SFC AD-H 20 × 250 mm, 5 μm 60:30 CO₂/MeOH (0.5% NH₄OH) FME | MS (ESI): m/z 183 [M − 16]. ₁H-NMR of freebase (500 MHz, CDCl₃) δ 8.17 (d, J = 8.5 Hz, 1H), 7.87 (d, J = 8.0 Hz, 1H), 7.76 (d, J = 8.5 Hz, 1H), 7.63-7.59 (m, 1H), 7.53-7.50 (m, 1H), 7.12 (d, J = 8.5 Hz, 1H), 4.99-4.88 (m, 2H), 4.38 (s, 1H), 4.27 (d, J = 11.5 Hz, 1H), 4.00-3.97 (dd, J = 11.0, 2.5 Hz, 1H), 1.90 (s, 2H). |

TABLE 12-continued

Compounds Prepared by Chiral Separation

| Example | Separation Conditions | Analytical Data |
|---|---|---|
| 118 | SFC<br>AD-H 20 × 250 mm,<br>5 μm<br>60:40 CO$_2$/MeOH<br>(0.5% NH$_4$OH)<br>SME | MS (ESI): m/z 183 [M − 16]. $_1$H-NMR of freebase (500 MHz, CDCl$_3$) δ 8.16 (d, J = 9.0 Hz, 1H), 7.87 (d, J = 8.0 Hz, 1H), 7.76 (d, J = 8.5 Hz, 1H), 7.63-7.59 (m, 1H), 7.53-7.50 (m, 1H), 7.12 (d, J = 8.5 Hz, 1H), 4.99-4.88 (m, 2H), 4.39 (s, 1H), 4.28 (d, J = 11.5 Hz, 1H), 4.00-3.97 (dd, J = 11.0, 2.5 Hz, 1H), 1.92 (s, 2H). |
| 119 | SFC<br>AD 20 × 250 mm, 5 μm<br>60:30 CO$_2$/MeOH<br>(0.1% NH$_4$OH)<br>FME | MS (ESI): m/z 218 [M + H]. $^1$H NMR (400 MHz, CD$_3$OD) δ 7.64 (d, J = 8.4 Hz, 1H), 7.21 (d, J = 8.4 Hz, 1H), 4.96 (d, J = 15.9 Hz, 1H), 4.78 (d, J = 15.9 Hz, 1H), 4.67 (s, 1H), 4.32 (d, J = 13.0 Hz, 1H), 3.92 (dd, J = 13.0, 1.8 Hz, 1H). |
| 120 | SFC<br>AD 20 × 250 mm, 5 μm<br>60:40 CO$_2$/MeOH<br>(0.1% NH$_4$OH)<br>SME | MS (ESI): m/z 218 [M + H]. $^1$H NMR (400 MHz, CD$_3$OD) δ 7.64 (d, J = 8.4 Hz, 1H), 7.21 (d, J = 8.4 Hz, 1H), 4.96 (d, J = 15.9 Hz, 1H), 4.78 (d, J = 15.9 Hz, 1H), 4.66 (s, 1H), 4.32 (d, J = 13.0 Hz, 1H), 3.92 (dd, J = 13.0, 1.9 Hz, 1H). |
| 121 | SFC<br>AD 20 × 250 mm, 5 μm<br>75:25 CO$_2$/MeOH<br>(0.5% NH$_3$)<br>FME | MS (ESI): m/z 180 [M + H]. $^1$H NMR (400 MHz, CD$_3$OD) δ 7.11 (d, J = 8.5 Hz, 1H), 7.05 (d, J = 2.5 Hz, 1H), 7.00 (dd, J = 8.5, 2.6 Hz, 1H), 4.85 (d, J = 14.9 Hz, 1H), 4.73 (d, J = 14.9 Hz, 1H), 4.34 (s, 1H), 4.23 (dd, J = 12.8, 1.4 Hz, 1H), 3.95 (dd, J = 12.8, 2.3 Hz, 1H), 3.83 (s, 3H). |
| 122 | SFC<br>AD 20 × 250 mm, 5 μm<br>75:25 CO$_2$/MeOH<br>(0.5% NH$_3$)<br>SME | MS (ESI): m/z 180 [M + H]. $^1$H NMR (400 MHz, CD$_3$OD) δ 7.11 (d, J = 8.4 Hz, 1H), 7.05-6.96 (m, 2H), 4.85 (d, J = 14.9 Hz, 1H), 4.74 (d, J = 14.9 Hz, 1H), 4.32 (s, 1H), 4.22 (dd, J = 12.8, 2.0 Hz, 1H), 3.95 (dd, J = 12.8, 2.3 Hz, 1H), 3.83 (s, 3H). |
| 123 | SFC<br>AY 20 × 250 mm, 5 μm<br>90:10 CO$_2$/MeOH<br>(0.5% NH$_3$)<br>FME | MS (ESI): m/z 164 [M + H]. $^1$H NMR (400 MHz, CD$_3$OD) δ 7.28-7.24 (m, 2H), 7.07 (d, J = 8.0 Hz, 1H), 4.91-4.88 (m, 1H), 4.76 (d, J = 15.2 Hz, 1 H), 4.32 (s, 1H), 4.23 (d, J = 12.8 Hz, 1H), 3.95 (dd, J = 12.8, 2.4 Hz, 1H), 2.37 (s, 3H). |
| 124 | SFC<br>AY 20 × 250 mm, 5 μm<br>90:10 CO$_2$/MeOH<br>(0.5% NH$_3$)<br>SME | MS (ESI): m/z 164 [M + H]. $^1$H NMR (400 MHz, CD$_3$OD) δ 7.28-7.23 (m, 2H), 7.07 (d, J = 8.0 Hz, 1H), 4.92-4.88 (m, 1H), 4.75 (d, J = 15.2 Hz, 1 H), 4.32 (s, 1H), 4.23 (dd, J = 12.8, 1.2Hz, 1H), 3.95 (dd, J = 12.8, 2.4 Hz, 1H), 2.37 (s, 3H). |

TABLE 12-continued

Compounds Prepared by Chiral Separation

| Example | Separation Conditions | Analytical Data |
|---|---|---|
| 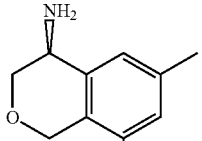<br>125 | HPLC<br>AS-H 20 × 250, 10 μm<br>95:5 Hexanes/EtOH<br>(0.1% DEA)<br>FME | MS (ESI): m/z 178 [M + H]. $^1$H NMR (500 MHz, CD$_3$OD) δ 7.10 (d, J = 7.2 Hz, 2H), 4.89 (s, 1H), 4.68 (d, J = 15.5 Hz, 1H), 4.30 (s, 1H), 4.22 (d, J = 12.7 Hz, 1H), 3.92 (d, J = 12.6 Hz, 1H), 2.35 (s, 3H), 2.18 (s, 3H). |
| 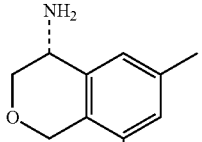<br>126 | HPLC<br>AS-H 20 × 250, 10 μm<br>95:5 Hexanes/EtOH<br>(0.1% DEA)<br>SME | MS (ESI): m/z 178 [M + H]. $^1$H NMR (500 MHz, CD$_3$OD) δ 7.11 (d, J = 15.7 Hz, 2H), 4.89 (s, 1H), 4.67 (d, J = 15.5 Hz, 1H), 4.31 (s, 1H), 4.23 (d, J = 12.7 Hz, 1H), 3.92 (d, J = 12.6 Hz, 1H), 2.35 (s, 3H), 2.18 (s, 3H). |
| 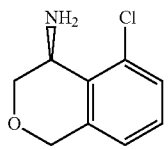<br>127 | SFC<br>AD 20 × 250 mm, 5 μm<br>70:30 CO$_2$/MeOH<br>(0.5% NH$_3$)<br>SME | MS (ESI): m/z 184.0 [M + H]. $^1$H NMR (400 MHz, CD$_3$OD) δ 7.47-7.42 (m, 2H), 7.19 (dd, J = 6.0, 3.2 Hz, 1 H), 5.00-4.78 (m, 2 H), 4.63 (s, 1 H), 4.33 (dd, J = 12.8, 0.8 Hz, 1 H), 3.93 (dd, J = 13.2, 2.0 Hz, 1 H). |
| 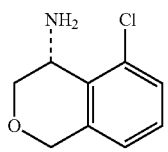<br>128 | SFC<br>AD 20 × 250 mm, 5 μm<br>70:30 CO$_2$/MeOH<br>(0.5% NH$_3$)<br>FME | MS (ESI): m/z 184.0 [M + H]. $^1$H NMR (400 MHz, CD$_3$OD) δ 7.46-7.42(m, 2H), 7.20 (m, 1 H), 4.99-4.78 (m, 2 H), 4.62 (s, 1 H), 4.34-4.31 (m, 1 H), 3.93 (dd, J = 12.8, 1.6 Hz, 1 H). |
| 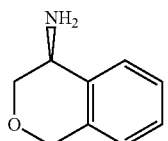<br>129 | SFC<br>AY 20 × 250 mm, 5 μm<br>50:50 CO$_2$/MeOH<br>(0.5% NH$_3$)<br>FME | MS (ESI): m/z 164.1 [M + H]. $^1$H NMR (400 MHz, DMSO-d6) δ 8.73 (br s, 3 H), 7.42 (d, J = 6.8 Hz, 1 H), 7.24-7.18 (m, 2 H), 4.79-4.59 (m, 2H), 4.28 (s, 1 H), 4.22 (dd, J = 12.4, 2.0 Hz, 1H), 3.84 (dd, J = 12.4, 2.0 Hz, 1 H), 2.13 (s, 3 H). |
| 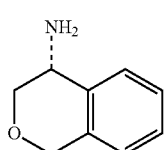<br>130 | SFC<br>AY 20 × 250 mm, 5 μm<br>50:50 CO$_2$/MeOH<br>(0.5% NH$_3$)<br>SME | MS (ESI): m/z 164.1 [M + H]. $^1$H NMR (400 MHz, DMSO-d6) δ 8.69 (br s, 3 H), 7.42 (d, J = 6.8 Hz, 1 H), 7.24-7.18 (m, 2 H), 4.79-4.59 (m, 2H), 4.28 (s, 1 H), 4.20 (dd, J = 12.4, 1.6 Hz, 1 H), 3.83 (dd, J = 12.4, 2.4 Hz, 1 H), 2.13 (s, 3 H). |
| 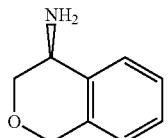<br>131 | SFC<br>OJ 20 × 250 mm, 5 μm<br>70:30 CO$_2$/MeOH<br>(0.5% NH$_3$)<br>FME | MS (ESI): m/z 184 [M + H]. $^1$H NMR (400 MHz, DMSO-d6) δ 8.88 (br s, 3H), 7.64 (d, J = 7.6 Hz, 1H), 7.50-7.48 (m, 1H), 7.38 (t, J = 8.0 Hz, 1H), 4.82-4.61 (m, 2H), 4.36 (s, 1H), 4.28-4.25 (m, 1H), 3.88 (dd, J = 12.4, 2.4 Hz, 1H). |

TABLE 12-continued

Compounds Prepared by Chiral Separation

| Example | Separation Conditions | Analytical Data |
|---|---|---|
| 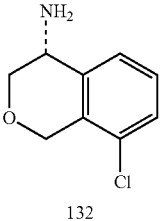 [SMILES: N[C@H]1COCc2c(Cl)cccc21] 132 | SFC<br>OJ 20 × 250 mm, 5 μm<br>70:30 CO$_2$/MeOH<br>(0.5% NH$_3$)<br>SME | MS (ESI): m/z 184 [M + H]. $^1$H NMR (400 MHz, DMSO-d6) δ 8.87 (br s, 3H), 7.64 (d, J = 7.2 Hz, 1H), 7.48 (dd, J = 8.4, 0.8 Hz, 1H), 7.38 (t, J = 8.0 Hz, 1H), 4.82-4.61 (m, 2H), 4.37 (s, 1H), 4.28-4.25 (m, 1H), 3.88 (dd, J = 12.8, 2.4 Hz, 1H). |
| 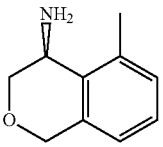 133 | SFC<br>IC 30 × 250 mm, 5 μm<br>90:10 CO$_2$/MeOH<br>(0.1% NH$_4$OH)<br>FME | MS (ESI): m/z 164 [M + H]. $^1$H NMR (400 MHz, DMSO-d6) δ 8.56 (br s, 3H), 7.25 (d, J = 7.6 Hz, 1H), 7.12 (d, J = 7.2 Hz, 1H), 6.97 (d, J = 8.0 Hz, 1H), 4.87-4.68 (m, 2H), 4.32 (s, 1H), 4.30 (d, J = 12.0 Hz, 1H), 3.75 (d, J = 11.2 Hz, 1H), 2.42 (s, 3H). |
| 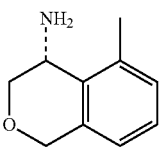 134 | SFC<br>IC 30 × 250 mm, 5 μm<br>90:10 CO$_2$/MeOH<br>(0.1% NH$_4$OH)<br>SME | MS (ESI): m/z 164 [M + H]. $^1$H NMR (400 MHz, DMSO-d6) δ 8.54 (br s, 3H), 7.26 (t, J = 7.6 Hz, 1H), 7.12 (d, J = 7.2 Hz, 1H), 6.97 (d, J = 7.6 Hz, 1H), 4.87-4.68 (m, 2H), 4.39 (s, 1H), 4.30 (d, J = 12.0 Hz, 1H), 3.78-3.75 (m, 1H), 2.42 (s, 3H). |
| 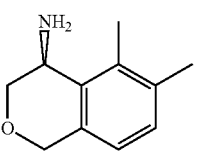 135 | SFC<br>AD 20 × 250 mm, 5 μm<br>55:45 CO$_2$/MeOH<br>(0.5% NH$_3$)<br>FME | MS (ESI): m/z 178 [M + H]. $^1$H NMR (500 MHz, CD$_3$OD) δ 7.22 (d, J = 8.0 Hz, 1H), 6.92 (d, J = 8.0 Hz, 1H), 4.93 (d, J = 15.0 Hz, 1H), 4.79 (d, J = 15.0 Hz, 1H), 4.58 (s, 1H), 4.30 (dd, J = 12.5, 1.0 Hz, 1H), 3.90 (d, J = 12.5 Hz, 1H), 2.34 (s, 3H), 2.33 (s, 3H). |
| 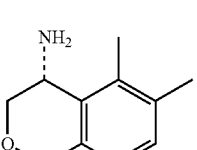 136 | SFC<br>AD 20 × 250 mm, 5 μm<br>55:45 CO$_2$/MeOH<br>(0.5% NH$_3$)<br>SME | MS (ESI): m/z 178 [M + H]. $^1$H NMR (500 MHz, CD$_3$OD) δ 7.23 (d, J = 7.5 Hz, 1H), 6.93 (d, J = 7.5 Hz, 1H), 4.93 (d, J = 15.0 Hz, 1H), 4.79 (d, J = 15.0 Hz, 1H), 4.61 (s, 1H), 4.30 (dd, J = 12.5, 1.0Hz, 1H), 3.91 (d, J = 12.5 Hz, 1H), 2.34 (s, 3H), 2.33 (s, 3H). |
| 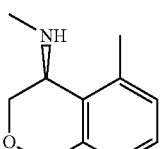 137 | SFC<br>AY 4.6 × 250 mm, 5 μm<br>85:15 CO$_2$/EtOH<br>(0.1% NH$_3$)<br>FME | MS (ESI): m/z 178 [M + H]. $^1$H NMR (500 MHz, CD$_3$OD) δ 7.35 (d, J = 7.6 Hz, 1H), 7.25 (d, J = 7.5 Hz, 1H), 7.05 (d, J = 7.7 Hz, 1H), 5.00 (d, J = 15.6 Hz, 1H), 4.84 (d, J = 15.6 Hz, 1H), 4.55-4.41 (m, 2H), 3.90 (dd, J = 13.1, 1.3 Hz, 1H), 2.85 (s, 3H), 2.47 (s, 3H). |
| 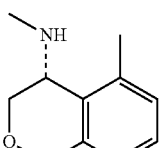 138 | SFC<br>AY 4.6 × 250 mm, 5 μm<br>85:15 CO$_2$/EtOH<br>(0.1% NH$_3$)<br>SME | MS (ESI): m/z 178 [M + H]. $^1$H NMR (500 MHz, CD$_3$OD) δ 7.36 (t, J = 7.6 Hz, 1H), 7.25 (d, J = 7.5 Hz, 1H), 7.04 (d, J = 7.7 Hz, 1H), 4.99 (d, J = 15.6 Hz, 1H), 4.84 (d, J = 15.7 Hz, 1H), 4.53-4.42 (m, 2H), 3.90 (dd, J = 13.1, 1.2 Hz, 1H), 2.85 (s, 3H), 2.47 (s, 3H). |

TABLE 12-continued

| | Compounds Prepared by Chiral Separation | |
|---|---|---|
| Example | Separation Conditions | Analytical Data |
| 139 | HPLC<br>AY-H 4.6 × 250 mm,<br>5 μm<br>90:10 Hexanes/EtOH<br>(0.1% DEA)<br>FME | MS (ESI) m/z 194 [M + H]. $^1$H NMR (400 MHz, CD$_3$OD) δ 7.14 (d, J = 8.5 Hz, 1H), 7.10-7.01 (m, 2H), 4.91 (d, J = 12.0 Hz, 4H), 4.76 (d, J = 15.0 Hz, 1H), 4.43 (dd, J = 13.3, 0.8 Hz, 1H), 4.25 (s, 1H), 3.91 (dd, J = 13.3, 1.9 Hz, 1H), 3.85 (s, 3H), 2.77 (s, 3H). |
| 140 | HPLC<br>AY-H 4.6 × 250 mm,<br>5 μm<br>90:10 Hexanes/EtOH<br>(0.1% DEA)<br>SME | MS (ESI): m/z 194 [M + H]. $^1$H NMR (400 MHz, CD$_3$OD) δ 7.14 (d, J = 8.5 Hz, 1H), 7.10-7.02 (m, 2H), 4.90 (d, J = 12.0 Hz, 1H), 4.76 (d, J = 15.0 Hz, 1H), 4.43 (dd, J = 13.2, 1.0 Hz, 1H), 4.25 (s, 1H), 3.91 (dd, J = 13.2, 1.9 Hz, 1H), 3.85 (s, 3H), 2.77 (s, 3H). |
| 141 | HPLC<br>AY-H 4.6 × 250 mm,<br>5 μm<br>90:10 Hexanes/EtOH<br>(0.1% DEA)<br>FME | MS (ESI): m/z 178 [M + H]. $^1$H NMR (400 MHz, CD$_3$OD) δ 7.32 (s, 1H), 7.28 (d, J = 8.0 Hz, 1H), 7.10 (d, J = 8.0 Hz, 1H), 4.93 (d, J = 15.2 Hz, 1H), 4.78 (d, J = 15.2 Hz, 1H), 4.43 (d, J = 12.8 Hz, 1H), 4.23 (s, 1H), 3.92 (dd, J = 13.2, 2.0 Hz, 1H), 2.76 (s, 3H), 2.38 (s, 3H). |
| 142 | HPLC<br>AY-H 4.6 × 250 mm,<br>5 μm<br>90:10 Hexanes/EtOH<br>(0.1% DEA)<br>SME | MS (ESI): m/z 178 [M + H]. $^1$H NMR (400 MHz, CD$_3$OD) δ 7.32 (s, 1H), 7.28 (d, J = 8.0 Hz, 1H), 7.10 (d, J = 8.0 Hz, 1H), 4.93 (d, J = 15.2 Hz, 1H), 4.78 (d, J = 15.2 Hz, 1H), 4.43 (d, J = 12.8 Hz, 1H), 4.23 (s, 1H), 3.92 (dd, J = 13.2, 2.0 Hz, 1H), 2.76 (s, 3H), 2.38 (s, 3H). |
| 143 | SFC<br>AY-H 4.6 × 250 mm,<br>5 μm<br>80:20 CO$_2$/EtOH<br>(1% NH$_3$)<br>FME | MS (ESI): m/z 192 [M +H]. $^1$H NMR (400 MHz, CD$_3$OD) δ 7.25 (d, J = 7.8 Hz, 1H), 6.93 (d, J = 7.8 Hz, 1H), 4.94 (d, J = 15.4 Hz, 1H), 4.80 (d, J = 15.4 Hz, 1H), 4.53~4.43 (m, 2H), 3.91~3.82 (m, 1H), 2.83 (s, 3H), 2.33 (s, 6H). |
| 144 | SFC<br>AY-H 4.6 × 250 mm,<br>5 μm<br>80:20 CO$_2$/EtOH<br>(1% NH$_3$)<br>SME | MS (ESI): m/z 192 [M +H]. $^1$H NMR (400 MHz, CD$_3$OD) δ 7.27 (d, J = 8.0 Hz, 1H), 6.94 (d, J = 8.0 Hz, 1H), 4.94 (d, J = 15.4 Hz, 1H), 4.80 (d, J = 15.3 Hz, 1H), 4.48 (dd, J = 15.2, 1.9 Hz, 2H), 3.86 (dd, J = 12.9, 0.9 Hz, 1H), 2.82 (s, 3H), 2.33 (s, 6H). |
| 145 | HPLC<br>AY-H 4.6 × 250 mm,<br>5 μm<br>80:20 Hexanes/EtOH<br>(0.1% DEA)<br>FME | MS (ESI): m/z 198 [M + H]. $^1$H NMR (500 MHz, CD$_3$OD) δ 7.36 (t, J = 7.6 Hz, 1H), 7.25 (d, J = 7.5 Hz, 1H), 7.04 (d, J = 7.7 Hz, 1H), 4.99 (d, J = 15.6 Hz, 1H), 4.84 (d, J = 15.7 Hz, 1H), 4.53-4.42 (m, 2H), 3.90 (dd, J = 13.1, 1.2 Hz, 1H), 2.85 (s, 3H), 2.47 (s, 3H). |

TABLE 12-continued

Compounds Prepared by Chiral Separation

| Example | Separation Conditions | Analytical Data |
|---|---|---|
| 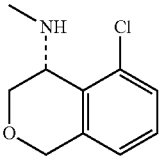 146 | HPLC AY-H 4.6 × 250 mm, 5 μm 80:20 Hexanes/EtOH (0.1% DEA) SME | MS (ESI): m/z 198 [M + H]. $^1$H NMR (500 MHz, CD$_3$OD) δ 7.53-7.47 (m, 2H), 7.22 (dd, J = 8.6, 6.6 Hz, 1H), 5.01 (d, J = 15.9 Hz, 1H), 4.83 (d, J = 15.9 Hz, 1H), 4.59-4.46 (m, 2H), 3.92 (dd, J = 13.4, 1.6 Hz, 1H), 2.88 (s, 3H). |
| 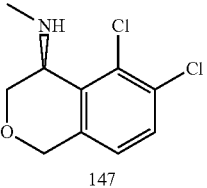 147 | HPLC AY-H 4.6 × 250 mm, 5 μm 90:10 Hexanes/EtOH (0.1% DEA) FME | MS (ESI): m/z 232 [M + H]. $^1$H NMR (400 MHz, CD$_3$OD) δ 7.67 (d, J = 8.8 Hz, 1H), 7.23 (d, J = 8.4 Hz, 1H), 4.99 (d, J = 16.0 Hz, 1H), 4.79 (d, J = 16.4 Hz, 1H), 4.59 (s, 1H), 4.52 (d, J = 13.6 Hz, 1H), 3.89 (dd, J = 12.8, 1.2 Hz, 1H), 2.89 (s, 3H). |
| 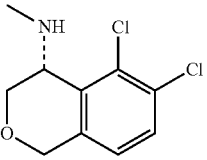 148 | HPLC AY-H 4.6 × 250 mm, 5 μm 90:10 Hexanes/EtOH (0.1% DEA) SME | MS (ESI): m/z 232 [M + H]. $^1$H NMR (400 MHz, CD$_3$OD) δ 7.67 (d, J = 8.8 Hz, 1H), 7.21 (d, J = 8.4 Hz, 1H), 4.99 (d, J = 16.0 Hz, 1H), 4.79 (d, J = 16.4 Hz, 1H), 4.59 (s, 1H), 4.52 (d, J = 13.6 Hz, 1H), 3.89 (dd, J = 12.8, 1.2 Hz, 1H), 2.89 (s, 3H). |
| 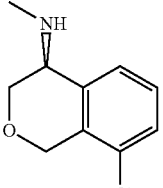 149 | SFC AY 20 × 250 mm, 5 μm 80:20 CO$_2$/EtOH (0.2% NH$_3$) FME | MS (ESI): m/z 198 [M + H]. $^1$H NMR (400 MHz, CD$_3$OD) δ 7.52 (dd, J = 13.3, 8.0 Hz, 2H), 7.42 (t, J = 7.8 Hz, 1H), 5.03 (d, J = 16.3 Hz, 1H), 4.74 (d, J = 16.3 Hz, 1H), 4.46 (d, J = 13.2 Hz, 1H), 4.33 (s, 1H), 3.93 (dd, J = 13.2, 1.5 Hz, 1H), 2.79 (s, 3H). |
| 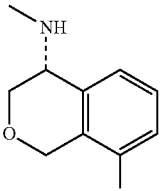 150 | SFC AY-H 20 × 250 mm, 5 μm 80:20 CO$_2$/EtOH (0.2% NH$_3$) SME | MS (ESI): m/z 198 [M + H]. $^1$H NMR (400 MHz, CD$_3$OD) δ 7.41 (dd, J = 16.0, 6.6 Hz, 2H), 7.31 (t, J = 7.8 Hz, 1H), 4.92 (d, J = 16.3 Hz, 1H), 4.63 (d, J = 16.3 Hz, 1H), 4.35 (d, J = 13.3 Hz, 1H), 4.22 (s, 1H), 3.82 (dd, J = 13.2, 1.5 Hz, 1H), 2.68 (s, 3H). |
| 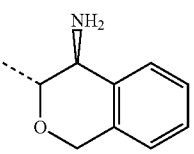 151 | SFC OD 4.6 × 250 mm, 5 μm 90:10 CO$_2$/MeOH (0.2% NH$_3$) FME | MS (ESI): m/z 164 [M + H]. $^1$H NMR (400 MHz, CD$_3$OD) δ 7.47 (m, 1H), 7.43 (ddd, J = 7.2, 7.2, 0.8 Hz, 1H), 7.37 (dd, J = 8.0, 8.0 Hz, 1H), 7.20 (d, J = 7.2 Hz, 1H), 4.86 (s, 2H), 4.30 (m, 1H), 4.21 (s, 1H), 1.33 (d, J = 6.8 Hz, 3H). |
| 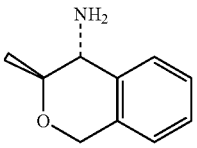 152 | SFC OD 4.6 × 250 mm, 5 μm 90:10 CO$_2$/MeOH (0.2% NH$_3$) SME | MS (ESI): m/z 164 [M + H]. $^1$H NMR (400 MHz, CD$_3$OD) δ 7.48 (m, 1H), 7.42 (ddd, J = 7.6, 7.6, 1.2 Hz, 1H), 7.37 (dd, J = 7.6, 7.6, Hz, 1H), 7.20 (d, J = 7.2 Hz, 1H), 4.86 (s, 2H), 4.31 (m, 1H), 4.22 (s, 1H), 1.33 (d, J = 6.8 Hz, 3H). |

TABLE 12-continued

Compounds Prepared by Chiral Separation

| Example | Separation Conditions | Analytical Data |
|---|---|---|
| 153 | SFC<br>IC 20 × 250 mm, 5 μm<br>85:15 CO$_2$/MeOH<br>(0.5% NH$_3$)<br>FME | MS (ESI): m/z 164 [M + H]. $^1$H NMR (400 MHz, CD$_3$OD) δ 7.45-7.34 (m, 3H), 7.20 (d, J = 7.2 Hz, 1H), 4.98 (d, J = 15.6 Hz, 1H), 4.90-4.86 (m, 1H), 4.28 (s, 1H), 4.08-4.03 (m, 1H), 1.42 (d, J = 6.4 Hz, 3H). |
| 154 | SFC<br>IC 20 × 250 mm, 5 μm<br>85:15 CO$_2$/MeOH<br>(0.5% NH$_3$)<br>SME | MS (ESI): m/z 164 [M + H]. $^1$H NMR (400 MHz, CD$_3$OD) δ 7.47-7.34 (m, 3H), 7.20 (d, J = 7.6 Hz, 1H), 4.98 (d, J = 15.6 Hz, 1H), 4.90-4.86 (m, 1H), 4.29 (s, 1H), 4.07-4.03 (m, 1H), 1.42 (d, J = 6.4 Hz, 3H). |
| 155 | SFC<br>AD 4.6 × 250 mm, 5 μm<br>85:15 CO$_2$/MeOH<br>(0.2% NH$_3$)<br>FME | MS (ESI): m/z 178 [M + H]. $^1$H NMR (500 MHz, CD$_3$OD) δ 7.27 (s, 1H), 7.26 (d, J = 8.2 Hz, 1H), 7.09 (d, J = 7.7 Hz, 1H), 4.83 (d, J = 2.2 Hz, 2H), 4.27 (qd, J = 6.7, 2.6 Hz, 1H), 4.15 (d, J = 2.4 Hz, 1H), 2.39 (s, 3H), 1.33 (d, J = 6.7 Hz, 3H). |
| 156 | SFC<br>AD 4.6 × 250 mm, 5 μm<br>85:15 CO$_2$/MeOH<br>(0.2% NH$_3$)<br>SME | MS (ESI): m/z 178 [M + H]. $^1$H NMR (500 MHz, CD$_3$OD) δ 7.27 (s, 1H), 7.26 (d, J = 8.6 Hz, 1H), 7.09 (d, J = 7.7 Hz, 1H), 4.83 (s, 2H), 4.28 (qd, J = 6.6, 2.6 Hz, 1H), 4.15 (d, J = 2.4 Hz, 1H), 2.39 (s, 3H), 1.33 (d, J = 6.7 Hz, 3H). |
| 157 | HPLC<br>AY-H 4.6 × 250 mm, 5 μm<br>90:10 Hexanes/EtOH<br>(0.1% Et$_2$NH)<br>FME | MS (ESI): m/z 178 [M + H]. $^1$H NMR (400 MHz, CD$_3$OD) δ 7.26 (s, 1H), 7.24 (d, J = 8.0 Hz, 1H), 7.08 (d, J = 8.0 Hz, 1H), 4.93 (s, J = 12.0 Hz, 1H), 4.84 (d, J = 15.3 Hz, 1H), 4.22 (s, 1H), 4.03 (dd, J = 6.6, 1.6 Hz, 1H), 2.38 (s, 3H), 1.41 (d, J = 6.6 Hz, 3H). |
| 158 | HPLC<br>AY-H 4.6 × 250 mm, 5 μm<br>90:10 Hexanes/EtOH<br>(0.1% Et$_2$NH)<br>SME | MS (ESI): m/z 178 [M + H]. $^1$H NMR (400 MHz, CD$_3$OD) δ 7.26 (s, 1H), 7.25 (d, J = 8.1 Hz, 1H), 7.08 (d, J = 7.7 Hz, 1H), 4.94 (d, J = 12.0 Hz, 1H), 4.84 (d, J = 15.4 Hz, 1H), 4.23 (s, 1H), 4.03 (dd, J = 6.6, 1.6 Hz, 1H), 2.38 (s, 3H), 1.41 (d, J = 6.6 Hz, 3H). |
| 159 | SFC<br>IC 20 × 250 mm, 5 μm<br>80:20 CO$_2$/MeOH<br>(0.2% NH$_3$)<br>FME | MS (ESI): m/z 198 [M + H]. $^1$H NMR (400 MHz, CD$_3$OD) δ 7.47-7.44 (m, 2H), 7.27-7.17 (m, 1H), 4.88 (s, 2H), 4.48-4.43 (m, 2H), 1.28 (d, J = 6.8 Hz, 3H). |
| 160 | SFC<br>IC 20 × 250 mm, 5 μm<br>80:20 CO$_2$/MeOH<br>(0.2% NH$_3$)<br>SME | MS (ESI): m/z 198 [M + H]. $^1$H NMR (400 MHz, CD$_3$OD) δ 7.52-7.41 (m, 2H), 7.25-7.16 (m, 1H), 4.88 (s, 2H), 4.53-4.39 (m, 2H), 1.28 (d, J = 6.8 Hz, 3H). |

TABLE 12-continued

Compounds Prepared by Chiral Separation

| Example | Separation Conditions | Analytical Data |
|---|---|---|
| 165 | SFC<br>AY 30 × 250 mm, 5 μm<br>80:20 CO$_2$/MeOH<br>(0.1% NH$_4$OH)<br>FME | MS (ESI): m/z 161 [M − 16]. $^1$H NMR (400 MHz, CD$_3$OD) δ 8.48 (bs, 3 H), 7.10 (dd, J$_1$ = 6.4 Hz, J$_2$ =20 Hz, 2 H), 4.80 (d, J = 12.4 Hz, 1 H), 4.61 (d, J = 12.8 Hz, 1 H), 4.39 (s, 1 H), 4.27 (d, J = 9.6 Hz, 1 H), 3.73 (d, J = 9.6 Hz, 1 H), 2.38 (s, 3 H), 2.10 (s, 3 H). |
| 166 | SFC<br>AY 30 × 250 mm, 5 μm<br>80:20 CO$_2$/MeOH<br>(0.1% NH$_4$OH)<br>SME | MS (ESI): m/z 161 [M − 16]. $^1$H NMR (400 MHz, CD$_3$OD) δ 8.52 (bs, 3 H), 7.09 (m, 2 H), 4.81 (d, J = 13.2 Hz, 1 H), 4.61 (d, J = 12.4 Hz, 1 H), 4.39 (d, J = 2.8 Hz, 1 H), 4.28 (d, J = 10.0 Hz, 1 H), 3.72 (d, J = 9.6 Hz, 1 H), 2.39 (s, 3 H), 2.09 (s, 3 H). |
| 167 | SFC<br>IC 4.6 × 250 mm, 5 μm<br>85:15 CO$_2$/MeOH<br>(0.2% NH$_3$)<br>FME | MS (ESI): m/z 178 [M + H]. $^1$H NMR (400 MHz, CD$_3$OD) δ 7.34 (t, J = 7.6 Hz, 1H), 7.23 (d, J = 7.5 Hz, 1H), 7.03 (d, J = 7.7 Hz, 1H), 4.88 (s, 2H), 4.49-4.35 (m, 2H), 2.45 (s, 3H), 1.27 (d, J = 6.7 Hz, 3H). |
| 168 | SFC<br>IC 4.6 × 250 mm, 5 μm<br>85:15 CO$_2$/MeOH<br>(0.2% NH$_3$)<br>SME | MS (ESI): m/z 178 [M + H]. $^1$H NMR (400 MHz, CD$_3$OD) δ 7.34 (t, J = 7.6 Hz, 1H), 7.23 (d, J = 7.5 Hz, 1H), 7.03 (d, J = 7.7 Hz, 1H), 4.88 (s, 2H), 4.48-4.37 (m, 2H), 2.46 (s, 3H), 1.27 (d, J = 6.7 Hz, 3H). |
| 169 | HPLC<br>AY-H 20 × 250 mm,<br>5 μm<br>90:10 Hexanes/EtOH<br>(0.1% Et$_2$NH)<br>FME | MS (ESI): m/z 178 [M + H]. $^1$H NMR (400 MHz, CD$_3$OD) δ 7.32 (t, J = 7.6 Hz, 1H), 7.22 (d, J = 7.5 Hz, 1H), 7.02 (d, J = 7.7 Hz, 1H), 4.99 (d, J = 15.6 Hz, 1H), 4.87 (s, 1H), 4.44 (s, 1H), 4.08-3.99 (m, 1H), 2.45 (s, 3H), 1.44 (d, J = 6.6 Hz, 3H). |
| 170 | HPLC<br>AY-H 20 × 250 mm,<br>5 μm<br>90:10 Hexanes/EtOH<br>(0.1% Et$_2$NH)<br>SME | MS (ESI): m/z 178 [M + H]. $^1$H NMR (400 MHz, CD$_3$OD) δ 7.32 (t, J = 7.6 Hz, 1H), 7.22 (d, J = 7.5 Hz, 1H), 7.02 (d, J = 7.6 Hz, 1H), 4.99 (d, J = 15.6 Hz, 1H), 4.87 (s, 1H), 4.43 (s, 1H), 4.03 (d, J = 6.6 Hz, 1H), 2.44 (s, 3H), 1.43 (d, J = 6.6 Hz, 3H). |
| 171 | SFC<br>OD 20 × 250 mm, 5 μm<br>85:15 CO$_2$/MeOH<br>(0.2% NH$_3$)<br>FME | MS (ESI): m/z 194 [M + H]. $^1$H NMR (400 MHz, CD$_3$OD) δ 7.13 (d, J = 8.2 Hz, 1H), 7.04-7.01 (m, 2H), 4.86-4.75 (m, 2H), 4.25 (tt, J = 6.7, 3.3 Hz, 1H), 4.17 (d, J = 2.3 Hz, 1H), 3.85 (s, 3H), 1.34 (d, J = 6.7 Hz, 3H). |

TABLE 12-continued

Compounds Prepared by Chiral Separation

| Example | Separation Conditions | Analytical Data |
|---|---|---|
| 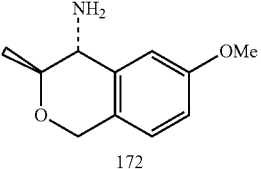 172 | SFC<br>OD 20 × 250 mm, 5 μm<br>85:15 CO$_2$/MeOH<br>(0.2% NH$_3$)<br>SME | MS (ESI): m/z 194 [M + H]. $^1$H NMR (400 MHz, CD$_3$OD) δ 7.13 (d, J = 9.3 Hz, 1H), 7.04-7.01 (m, 2H), 4.81 (d, J = 1.7 Hz, 2H), 4.25 (dd, J = 6.6, 2.4 Hz, 1H), 4.17 (s, 1H), 3.85 (s, 3H), 1.34 (d, J = 6.7 Hz, 3H). |
| 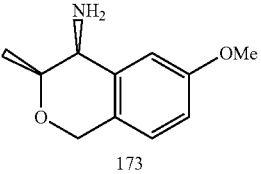 173 | SFC<br>AD 4.6 × 250 mm, 5 μm<br>90:10 CO$_2$/MeOH<br>(0.2% NH$_3$)<br>FME | MS (ESI): m/z 194 [M + H]. $^1$H NMR (400 MHz, CD$_3$OD) δ 7.11 (s, 1H), 7.02 (d, J = 6.4 Hz, 2H), 4.90 (s, 1H), 4.84 (s, 1H), 4.24 (s, 1H), 4.03 (s, 1H), 1.41 (d, J = 6.6 Hz, 3H). |
| 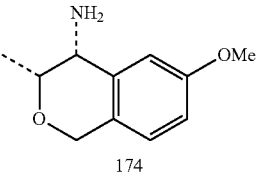 174 | SFC<br>AD 4.6 × 250 mm, 5 μm<br>90:10 CO$_2$/MeOH<br>(0.2% NH$_3$)<br>SME | MS (ESI): m/z 194 [M + H]. $^1$H NMR (400 MHz, CD$_3$OD) δ 7.12 (d, J = 9.2 Hz, 1H), 7.05-6.99 (m, 2H), 4.90 (s, 1H), 4.82 (d, J = 15.0 Hz, 1H), 4.24 (s, 1H), 4.03 (dd, J = 6.6, 1.6 Hz, 1H), 3.85 (s, 3H), 1.41 (d, J = 6.6 Hz, 3H). |
| 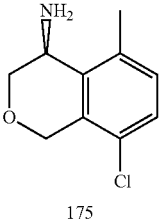 175 | SFC<br>IC 30 × 250 mm, 5 μm<br>80:20 CO$_2$/MeOH<br>(0.1% NH$_4$OH)<br>FME | MS (ESI): m/z 198 [M + H]. $^1$H NMR (400 MHz, CD$_3$OD) δ 7.39 (d, J = 8.0 Hz, 1 H), 7.27 (d, J = 8.4 Hz, 1 H), 5.04 (d, J = 16.0 Hz, 1 H), 4.72 (d, J = 16.4 Hz, 1 H), 4.59-4.58 (m, 1 H), 4.35-4.30 (m, 1 H), 3.90 (dd, J = 12.8, 1.2 Hz, 1 H), 2.48-2.47 (m, 3 H). |
| 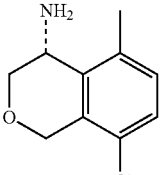 176 | SFC<br>IC 30 × 250 mm, 5 μm<br>80:20 CO$_2$/MeOH<br>(0.1% NH$_4$OH)<br>SME | MS (ESI): m/z 198 [M + H]. $^1$H NMR (400 MHz, CD$_3$OD) δ 7.39 (d, J = 8.0 Hz, 1 H), 7.26 (d, J = 8.4 Hz, 1 H), 5.04 (d, J = 16.4 Hz, 1 H), 4.71 (d, J = 16.0 Hz, 1 H), 4.58-4.56 (m, 1 H), 4.33-4.29 (m, 1 H), 3.90 (dd, J = 12.4, 1.2 Hz, 1 H), 2.47-2.46 (m, 3 H). |
| 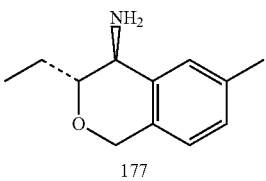 177 | SFC<br>AD-H 20 × 250 mm, 5 μm<br>90:10 CO$_2$/MeOH<br>(0.2% NH$_3$)<br>FME | MS (ESI): m/z 175 [M − 16]. $^1$H NMR (400 MHz, CD$_3$OD) δ 7.29 (s, 1H), 7.26-7.24 (d, J = 8.0 Hz, 1H), 7.09-7.07 (d, J = 7.9 Hz, 1H), 4.80 (s, 2H), 4.21 (s, 1H), 4.03-3.99 (m, 1H), 2.39 (s, 3H), 1.66-1.56 (m, 2H), 1.10-1.06 (t, J = 7.4 Hz, 3H). |
| 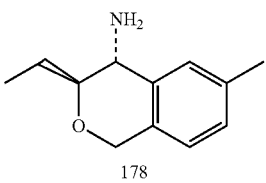 178 | SFC<br>AD-H 20 × 250 mm, 5 μm<br>90:10 CO$_2$/MeOH<br>(0.2% NH$_3$)<br>SME | MS (ESI): m/z 175 [M − 16]. $^1$H NMR (400 MHz, CD$_3$OD) δ 7.30 (s, 1H), 7.26-7.24 (d, J = 8.0 Hz, 1H), 7.09-7.07 (d, J = 7.9 Hz, 1H), 4.80 (s, 2H), 4.21 (s, 1H), 4.04-4.00 (m, 1H), 2.39 (s, 3H), 1.66-1.57 (m, 2H), 1.10-1.06 (t, J = 7.4 Hz, 3H). |

TABLE 12-continued

Compounds Prepared by Chiral Separation

| Example | Separation Conditions | Analytical Data |
|---|---|---|
| 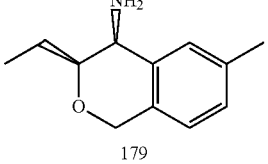 179 | HPLC AY-H 50 × 250 mm, 5 μm 90:10 Hexanes/EtOH (0.1% Et$_2$NH) FME | MS (ESI): m/z 192 [M + H]. $^1$H NMR (400 MHz, CD$_3$OD) δ 7.27-7.25 (m, 2H), 7.09 (d, J = 7.6 Hz, 1H), 4.98 (d, J = 15.2 Hz, 1H), 4.83 (d, J = 15.6 Hz, 1H), 4.29 (s, 1H), 3.75-3.72 (m, 1H), 2.39 (s, 3H), 1.76-1.66 (m, 2H), 1.16 (t, J = 7.2 Hz, 3H). |
| 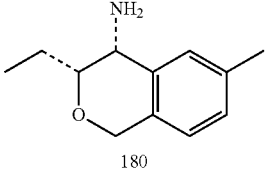 180 | HPLC AY-H 50 × 250 mm, 5 μm 90:10 Hexanes/EtOH (0.1% Et$_2$NH) SME | MS (ESI): m/z 192 [M + H]. $^1$H NMR (400 MHz, CD$_3$OD) δ 7.27-7.25 (m, 2H), 7.09 (d, J = 7.6 Hz, 1H), 4.98 (d, J = 15.6 Hz, 1H), 4.83 (d, J = 15.2 Hz, 1H), 4.29 (s, 1H), 3.75-3.72 (m, 1H), 2.39 (s, 3H), 1.76-1.66 (m, 2H), 1.14 (t, J = 7.6 Hz, 3H). |
| 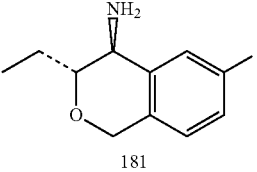 181 | SFC IC 30 × 250 mm, 5 μm 90:10 CO$_2$/MeOH (0.1% NH$_4$OH) FME | MS (ESI): m/z 196 [M + H]. $^1$H NMR (400 MHz, CD$_3$OD) δ 7.30-7.20 (m, 3H), 4.82 (s, 2H), 4.29 (s, 1H), 4.03-4.00 (m, 1H), 1.70-1.56 (m, 2H), 1.09 (t, J = 7.6 Hz, 3H). |
| 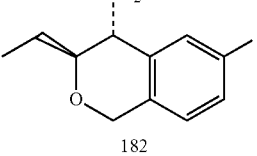 182 | SFC IC 30 × 250 mm, 5 μm 90:10 CO$_2$/MeOH (0.1% NH$_4$OH) SME | MS (ESI): m/z 196 [M + H]. $^1$H NMR (400 MHz, CD$_3$OD) δ 7.27-7.18 (m, 3H), 4.82 (s, 2H), ), 4.27 (d, J = 2.0 Hz, 1H), 4.02-3.98 (m, 1H), 1.70-1.54 (m, 2H), 1.09 (t, J = 7.6 Hz, 3H). |
| 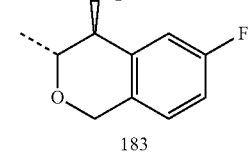 183 | SFC IC 30 × 250 mm 5 μm 90:10 CO$_2$/MeOH (0.1% NH$_4$OH) FME | MS (ESI): m/z 182 [M + H]. $^1$H NMR (400 MHz, CD$_3$OD) δ 7.26-7.20 (m, 3H), 4.84 (s, 2H), 4.27-4.22 (m, 2H), 1.33 (d, J = 6.8 Hz, 3H). |
| 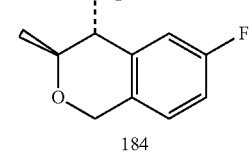 184 | SFC IC 30 × 250 mm, 5 μm 90:10 CO$_2$/MeOH (0.1% NH$_4$OH) SME | MS (ESI): m/z 196 [M + H]. $^1$H NMR (400 MHz, CD$_3$OD) δ 7.26-7.19 (m, 3H), 4.84 (s, 2H), 4.28-4.22 (m, 2H), 1.33 (d, J = 6.8 Hz, 2H). |
| 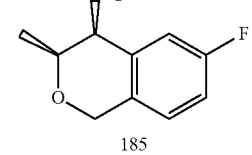 185 | SFC IC 20 × 250 mm, 5 μm 85:15 CO$_2$/MeOH (0.2% NH$_3$) FME | MS (ESI): m/z 182 [M + H]. $^1$H NMR (400 MHz, CD$_3$OD) δ 7.27-7.17 (m, 3 H), 4.96 (d, J = 15.6 Hz, 1 H), 4.85 (d, J = 15.6 Hz, 1 H), 4.32 (s, 1 H), 4.07-4.02 (m, 1 H), 1.42 (d, J = 6.4 Hz, 3 H). |
| 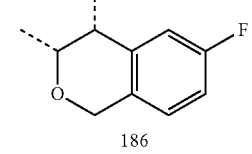 186 | SFC IC 20 × 250 mm, 5 μm 85:15 CO$_2$/MeOH (0.2% NH$_3$) SME | MS (ESI): m/z 182 [M + H]. $^1$H NMR (400 MHz, CD$_3$OD) δ 7.27-7.17 (m, 3 H), 4.96 (d, J = 15.2 Hz, 1 H), 4.85 (d, J = 15.6 Hz, 1 H), 4.32 (s, 1 H), 4.07-4.02 (m, 1 H), 1.42 (d, J = 6.4 Hz, 3 H). |

TABLE 12-continued

Compounds Prepared by Chiral Separation

| Example | Separation Conditions | Analytical Data |
|---|---|---|
| 187 | SFC<br>IC 30 × 250 mm, 5 μm<br>90:10 CO$_2$/MeOH<br>(0.1% NH$_4$OH)<br>FME | MS (ESI): m/z 196 [M + H]. $^1$H NMR (400 MHz, CD$_3$OD) δ 7.26-7.18 (m, 3H), 5.03 (d, J = 15.2 Hz, 1H), 4.86-4.83 (d, J = 15.2 Hz, 1H), 4.37 (s, 1H), 3.77-3.73 (m, 1H), 1.79-1.65 (m, 2H), 1.16-1.12 (t, J = 7.6 Hz, 3H). |
| 188 | SFC<br>IC 30 × 250 mm, 5 μm<br>90:10 CO$_2$/MeOH<br>(0.1% NH$_4$OH)<br>SME | MS (ESI): m/z 196 [M + H]. $^1$H NMR (400 MHz, CD$_3$OD) δ 7.26-7.18 (m, 3H), 5.03 (d, J = 15.2 Hz, 1H), 4.86-4.83 (d, J = 15.2 Hz, 1H), 4.37 (s, 1H), 3.77-3.73 (m, 1H), 1.79-1.65 (m, 2H), 1.16-1.12 (t, J = 7.6 Hz, 3H). |
| 189 | SFC<br>AY-H 4.7 × 100 mm,<br>5 μm<br>EtOH (1% NH$_3$)<br>FME | MS (ESI): m/z 161 [M − 16]. $^1$H NMR (400 MHz, CD$_3$OD) δ 7.33 (d, J = 8.0 Hz, 1H), 7.17 (d, J = 8.0 Hz, 1H), 7.01 (s, 1H), 4.95-4.82 (m, 2H), 4.23 (s, 1H), 4.05-4.04 (m, 1H), 2.35 (s, 3H), 1.41 (d, J = 6.8 Hz, 3H). |
| 190 | SFC<br>AY-H 4.7 × 100 mm,<br>5 μm<br>EtOH (1% NH$_3$)<br>SME | MS (ESI): m/z 161 [M − 16]. $^1$H NMR (400 MHz, CD$_3$OD) δ 7.33 (d, J = 8.0 Hz, 1H), 7.17 (d, J = 8.0 Hz, 1H), 7.01 (s, 1H), 4.95-4.82 (m, 2H), 4.23 (s, 1H), 4.05-4.04 (m, 1H), 2.35 (s, 3H), 1.41 (d, J = 6.8 Hz, 3H). |
| 191 | HPLC<br>AY 20 × 250 mm, 10 μm<br>90:10 Hexanes/EtOH<br>(0.1% Et$_2$NH)<br>FME | MS (ESI): m/z 178 [M + H]. $^1$H NMR (400 MHz, CD$_3$OD) δ 7.47-7.42 (m, 2H), 7.38 (t, J = 7.6 Hz, 1H), 7.22 (d, J = 7.6 Hz, 1H), 5.05 (d, J = 15.6 Hz, 1H), 4.90 (d, J = 15.6 Hz, 1H), 4.35 (s, 1H), 3.78-3.75 (m, 1H), 1.79-1.66 (m, 2H), 1.16 (t, J = 7.2 Hz, 3H). |
| 192 | HPLC<br>AY 20 × 250 mm, 10 μm<br>90:10 Hexanes/EtOH<br>(0.1% Et$_2$NH)<br>SME | MS (ESI): m/z 178 [M + H]. $^1$H NMR (400 MHz, CD$_3$OD) δ 7.48-7.42 (m, 2H), 7.38 (t, J = 7.2 Hz, 1H), 7.22 (d, J = 7.6 Hz, 1H), 5.05 (d, J = 15.2 Hz, 1H), 4.90 (d, J = 15.2 Hz, 1H), 4.36 (s, 1H), 3.78-3.75 (m, 1H), 1.78-1.69 (m, 2H), 1.16 (t, J = 7.2 Hz, 3H). |
| 193 | SFC<br>OD-H 20 × 250 mm<br>5 μm<br>90:10 CO$_2$/MeOH<br>(1% NH$_3$)<br>FME | MS (ESI): m/z 161 [M − 16]. $^1$H NMR (400 MHz, CD$_3$OD) δ 7.48-7.36 (m, 3H), 7.21-7.19 (d, J = 7.5 Hz, 1H), 4.85 (s, 2H), 4.27 (d, J = 2.1 Hz, 1H), 4.05-4.01 (m, 1H), 1.67-1.56 (m, 2H), 1.09-1.07 (t, J = 7.4 Hz, 3H). |
| 195 | SFC<br>OD-H 20 × 250 mm,<br>5 μm<br>90:10 CO$_2$/MeOH<br>(1% NH$_3$)<br>SME | MS (ESI): m/z 161 [M − 16]. $^1$H NMR (400 MHz, CD$_3$OD) δ 7.46-7.36 (m, 3H), 7.21-7.19 (d, J = 7.5 Hz, 1H), 4.85 (s, 2H), 4.25 (d, J = 2.1 Hz, 1H), 4.04-4.00 (m, 1H), 1.66-1.55 (m, 2H), 1.11-1.07 (t, J = 7.4 Hz, 3H) |

TABLE 12-continued

Compounds Prepared by Chiral Separation

| Example | Separation Conditions | Analytical Data |
|---|---|---|
| 252 | SFC<br>OZ 20 × 250 mm, 5 μm<br>75:25 CO$_2$/EtOH<br>(1% NH$_3$)<br>FME | MS (ESI): m/z 178 [M +H]$^+$. $^1$H NMR (400 MHz, CD$_3$OD) δ 7.32 (d, J = 7.6 Hz, 1H), 7.29 (d, J = 8.0 Hz, 1H), 7.03 (s, 1H), 4.87 (s, 2H), 4.28-4.23 (m, 1H), 4.15 (d, J = 2.0 Hz, 1H), 2.37 (s, 3H), 1.32 (d, J = 2.8 Hz, 3H). |
| 253 | SFC<br>OZ 20 × 250 mm, 5 μm<br>75:25 CO$_2$/EtOH<br>(1% NH$_3$)<br>SME | MS (ESI): m/z 178 [M + H]$^+$. $^1$H NMR (400 MHz, CD$_3$OD) δ d 7.35 (d, J = 6.0 Hz, 1H), 7.29 (d, J = 8.0 Hz, 1H), 7.03 (s, 1H), 4.88 (s, 2H), 4.30-4.26 (m, 1H), 4.16 (s, 1H), 2.37 (s, 3H), 1.32 (d, J = 2.4 Hz, 3H). |
| 254 | HPLC<br>AY-H 4.6 × 250 mm,<br>5 μm<br>90:10 Hexanes/EtOH<br>(0.1% Et$_2$NH)<br>FME | MS (ESI): m/z 178 [M + H]$^+$. $^1$H NMR (400 MHz, D$_2$O) δ 7.22-7.21 (m, 2H), 7.19-7.16 (m, 1H), 5.15 (q, J = 6.8 Hz, 1H), 4.34-4.31 (m, 2H), 3.95 (dd, J = 14.0, 2.0 Hz, 1H), 2.17 (s, 3H), 1.40 (d, J = 7.8 Hz, 3H). |
| 255 | HPLC<br>AY-H 4.6 × 250 mm,<br>5 μm<br>90:10 Hexanes/EtOH<br>(0.1% Et$_2$NH)<br>SME | MS (ESI): m/z 178 [M + H]$^+$. $^1$H NMR (400 MHz, D$_2$O) δ 7.22-7.21 (m, 2H), 7.19-7.16 (m, 1H), 5.15 (q, J = 6.8 Hz, 1H), 4.34-4.31 (m, 2H), 3.95 (dd, J = 14.0, 2.0 Hz, 1H), 2.17 (s, 3H), 1.40 (d, J = 7.8 Hz, 3H). |

Chiral Separation of tert-butyl (2,4,7,8,9,10-hexahydro-1H-7,10-methanobenzo-[f]isochromen-1-yl)carbamate

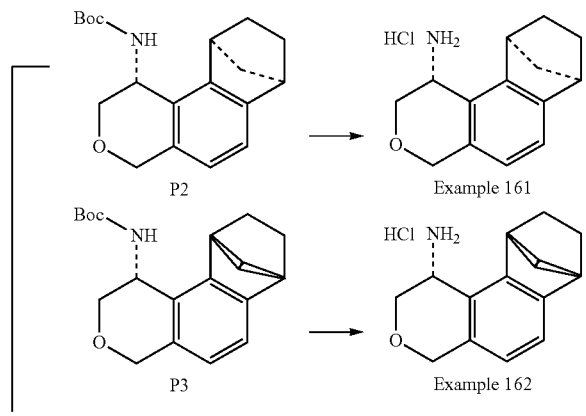

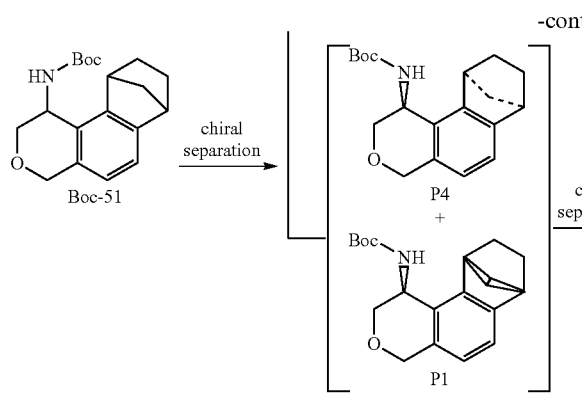

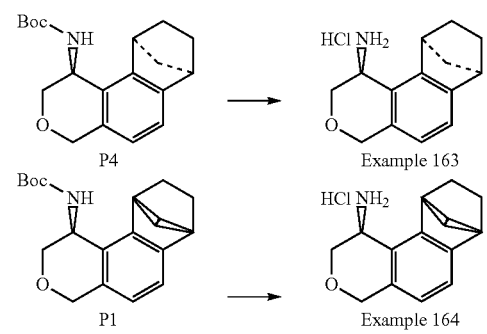

As previously described in the General Procedure for Chiral Separation above compound Boc-51 (prepared as previously described in Example 51) was separated into 3 peaks consisting of a mixture of enantiomers (P1 and P4) and the individual enantiomers P2 and P3 using an AD 20×250 mm, 5 um column and a mobile phase of 85:15 $CO_2$/MeOH/0.5% $NH_3$. The mixture of P1 and P4 was further separated by SFC into enantiomers P1 and P4 using a Whelk 20×250 mm, 5 um column and a mobile phase of 85:15 $CO_2$/MeOH (0.5% $NH_3$).

The individual Boc-protected enantiomers were deprotected and converted to the corresponding HCl salts as previously described in Example 1.

Example 161

FME on AD column, MS (ESI): m/z 216 [M+H]. $^1$H NMR (400 MHz, $CD_3OD$): δ 7.22 (d, J=7.6 Hz, 1H), 6.87 (d, J=7.6 Hz, 1H), 4.89 (d, J=15.2 Hz, 1H), 4.79 (d, J=15.2 Hz, 1H), 4.56 (s, 1H), 4.32 (dd, J=12.8, 1.2 Hz, 1H), 3.91 (d, J=12.8, 2.0 Hz, 1H), 3.61 (s, 1H), 3.41 (d, J=2.0 Hz, 1H), 2.06-2.01 (m, 2H), 1.73-1.70 (m, 1H), 1.64-1.61 (m, 1H), 1.20-1.15 (m, 2H).

Example 162

SME on AD column, MS (ESI): m/z 216 [M+H]. $^1$H NMR (400 MHz, $CD_3OD$): δ 7.20 (d, J=7.6 Hz, 1H), 6.87 (d, J=7.6 Hz, 1H), 4.94 (d, J=15.6 Hz, 1H), 4.77 (d, J=15.2 Hz, 1H), 4.43 (s, 1H), 4.25 (dd, J=12.8, 0.8 Hz, 1H), 3.91 (dd, J=12.8, 2.0 Hz, 1H), 3.66 (s, 1H), 3.39 (s, 1H), 1.96-1.99 (m, 2H), 1.84-1.81 (m, 1H), 1.65-1.62 (m, 1H), 1.10-1.06 (m, 2H).

Example 163

FME on Whelk column, MS (ESI): m/z 216 [M+H]. $^1$H NMR (400 MHz, $CD_3OD$): δ 7.20 (d, J=7.6 Hz, 1H), 6.87 (d, J=7.6 Hz, 1H), 4.94 (d, J=15.6 Hz, 1H), 4.77 (d, J=15.2 Hz, 1H), 4.43 (s, 1H), 4.25 (dd, J=12.8, 0.8 Hz, 1H), 3.91 (dd, J=12.8, 2.0 Hz, 1H), 3.66 (s, 1H), 3.39 (s, 1H), 1.99-1.96 (m, 2H), 1.84-1.81 (m, 1H), 1.65-1.62 (m, 1H), 1.10-1.06 (m, 2H).

Example 164

SME on Whelk column, MS (ESI): m/z 216 [M+H]. $^1$H NMR (400 MHz, $CD_3OD$): δ 7.22 (d, J=7.6 Hz, 1H), 6.87 (d, J=7.6 Hz, 1H), 4.89 (d, J=15.2 Hz, 1H), 4.79 (d, J=15.2 Hz, 1H), 4.56 (s, 1H), 4.32 (dd, J=12.8, 1.2 Hz, 1H), 3.91 (dd, J=12.8, 2.0 Hz, 1H), 3.61 (s, 1H), 3.41 (d, J=2.0 Hz, 1H), 2.06-2.01 (m, 2H), 1.73-1.70 (m, 1H), 1.64-1.61 (m, 1H), 1.20-1.15 (m, 2H).

Example 289

In Vivo Biological Studies

Neuropharmacological Assay (SmartCube™)

In order to demonstrate the utility of the provided compounds to treat neurological and psychiatric diseases and disorders, exemplary compounds were evaluated using the neuropharmacological screen described in S. L. Roberds et al., *Front. Neurosci.* 2011 Sep. 9; 5:103 (doi: 10.3389/fnins.2011.00103) ("Roberds"). As reported in Roberds, because psychiatric diseases generally result from disorders of cell-cell communication or circuitry, intact systems are useful in detecting improvement in disease-relevant endpoints. These endpoints are typically behavioral in nature, often requiring human observation and interpretation. To facilitate testing of multiple compounds for behavioral effects relevant to psychiatric disease, PsychoGenics, Inc. (Tarrytown, N.Y., "PGI") developed SmartCube™, an automated system in which behaviors of compound-treated mice are captured by digital video and analyzed with computer algorithms. (D. Brunner et al., *Drug Discov. Today* 2002, 7:S107-S112). PGI Analytical Systems uses data from SmartCube™ to compare the behavioral signature of a test compound to a database of behavioral signatures obtained using a large set of diverse reference compounds. (The composition of the database as well as validation of the method is further described in Roberds). In this way, the neuropharmacological effects of a test compound can be predicted by similarity to major classes of compounds, such as antipsychotics, anxiolytics and antidepressants.

Figure 2:
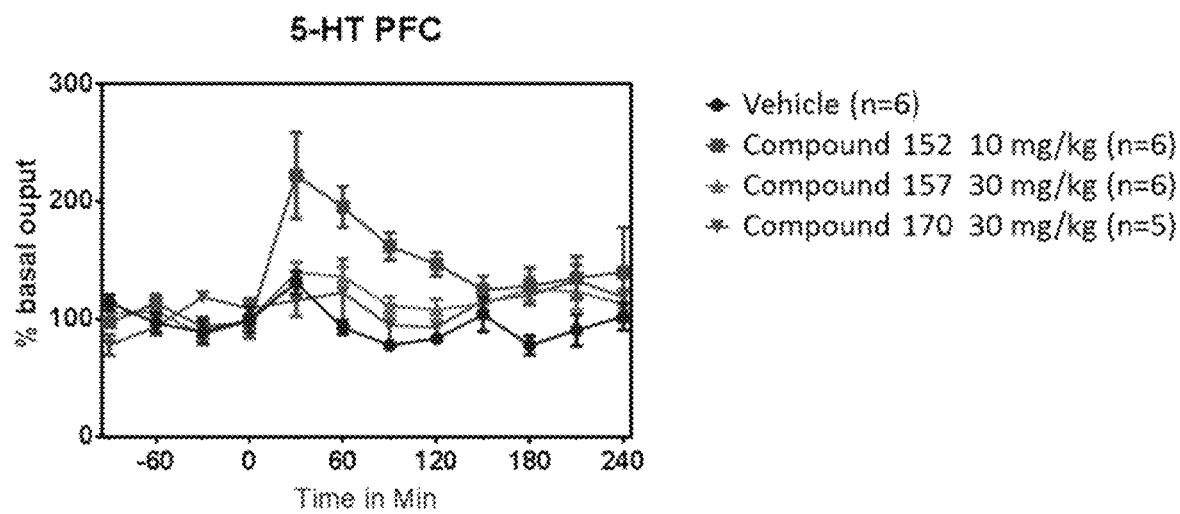
FIG. 2 shows the effect the effect of representative compounds of the invention on treatment on 5-HT release in the PFC.
Figure 3:
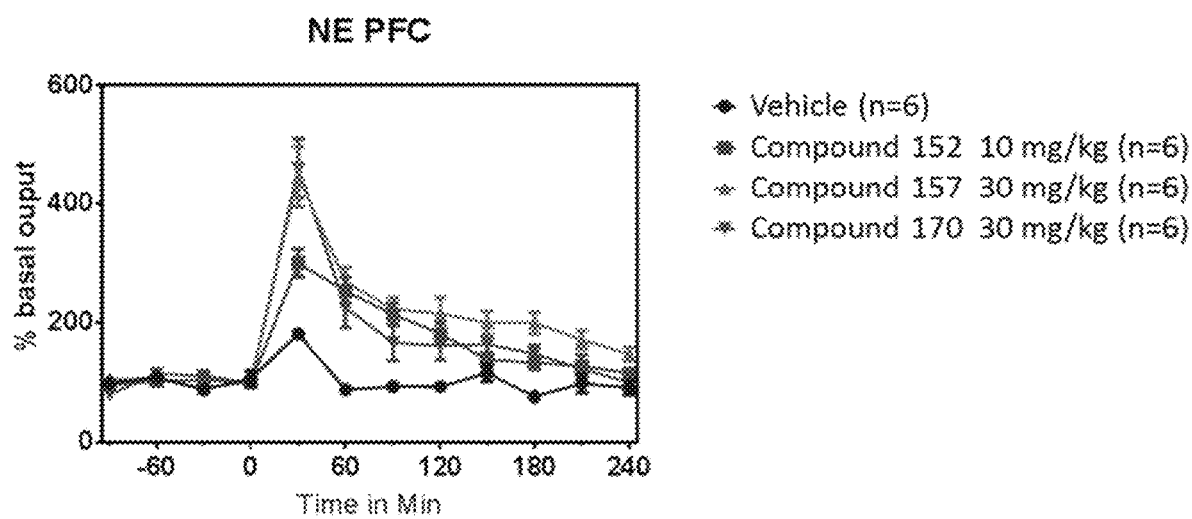
FIG. 3 shows the effect of representative compounds of the invention on treatment on NE release in the PFC.

The SmartCube™ system produces an activity signature indicating the probability that the activity of the test compound at the administered dose matches a given class of neuropharmacological agents. (See, e.g., Roberds, FIGS. 2 and 3). The test compound is simultaneously compared against multiple classes of agents; thus, a separate probability is generated for each behavioral effect measured (e.g., anxiolytic activity, analgesic activity, etc.). In the table below, these probabilities are reported for each behavioral effect measured as follows:

| LOQ ≤ | + | <5% |
|---|---|---|
| 5% ≤ | ++ | <25% |

| | | |
|---|---|---|
| 25% ≤ | +++ | <50% |
| 50% ≤ | ++++ | | where LOQ is the limit of quantification.

Provided compounds were dissolved in a mixture of Pharmasolve™ (N-methyl-2-pyrrolidone), polyethylene glycol and propylene glycol, and were injected i.p. 15 min. before the behavioral test. For each compound, injections were administered at 3 different doses. For each behavioral effect measured, results for the most efficacious dose(s) are presented. In the table below, DP: anti-depressant; AX: anxiolytic; SD: sedative hypnotic; PS: anti-psychotic; MS: mood stabilizer; AD: ADHD; CE: cognitive enhancer; AG: analgesic; UN: uncharacterized CNS activity.

The potency of many of the compounds in the table was also determined in the SmartCube™ system. Test compounds were routinely examined at dose levels of 0.3, 1, 3, 10 and 30 mg per kg (mpk), although the dose range was increased or decreased if necessary to obtain a full dose response curve. A compound's minimal effective dose (MED) is a measure of the compounds potency. The MED was defined as the dose (in mpk) having 50% or more total activity in SmartCube. The potencies of the compounds are shown in the table below, with potency values in mpk binned in the following manner:

| MED mpk range | BIN |
|---|---|
| ≤3 mpk | A |
| >3 to 10 mpk | B |
| >10 to ≤30 mpk | C |
| >30 mpk | D |

| Example | DP | AX | SD | PS | MS | AD | CE | AG | UN | Potency |
|---|---|---|---|---|---|---|---|---|---|---|
| 1 | + | ++ | ++ | ++ | + | + | ++ | ++ | ++ | C |
| 2 | + | ++ | + | + | + | + | + | ++ | +++ | C |
| 3 | ++ | ++ | ++ | + | + | + | + | ++ | +++ | C |
| 4 | ++ | +++ | ++ | ++ | + | + | ++ | ++ | + | C |
| 5 | ++ | ++ | ++ | ++ | + | + | ++ | ++ | +++ | A |
| 6 | ++ | ++ | ++ | + | + | + | + | ++ | ++++ | B |
| 7 | ++ | ++ | + | ++ | ++ | + | ++ | + | +++ | C |
| 8 | ++ | ++ | +++ | ++ | + | + | ++ | ++ | ++ | C |
| 9 | ++ | ++ | + | ++ | + | + | ++ | ++ | +++ | B |
| 10 | ++ | ++ | ++ | +++ | + | + | +++ | ++ | ++ | B |
| 11 | ++ | + | ++ | + | + | + | ++ | + | + | C |
| 12 | ++ | ++ | + | ++ | + | + | ++ | ++ | +++ | C |
| 13 | ++ | ++ | + | ++ | + | + | ++ | ++ | ++++ | B |
| 14 | ++ | ++ | + | + | + | + | + | ++ | ++++ | C |
| 15 | + | + | + | + | + | + | + | + | + | D |
| 16 | + | +++ | + | ++ | + | + | ++ | ++ | +++ | C |
| 17 | ++ | +++ | + | ++ | + | + | ++ | ++ | +++ | C |
| 18 | ++ | ++ | ++ | ++ | + | + | ++ | +++ | + | C |
| 19 | + | +++ | ++ | ++ | + | + | ++ | ++ | +++ | C |
| 20 | ++ | +++ | ++ | +++ | + | + | ++ | ++ | ++ | B |
| 21 | ++ | ++ | ++ | ++ | + | + | ++ | ++ | +++ | B |
| 22 | ++ | ++ | + | ++ | + | + | ++ | ++ | +++ | C |
| 23 | ++ | +++ | + | ++ | + | + | ++ | ++ | ++ | C |
| 24 | ++ | ++ | ++ | ++ | + | + | + | + | + | C |
| 25 | ++ | ++ | + | ++ | + | + | ++ | ++ | +++ | C |
| 26 | ++ | ++ | + | ++ | + | + | ++ | ++ | ++++ | A |
| 27 | ++ | ++ | + | ++ | ++ | + | ++ | ++ | +++ | B |
| 28 | ++ | ++ | + | ++ | + | + | ++ | ++ | +++ | B |
| 29 | ++ | ++ | + | + | + | + | + | +++ | + | C |
| 30 | + | + | + | + | + | + | + | ++ | + | D |
| 31 | ++ | ++ | + | + | + | + | + | ++ | +++ | C |
| 32 | ++ | ++ | ++ | ++ | + | + | + | ++ | + | C |
| 33 | + | ++ | + | ++ | + | + | ++ | ++ | +++ | C |
| 34 | + | +++ | ++ | ++ | + | + | ++ | ++ | +++ | B |
| 35 | ++ | +++ | + | ++ | + | + | ++ | ++ | +++ | B |
| 36 | ++ | ++ | ++ | ++ | + | + | +++ | ++ | ++ | B |
| 37 | + | ++ | + | ++ | + | + | ++ | ++ | +++ | C |
| 38 | ++ | ++ | + | ++ | + | + | + | ++ | +++ | C |
| 39 | ++ | +++ | + | + | + | + | ++ | ++ | ++++ | B |
| 40 | + | +++ | + | ++ | + | + | ++ | ++ | ++ | B |
| 41 | ++ | ++ | + | + | + | + | ++ | ++ | +++ | C |
| 42 | ++ | ++ | ++ | +++ | + | + | ++ | +++ | +++ | A |
| 43 | + | +++ | ++ | ++ | + | + | ++ | ++ | + | C |
| 44 | ++ | +++ | ++ | ++ | + | + | ++ | ++ | +++ | B |
| 45 | ++ | +++ | ++ | ++ | + | + | ++ | ++ | ++++ | B |
| 46 | + | ++ | ++ | + | + | + | ++ | ++ | ++++ | A |
| 47 | ++ | ++ | + | ++ | ++ | + | ++ | ++ | ++++ | A |
| 48 | + | +++ | ++ | ++ | + | + | +++ | ++ | ++ | A |
| 49 | ++ | ++ | + | ++ | + | + | ++ | ++ | ++++ | B |
| 50 | +++ | ++ | + | ++ | + | + | ++ | ++ | ++ | C |
| 51 | ++ | ++ | + | ++ | + | + | ++ | ++ | ++++ | B |
| 52 | ++ | +++ | ++ | ++ | + | + | ++ | ++ | + | B |
| 53 | ++ | ++ | ++ | ++ | + | + | ++ | ++ | ++++ | B |
| 54 | ++ | ++ | + | ++ | + | + | + | ++ | +++ | C |

-continued

|     |     |     |     |     |     |     |     |     |      |   |
|-----|-----|-----|-----|-----|-----|-----|-----|-----|------|---|
| 55  | +   | ++  | +   | ++  | +   | +   | ++  | ++  | +++  | B |
| 56  | ++  | ++  | +   | +   | +   | +   | ++  | +++ | +    | C |
| 57  | ++  | ++  | ++  | ++  | +   | +   | +++ | ++  | +++  | B |
| 58  | ++  | ++  | ++  | ++  | +   | +   | ++  | ++  | +++  | B |
| 59  | ++  | ++  | ++  | ++  | +   | +   | ++  | +++ | +++  | B |
| 60  | ++  | +++ | +   | ++  | +   | +   | ++  | ++  | +    | C |
| 61  | +   | ++  | +   | ++  | +   | +   | ++  | ++  | ++++ | C |
| 62  | ++  | ++  | +   | ++  | ++  | +   | +++ | ++  | ++++ | B |
| 63  | ++  | ++  | +   | +   | +   | +   | ++  | ++  | ++   | C |
| 68  | ++  | ++  | +   | ++  | +   | +   | ++  | ++  | ++   | C |
| 72  | ++  | ++  | ++  | ++  | +   | +   | ++  | ++  | +++  | B |
| 73  | ++  | +++ | +   | ++  | +   | +   | ++  | ++  | +++  | A |
| 74  | ++  | ++  | +   | +   | +   | +   | +   | ++  | +++  | C |
| 75  | +   | ++  | +   | ++  | +   | +   | ++  | ++  | +++  | C |
| 76  | ++  | ++  | +   | ++  | +   | +   | ++  | ++  | +++  | A |
| 77  | ++  | ++  | +   | ++  | +   | +   | ++  | ++  | +++  | A |
| 78  | ++  | ++  | +   | +++ | +   | +   | ++  | ++  | ++++ | B |
| 79  | ++  | +++ | ++  | ++  | +   | +   | ++  | ++  | ++   | B |
| 80  | +   | +++ | ++  | ++  | +   | +   | +   | ++  | +++  | A |
| 81  | ++  | +++ | ++  | ++  | +   | +   | ++  | ++  | +++  | A |
| 82  | ++  | +++ | ++  | ++  | +   | +   | ++  | ++  | +++  | A |
| 83  | +   | ++  | +   | ++  | +   | +   | ++  | ++  | ++++ | B |
| 84  | ++  | ++++| +   | ++  | +   | +   | ++  | ++  | +++  | B |
| 85  | ++  | ++  | +   | +   | +   | +   | ++  | +++ | +++  | B |
| 86  | +   | ++  | +   | ++  | +   | +   | ++  | ++  | +++  | C |
| 87  | ++  | ++  | ++  | ++  | +   | +   | ++  | ++  | +++  | B |
| 88  | +   | +++ | ++  | ++  | +   | +   | ++  | ++  | +++  | A |
| 89  | +   | ++  | ++  | ++  | +   | +   | ++  | ++  | ++++ | A |
| 90  | ++  | +++ | ++  | +   | +   | +   | ++  | ++  | +    | C |
| 91  | +   | +   | ++  | ++  | +   | +   | ++  | ++  | +++  | C |
| 92  | ++  | ++  | +   | +   | +   | +   | +   | +   | ++++ | C |
| 93  | ++  | +++ | +   | ++  | +   | +   | +   | ++  | +    | C |
| 94  | +   | ++  | +   | +   | +   | +   | +   | ++  | ++   | C |
| 95  | ++  | ++  | +   | +++ | +   | +   | ++  | ++  | +++  | A |
| 96  | ++  | +++ | +   | ++  | +   | +   | ++  | ++  | +++  | A |
| 97  | +   | ++  | ++  | ++  | +   | +   | ++  | +   | ++++ | B |
| 98  | ++  | ++  | ++  | ++  | +   | +   | ++  | ++  | ++++ | B |
| 99  | ++  | +++ | +   | ++  | +   | +   | ++  | ++  | +++  | B |
| 100 | ++  | ++  | ++  | +++ | +   | +   | ++  | ++  | +++  | A |
| 101 | ++  | +++ | ++  | ++  | +   | +   | +   | ++  | +    | C |
| 104 | ++  | ++  | ++  | ++  | +   | +   | ++  | ++  | +++  | B |
| 105 | ++  | ++  | +   | ++  | ++  | +   | ++  | ++  | +++  | C |
| 106 | +   | ++  | ++  | ++  | +   | +   | ++  | +   | ++++ | B |
| 107 | +   | ++  | +   | ++  | +   | +   | ++  | ++  | +++  | B |
| 111 | ++  | ++  | +   | ++  | +   | +   | ++  | ++  | +++  | B |
| 112 | ++  | ++  | +   | ++  | +   | +   | +++ | ++  | +    | C |
| 113 | ++  | ++  | +   | ++  | +   | +   | ++  | ++  | +++  | B |
| 114 | ++  | ++  | +   | ++  | +   | +   | ++  | ++  | +++  | C |
| 115 | ++  | ++  | ++  | +++ | +   | +   | ++  | ++  | +++  | B |
| 116 | ++  | ++  | +++ | ++  | +   | +   | ++  | ++  | +++  | B |
| 117 | ++  | ++  | +   | +++ | ++  | +   | ++  | ++  | +    | B |
| 118 | +++ | ++  | ++  | ++  | +   | +   | ++  | ++  | +    | B |
| 119 | ++  | +++ | ++  | ++  | +   | +   | ++  | ++  | ++++ | A |
| 120 | ++  | +++ | ++  | ++  | +   | +   | ++  | ++  | ++   | B |
| 121 | ++  | ++  | ++  | ++  | +   | +   | ++  | ++  | +++  | A |
| 122 | ++  | +++ | ++  | ++  | +   | +   | +++ | ++  | +++  | A |
| 123 | ++  | ++  | ++  | ++  | +   | +   | +   | ++  | +++  | A |
| 124 | ++  | +++ | ++  | ++  | +   | +   | ++  | ++  | +++  | B |
| 125 | ++  | ++  | ++  | ++  | +   | +   | ++  | +   | ++++ | A |
| 126 | ++  | ++  | +   | +++ | +   | +   | ++  | ++  | ++++ | A |
| 127 | ++  | ++  | +   | ++  | +   | +   | ++  | ++  | +++  | A |
| 128 | ++  | ++  | +   | ++  | +   | +   | +++ | ++  | +++  | A |
| 129 | ++  | +++ | ++  | ++  | +   | +   | ++  | ++  | +++  | B |
| 130 | ++  | ++  | ++  | +++ | +   | +   | ++  | ++  | ++++ | B |
| 131 | ++  | ++  | ++  | ++  | ++  | +   | +++ | +   | +++  | A |
| 132 | ++  | +++ | ++  | ++  | +   | +   | +++ | ++  | +++  | A |
| 133 | ++  | ++  | +   | +++ | +   | +   | ++  | ++  | ++++ | A |
| 134 | ++  | +++ | ++  | ++  | +   | +   | ++  | ++  | +++  | B |
| 135 | ++  | +++ | ++  | ++  | +   | +   | ++  | ++  | +++  | A |
| 136 | ++  | ++  | +   | ++  | +   | +   | ++  | ++  | +++  | B |
| 137 | +   | ++  | +   | ++  | +   | +   | ++  | ++  | +++  | B |
| 138 | ++  | ++  | ++  | ++  | +   | +   | ++  | ++  | +++  | B |
| 139 | ++  | ++  | +   | ++  | +   | +   | ++  | ++  | +++  | B |
| 140 | ++  | ++  | +   | +++ | ++  | +   | ++  | ++  | +    | C |
| 141 | ++  | +++ | +   | ++  | ++  | +   | ++  | ++  | +++  | B |
| 142 | ++  | ++  | +   | +   | +   | +   | ++  | ++  | ++++ | B |
| 143 | ++  | ++  | ++  | +   | +   | +   | ++  | +++ | ++   | B |
| 144 | ++  | ++  | ++  | ++  | +   | +   | ++  | ++  | +++  | B |
| 145 | +   | ++  | +   | +   | +   | +   | ++  | ++  | +++  | C |

-continued

| | | | | | | | | | | |
|---|---|---|---|---|---|---|---|---|---|---|
| 146 | + | +++ | + | + | + | + | ++ | ++ | ++ | B |
| 147 | ++ | ++ | + | + | + | + | + | ++ | ++++ | B |
| 148 | ++ | ++ | ++ | ++ | ++ | + | ++ | ++ | +++ | B |
| 149 | ++ | ++ | ++ | +++ | + | + | ++ | ++ | +++ | A |
| 150 | + | ++ | + | ++ | + | + | + | ++ | ++++ | B |
| 151 | ++ | +++ | ++ | ++ | + | + | ++ | ++ | ++ | B |
| 152 | ++ | +++ | + | ++ | + | + | ++ | ++ | +++ | A |
| 153 | + | ++ | + | ++ | + | + | ++ | ++ | +++ | B |
| 154 | + | ++ | ++ | ++ | + | + | ++ | ++ | ++++ | B |
| 155 | ++ | ++++ | ++ | ++ | + | + | ++ | ++ | ++ | B |
| 156 | + | ++ | + | + | + | + | ++ | ++ | +++ | B |
| 157 | ++ | ++ | + | +++ | ++ | + | ++ | ++ | ++++ | A |
| 158 | ++ | ++ | ++ | +++ | + | + | ++ | ++ | ++ | B |
| 159 | +++ | +++ | + | + | + | + | + | + | ++ | B |
| 160 | + | ++ | + | ++ | + | + | ++ | ++ | +++ | A |
| 161 | ++ | +++ | + | ++ | + | + | ++ | ++ | ++ | B |
| 162 | + | +++ | + | ++ | + | + | ++ | ++ | +++ | B |
| 163 | ++ | ++ | ++ | +++ | + | + | ++ | ++ | +++ | B |
| 164 | + | +++ | ++ | ++ | + | + | ++ | ++ | +++ | B |
| 165 | ++ | ++ | + | ++ | + | + | ++ | + | ++++ | B |
| 166 | + | ++ | ++ | ++ | + | + | ++ | + | ++++ | B |
| 167 | + | ++ | + | ++ | + | + | + | ++ | ++++ | A |
| 168 | ++ | ++ | + | +++ | + | + | ++ | + | ++++ | B |
| 169 | ++ | ++ | ++ | ++ | + | + | ++ | ++ | ++++ | A |
| 170 | ++ | ++ | + | ++ | + | + | ++ | ++ | ++++ | A |
| 171 | ++ | +++ | ++ | ++ | + | + | ++ | ++ | +++ | A |
| 172 | + | ++ | + | ++ | + | + | + | ++ | +++ | C |
| 173 | + | ++ | + | + | + | + | ++ | ++ | ++++ | B |
| 174 | ++ | ++ | + | ++ | + | + | ++ | ++ | ++++ | B |
| 175 | ++ | ++ | + | ++ | + | + | ++ | ++ | +++ | A |
| 176 | ++ | ++ | + | ++ | + | + | ++ | + | ++++ | B |
| 177 | + | ++++ | + | ++ | + | + | ++ | ++ | ++++ | A |
| 178 | ++ | ++ | ++ | ++ | + | + | + | ++ | +++ | C |
| 179 | +++ | ++ | + | ++ | + | + | ++ | + | ++++ | A |
| 180 | ++ | ++ | + | ++ | + | + | ++ | ++ | ++++ | B |
| 181 | + | ++ | +++ | ++ | + | + | ++ | ++ | ++++ | A |
| 182 | ++ | ++ | + | +++ | + | + | ++ | + | ++++ | A |
| 183 | ++ | ++ | ++ | ++ | + | + | ++ | ++ | ++++ | A |
| 184 | ++ | ++ | + | ++ | + | + | ++ | + | ++++ | A |
| 185 | + | +++ | + | ++ | + | + | ++ | ++ | ++++ | A |
| 186 | ++ | ++ | + | ++ | + | + | ++ | ++ | +++ | B |
| 187 | + | ++ | + | +++ | + | + | ++ | ++ | ++++ | A |
| 188 | ++ | ++ | + | ++ | + | + | + | ++ | ++++ | A |
| 189 | ++ | ++ | + | ++ | + | + | ++ | ++ | +++ | C |
| 190 | + | ++ | ++ | ++ | + | + | ++ | + | ++++ | B |
| 191 | ++ | ++ | ++ | ++ | + | + | ++ | ++ | ++++ | A |
| 192 | + | ++ | ++ | ++ | + | + | ++ | + | ++++ | A |
| 193 | + | ++ | ++ | ++ | + | + | ++ | ++ | ++++ | B |
| 194 | ++ | ++ | + | ++ | + | + | ++ | ++ | ++++ | B |
| 195 | ++ | ++ | ++ | ++ | + | + | ++ | ++ | ++++ | A |
| 196 | + | ++ | + | ++ | + | + | ++ | + | +++ | C |
| 197 | + | ++ | + | + | + | + | + | + | ++++ | B |
| 198 | ++ | ++ | + | +++ | + | + | ++ | + | +++ | A |
| 199 | + | ++++ | ++ | ++ | + | + | ++ | ++ | ++++ | A |
| 200 | ++ | +++ | + | ++ | + | + | ++ | ++ | ++++ | B |
| 201 | + | ++ | + | ++ | + | + | ++ | + | ++++ | B |
| 202 | ++ | +++ | + | ++ | + | + | ++ | ++ | ++++ | A |
| 203 | ++ | ++ | ++ | +++ | + | + | ++ | ++ | ++++ | B |
| 204 | + | ++ | ++ | ++ | + | + | ++ | + | ++++ | B |
| 205 | ++ | +++ | ++ | ++ | + | + | ++ | + | +++ | B |
| 206 | ++ | ++++ | + | ++ | + | + | ++ | ++ | +++ | B |
| 207 | ++ | ++ | + | ++ | + | + | ++ | ++ | ++++ | B |
| 208 | ++ | +++ | + | ++ | ++ | + | ++ | + | +++ | B |
| 209 | ++ | ++ | ++ | ++ | + | + | ++ | +++ | +++ | B |
| 210 | + | ++ | + | + | + | + | ++ | ++ | ++++ | B |
| 211 | ++ | ++ | +++ | ++ | + | + | + | + | ++++ | B |
| 212 | + | ++ | + | + | + | + | + | ++ | ++++ | C |
| 213 | ++ | ++ | + | ++ | + | + | ++ | ++ | +++ | B |
| 214 | ++ | ++ | ++ | ++ | + | ++ | ++ | ++ | ++++ | B |
| 215 | ++ | +++ | ++ | ++ | + | + | ++ | ++ | ++++ | B |
| 216 | ++ | ++ | + | + | + | + | + | ++ | ++++ | B |
| 217 | ++ | +++ | + | ++ | + | + | ++ | + | ++++ | C |
| 218 | + | ++ | + | ++ | + | + | ++ | ++ | ++++ | A |
| 219 | + | ++ | + | + | + | + | ++ | ++ | ++++ | B |
| 220 | + | ++++ | + | + | + | + | ++ | ++ | ++++ | B |
| 221 | ++ | ++ | + | ++ | + | + | + | + | ++++ | B |
| 222 | + | ++ | + | + | + | + | + | + | ++++ | B |
| 223 | ++ | ++ | ++ | + | + | + | + | + | +++ | B |
| 224 | + | ++ | ++ | + | + | + | +++ | ++ | ++ | C |

-continued

| | | | | | | | | | | |
|---|---|---|---|---|---|---|---|---|---|---|
| 225 | ++ | ++ | ++ | ++ | + | + | ++ | ++ | ++++ | B |
| 226 | ++ | ++ | + | +++ | + | + | ++ | + | ++ | C |
| 227 | + | ++ | + | ++ | + | + | + | ++ | ++++ | B |
| 228 | ++ | ++ | + | ++ | + | + | + | ++ | +++ | C |
| 229 | ++ | ++ | + | ++ | + | + | ++ | + | +++ | B |
| 230 | + | ++ | + | ++ | + | + | ++ | + | ++++ | B |
| 231 | ++ | ++ | + | + | + | + | ++ | ++ | +++ | C |
| 232 | + | ++ | + | + | + | + | + | ++ | ++ | C |
| 233 | + | ++ | + | + | + | + | ++ | ++ | + | D |
| 234 | + | +++ | ++ | ++ | + | + | ++ | ++ | ++ | C |
| 235 | + | ++ | + | + | + | + | + | + | + | D |
| 236 | ++ | ++ | + | ++ | + | + | + | ++ | ++++ | B |
| 237 | + | ++ | +++ | ++ | + | + | + | + | ++ | C |
| 238 | + | ++ | + | ++ | + | + | ++ | + | ++++ | C |
| 239 | ++ | ++ | + | ++ | + | ++ | ++ | ++ | +++ | B |
| 240 | ++ | ++ | ++ | ++ | + | + | ++ | ++ | +++ | B |
| 248 | + | ++ | + | + | + | + | ++ | ++ | +++ | C |
| 249 | + | ++ | + | ++ | + | + | ++ | ++ | +++ | B |
| 250 | + | ++ | ++ | ++ | ++ | ++ | + | + | + | B |
| 251 | + | ++ | ++ | ++ | ++ | ++ | + | + | ++ | B |
| 252 | ++ | + | ++ | ++ | ++ | + | + | + | ++++ | A |
| 253 | ++ | + | ++ | ++ | ++ | + | + | + | ++ | B |
| 254 | + | + | ++ | + | + | + | + | + | ++ | B |
| 255 | + | + | ++ | + | + | + | + | + | ++ | C |
| 256 | + | ++ | ++ | +++ | ++ | ++ | + | + | ++ | B |
| 257 | ++ | + | +++ | ++ | ++ | + | + | + | ++ | B |
| 258 | ++ | + | ++ | + | ++ | + | + | + | + | B |
| 259 | ++ | + | +++ | + | + | + | + | + | ++ | C |
| 260 | + | + | ++ | + | ++ | ++ | + | + | + | B |
| 261 | ++++ | + | ++ | + | + | ++ | + | + | ++ | C |
| 262 | ++ | + | ++ | + | + | + | + | + | ++ | C |
| 263 | + | + | ++ | + | + | + | + | + | + | A |
| 264 | ++ | ++ | ++ | +++ | ++ | ++ | + | + | + | B |
| 265 | ++ | + | ++ | + | + | + | + | + | + | B |
| 266 | + | + | ++ | + | ++ | + | + | + | + | B |
| 267 | ++ | + | ++ | + | ++ | + | + | + | ++ | A |
| 268 | + | ++ | ++ | +++ | ++ | ++ | + | + | ++ | B |
| 269 | ++ | + | ++ | + | ++ | + | + | + | ++ | B |
| 270 | ++ | ++ | ++ | + | ++++ | ++ | + | + | ++ | A |
| 271 | ++ | ++ | ++ | + | +++ | ++ | + | + | ++ | B |
| 272 | + | ++ | ++ | ++ | ++ | + | + | + | ++ | B |
| 273 | ++ | + | +++ | + | ++ | + | + | ++ | ++ | A |
| 274 | ++ | + | ++ | ++ | +++ | + | + | + | ++ | A |
| 275 | + | + | +++ | + | ++ | + | + | + | ++ | B |
| 276 | + | + | ++ | + | ++ | + | + | + | + | B |
| 277 | + | + | + | + | + | + | + | + | + | D |
| 278 | + | + | + | + | + | + | + | + | + | D |
| 279 | ++ | + | ++ | ++ | +++ | + | + | + | ++ | B |
| 280 | ++ | + | ++ | + | ++ | + | ++ | + | + | B |
| 281 | + | + | + | + | + | + | + | + | + | D |
| 282 | + | + | ++ | + | + | + | + | + | + | D |
| 283 | ++ | ++ | ++ | ++ | +++ | ++ | + | + | ++ | B |
| 284 | ++ | ++ | ++ | ++ | +++ | + | + | + | + | C |
| 285 | ++ | ++ | + | ++++ | ++++ | ++ | + | + | ++ | B |
| 286 | ++ | + | ++ | + | ++ | + | + | + | ++ | C |
| 287 | + | + | ++ | + | + | + | + | + | + | D |
| 288 | ++ | + | ++ | + | + | + | + | + | + | D |

Marble Burying Test

The marble burying assay is used to evaluate the anxiolytic activity of a test compound. After placement in a novel cage containing glass marbles, mice will bury the marbles. Acute administration of anxiolytic agents, as well as antidepressants, decrease this activity at non-sedating doses. Male C57Bl/6J mice from Jackson Laboratories were used in this study and were acclimatized to the experimental room for at least 1 hour prior to testing. Mice (n=10 per group) were administered sterile water or test compound intraperitoneally (i.p.) or orally by gavage (p.o.), or the positive control chlordiazepoxide (15 mg/kg, i.p.), in 10 mL/kg injection volumes, and returned to their home cages for a 30-minute pretreatment period. The mice were then placed individually in clean cages, containing hard wood bedding and twenty black marbles placed in spaced rows of 4×5. After a 30-minute test session, the number of buried marbles was counted. A marble was considered buried if it was pushed at least two thirds into the bedding. Locomotor activity was monitored by measuring the distance traveled using an overhead camera and Video Tracker Software (ViewPoint Life Sciences Software, France). A reduction in the number of marbles buried relative to the vehicle condition indicates an anxiolytic drug-like effect.

Effects of Compounds on Marble Burying in Mice.

| Compound | Dose | Marbles Buried |
|---|---|---|
| 111 | 3 mg/kg (p.o.) | − |
| | 10 mg/kg (p.o.) | + |
| | 30 mg/kg (p.o.) | + |
| 123 | 3 mg/kg (p.o.) | − |
| | 10 mg/kg (p.o.) | + |
| | 30 mg/kg (p.o.) | + |

| Compound | Dose | Marbles Buried |
|---|---|---|
| 114 | 1 mg/kg (p.o.) | − |
|  | 3 mg/kg (p.o.) | + |
|  | 10 mg/kg (p.o.) | + |
|  | 30 mg/kg (p.o.) | + |
| 117 | 1 mg/kg (p.o.) | − |
|  | 3 mg/kg (p.o.) | + |
|  | 10 mg/kg (p.o.) | + |
|  | 30 mg/kg (p.o.) | + |
| 118 | 3 mg/kg (p.o.) | − |
|  | 10 mg/kg (p.o.) | + |
|  | 30 mg/kg (p.o.) | + |
| 124 | 3 mg/kg (p.o.) | − |
|  | 10 mg/kg (p.o.) | + |
|  | 30 mg/kg (p.o.) | + |
| 152 | 1 mg/kg (i.p.) | − |
|  | 3 mg/kg (i.p.) | − |
|  | 10 mg/kg (i.p.) | + |
| 157 | 1 mg/kg (i.p.) | − |
|  | 3 mg/kg (i.p.) | − |
|  | 10 mg/kg (i.p.) | + |
| 160 | 1 mg/kg (i.p.) | − |
|  | 3 mg/kg (i.p.) | − |
|  | 10 mg/kg (i.p.) | + |
| 170 | 1 mg/kg (i.p.) | − |
|  | 3 mg/kg (i.p.) | − |
|  | 10 mg/kg (i.p.) | + |
| 195 | 1 mg/kg (i.p.) | − |
|  | 3 mg/kg (i.p.) | − |
|  | 10 mg/kg (i.p.) | + |

−: No reduction in number of marbles buried
+: Significant reduction in number of marbles buried ($P < 0.05$ vs vehicle)

Stress Induced Hyperthermia Assay

Stress-induced hyperthermia (SIH), mediated by the autonomic nervous system, is well known to occur prior to and during exposure to stress and/or anxiety-inducing situations. In many human anxiety disorders, it occurs as an integral part of the pathology and is often considered a representative symptom of the disease, e.g. in generalized anxiety disorder as defined in DSM-IV. In rodents, acute administration of anxiolytic drugs, such as buspirone or chlordiazepoxide (CDP), are known to reduce the SIH response to stressors such as handling, noise, heat, novelty, or pain. The test involves two measures of rectal temperature repeated in the same animal with a 10-minute interval. On the day prior to testing, male Sprague-Dawley rats from Envigo (n=10 per group) were brought to the experimental room approximately one hour before scheduled lights out and singly housed overnight with food and water ad libitum. On the morning of the experiment, animals were first injected with either vehicle or test compound orally by gavage, or CDP (10 mg/kg, i.p.). One hour following injection, each animal was removed from the holding cage and held in a supine position while the rectal temperature was measured by slowly inserting a rectal probe into the animal's rectum at a length of approximately 0.5 cm. The rectal probe was attached to a PhysiTemp digital thermometer (Fisher Scientific) which provides temperature readings at 0.1° C. accuracy. The probe remained inside the animal for approximately 5 seconds or until body temperature reaches stability. This temperature was recorded as the baseline rectal temperature (T1). The animal was immediately placed back to the holding cage and after a 10-min interval the second rectal temperature (T2) was taken using the same procedure as in measuring T1. Before each insertion, the rectal probe was cleaned with an alcohol pad and lubricated with sterile K-Y jelly. All SIH studies were conducted between 8:00-11:00 a.m. The SIH response was calculated as the difference in temperature between the second and first temperature reading (Delta T, $\Delta T$). A reduction in $\Delta T$ relative to the vehicle condition indicates an anxiolytic drug-like response.

Effects of Compounds on Stress-induced Hyperthermia (SIH) in Rats.

| Compound | Dose (mg/kg, PO) | Delta T ($\Delta T$) |
|---|---|---|
| 152 | 0.3 mg/kg | − |
|  | 1 mg/kg | + |
|  | 3 mg/kg | + |
|  | 10 mg/kg | + |
|  | 30 mg/kg | + |
| 157 | 1 mg/kg | − |
|  | 3 mg/kg | + |
|  | 10 mg/kg | + |
|  | 30 mg/kg | + |
| 170 | 3 mg/kg | − |
|  | 10 mg/kg | + |
|  | 30 mg/kg | + |

−: No change in Delta T ($\Delta T$)
+: Significant decrease in Delta T ($\Delta T$) ($P < 0.05$ vs vehicle)

Amphetamine Induced Hyperlocomotion Assay

Psychostimulants such as amphetamine (AMPH) are frequently used to induce or mimic a manic-like or psychotic-like state. AMPH administration to rodents increases horizontal locomotion, vertical rearing and repetitive stereotyped behaviors, and typical antipsychotic drugs, such as haloperidol, can reduce these behaviors. The antimanic/antipsychotic-like effects of test compounds were evaluated in male C57Bl/6J mice from Jackson Laboratories Mice were acclimatized to the experimental room for at least 1 hour prior to testing. The mice (n=10 per group) were administered vehicle or test compound orally by gavage (10 mL/kg injection volume) and placed individually in the novel open field (OF) chambers (Med Associates) for 30 minutes of baseline activity measurement. Mice were then injected with either water or AMPH (4 mg/kg, i.p., 10 mL/kg) and placed back in the same individual OF chambers for a 60-minute testing session during which the effects of test compounds on stimulant-induced behaviors (total distance traveled, rearing and stereotypy) were measured. A reduction in total distance traveled relative to the vehicle+AMPH condition indicates an antimanic/antipsychotic drug-like response.

Effects of Compounds on AMPH-Induced Hyperlocomotion in Mice.

| Compound | Dose (PO, mg/kg) | Total Distance Traveled (cm) |
|---|---|---|
| 111 | 3 mg/kg Compound + AMPH | # |
|  | 10 mg/kg Compound + AMPH | − |
|  | 30 mg/kg Compound + AMPH | + |
| 123 | 3 mg/kg Compound + AMPH | # |
|  | 10 mg/kg Compound + AMPH | − |
|  | 30 mg/kg Compound + AMPH | + |
| 114 | 3 mg/kg Compound + AMPH | − |
|  | 10 mg/kg Compound + AMPH | − |
|  | 30 mg/kg Compound + AMPH | + |
| 117 | 3 mg/kg Compound + AMPH | − |
|  | 10 mg/kg Compound + AMPH | − |
|  | 30 mg/kg Compound + AMPH | + |
| 118 | 3 mg/kg Compound + AMPH | − |
|  | 10 mg/kg Compound + AMPH | − |
|  | 30 mg/kg Compound + AMPH | + |

-continued

| Compound | Dose (PO, mg/kg) | Total Distance Traveled (cm) |
|---|---|---|
| 124 | 3 mg/kg Compound + AMPH | − |
|  | 10 mg/kg Compound + AMPH | − |
|  | 30 mg/kg Compound + AMPH | + |

: Significant increase in total distance traveled (P < 0.05 vs vehicle + AMPH group)
−: No change in total distance traveled
+: Significant decrease in total distance traveled (P < 0.05 vs vehicle + AMPH group)

Tail Suspension Test

The tail suspension test (TST) is a rodent screening test for potential (human) antidepressant drugs. It is based on the assumption that an animal will actively try to escape an aversive (stressful) stimulus. If escape is impossible, the animal will eventually stop trying ("give up"). In the TST, a mouse is suspended by the tail so that its body dangles in the air, head downward. Mice initially struggle to face upward and climb to a solid surface. When the animal stops struggling and hangs immobile it is considered to have "given up". Shorter periods of immobility are characteristic of antidepressant-like activity. Accordingly, longer periods of immobility are considered indicative of a depressive-like state. It has been shown that treatment with an antidepressant drug will decrease the time the animal spends immobile. See generally L. Steru et al., *Psychopharmacology (Berl)*. 1985; 85(3):367-70; B. Thierry et al., *Psychopharmacology* 1986; 90:284-85.

Procedure.

Adult male AJ mice from Jackson Laboratories received vehicle (sterile water) or test compound orally by gavage, or the positive control desipramine (20 mg/kg, i.p.), in 10 mL/kg injection volumes, 30 min before being subjected to the Tail Suspension Test. In this test, mice are placed in the Tail Suspension chambers (white polyvinylchloride cubicles measuring 33×33×31.75 cm Med Associates, Inc. St. Albans, Vt.) by a piece of transparent (Scotch®) tape attached to the tail, from about the mid-tail, with approximately 2 cm of tape past the end of the tail for 10 min during which the time spent immobile is measured. A reduction in total time immobile relative to the vehicle condition indicates an antidepressant drug-like response.

Effects of Compounds in a Tail-Suspension Test (TST) in Mice.

| Compound | Dose (PO, mg/kg) | Mean Total Time Immobile (sec) |
|---|---|---|
| 111 | 3 mg/kg | − |
|  | 10 mg/kg | − |
|  | 30 mg/kg | − |
| 123 | 3 mg/kg | − |
|  | 10 mg/kg | − |
|  | 30 mg/kg | − |
| 114 | 3 mg/kg | − |
|  | 10 mg/kg | − |
|  | 30 mg/kg | + |
| 117 | 3 mg/kg | − |
|  | 10 mg/kg | + |
|  | 30 mg/kg | − |
| 118 | 3 mg/kg | − |
|  | 10 mg/kg | − |
|  | 30 mg/kg | − |
| 124 | 3 mg/kg | − |
|  | 10 mg/kg | − |
|  | 30 mg/kg | − |

−: No decrease in Mean Total Time Immobile
+: Significant decrease in Mean Total Time Immobile (P < 0.05 vs vehicle)

Prepulse Inhibition of Startle

The acoustic startle is an unconditioned reflex response to an external auditory stimulus. Prepulse inhibition of startle (PPI) refers to the reduction in the startle response caused by the presentation of a low-intensity auditory stimulus prior to the startle stimulus. The PPI paradigm is used for the study of schizophrenia and antipsychotic action due to the similarities between the results from human and rodent studies. PPI has been used as a tool for the assessment of deficiencies in sensory-motor gating observed in schizophrenia and to screen for potential antipsychotic drugs. Various psychotomimetic drugs, such as phencyclidine (PCP), can disrupt PPI. In mice, antipsychotic drugs such as haloperidol can increase PPI and clozapine can reverse the disruption of PPI induced by PCP.

Male C57Bl/6J mice from Jackson Laboratories were placed in the PPI chambers (Med Associates) for a 5 min session of white noise (70 dB) habituation. After the habituation period, the test session was initiated. The session started with a habituation block of 6 presentations of the startle stimulus alone, followed by 10 PPI blocks, each of which consisted of 6 different types of trials. Trial types were: 'null' (no stimuli), 'startle' (120 dB), 'startle plus prepulse' (4, 8, and 12 dB over background noise, i.e., 74, 78, or 82 dB) and 'prepulse' (82 dB). Trial types were presented in a random order within each block. Each trial started with a 50 ms stimulus-free period during which baseline movements were recorded. This was followed by a subsequent 20 ms period during which the prepulse stimulus was presented and responses to the prepulse measured. After a further 100 ms period, the startle stimulus was presented for 40 ms and responses recorded for 100 ms from startle onset. Responses were sampled every ms. The inter-trial interval was variable with an average of 15 s (range from 10 to 20 s). In 'startle' trials, the basic auditory startle response was measured. The basic startle response was calculated as the mean startle response of all 'startle' trials (i.e., excluding the first habituation block). In 'startle plus prepulse' trials, the degree of inhibition of the normal startle was calculated and expressed as a percentage of the basic startle response.

Mice were treated with vehicle or test compound orally by gavage, or haloperidol (1 mg/kg, i.p.), in 10 mL/kg injection volumes, 30 min prior to PPI test. The PPI enclosures were cleaned following each test. An increase in the percent PPI relative to the vehicle condition indicates an antipsychotic drug-like response.

Effects of Compounds on Pre-Pulse Inhibition (PPI) in Mice.

| Compound | Dose (PO, mg/kg) | Effect |
|---|---|---|
| 111 | 3 mg/kg | − |
|  | 10 mg/kg | − |
|  | 30 mg/kg | +++ |
| 123 | 3 mg/kg | − |
|  | 10 mg/kg | − |
|  | 30 mg/kg | − |
| 114 | 3 mg/kg | − |
|  | 10 mg/kg | − |
|  | 30 mg/kg | − |
| 117 | 3 mg/kg | − |
|  | 10 mg/kg | − |
|  | 30 mg/kg | +++ |
| 118 | 3 mg/kg | − |
|  | 10 mg/kg | − |
|  | 30 mg/kg | − |

| Compound | Dose (PO, mg/kg) | Effect |
|---|---|---|
| 124 | 3 mg/kg | − |
|  | 10 mg/kg | − |
|  | 30 mg/kg | − |

−: No change in PPI
+: Significant increase in PPI at one pre-pulse intensity (P < 0.05 vs vehicle)
++: Significant increase in PPI at two pre-pulse intensities (P < 0.05 vs vehicle)
+++: Significant increase in PPI at three pre-pulse intensities (P < 0.05 vs vehicle)

In Vivo Microdialysis of the Prefrontal Cortex and Nucleus Accumbens

In vivo microdialysis is a biological sampling technique used to evaluate the extracellular concentrations of neurotransmitters in specific brain regions following administration of a test compound to animals. Dysfunctions of brain neurotransmitter systems, such as dopamine (DA), norepinephrine (NE), serotonin (5-HT) and/or acetylcholine (ACh), have been linked to cognitive deficits (e.g., memory impairment, inattention, etc.), which may be observed in human aging, Alzheimer's disease (AD) and Attention Deficit Hyperactivity Disorder (ADHD). Drugs that increase extracellular concentrations of DA, NE, 5-HT and/or ACh in the prefrontal cortex (PFC), such as donepezil and methylphenidate, can reverse cognitive deficits in humans and animals.

Adult male C57Bl/6 mice (n=6 per group) from Jackson Laboratories were anesthetized using isoflurane (2%, 800 mL/min $O_2$). Bupivacaine/epinephrine was used for local anesthesia and carprofen was used for peri-/post-operative analgesia. The animals were placed in a stereotaxic frame (Kopf instruments, USA) and I-shaped microdialysis probes (polyacrylonitril membrane, BrainLink, the Netherlands) were inserted into the PFC (2 mm exposed membrane; coordinates for the tips of the probes: posterior (AP)=+2.0 mm to bregma, lateral (L)=−0.5 mm to midline and ventral (V)=−3.3 mm to dura, the toothbar set at 0.0 mm) and the NAcc (coordinates for the tips of the probes: posterior (AP)=+0.8 mm to bregma, lateral (L)=+0.9 mm to midline and ventral (V)=−4.2 mm to dura, the toothbar set at 0.0 mm (Paxinos and Franklin, 2001)). After surgery, animals were housed individually in cages and provided food and water ad libitum. In vivo microdialysis experiments were performed one day after surgery. On the day of the experiment, the microdialysis probes were connected with flexible PEEK tubing to a microperfusion pump (Harvard PHD 2000 Syringe pump, Holliston, Mass. or similar). Microdialysis probes were perfused with artificial cerebrospinal fluid (aCSF) containing 147 mM NaCl, 3.0 mM KCl, 1.2 mM $CaCl_2$ and 1.2 mM $MgCl_2$, at a flow rate of 1.5 L/min. Microdialysis samples were collected for 30 minute periods by an automated fraction collector (820 Microsampler, Univentor, Malta or similar) into polystyrene mini-vials already containing 15 µL of 0.02 M formic acid (FA) and 0.04% ascorbic acid in ultrapurified $H_2O$. Four basal samples were collected before the administration of vehicle or test compound (i.p., 5 mL/kg injection volumes). Samples were collected for an additional 240 min following vehicle or compound administration. All the dialysis samples were stored at −80° C. awaiting analysis. After the experiment, the mice were sacrificed and brain tissue was collected for probe verification. Each dialysis sample was analyzed for concentrations of DA, NE, 5-HT and ACh as determined by HPLC with tandem mass spectrometry (MS/MS) detection using labeled isotopes of the analytes of interest as internal standards. Data was expressed as a percentage of basal output, calculated by dividing each post-dose time point with the average basal output=100%. An increase in the post-dose percent basal output of DA, NE, 5-HT and/or ACh in the PFC relative to the vehicle condition indicates a potential cognition-enhancing drug-like response. Graphical representations of the observed changes in neurotransmitter concentrations are shown in the indicated Figures.

Effects of Compounds on Neurotransmitters in the PFC and NAcc in Mice.

Figure 4:
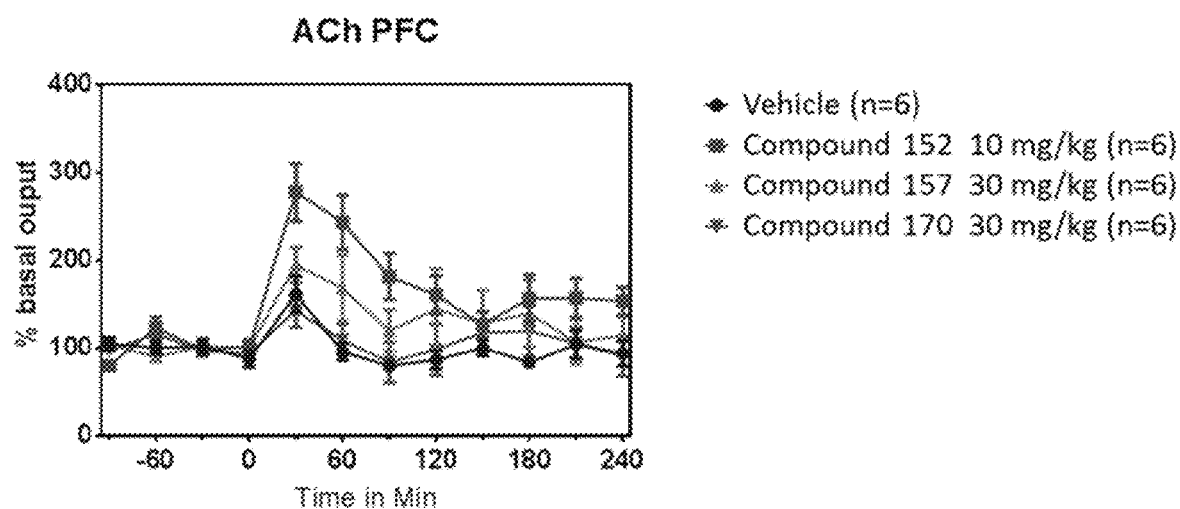
FIG. 4 shows the effect of representative compounds of the invention on treatment on ACh release in the PFC

| Compound | Dose (mg/kg, IP) | PFC [DA] (FIG. 1) | PFC [5-HT] (FIG. 2) | PFC [NE] (FIG. 3) | PFC [ACh] (FIG. 4) |
|---|---|---|---|---|---|
| 152 | 10 mg/kg | + | + | + | + |
| 157 | 30 mg/kg | + | + | + | − |
| 170 | 30 mg/kg | + | − | + | − |

Figure 5:
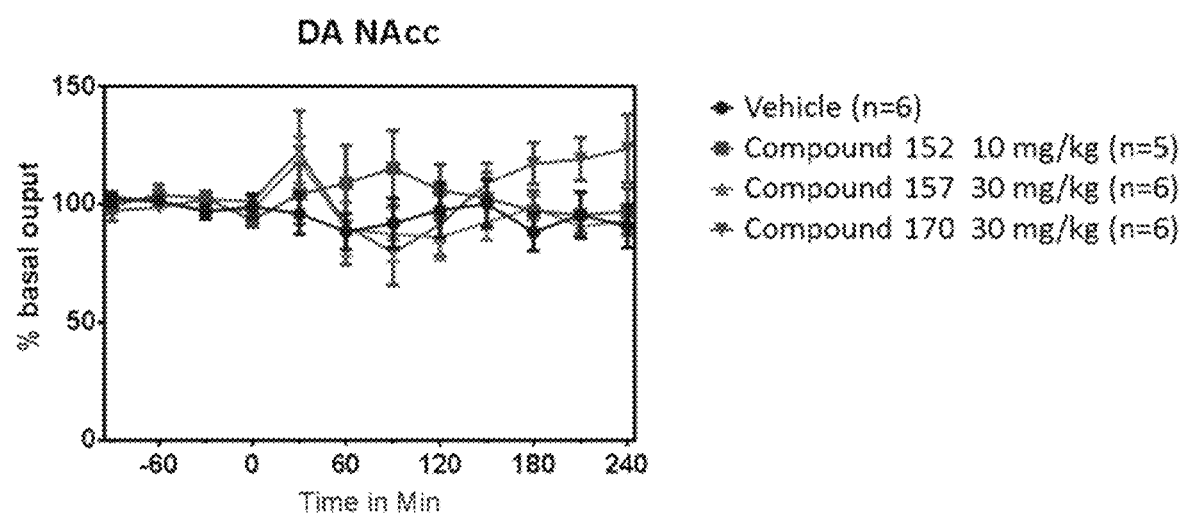
FIG. 5 shows the effect of representative compounds of the invention on treatment on DA release in the NAcc.
Figure 6:
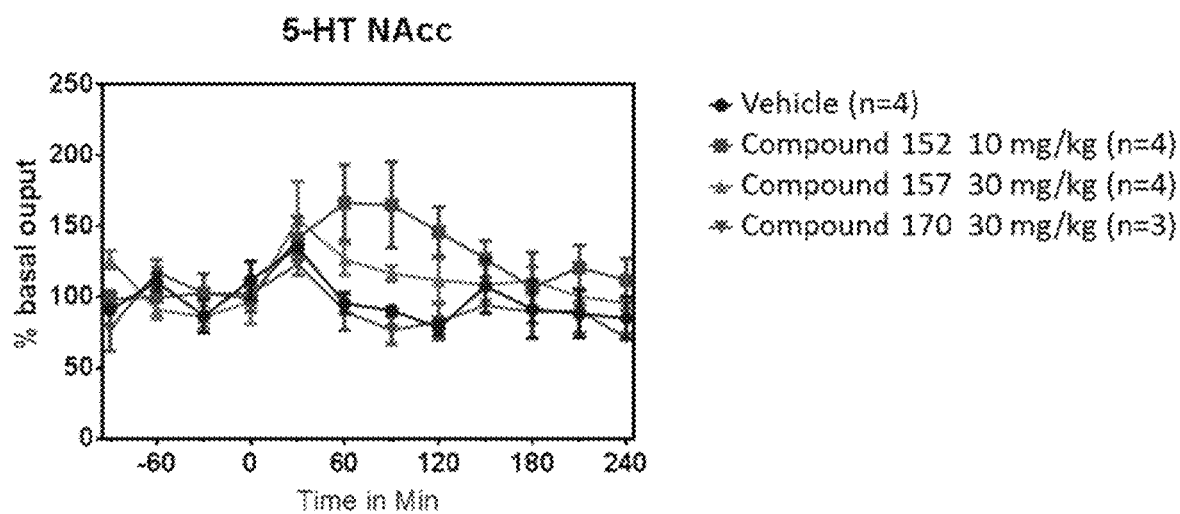
FIG. 6 shows the effect of representative compounds of the invention on treatment on 5-HT release in the NAcc.
Figure 7:
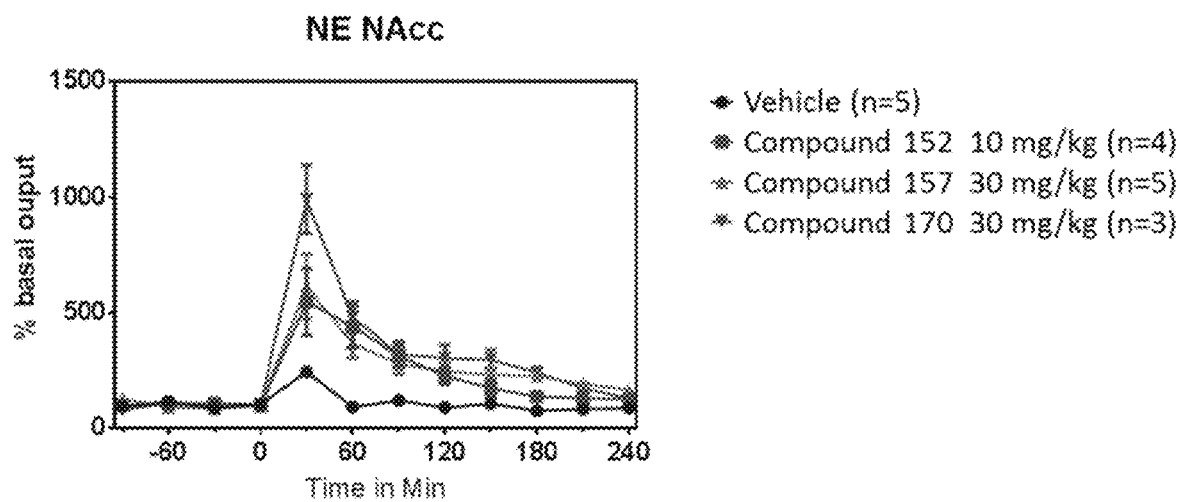
FIG. 7 shows the effect of representative compounds of the invention on treatment on NE release in the NAcc.
Figure 8:
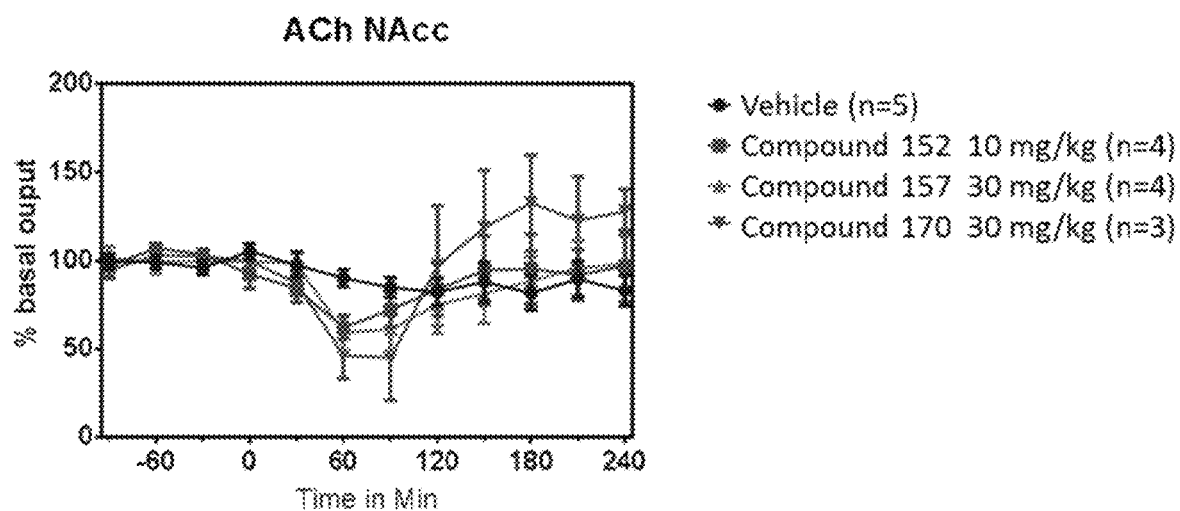
FIG. 8 shows the effect of representative compounds of the invention on treatment on ACh release in the NAcc.

| Compound | Dose (mg/kg, IP) | NAcc [DA] (FIG. 5) | NAcc [5-HT] (FIG. 6) | NAcc [NE] (FIG. 7) | NAcc [ACh] (FIG. 8) |
|---|---|---|---|---|---|
| 152 | 10 mg/kg | − | + | + | − |
| 157 | 30 mg/kg | − | − | + | − |
| 170 | 30 mg/kg | − | − | + | − |

−: No change in extracellular concentration (P < 0.05 vs vehicle)
+: Significant increase in extracellular concentration (P < 0.05 vs vehicle)

LIST OF ABBREVIATIONS

5-HT 5-hydroxytrytophan (serotonin)
ACh acetylcholine
ACN acetonitrile
aCSF artificial cerebrospinal fluid
AMPH Amphetamine
AP anterior-posterior
° C. degrees Celsius
CDP chlordiazepoxide
cm centimeter
DA dopamine
FA formic acid
g gram
HPLC high performance liquid chromatography
IP intraperitoneal
L lateral
LC liquid chromatography
µL microliter
MD microdialysis
mg/kg milligram per kilogram
mL milliliter
mm millimeter
mM millimolar
min/Min minute
MRM multiple reaction monitoring
MS mass spectrometry
MSq mean squared
NAcc nucleus accumbens
NE norepinephrine
nM nanomolar
P p-value
PCP Phencyclidine
PPI Pre-pulse Inhibition
% percentage
PFC prefrontal cortex
pmol picomole
PSIG pounds per square inch gage
QC quality control sec seconds
SEM standard error of the mean
SIH stress-induced hyperthermia
TST tail suspension test
V ventral
UP ultra-pure It may be found upon examination that additional species and genera not presently excluded from the claims to pharmaceutical compositions and chemical compounds are not patentable to the inventors in this application. In that case, the subsequent exclusion of species and genera in applicants' claims are to be considered artifacts of patent prosecution and not reflective of the inventors' concept or description of their invention. The invention, in a composition aspect, is all compounds of formula I except those that are in the public's possession.

It is to be understood that the invention is not limited to the particular embodiments of the invention described above, as variations of the particular embodiments may be made and still fall within the scope of the appended claims.

The invention claimed is:

1. A composition comprising a compound, wherein said compound is:

[four stereoisomer structures of 3-methyl-isochroman-4-amine]

or a pharmaceutically acceptable salt thereof, and wherein said composition is greater than 90% enantiomerically pure.

2. The composition according to claim 1, wherein said composition is greater than 95% enantiomerically pure.

3. A composition comprising a compound, wherein said compound is:

[two stereoisomer structures]

or a pharmaceutically acceptable salt thereof, and wherein said composition is greater than 90% enantiomerically pure.

4. The composition according to claim 3, wherein said composition is greater than 95% enantiomerically pure.

5. A pharmaceutical composition comprising a compound, wherein said compound is:

[structure]

or a pharmaceutically acceptable salt thereof, and a pharmaceutically acceptable carrier, adjuvant, or vehicle.

6. A pharmaceutical composition comprising a compound, wherein said compound is:

[four stereoisomer structures]

or a pharmaceutically acceptable salt thereof, and a pharmaceutically acceptable carrier, adjuvant, or vehicle.

7. The pharmaceutical composition of claim 6, wherein said compound is:

[two structures]

or a pharmaceutically acceptable salt thereof.

8. The pharmaceutical composition of claim 5, wherein said compound is:

[structure]

or a pharmaceutically acceptable salt thereof.

9. The pharmaceutical composition of claim 5, wherein said compound is:

[structure]

or a pharmaceutically acceptable salt thereof.

10. The pharmaceutical composition of claim 5, wherein said compound is:

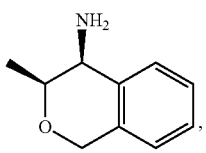

or a pharmaceutically acceptable salt thereof.

11. The pharmaceutical composition of claim 5, wherein said compound is:

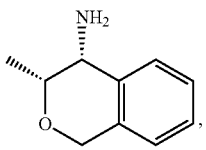

or a pharmaceutically acceptable salt thereof.

12. A method for alleviating or inhibiting the progress of a neurological or psychiatric disease or disorder selected from the group consisting of depression, bipolar disorder, pain, schizophrenia, obsessive compulsive disorder, addiction, social disorder, attention deficit hyperactivity disorder, an anxiety disorder, a movement disorder, epilepsy, Alzheimer's disease, Parkinson's disease, autism and cognitive impairments in a subject in need thereof, comprising administering to said subject an effective amount of a compound, wherein said compound is:

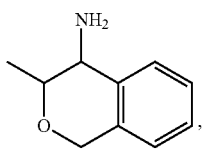

or a pharmaceutically acceptable salt thereof.

13. The method of claim 12, wherein said neurological or psychiatric disorder is depression.

14. The method of claim 13, wherein the depression is treatment-resistant depression (TRD), major depressive disorder (MDD), unipolar depression, bipolar depression or depression associated with another disease or disorder.

15. The method of claim 12, wherein said neurological or psychiatric disorder is bipolar disorder.

16. The method of claim 12, wherein said neurological or psychiatric disorder is pain.

17. The method of claim 12, wherein said neurological or psychiatric disorder is schizophrenia.

18. The method of claim 12, wherein said neurological or psychiatric disorder is obsessive compulsive disorder.

19. The method of claim 12, wherein said neurological or psychiatric disorder is addiction.

20. The method of claim 12, wherein said neurological or psychiatric disorder is social disorder.

21. The method of claim 12, wherein said neurological or psychiatric disorder is attention deficit hyperactivity disorder.

22. The method of claim 12, wherein said neurological or psychiatric disorder is an anxiety disorder.

23. The method of claim 12, wherein said neurological or psychiatric disorder is a movement disorder.

24. The method of claim 12, wherein said neurological or psychiatric disorder is Alzheimer's disease.

25. The method of claim 12, wherein said neurological or psychiatric disorder is Parkinson's disease.

26. The method of claim 12, wherein said neurological or psychiatric disorder is autism.

27. The method of claim 12, wherein said neurological or psychiatric disorder is cognitive impairments.

28. A method of alleviating or inhibiting the progress of a neurological or psychiatric disease or disorder selected from the group consisting of depression, bipolar disorder, pain, schizophrenia, obsessive compulsive disorder, addiction, social disorder, attention deficit hyperactivity disorder, an anxiety disorder, a movement disorder, epilepsy, Alzheimer's disease, Parkinson's disease, autism and cognitive impairments in a subject in need thereof, comprising administering to said subject an effective amount of a compound, wherein said compound is:

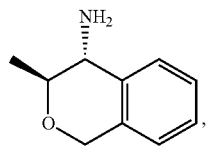

or a pharmaceutically acceptable salt thereof.

29. The method of claim 28, wherein said neurological or psychiatric disorder is depression.

30. The method of claim 29, wherein the depression is treatment-resistant depression (TRD), major depressive disorder (MDD), unipolar depression, bipolar depression or depression associated with another disease or disorder.

31. The method of claim 28, wherein said neurological or psychiatric disorder is bipolar disorder.

32. The method of claim 28, wherein said neurological or psychiatric disorder is pain.

33. The method of claim 28, wherein said neurological or psychiatric disorder is schizophrenia.

34. The method of claim 28, wherein said neurological or psychiatric disorder is obsessive compulsive disorder.

35. The method of claim 28, wherein said neurological or psychiatric disorder is addiction.

36. The method of claim 28, wherein said neurological or psychiatric disorder is social disorder.

37. The method of claim 28, wherein said neurological or psychiatric disorder is attention deficit hyperactivity disorder.

38. The method of claim 28, wherein said neurological or psychiatric disorder is an anxiety disorder.

39. The method of claim 28, wherein said neurological or psychiatric disorder is a movement disorder.

40. The method of claim 28, wherein said neurological or psychiatric disorder is Alzheimer's disease.

41. The method of claim 28, wherein said neurological or psychiatric disorder is Parkinson's disease.

42. The method of claim 28, wherein said neurological or psychiatric disorder is autism.

43. The method of claim 28, wherein said neurological or psychiatric disorder is cognitive impairments.

44. The method of claim 12, wherein said neurological or psychiatric disorder is epilepsy.

45. The method of claim 28, wherein said neurological or psychiatric disorder is epilepsy.

* * * * *